US012712082B2

(12) United States Patent
Min et al.

(10) Patent No.: US 12,712,082 B2
(45) Date of Patent: Aug. 18, 2026

(54) SYSTEMS, DEVICES, AND METHODS FOR NON-INVASIVE IMAGE-BASED PLAQUE ANALYSIS AND RISK DETERMINATION

(71) Applicant: Cleerly, Inc., Denver, CO (US)

(72) Inventors: James K. Min, Durham, NC (US); James P. Earls, Alexandria, VA (US); Shant Malkasian, Pasadena, CA (US); Hugo Miguel Rodrigues Marques, Lisbon (PT); Chung Chan, Northbrook, IL (US); Shai Ronen, Westminster, CO (US)

(73) Assignee: Cleerly, Inc., Denver, CO (US)

( * ) Notice: Subject to any disclaimer, the term of this patent is extended or adjusted under 35 U.S.C. 154(b) by 234 days.

(21) Appl. No.: 18/614,592

(22) Filed: Mar. 22, 2024

(65) Prior Publication Data

US 2024/0266065 A1 Aug. 8, 2024

Related U.S. Application Data

(63) Continuation of application No. 18/390,555, filed on Dec. 20, 2023, which is a continuation-in-part of (Continued)

(51) Int. Cl.
*G16H 50/30* (2018.01)
*A61B 5/00* (2006.01)
(Continued)

(52) U.S. Cl.
CPC ......... *G16H 50/30* (2018.01); *A61B 5/02028* (2013.01); *A61B 5/4848* (2013.01); (Continued)

(58) Field of Classification Search
CPC ........ G16H 50/30; G16H 30/40; G16H 50/20; A61B 5/02028; A61B 5/4848;
(Continued)

(56) References Cited

U.S. PATENT DOCUMENTS

| | | |
|---|---|---|
| 4,296,901 A | 10/1981 | Perrott |
| 4,945,478 A | 7/1990 | Merickel et al. |

(Continued)

FOREIGN PATENT DOCUMENTS

| | | |
|---|---|---|
| AU | 2023200986 A1 | 3/2023 |
| CA | 2368390 A1 | 9/2000 |

(Continued)

OTHER PUBLICATIONS

US 11,791,027 B2, 10/2023, Buckler et al. (withdrawn)
(Continued)

*Primary Examiner* — Ming Y Hon
*Assistant Examiner* — Amanda H Pearson
(74) *Attorney, Agent, or Firm* — Ashurst Perkins Coie US LLP

(57) ABSTRACT

Various embodiments described herein relate to systems, devices, and methods for non-invasive image-based plaque analysis and risk determination. In particular, in some embodiments, the systems, devices, and methods described herein are related to analysis of one or more regions of plaque, such as for example coronary plaque, using non-invasively obtained images that can be analyzed using computer vision or machine learning to identify, diagnose, characterize, treat and/or track coronary artery disease.

20 Claims, 35 Drawing Sheets

Related U.S. Application Data application No. 18/508,098, filed on Nov. 13, 2023, now abandoned, which is a continuation-in-part of application No. 18/179,921, filed on Mar. 7, 2023, now Pat. No. 12,406,365.

(60) Provisional application No. 63/501,490, filed on May 11, 2023, provisional application No. 63/478,128, filed on Dec. 31, 2022, provisional application No. 63/478,127, filed on Dec. 31, 2022, provisional application No. 63/478,124, filed on Dec. 31, 2022, provisional application No. 63/478,126, filed on Dec. 31, 2022, provisional application No. 63/478,084, filed on Dec. 30, 2022, provisional application No. 63/477,961, filed on Dec. 30, 2022, provisional application No. 63/478,076, filed on Dec. 30, 2022, provisional application No. 63/477,985, filed on Dec. 30, 2022, provisional application No. 63/477,947, filed on Dec. 30, 2022, provisional application No. 63/477,640, filed on Dec. 29, 2022, provisional application No. 63/477,661, filed on Dec. 29, 2022, provisional application No. 63/477,632, filed on Dec. 29, 2022, provisional application No. 63/477,650, filed on Dec. 29, 2022, provisional application No. 63/477,643, filed on Dec. 29, 2022, provisional application No. 63/477,638, filed on Dec. 29, 2022, provisional application No. 63/477,656, filed on Dec. 29, 2022, provisional application No. 63/476,577, filed on Dec. 21, 2022, provisional application No. 63/476,522, filed on Dec. 21, 2022, provisional application No. 63/476,255, filed on Dec. 20, 2022, provisional application No. 63/476,245, filed on Dec. 20, 2022, provisional application No. 63/476,251, filed on Dec. 20, 2022, provisional application No. 63/386,376, filed on Dec. 7, 2022, provisional application No. 63/386,297, filed on Dec. 6, 2022, provisional application No. 63/385,472, filed on Nov. 30, 2022, provisional application No. 63/385,179, filed on Nov. 28, 2022, provisional application No. 63/383,904, filed on Nov. 15, 2022, provisional application No. 63/383,632, filed on Nov. 14, 2022, provisional application No. 63/381,210, filed on Oct. 27, 2022, provisional application No. 63/368,293, filed on Jul. 13, 2022, provisional application No. 63/365,381, filed on May 26, 2022, provisional application No. 63/364,084, filed on May 3, 2022, provisional application No. 63/364,078, filed on May 3, 2022, provisional application No. 63/362,856, filed on Apr. 12, 2022, provisional application No. 63/362,108, filed on Mar. 29, 2022, provisional application No. 63/269,136, filed on Mar. 10, 2022.

(51) Int. Cl.

| | |
|---|---|
| ***A61B 5/02*** | (2006.01) |
| ***G06T 7/00*** | (2017.01) |
| ***G06T 7/10*** | (2017.01) |
| ***G06T 7/60*** | (2017.01) |
| ***G06V 20/50*** | (2022.01) |
| ***G16H 30/40*** | (2018.01) |

(52) U.S. Cl.

CPC .............. *G06T 7/0016* (2013.01); *G06T 7/10* (2017.01); *G06T 7/60* (2013.01); *G06V 20/50* (2022.01); *G16H 30/40* (2018.01); *G06T 2207/10048* (2013.01); *G06T 2207/10081* (2013.01); *G06T 2207/10088* (2013.01); *G06T 2207/10101* (2013.01); *G06T 2207/10104* (2013.01); *G06T 2207/10108* (2013.01); *G06T 2207/10116* (2013.01); *G06T 2207/10132* (2013.01); *G06T 2207/20081* (2013.01); *G06T 2207/30048* (2013.01); *G06T 2207/30101* (2013.01); *G06V 2201/031* (2022.01)

(58) Field of Classification Search

CPC . A61B 5/0044; A61B 5/02007; G06T 7/0016; G06T 7/10; G06T 7/60; G06T 2207/10048; G06T 2207/10081; G06T 2207/10088; G06T 2207/10101; G06T 2207/10104; G06T 2207/10108; G06T 2207/10116; G06T 2207/10132; G06T 2207/30048; G06T 2207/30101; G06T 7/0012; G06V 2201/031

See application file for complete search history.

(56) References Cited

U.S. PATENT DOCUMENTS

| | | | |
|---|---|---|---|
| 5,056,130 | A | 10/1991 | Engel |
| 5,722,408 | A | 3/1998 | Dehner et al. |
| 5,891,030 | A | 4/1999 | Johnson et al. |
| 5,944,689 | A | 8/1999 | Houser et al. |
| 6,047,080 | A | 4/2000 | Chen et al. |
| 6,320,931 | B1 | 11/2001 | Arnold |
| 6,591,004 | B1 | 7/2003 | Vanessen et al. |
| 6,993,382 | B2 | 1/2006 | Casscells et al. |
| 7,008,401 | B2 | 3/2006 | Thompson et al. |
| 7,011,655 | B2 | 3/2006 | Thompson et al. |
| 7,045,238 | B2 | 5/2006 | Gottmann et al. |
| 7,191,110 | B1 | 3/2007 | Charbel et al. |
| 7,276,044 | B2 | 10/2007 | Ferry et al. |
| 7,351,214 | B2 | 4/2008 | Burgermeister |
| 7,371,248 | B2 | 5/2008 | Dapolito et al. |
| 7,535,986 | B2 | 5/2009 | Hempel |
| 7,558,611 | B2 | 7/2009 | Arnold et al. |
| 7,570,983 | B2 | 8/2009 | Becker et al. |
| 7,705,490 | B2 | 4/2010 | Srinivasan et al. |
| 7,711,165 | B2 | 5/2010 | Lesage et al. |
| 7,715,626 | B2 | 5/2010 | Florin et al. |
| 7,766,856 | B2 | 8/2010 | Ferry et al. |
| 7,803,130 | B2 | 9/2010 | Ryan et al. |
| 7,805,385 | B2 | 9/2010 | Steck et al. |
| 7,813,549 | B2 | 10/2010 | Buelow et al. |
| 7,840,062 | B2 | 11/2010 | Boroczky et al. |
| 7,860,283 | B2 | 12/2010 | Begelman et al. |
| 7,876,939 | B2 | 1/2011 | Yankelevitz et al. |
| 7,899,764 | B2 | 3/2011 | Martin et al. |
| 7,904,977 | B1 | 3/2011 | Singh |
| 7,907,766 | B2 | 3/2011 | Lehel et al. |
| 7,912,528 | B2 | 3/2011 | Krishnan et al. |
| 7,940,974 | B2 | 5/2011 | Skinner et al. |
| 7,940,977 | B2 | 5/2011 | Begelman et al. |
| 7,953,266 | B2 | 5/2011 | Gulsun et al. |
| 7,974,681 | B2 | 7/2011 | Wallace et al. |
| 7,993,274 | B2 | 8/2011 | Pruvot et al. |
| 7,998,020 | B2 | 8/2011 | Kidd et al. |
| 8,009,793 | B2 | 8/2011 | Langheinrich et al. |
| 8,021,326 | B2 | 9/2011 | Moll et al. |
| 8,046,488 | B2 | 10/2011 | Cherukuri et al. |
| 8,068,894 | B2 | 11/2011 | Huizenga et al. |
| 8,107,695 | B2 | 1/2012 | Wollenweber |
| 8,108,069 | B2 | 1/2012 | Stahler et al. |
| 8,114,097 | B2 | 2/2012 | Brock et al. |
| 8,139,836 | B2 | 3/2012 | Arnold et al. |
| 8,144,949 | B2 | 3/2012 | Simon et al. |
| 8,186,880 | B1 | 5/2012 | Arnold |
| 8,200,466 | B2 | 6/2012 | Spilker et al. |
| 8,211,084 | B2 | 7/2012 | Kassab et al. |
| 8,257,302 | B2 | 9/2012 | Beyar et al. |
| 8,317,744 | B2 | 11/2012 | Kirschenman |
| 8,386,188 | B2 | 2/2013 | Taylor et al. |
| 8,390,438 | B2 | 3/2013 | Olson et al. |

(56) References Cited

U.S. PATENT DOCUMENTS

| | | | |
|---|---|---|---|
| 8,460,236 | B2 | 6/2013 | Roelle et al. |
| 8,494,244 | B2 | 7/2013 | Dutta et al. |
| 8,526,699 | B2 | 9/2013 | Mittal et al. |
| 8,551,084 | B2 | 10/2013 | Hauck et al. |
| 8,582,854 | B2 | 11/2013 | Zhang et al. |
| 8,603,068 | B2 | 12/2013 | Weitzner et al. |
| 8,605,979 | B2 | 12/2013 | Arnold et al. |
| 8,615,288 | B2 | 12/2013 | Govari et al. |
| 8,660,326 | B2 | 2/2014 | Ohayon et al. |
| 8,684,953 | B2 | 4/2014 | Cabiri |
| 8,740,840 | B2 | 6/2014 | Foley et al. |
| 8,774,479 | B2 | 7/2014 | Madabhushi et al. |
| 8,777,854 | B2 | 7/2014 | Patwardhan et al. |
| 8,790,297 | B2 | 7/2014 | Bromander et al. |
| 8,867,822 | B2 | 10/2014 | Oh et al. |
| 8,885,905 | B2 | 11/2014 | Dey et al. |
| 8,938,106 | B2 | 1/2015 | Aulbach et al. |
| 9,005,217 | B2 | 4/2015 | Govari et al. |
| 9,008,392 | B1 | 4/2015 | Bai et al. |
| 9,058,692 | B1 | 6/2015 | Grady et al. |
| 9,066,740 | B2 | 6/2015 | Carlson et al. |
| 9,070,214 | B1 | 6/2015 | Grady et al. |
| 9,081,721 | B1 | 7/2015 | Grady et al. |
| 9,129,417 | B2 | 9/2015 | Zheng et al. |
| 9,138,566 | B2 | 9/2015 | Cabiri |
| 9,155,512 | B2 | 10/2015 | Choi et al. |
| 9,159,159 | B2 | 10/2015 | Bai et al. |
| 9,195,801 | B1 | 11/2015 | Sankaran et al. |
| 9,220,418 | B2 | 12/2015 | Choi et al. |
| 9,220,419 | B2 | 12/2015 | Choi et al. |
| 9,220,568 | B2 | 12/2015 | Bromander et al. |
| 9,235,887 | B2 | 1/2016 | Buckler et al. |
| 9,239,905 | B1 | 1/2016 | Sankaran et al. |
| 9,280,639 | B2 | 3/2016 | Sankaran et al. |
| 9,295,397 | B2 | 3/2016 | Liu et al. |
| 9,295,429 | B2 | 3/2016 | Ong et al. |
| 9,295,527 | B2 | 3/2016 | Kirschenman et al. |
| 9,320,573 | B2 | 4/2016 | Sandhu et al. |
| 9,333,324 | B2 | 5/2016 | Cohen et al. |
| 9,378,580 | B2 | 6/2016 | Grady et al. |
| 9,430,827 | B2 | 8/2016 | Kelm et al. |
| 9,538,925 | B2 | 1/2017 | Sharma et al. |
| 9,545,246 | B2 | 1/2017 | Lavender |
| 9,586,029 | B2 | 3/2017 | Shekalim et al. |
| 9,610,272 | B2 | 4/2017 | Soni |
| 9,633,277 | B2 | 4/2017 | Feldman et al. |
| 9,642,586 | B2 | 5/2017 | Kelm et al. |
| 9,649,171 | B2 | 5/2017 | Sankaran et al. |
| 9,655,563 | B2 | 5/2017 | Liu et al. |
| 9,679,374 | B2 | 6/2017 | Choi et al. |
| 9,700,219 | B2 | 7/2017 | Sharma et al. |
| 9,715,562 | B2 | 7/2017 | Goldstein et al. |
| 9,721,340 | B2 | 8/2017 | Gillies et al. |
| 9,761,004 | B2 | 9/2017 | Mittal et al. |
| 9,763,650 | B2 | 9/2017 | Chen et al. |
| 9,767,557 | B1 | 9/2017 | Gulsun et al. |
| 9,770,303 | B2 | 9/2017 | Choi et al. |
| 9,785,748 | B2 | 10/2017 | Koo et al. |
| 9,805,463 | B2 | 10/2017 | Choi et al. |
| 9,805,470 | B2 | 10/2017 | Bhatia et al. |
| 9,814,490 | B2 | 11/2017 | Neoh et al. |
| 9,836,653 | B2 | 12/2017 | Schnittman |
| 9,839,399 | B2 | 12/2017 | Fonte et al. |
| 9,839,484 | B2 | 12/2017 | Taylor |
| 9,881,372 | B2 | 1/2018 | Gulsun et al. |
| 9,965,891 | B2 | 5/2018 | Grady et al. |
| 9,980,960 | B2 | 5/2018 | Chance |
| 10,010,255 | B2 | 7/2018 | Fonte et al. |
| 10,010,700 | B2 | 7/2018 | Romoscanu |
| 10,052,031 | B2 | 8/2018 | Sharma et al. |
| 10,078,124 | B2 | 9/2018 | Horkay et al. |
| 10,082,553 | B2 | 9/2018 | Boss |
| 10,082,793 | B1 | 9/2018 | Glaser |
| 10,130,242 | B2 | 11/2018 | Ostrovsky et al. |
| 10,149,728 | B2 | 12/2018 | Bencteux et al. |
| 10,170,206 | B2 | 1/2019 | Koo et al. |
| 10,176,408 | B2 | 1/2019 | Paik et al. |
| 10,307,131 | B2 | 6/2019 | Taylor et al. |
| 10,352,411 | B2 | 7/2019 | Fojtik |
| 10,354,360 | B2 | 7/2019 | Sakamoto |
| 10,357,230 | B2 | 7/2019 | Bolduc |
| 10,359,783 | B2 | 7/2019 | Williams et al. |
| 10,398,331 | B2 | 9/2019 | Relan et al. |
| 10,433,740 | B2 | 10/2019 | Fonte et al. |
| 10,448,811 | B2 | 10/2019 | London et al. |
| 10,451,409 | B2 | 10/2019 | Tojo et al. |
| 10,453,191 | B2 | 10/2019 | Shalev et al. |
| 10,456,094 | B2 | 10/2019 | Fonte et al. |
| 10,456,556 | B2 | 10/2019 | Cabiri |
| 10,463,835 | B2 | 11/2019 | Jungles |
| 10,470,793 | B2 | 11/2019 | Mcarthur et al. |
| 10,478,130 | B2 | 11/2019 | Sharma et al. |
| 10,478,595 | B2 | 11/2019 | Kokish |
| 10,483,006 | B2 | 11/2019 | Itu et al. |
| 10,492,755 | B2 | 12/2019 | Lin et al. |
| 10,498,755 | B2 | 12/2019 | Harris et al. |
| 10,500,373 | B2 | 12/2019 | Barrish et al. |
| 10,507,037 | B2 | 12/2019 | Doud et al. |
| 10,517,677 | B2 | 12/2019 | Sankaran et al. |
| 10,542,878 | B2 | 1/2020 | Dewaele et al. |
| 10,549,071 | B2 | 2/2020 | Falb et al. |
| 10,610,203 | B2 | 4/2020 | Liang et al. |
| 10,632,287 | B2 | 4/2020 | Romoscanu et al. |
| 10,667,673 | B2 | 6/2020 | Su et al. |
| 10,695,023 | B2 | 6/2020 | Antoniades et al. |
| 10,695,533 | B2 | 6/2020 | Deboeuf et al. |
| 10,695,536 | B2 | 6/2020 | Weitzner et al. |
| 10,709,510 | B2 | 7/2020 | Kottenstette |
| 10,740,880 | B2 | 8/2020 | Paik et al. |
| 10,744,301 | B2 | 8/2020 | Pacheco et al. |
| 10,755,810 | B2 | 8/2020 | Buckler et al. |
| 10,762,624 | B2 | 9/2020 | Daughton et al. |
| 10,776,988 | B2 | 9/2020 | Grady et al. |
| 10,799,305 | B2 | 10/2020 | Murphy et al. |
| 10,799,677 | B2 | 10/2020 | Khuu et al. |
| 10,806,897 | B2 | 10/2020 | Furnish |
| 10,813,612 | B2 | 10/2020 | Min |
| 10,813,708 | B2 | 10/2020 | Reinstein et al. |
| 10,828,468 | B2 | 11/2020 | Selkee |
| 10,835,716 | B2 | 11/2020 | Kim et al. |
| 10,871,536 | B2 | 12/2020 | Golden et al. |
| 10,888,234 | B2 | 1/2021 | Sharma et al. |
| 10,929,828 | B2 | 2/2021 | Matsukura |
| 10,933,221 | B2 | 3/2021 | Lepak et al. |
| 10,939,828 | B2 | 3/2021 | Fonte et al. |
| 10,939,960 | B2 | 3/2021 | Choi et al. |
| 10,943,142 | B2 | 3/2021 | Karimabadi |
| 10,945,606 | B2 | 3/2021 | Sanders et al. |
| 10,951,715 | B2 | 3/2021 | Hart et al. |
| 10,959,789 | B2 | 3/2021 | Yi et al. |
| 10,964,071 | B2 | 3/2021 | Grady et al. |
| 10,966,619 | B2 | 4/2021 | Fonte et al. |
| 10,973,469 | B2 | 4/2021 | Daughton et al. |
| 10,973,583 | B2 | 4/2021 | Taylor et al. |
| 10,978,210 | B2 | 4/2021 | Grady et al. |
| 10,984,535 | B2 | 4/2021 | Grady et al. |
| 10,987,010 | B2 | 4/2021 | Grady et al. |
| 10,990,652 | B2 | 4/2021 | Taylor et al. |
| 10,991,465 | B2 | 4/2021 | Grady |
| 10,994,097 | B2 | 5/2021 | Ludwin et al. |
| 11,013,425 | B2 | 5/2021 | Fonte et al. |
| 11,017,904 | B2 | 5/2021 | Sankaran et al. |
| 11,033,332 | B2 | 6/2021 | Taylor |
| 11,042,822 | B2 | 6/2021 | Sankaran et al. |
| 11,071,501 | B2 | 7/2021 | Buckler et al. |
| 11,076,924 | B2 | 8/2021 | Kim et al. |
| 11,083,524 | B2 | 8/2021 | Taylor |
| 11,087,459 | B2 | 8/2021 | Buckler et al. |
| 11,087,460 | B2 | 8/2021 | Buckler et al. |
| 11,087,884 | B2 | 8/2021 | Sankaran et al. |
| 11,090,118 | B2 | 8/2021 | Taylor |
| 11,094,058 | B2 | 8/2021 | Buckler et al. |
| 11,094,060 | B1 | 8/2021 | Min et al. |
| 11,094,061 | B1 | 8/2021 | Min et al. |

(56) References Cited

U.S. PATENT DOCUMENTS 11,113,811 B2 9/2021 Min et al.
11,113,812 B2 9/2021 Buckler et al.
11,116,575 B2 9/2021 Taylor
11,120,312 B2 9/2021 Buckler et al.
11,120,549 B2 9/2021 Min et al.
11,120,550 B2 9/2021 Min et al.
11,120,893 B2 9/2021 Choi et al.
11,127,503 B2 9/2021 Rabbat et al.
11,132,796 B2 9/2021 Min et al.
11,135,012 B2 10/2021 Taylor
11,138,337 B2 10/2021 Yousfi et al.
11,141,566 B2 10/2021 Cabiri
11,147,950 B2 10/2021 Destrebecq et al.
11,154,361 B2 10/2021 Taylor
11,169,538 B2 11/2021 Williams et al.
11,185,368 B2 11/2021 Spilker et al.
11,185,666 B2 11/2021 Choi et al.
11,187,307 B2 11/2021 Asselin et al.
11,196,068 B2 12/2021 Weingaertner et al.
11,210,786 B2 12/2021 Min et al.
11,213,356 B2 1/2022 Tanner et al.
11,229,775 B2 1/2022 Kim et al.
11,232,564 B2 1/2022 Min et al.
11,234,767 B2 2/2022 Viswanathan et al.
11,238,587 B2 2/2022 Min et al.
11,244,451 B1 2/2022 Min et al.
11,257,584 B2 2/2022 Buckler et al.
11,257,585 B2 2/2022 Bhatia et al.
11,266,424 B2 3/2022 Hofmann et al.
11,272,995 B2 3/2022 Landey et al.
11,273,038 B2 3/2022 Tang et al.
11,276,170 B2 3/2022 Min et al.
11,278,703 B2 3/2022 Kokish et al.
11,288,799 B2 3/2022 Min et al.
11,288,813 B2 3/2022 Grady et al.
11,291,515 B2 4/2022 Sharon et al.
11,295,865 B2 4/2022 Rabbat et al.
11,298,187 B2 4/2022 Taylor
11,298,198 B2 4/2022 Fournier et al.
11,298,505 B2 4/2022 Bailey et al.
11,302,001 B2 4/2022 Min et al.
11,302,002 B2 4/2022 Min et al.
11,308,617 B2 4/2022 Min et al.
11,311,699 B2 4/2022 Weisz et al.
11,315,247 B2 4/2022 Min et al.
11,317,883 B2 5/2022 Min
11,318,302 B2 5/2022 Asleson et al.
11,321,840 B2 5/2022 Min et al.
11,328,824 B2 5/2022 Fonte
11,337,764 B2 5/2022 Deboeuf et al.
11,341,644 B2 5/2022 Min et al.
11,350,899 B2 6/2022 Min
11,357,469 B2 6/2022 Taylor et al.
11,367,190 B2 6/2022 Min et al.
11,382,569 B2 7/2022 Grady et al.
11,386,563 B2 7/2022 Figueroa-Alvarez et al.
11,398,029 B2 7/2022 Grady et al.
11,399,729 B2 8/2022 Fonte et al.
11,423,805 B2 8/2022 Sankaran et al.
11,424,036 B2 8/2022 Fonte et al.
11,424,038 B2 8/2022 Grady et al.
11,430,113 B2 8/2022 Daughton et al.
11,462,329 B2 10/2022 Rabbat et al.
11,482,339 B2 10/2022 Koo et al.
11,494,904 B2 11/2022 Fonte et al.
11,501,436 B2 11/2022 Min et al.
11,501,485 B2 11/2022 Grady et al.
11,504,019 B2 11/2022 Fonte et al.
11,508,063 B2 11/2022 Buckler
11,521,755 B2 12/2022 Taylor et al.
11,540,931 B2 1/2023 Grady et al.
11,547,367 B2 1/2023 Taylor
11,564,746 B2 1/2023 Spilker et al.
11,576,626 B2 2/2023 Fonte et al.
11,583,340 B2 2/2023 Taylor
11,589,924 B2 2/2023 Passerini et al.
11,592,836 B2 2/2023 Williams et al.
11,593,926 B2 2/2023 Buckler et al.
11,594,319 B2 2/2023 Yousfi et al.
11,599,996 B2 3/2023 Isgum et al.
11,605,466 B2 3/2023 Grady et al.
11,607,179 B2 3/2023 Buckler et al.
11,610,318 B2 3/2023 Grady et al.
11,617,620 B2 4/2023 Tran et al.
11,622,812 B2 4/2023 Grady et al.
11,638,609 B2 5/2023 Sankaran et al.
11,642,092 B1 5/2023 Min
11,642,171 B2 5/2023 Jaquet et al.
11,644,849 B2 5/2023 Williams et al.
11,646,118 B2 5/2023 Grady et al.
11,653,833 B2 5/2023 Sanders et al.
11,657,486 B2 5/2023 Buckler et al.
11,660,058 B2 5/2023 Min et al.
11,660,143 B2 5/2023 Taylor et al.
11,663,715 B2 5/2023 Choi et al.
11,672,497 B2 6/2023 Min et al.
11,676,359 B2 6/2023 Buckler et al.
11,678,937 B2 6/2023 Choi et al.
11,690,586 B2 7/2023 Min et al.
11,696,735 B2 7/2023 Buckler et al.
11,701,175 B2 7/2023 Bai et al.
11,707,325 B2 7/2023 Sankaran et al.
11,715,187 B2 8/2023 Buckler et al.
11,715,198 B2 8/2023 Kim et al.
11,730,437 B2 8/2023 Min et al.
11,737,718 B2 8/2023 Min et al.
11,742,070 B2 8/2023 Grady et al.
11,751,826 B2 9/2023 Min et al.
11,751,829 B2 9/2023 Min et al.
11,751,830 B2 9/2023 Min et al.
11,751,831 B2 9/2023 Min
11,756,690 B2 9/2023 Koo et al.
11,759,161 B2 9/2023 Min
11,766,229 B2 9/2023 Min et al.
11,766,230 B2 9/2023 Min et al.
11,779,292 B2 10/2023 Min et al.
11,784,329 B1 10/2023 Basu et al.
11,803,965 B2 10/2023 Fonte et al.
11,817,219 B2 11/2023 Rabbat et al.
11,826,106 B2 11/2023 Hart et al.
11,832,982 B2 12/2023 Min et al.
11,837,353 B2 12/2023 Bhatia et al.
11,847,781 B2 12/2023 Grady et al.
11,854,704 B2 12/2023 Grady et al.
11,861,831 B2 1/2024 Choi et al.
11,861,833 B2 1/2024 Min et al.
11,862,342 B2 1/2024 Grady et al.
11,865,195 B2 1/2024 Sinusas et al.
11,869,186 B2 1/2024 Buckler et al.
11,869,669 B2 1/2024 Spilker et al.
11,883,225 B2 1/2024 Sankaran et al.
11,887,305 B1 1/2024 Grady et al.
11,887,701 B2 1/2024 Buckler et al.
11,887,713 B2 1/2024 Buckler et al.
11,887,734 B2 1/2024 Buckler et al.
11,896,415 B2 2/2024 Min et al.
11,901,076 B1 2/2024 Daughton et al.
11,915,822 B2 2/2024 Yi et al.
11,918,293 B2 3/2024 Grady et al.
11,941,152 B2 3/2024 Yousfi et al.
11,967,078 B2 4/2024 Min et al.
11,986,280 B2 5/2024 Grady et al.
11,992,293 B2 5/2024 Fonte et al.
11,996,182 B2 5/2024 Lee et al.
12,004,841 B2 6/2024 Sanders et al.
12,008,751 B2 6/2024 Buckler et al.
12,016,635 B2 6/2024 Taylor
12,020,432 B2 6/2024 Ross et al.
12,026,868 B2 7/2024 Buckler et al.
12,027,275 B2 7/2024 Koo et al.
12,029,494 B2 7/2024 Taylor
12,035,976 B2 7/2024 Choi et al.
12,039,765 B2 7/2024 Buckler et al.
12,045,983 B2 7/2024 Buckler et al.

(56) References Cited

U.S. PATENT DOCUMENTS 12,046,367 B2 7/2024 Yi et al.
12,048,490 B2 7/2024 Grady et al.
12,051,497 B2 7/2024 Grady et al.
12,059,288 B2 8/2024 Taylor et al.
12,068,079 B2 8/2024 Sankaran et al.
12,073,561 B2 8/2024 Buckler et al.
12,073,943 B2 8/2024 Yu et al.
12,079,921 B2 9/2024 Grady et al.
12,079,988 B2 9/2024 Yi et al.
12,096,990 B2 9/2024 Sankaran et al.
12,100,149 B2 9/2024 Buckler et al.
12,106,477 B2 10/2024 Buckler et al.
12,112,483 B2 10/2024 Grady et al.
12,114,933 B2 10/2024 Seo et al.
12,118,694 B2 10/2024 Buckler et al.
12,125,261 B2 10/2024 Petersen et al.
12,125,571 B2 10/2024 Buckler et al.
12,125,572 B2 10/2024 Buckler et al.
12,131,147 B2 10/2024 Reasor
12,131,471 B2 10/2024 Buckler et al.
12,131,472 B2 10/2024 Buckler et al.
12,136,214 B2 11/2024 Buckler et al.
2001/0047137 A1 11/2001 Moreno et al.
2002/0045153 A1 4/2002 Kaufman et al.
2002/0172663 A1 11/2002 Palasis
2003/0152519 A1 8/2003 Koenig et al.
2003/0176780 A1 9/2003 Arnold et al.
2004/0017936 A1 1/2004 Gopinath et al.
2004/0059260 A1 3/2004 Truwit
2004/0101181 A1 5/2004 Giger et al.
2004/0133094 A1 7/2004 Becker et al.
2004/0133100 A1 7/2004 Naghavi et al.
2004/0135031 A1 7/2004 Stupakis
2004/0136491 A1 7/2004 Iatrou et al.
2004/0147838 A1 7/2004 Londt et al.
2004/0254566 A1 12/2004 Plicchi et al.
2005/0020998 A1 1/2005 Bonnette et al.
2005/0038575 A1 2/2005 Wu
2005/0043614 A1 2/2005 Huizenga et al.
2005/0110791 A1 5/2005 Krishnamoorthy et al.
2005/0118632 A1 6/2005 Chen et al.
2005/0171508 A1 8/2005 Gilboa
2005/0245862 A1 11/2005 Seward et al.
2006/0013460 A1 1/2006 Dehmeshki
2006/0036167 A1 2/2006 Shina
2006/0101075 A1 5/2006 Lehel et al.
2006/0146010 A1 7/2006 Schneider
2007/0018558 A1 1/2007 Chua et al.
2007/0019778 A1 1/2007 Clouse et al.
2007/0172447 A1 7/2007 Sakurada et al.
2007/0239140 A1 10/2007 Chechelski et al.
2007/0248250 A1 10/2007 Gulsun et al.
2007/0260141 A1 11/2007 Margolis et al.
2008/0058642 A1 3/2008 Gould
2008/0100621 A1 5/2008 Aharon et al.
2008/0103389 A1 5/2008 Begelman et al.
2008/0118131 A1 5/2008 Skinner et al.
2008/0119713 A1 5/2008 Le et al.
2008/0119734 A1 5/2008 Pruvot et al.
2008/0123926 A1 5/2008 Capolunghi et al.
2008/0187199 A1 8/2008 Gulsun et al.
2008/0188962 A1 8/2008 Suryanarayanan et al.
2008/0226017 A1 9/2008 Altman et al.
2009/0012382 A1 1/2009 Dutta et al.
2009/0012533 A1 1/2009 Barbagli et al.
2009/0016588 A1 1/2009 Slabaugh et al.
2009/0082722 A1 3/2009 Munger et al.
2009/0129673 A1 5/2009 Simon et al.
2009/0264771 A1 10/2009 Houben et al.
2009/0276161 A1 11/2009 Cobain
2009/0278846 A1 11/2009 Gulsun et al.
2009/0299645 A1 12/2009 Colby et al.
2009/0307179 A1 12/2009 Colby et al.
2010/0030035 A1 2/2010 Chan et al.
2010/0092053 A1 4/2010 Manabe et al.
2010/0137711 A1 6/2010 Hamilton et al.
2010/0156898 A1 6/2010 Voros et al.
2010/0177945 A1 7/2010 Moriya
2010/0201786 A1 8/2010 Schaefer et al.
2010/0204646 A1 8/2010 Plicchi et al.
2010/0215225 A1 8/2010 Kadomura et al.
2010/0278405 A1 11/2010 Kakadiaris et al.
2010/0316274 A1 12/2010 Langheinrich et al.
2011/0026798 A1 2/2011 Madabhushi et al.
2011/0077591 A1 3/2011 Plicchi et al.
2011/0116697 A1 5/2011 Dafni et al.
2011/0144576 A1 6/2011 Rothe et al.
2011/0144658 A1 6/2011 Wenderow et al.
2011/0206247 A1 8/2011 Dachille et al.
2011/0218427 A1 9/2011 Kitamura
2011/0229002 A1 9/2011 Arnold et al.
2011/0238010 A1 9/2011 Kirschenman et al.
2011/0243412 A1 10/2011 Grass et al.
2011/0245650 A1 10/2011 Kerwin et al.
2011/0282182 A1 11/2011 Ohayon et al.
2012/0041323 A1 2/2012 Taylor et al.
2012/0075638 A1 3/2012 Rollins et al.
2012/0076377 A1 3/2012 Dutta et al.
2012/0128132 A1 5/2012 Coolens et al.
2012/0158011 A1 6/2012 Sandhu et al.
2012/0158432 A1 6/2012 Jain et al.
2012/0219198 A1 8/2012 Mohr
2012/0226227 A1 9/2012 Weitzner et al.
2012/0232005 A1 9/2012 Dasseux et al.
2012/0243764 A1 9/2012 Dey et al.
2012/0245595 A1 9/2012 Kesavadas et al.
2012/0263368 A1 10/2012 Nakano et al.
2012/0330335 A1 12/2012 Shekalim et al.
2013/0046168 A1 2/2013 Sui
2013/0066188 A1 3/2013 Taerum et al.
2013/0094749 A1 4/2013 Oh et al.
2013/0101187 A1 4/2013 Sundar et al.
2013/0190592 A1 7/2013 Coppini et al.
2013/0190595 A1 7/2013 Oraevsky et al.
2013/0202173 A1 8/2013 Buckler et al.
2013/0246034 A1 9/2013 Sharma et al.
2013/0304034 A1 11/2013 Cabiri
2013/0304035 A1 11/2013 Cabiri
2014/0058715 A1 2/2014 Sharma et al.
2014/0073976 A1 3/2014 Fonte et al.
2014/0114176 A1 4/2014 Hirschenbain et al.
2014/0276392 A1 9/2014 Wong et al.
2014/0276647 A1 9/2014 Yu
2014/0277333 A1 9/2014 Lewis et al.
2014/0306961 A1 10/2014 Nagata
2014/0343457 A1 11/2014 Shekalim et al.
2014/0350568 A1 11/2014 Shekalim et al.
2015/0009465 A1 1/2015 Park et al.
2015/0015702 A1 1/2015 Yamaguchi et al.
2015/0016702 A1 1/2015 Huizenga et al.
2015/0045287 A1 2/2015 Chen et al.
2015/0065846 A1 3/2015 Choi et al.
2015/0066818 A1 3/2015 Choi et al.
2015/0073340 A1 3/2015 Pacheco et al.
2015/0073342 A1 3/2015 Pacheco et al.
2015/0080907 A1 3/2015 Herrell et al.
2015/0090057 A1 4/2015 Pacheco et al.
2015/0099997 A1 4/2015 Cabiri
2015/0164342 A1 6/2015 Choi et al.
2015/0187025 A1 7/2015 Wasserkrug et al.
2015/0193944 A1 7/2015 Lang et al.
2015/0220240 A1 8/2015 Tsukijishin et al.
2015/0223832 A1 8/2015 Swaney et al.
2015/0265359 A1 9/2015 Camarillo
2015/0313677 A1 11/2015 Kidd et al.
2015/0314107 A1 11/2015 Rothe et al.
2015/0356734 A1 12/2015 Ooga et al.
2016/0012614 A1 1/2016 Goto
2016/0038002 A1 2/2016 Peters et al.
2016/0058303 A1 3/2016 Grady et al.
2016/0066861 A1 3/2016 Taylor
2016/0078309 A1 3/2016 Feldman et al.
2016/0103816 A1 4/2016 Grady et al.
2016/0104281 A1 4/2016 Grady et al.

(56) References Cited

U.S. PATENT DOCUMENTS

2016/0203263 A1 7/2016 Maier et al.
2016/0210428 A1 7/2016 Spilker et al.
2016/0239564 A1 8/2016 Sohma
2016/0271368 A1 9/2016 Falb et al.
2016/0291110 A1 10/2016 Balu et al.
2016/0292372 A1 10/2016 Kamen et al.
2016/0296288 A1 10/2016 Sankaran et al.
2016/0300350 A1 10/2016 Choi et al.
2016/0306944 A1 10/2016 Grady et al.
2016/0310702 A1 10/2016 Cabiri
2016/0342765 A1 11/2016 Sankaran et al.
2016/0346043 A1 12/2016 Jaquet et al.
2016/0358333 A1 12/2016 Lee et al.
2017/0014034 A1 1/2017 Koo et al.
2017/0018081 A1 1/2017 Taylor et al.
2017/0046484 A1 2/2017 Buckler et al.
2017/0046839 A1 2/2017 Paik et al.
2017/0103525 A1 4/2017 Hu et al.
2017/0119333 A1 5/2017 Zebaze et al.
2017/0161455 A1 6/2017 Grady et al.
2017/0199654 A1 7/2017 Wu et al.
2017/0202621 A1 7/2017 Taylor
2017/0245821 A1 8/2017 Itu et al.
2017/0252025 A1 9/2017 Cabiri et al.
2017/0258433 A1 9/2017 Gulsun et al.
2017/0265831 A1 9/2017 Sankaran et al.
2017/0265832 A1 9/2017 Antoniades
2017/0337343 A1 11/2017 Kakadiaris et al.
2017/0340393 A1 11/2017 Choi et al.
2017/0348060 A1 12/2017 Blacker
2017/0360372 A1 12/2017 Hauck et al.
2017/0367776 A1 12/2017 Kwok et al.
2018/0050626 A1 2/2018 Delp et al.
2018/0064910 A1 3/2018 Tegg
2018/0078139 A1 3/2018 Sanders et al.
2018/0125596 A1 5/2018 He et al.
2018/0126122 A1 5/2018 Cabiri
2018/0165811 A1 6/2018 Flohr et al.
2018/0179189 A1 6/2018 Macphee et al.
2018/0185104 A1 7/2018 Olson et al.
2018/0214675 A1 8/2018 Shekalim et al.
2018/0225847 A1 8/2018 Grady et al.
2018/0242944 A1 8/2018 Uber et al.
2018/0243033 A1 8/2018 Tran et al.
2018/0259976 A1 9/2018 Williams et al.
2018/0330477 A1 11/2018 Paik et al.
2018/0336319 A1 11/2018 Itu et al.
2018/0364738 A1 12/2018 Bridges
2019/0021608 A1 1/2019 Cope et al.
2019/0029519 A1 1/2019 Itu et al.
2019/0050807 A1 2/2019 Ferguson et al.
2019/0074082 A1 3/2019 Buckler et al.
2019/0076092 A1 3/2019 Saroha et al.
2019/0105112 A1 4/2019 Popovic et al.
2019/0110776 A1 4/2019 Yu et al.
2019/0111237 A1 4/2019 Cabiri
2019/0133456 A1 5/2019 Grady et al.
2019/0159737 A1 5/2019 Buckler et al.
2019/0167077 A1 6/2019 Hancock et al.
2019/0172197 A1 6/2019 Buckler et al.
2019/0174082 A1 6/2019 Taruki et al.
2019/0175130 A1 6/2019 Raman et al.
2019/0180153 A1 6/2019 Buckler et al.
2019/0180438 A1 6/2019 Buckler et al.
2019/0200881 A1 7/2019 Grady et al.
2019/0244347 A1 8/2019 Buckler et al.
2019/0244348 A1 8/2019 Buckler et al.
2019/0251713 A1 8/2019 Chen et al.
2019/0254690 A1 8/2019 Cabiri et al.
2019/0255289 A1 8/2019 Cabiri
2019/0282211 A1 9/2019 Merritt et al.
2019/0307987 A1 10/2019 Yu
2019/0318476 A1 10/2019 Isgum et al.
2019/0339712 A1 11/2019 Williams et al.
2019/0343404 A1 11/2019 Shekalim et al.
2019/0350538 A1 11/2019 Wilson et al.
2019/0388164 A1 12/2019 Gruionu et al.
2020/0000539 A1 1/2020 Sholev et al.
2020/0060820 A1 2/2020 Ben-Zvi et al.
2020/0069262 A1 3/2020 Fonte et al.
2020/0085501 A1 3/2020 Sankaran et al.
2020/0117851 A1 4/2020 Grady et al.
2020/0129252 A1 4/2020 Kokish et al.
2020/0129740 A1 4/2020 Kottenstette et al.
2020/0134897 A1 4/2020 Grady et al.
2020/0165309 A1 5/2020 Yount et al.
2020/0178815 A1 6/2020 Choi et al.
2020/0178990 A1 6/2020 Chu
2020/0179649 A1 6/2020 Kern et al.
2020/0188635 A1 6/2020 Barrish et al.
2020/0197111 A1 6/2020 Kim et al.
2020/0226749 A1 7/2020 Freiman et al.
2020/0237329 A1* 7/2020 Min ..................... A61B 6/504
2020/0237440 A1 7/2020 Zabar et al.
2020/0243076 A1 7/2020 Kim
2020/0243885 A1 7/2020 Weingaertner et al.
2020/0246089 A1 8/2020 Schlenk et al.
2020/0273579 A1 8/2020 Wright et al.
2020/0282181 A1 9/2020 Cabiri
2020/0294659 A1 9/2020 Gopinath et al.
2020/0297442 A1 9/2020 Adebar et al.
2020/0297971 A1 9/2020 Beeckler et al.
2020/0320775 A1 10/2020 Holladay et al.
2020/0337585 A1 10/2020 Shochat et al.
2020/0360659 A1 11/2020 Wong et al.
2020/0372701 A1 11/2020 Grady et al.
2020/0388391 A1 12/2020 Upton et al.
2020/0402234 A1 12/2020 Daughton et al.
2020/0402424 A1* 12/2020 Meyer ................. G09B 23/285
2020/0405182 A1 12/2020 Hoitink et al.
2020/0405413 A1 12/2020 Kokish et al.
2021/0007807 A1 1/2021 Sankaran et al.
2021/0023337 A1 1/2021 Debuys et al.
2021/0030478 A1 2/2021 Hart et al.
2021/0035287 A1 2/2021 Kim et al.
2021/0035687 A1 2/2021 Yi et al.
2021/0042918 A1 2/2021 Buckler
2021/0042927 A1 2/2021 Amis et al.
2021/0045764 A1 2/2021 Sholev et al.
2021/0060310 A1 3/2021 Kim et al.
2021/0074435 A1 3/2021 Taylor et al.
2021/0077196 A1 3/2021 Jaquet et al.
2021/0077209 A1 3/2021 Yu
2021/0082579 A1 3/2021 Grady et al.
2021/0085397 A1 3/2021 Passerini et al.
2021/0090694 A1 3/2021 Colley et al.
2021/0093384 A1 4/2021 Grady et al.
2021/0151171 A1 5/2021 Lee et al.
2021/0153749 A1 5/2021 Fonte et al.
2021/0153945 A1 5/2021 Choi et al.
2021/0161384 A1 6/2021 Sanders et al.
2021/0177375 A1 6/2021 Upton et al.
2021/0185131 A1 6/2021 Hart et al.
2021/0186448 A1 6/2021 Min
2021/0196387 A1 7/2021 Seo et al.
2021/0196391 A1 7/2021 Taylor et al.
2021/0201495 A1 7/2021 Yu et al.
2021/0202110 A1 7/2021 Grady et al.
2021/0209757 A1* 7/2021 Min ..................... A61B 6/504
2021/0210209 A1 7/2021 Taylor et al.
2021/0212565 A1 7/2021 Gardner et al.
2021/0217165 A1 7/2021 Min et al.
2021/0217534 A1 7/2021 Rabbat et al.
2021/0225006 A1 7/2021 Grady et al.
2021/0228094 A1 7/2021 Grady et al.
2021/0236105 A1 8/2021 Hansen et al.
2021/0236775 A1 8/2021 Schultz
2021/0236778 A1 8/2021 Kim et al.
2021/0241455 A1 8/2021 Min et al.
2021/0241920 A1 8/2021 Sankaran et al.
2021/0244475 A1 8/2021 Taylor
2021/0267690 A1 9/2021 Taylor
2021/0272030 A1 9/2021 Sankaran et al.
2021/0282719 A1 9/2021 Buckler et al.

(56) References Cited

U.S. PATENT DOCUMENTS

2021/0282860 A1 9/2021 Taylor
2021/0312622 A1 10/2021 Buckler et al.
2021/0319558 A1 10/2021 Min et al.
2021/0322102 A1 10/2021 Sankaran et al.
2021/0334961 A1 10/2021 Min et al.
2021/0334962 A1 10/2021 Min et al.
2021/0334964 A1 10/2021 Min et al.
2021/0334965 A1 10/2021 Min et al.
2021/0334966 A1 10/2021 Min et al.
2021/0335497 A1 10/2021 Sankaran et al.
2021/0338333 A1 11/2021 Sankaran et al.
2021/0343010 A1 11/2021 Min et al.
2021/0358634 A1 11/2021 Sankaran et al.
2021/0358635 A1 11/2021 Sankaran et al.
2021/0361366 A1 11/2021 Murphy et al.
2021/0366111 A1 11/2021 Min et al.
2021/0366112 A1 11/2021 Min et al.
2021/0366113 A1 11/2021 Min et al.
2021/0366114 A1 11/2021 Min et al.
2021/0366115 A1 11/2021 Min et al.
2021/0366116 A1 11/2021 Min et al.
2021/0374969 A1 12/2021 Grady et al.
2021/0375401 A1 12/2021 Choi et al.
2021/0375476 A1 12/2021 Rabbat et al.
2021/0386390 A1 12/2021 Min
2021/0390689 A1 12/2021 Buckler et al.
2021/0397746 A1 12/2021 Yousfi et al.
2022/0012865 A1 1/2022 Buckler et al.
2022/0012877 A1 1/2022 Buckler et al.
2022/0012878 A1 1/2022 Aoyama
2022/0026924 A1 1/2022 Williams et al.
2022/0028070 A1 1/2022 Min et al.
2022/0059856 A1 2/2022 Weingaertner et al.
2022/0079540 A1 3/2022 Sankaran et al.
2022/0079681 A1 3/2022 Grady et al.
2022/0084198 A1 3/2022 Viti
2022/0097817 A1 3/2022 Perry et al.
2022/0098249 A1 3/2022 Shah et al.
2022/0110687 A1 4/2022 Spilker et al.
2022/0110690 A1 4/2022 Sankaran et al.
2022/0111176 A1 4/2022 Dale et al.
2022/0114388 A1 4/2022 Li et al.
2022/0117683 A1 4/2022 Schnur et al.
2022/0122251 A1 4/2022 Min et al.
2022/0139529 A1 5/2022 Bhatia et al.
2022/0172353 A1 6/2022 Yi et al.
2022/0202857 A1 6/2022 Brewer et al.
2022/0211439 A1 7/2022 Sankaran et al.
2022/0211452 A1 7/2022 Clark et al.
2022/0216489 A1 7/2022 Perry
2022/0221861 A1 7/2022 Mcveen
2022/0222825 A1 7/2022 Yaacobi
2022/0230312 A1 7/2022 Choi et al.
2022/0241019 A1 8/2022 Taylor
2022/0253074 A1 8/2022 Williams et al.
2022/0253992 A1 8/2022 Buckler et al.
2022/0265239 A1 8/2022 Taylor et al.
2022/0277443 A1 9/2022 Min et al.
2022/0284572 A1 9/2022 Min et al.
2022/0322953 A1 10/2022 Fonte et al.
2022/0327695 A1 10/2022 Min et al.
2022/0327701 A1 10/2022 Grady et al.
2022/0330902 A1 10/2022 Forneris et al.
2022/0335603 A1 10/2022 Min et al.
2022/0335859 A1 10/2022 Sankaran et al.
2022/0359063 A1 11/2022 Tombropoulos et al.
2022/0366562 A1 11/2022 Yu et al.
2022/0367066 A1 11/2022 Grady et al.
2022/0375072 A1 11/2022 Min et al.
2022/0383464 A1 12/2022 Buckler et al.
2022/0383495 A1 12/2022 Petersen et al.
2022/0386979 A1 12/2022 Min et al.
2022/0392065 A1 12/2022 Min et al.
2022/0392070 A1 12/2022 Buckler
2022/0398706 A1 12/2022 Buckler et al.
2022/0400963 A1 12/2022 Buckler et al.
2022/0401050 A1 12/2022 Min
2022/0406459 A1 12/2022 Buckler et al.
2022/0406470 A1 12/2022 Fonte et al.
2022/0409160 A1 12/2022 Buckler et al.
2022/0415519 A1 12/2022 Buckler et al.
2023/0005582 A1 1/2023 Buckler et al.
2023/0005583 A1 1/2023 Buckler et al.
2023/0005622 A1 1/2023 Rabbat et al.
2023/0016104 A1 1/2023 Koo et al.
2023/0033594 A1 2/2023 Grady et al.
2023/0055828 A1 2/2023 Fonte et al.
2023/0113005 A1 4/2023 Antoniades et al.
2023/0117134 A1 4/2023 Clifton et al.
2023/0124826 A1 4/2023 Spilker et al.
2023/0130265 A1 4/2023 Kodali et al.
2023/0132940 A1 5/2023 Min et al.
2023/0137093 A1 5/2023 Min et al.
2023/0137934 A1 5/2023 Min et al.
2023/0138144 A1 5/2023 Min et al.
2023/0138468 A1 5/2023 Martinovski
2023/0138889 A1 5/2023 Min
2023/0139102 A1 5/2023 Taylor
2023/0142747 A1 5/2023 Min et al.
2023/0144293 A1 5/2023 Min et al.
2023/0144338 A1 5/2023 Min et al.
2023/0145596 A1 5/2023 Min et al.
2023/0147336 A1 5/2023 Min et al.
2023/0147995 A1 5/2023 Min et al.
2023/0148977 A1 5/2023 Fonte et al.
2023/0148981 A1 5/2023 Min et al.
2023/0154000 A1 5/2023 Min et al.
2023/0154620 A1 5/2023 Yi et al.
2023/0162603 A1 5/2023 Drr
2023/0165544 A1 6/2023 Hahn et al.
2023/0169702 A1 6/2023 Hahn et al.
2023/0172451 A1 6/2023 Seo et al.
2023/0196582 A1 6/2023 Grady et al.
2023/0197286 A1 6/2023 Grady et al.
2023/0205227 A1 6/2023 Williams et al.
2023/0207137 A1 6/2023 Buckler et al.
2023/0210602 A1 7/2023 Sankaran et al.
2023/0218346 A1 7/2023 Tran et al.
2023/0218347 A1 7/2023 Taylor
2023/0223148 A1 7/2023 Grady et al.
2023/0233261 A1 7/2023 Jaquet et al.
2023/0237654 A1 7/2023 Min et al.
2023/0237759 A1 7/2023 Buckler et al.
2023/0240619 A1 8/2023 Daughton et al.
2023/0245775 A1 8/2023 Buckler et al.
2023/0248242 A1 8/2023 Sanders et al.
2023/0277247 A1 9/2023 Taylor et al.
2023/0289939 A1 9/2023 Buckler et al.
2023/0289963 A1 9/2023 Min et al.
2023/0290433 A1 9/2023 Buckler et al.
2023/0290524 A1 9/2023 Taylor et al.
2023/0298168 A1 9/2023 Lee et al.
2023/0298176 A1 9/2023 Choi et al.
2023/0301720 A1 9/2023 Grady et al.
2023/0301722 A1 9/2023 Choi et al.
2023/0310085 A1 10/2023 Sankaran et al.
2023/0326166 A1 10/2023 Buckler et al.
2023/0342923 A1 10/2023 Lee et al.
2023/0342929 A1 10/2023 Kim et al.
2023/0343455 A1 10/2023 Kwon et al.
2023/0352152 A1 11/2023 Grady et al.
2023/0360803 A1 11/2023 Sankaran et al.
2023/0360804 A1 11/2023 Koo et al.
2023/0368365 A9 11/2023 Buckler et al.
2023/0386026 A1 11/2023 Buckler
2023/0386633 A1 11/2023 Buckler et al.
2023/0386634 A1 11/2023 Buckler et al.
2023/0397816 A1 12/2023 Forneris et al.
2023/0420130 A1 12/2023 Buckler et al.
2023/0420131 A1 12/2023 Buckler et al.
2023/0420143 A1 12/2023 Buckler et al.
2023/0420144 A1 12/2023 Buckler et al.
2024/0000414 A1 1/2024 Abdolmanafi et al.
2024/0006066 A1 1/2024 Buckler et al.

(56) References Cited

U.S. PATENT DOCUMENTS

| | | | |
|---|---|---|---|
| 2024/0013388 | A1 | 1/2024 | Fonte et al. |
| 2024/0021306 | A1 | 1/2024 | Buckler et al. |
| 2024/0023918 | A1 | 1/2024 | Min |
| 2024/0038398 | A1 | 2/2024 | Rabbat et al. |
| 2024/0046457 | A1 | 2/2024 | Buckler et al. |
| 2024/0047045 | A1 | 2/2024 | Bhatia et al. |
| 2024/0050159 | A1 | 2/2024 | Hart et al. |
| 2024/0057960 | A1 | 2/2024 | Min et al. |
| 2024/0062901 | A1 | 2/2024 | Buckler et al. |
| 2024/0070863 | A1 | 2/2024 | Grady et al. |
| 2024/0078671 | A1 | 3/2024 | Buckler et al. |
| 2024/0078672 | A1 | 3/2024 | Buckler et al. |
| 2024/0078673 | A1 | 3/2024 | Buckler et al. |
| 2024/0087742 | A1 | 3/2024 | Buckler et al. |
| 2024/0130702 | A1 | 4/2024 | Flack et al. |
| 2024/0153229 | A1 | 5/2024 | Buckler et al. |
| 2024/0153252 | A1 | 5/2024 | Phillips et al. |
| 2024/0161295 | A1 | 5/2024 | Buckler et al. |
| 2024/0161296 | A1 | 5/2024 | Buckler et al. |
| 2024/0161297 | A1 | 5/2024 | Buckler et al. |
| 2024/0202915 | A1 | 6/2024 | Buckler et al. |
| 2024/0212143 | A1 | 6/2024 | Buckler et al. |
| 2024/0232433 | A1 | 7/2024 | Yousfi et al. |
| 2024/0259352 | A1 | 8/2024 | Yousfi et al. |
| 2024/0274276 | A1 | 8/2024 | Lee et al. |
| 2024/0298894 | A1 | 9/2024 | Sanders et al. |
| 2024/0315777 | A1 | 9/2024 | Choi et al. |
| 2024/0331151 | A1 | 10/2024 | Seo et al. |
| 2024/0331848 | A1 | 10/2024 | Seo et al. |

FOREIGN PATENT DOCUMENTS

| | | | |
|---|---|---|---|
| CA | 3017610 | A1 | 9/2017 |
| CA | 3238598 | A1 | 5/2023 |
| CA | 3240201 | A1 | 6/2023 |
| CN | 1556688 | A | 12/2004 |
| CN | 102415894 | A | 4/2012 |
| CN | 106999122 | A | 8/2017 |
| CN | 107530041 | A | 1/2018 |
| CN | 110914866 | A | 3/2020 |
| CN | 112288731 | A | 1/2021 |
| CN | 112336365 | A | 2/2021 |
| CN | 112567378 | A | 3/2021 |
| CN | 113439287 | A | 9/2021 |
| CN | 115511995 | A | 12/2022 |
| CN | 117501379 | A | 2/2024 |
| CN | 117918872 | A | 4/2024 |
| CN | 118077008 | A | 5/2024 |
| CN | 118334070 | A | 7/2024 |
| EP | 3185762 | A1 | 7/2017 |
| EP | 3278254 | A1 | 2/2018 |
| EP | 3326092 | A1 | 5/2018 |
| EP | 3355762 | A1 | 8/2018 |
| EP | 3384413 | A1 | 10/2018 |
| EP | 3431005 | A1 | 1/2019 |
| EP | 3457959 | A1 | 3/2019 |
| EP | 3516561 | A1 | 7/2019 |
| EP | 3533410 | A1 | 9/2019 |
| EP | 3569150 | A2 | 11/2019 |
| EP | 3585253 | A1 | 1/2020 |
| EP | 3665702 | A2 | 6/2020 |
| EP | 3803687 | A1 | 4/2021 |
| EP | 3846176 | A1 | 7/2021 |
| EP | 3899864 | A1 | 10/2021 |
| EP | 3912550 | A1 | 11/2021 |
| EP | 4147632 | A1 | 3/2023 |
| EP | 4183344 | A1 | 5/2023 |
| EP | 4252186 | A1 | 10/2023 |
| EP | 4292098 | A1 | 12/2023 |
| EP | 4312776 | A1 | 2/2024 |
| EP | 4334941 | A1 | 3/2024 |
| EP | 4377885 | A1 | 6/2024 |
| EP | 4404141 | A2 | 7/2024 |
| EP | 4418280 | A2 | 8/2024 |
| EP | 4430534 | A1 | 9/2024 |
| EP | 4445835 | A2 | 10/2024 |
| EP | 4447838 | A1 | 10/2024 |
| FR | 2908976 | A1 | 5/2008 |
| GB | 2557263 | A | 6/2018 |
| GB | 2618468 | A | 11/2023 |
| IN | 202317079967 | | 9/2024 |
| JP | 2003-150703 | A | 5/2003 |
| JP | 2005-519657 | A | 7/2005 |
| JP | 2007-029129 | A | 2/2007 |
| JP | 2009-506854 | A | 2/2009 |
| JP | 2011-115481 | A | 6/2011 |
| JP | 2011-135938 | A | 7/2011 |
| JP | 2012-509122 | A | 4/2012 |
| JP | 2012-179360 | A | 9/2012 |
| JP | 2012-196436 | A | 10/2012 |
| JP | 5305821 | B2 | 10/2013 |
| JP | 2014-534822 | A | 12/2014 |
| JP | 2016-529037 | A | 9/2016 |
| JP | 6203410 | B2 | 9/2017 |
| JP | 2018-511791 | A | 4/2018 |
| JP | 2021-525929 | A | 9/2021 |
| JP | 2022-123103 | A | 8/2022 |
| JP | 7113916 | B2 | 8/2022 |
| JP | 2022-543330 | A | 10/2022 |
| JP | 2023-054309 | A | 4/2023 |
| JP | 2023-093605 | A | 7/2023 |
| JP | 2023-118960 | A | 8/2023 |
| JP | 2024-506605 | A | 2/2024 |
| JP | 2024-069343 | A | 5/2024 |
| JP | 7483079 | B2 | 5/2024 |
| JP | 7505093 | B2 | 6/2024 |
| JP | 2024-528679 | A | 7/2024 |
| JP | 2024-113185 | A | 8/2024 |
| JP | 2024-529232 | A | 8/2024 |
| JP | 7542578 | B2 | 8/2024 |
| KR | 10-2017-0120154 | A | 10/2017 |
| KR | 10-2020-0115489 | A | 10/2020 |
| KR | 10-2021-0042267 | A | 4/2021 |
| KR | 10-2021-0096942 | A | 8/2021 |
| KR | 10-2021-0121062 | A | 10/2021 |
| KR | 10-2022-0155828 | A | 11/2022 |
| KR | 10-2491988 | B1 | 1/2023 |
| KR | 10-2023-0069884 | A | 5/2023 |
| KR | 10-2023-0146038 | A | 10/2023 |
| KR | 10-2024-0054248 | A | 4/2024 |
| KR | 10-2024-0064617 | A | 5/2024 |
| KR | 10-2690881 | B1 | 8/2024 |
| KR | 10-2024-0133667 | A | 9/2024 |
| KR | 10-2024-0147616 | A | 10/2024 |
| KR | 10-2024-0147617 | A | 10/2024 |
| WO | 03/39601 | A1 | 5/2003 |
| WO | 2004/019256 | A2 | 3/2004 |
| WO | 2007/029129 | A2 | 3/2007 |
| WO | 2009/105530 | A2 | 8/2009 |
| WO | 2010/067276 | A1 | 6/2010 |
| WO | 2013/054947 | A1 | 4/2013 |
| WO | 2014/107402 | A1 | 7/2014 |
| WO | 2014/132829 | A1 | 9/2014 |
| WO | 2015/095282 | A1 | 6/2015 |
| WO | 2015/168682 | A1 | 11/2015 |
| WO | 2016/022533 | A1 | 2/2016 |
| WO | 2016/024128 | A1 | 2/2016 |
| WO | 2016/138449 | A1 | 9/2016 |
| WO | 2016/165432 | A1 | 10/2016 |
| WO | 2016/168292 | A1 | 10/2016 |
| WO | 2017/011555 | A1 | 1/2017 |
| WO | 2017/096407 | A1 | 6/2017 |
| WO | 2017/106819 | A1 | 6/2017 |
| WO | 2018/078395 | A1 | 5/2018 |
| WO | 2018/156961 | A1 | 8/2018 |
| WO | 2019/033098 | A2 | 2/2019 |
| WO | 2019/165432 | A1 | 8/2019 |
| WO | 2019/200108 | A1 | 10/2019 |
| WO | 2019/231844 | A1 | 12/2019 |
| WO | 2019/242227 | A1 | 12/2019 |
| WO | 2020/146360 | A1 | 7/2020 |
| WO | 2021/011518 | A1 | 1/2021 |
| WO | 2021/011533 | A1 | 1/2021 |
| WO | 2021/011551 | A1 | 1/2021 |

(56) References Cited

FOREIGN PATENT DOCUMENTS

| | | |
|---|---|---|
| WO | 2021/011554 A1 | 1/2021 |
| WO | 2021/026125 A1 | 2/2021 |
| WO | 2021/065312 A1 | 4/2021 |
| WO | 2021/117724 A1 | 6/2021 |
| WO | 2021/141135 A1 | 7/2021 |
| WO | 2021/141921 A1 | 7/2021 |
| WO | 2022/173534 A1 | 8/2022 |
| WO | 2022/221921 A1 | 10/2022 |
| WO | 2022/261506 A1 | 12/2022 |
| WO | 2023/004451 A1 | 2/2023 |
| WO | 2023/089559 A1 | 5/2023 |
| WO | 2023/111808 A1 | 6/2023 |
| WO | 2023/172273 A1 | 9/2023 |
| WO | 2024/095159 A1 | 5/2024 |
| WO | 2024/102879 A1 | 5/2024 |
| WO | 2024/105483 A1 | 5/2024 |
| WO | 2024/105484 A1 | 5/2024 |
| WO | 2024/171153 A1 | 8/2024 |

OTHER PUBLICATIONS

Dwivedi et al., "Evaluation of Atherosclerotic Plaque in Non-invasice Coronary Imaging", Korean Circulation Journal, Feb. 2018. 48(2), pp. 124-133.

Ehara et al. "Spotty calcification typifies the culprit plaque in patients with acute myocardial infarction: an intravascular ultrasound study." Circulation 2004; ■110(22): 3424-9.

Erickson BJ, et al. "Machine Learning for Medical Imaging." Radiographics 2017; 37(2) pp. 505-515.

Eskerud et al., "Total coronary atherosclerotic plaque burden is associated with myocardial ischemia in non-obstructive coronary artery disease", 2021 IJC Heart & Vasculature 35:100831 9 pages (Year: 2021), Elsevier B.V.

Fawaz, Ziad, "Design and Control of a Self-balancing Bicycle Using an Electric Linear Actuator," A thesis submitted in partial fulfillment of the requirements for the degree of Master of Science in Engineering (Electrical Engineering) in the University of Michigan-Dearborn 2019, https://deepblue.lib.umich.edu/bitstream/handle/2027.42/148871/MastersThesis_FinalDraft (3).pdf?sequence=1, 34 pp.

Ferencik et al., "Use of High-Risk Coronary Atherosclerotic Plaque Detection for Risk Stratification of Patients With Stable Chest Pain", JAMA Cardiol, Feb. 2018 in 19 pages.

Ferencik, et al. "Computed Tomography-Based High-Risk Coronary Plaque Score to Predict Acute Coronary Syndrome Among Patients with Acute Chest Pain—Results from the ROMICAT II Trial" J Cardiovascular Comput Tomogr., 2015 ; 9(6): 538-545. doi:10.1016/j.jcct.2015.07.003.

Fihn et al. "2012 ACCF/AHA/ACP/AATS/PCNA/SCAI/STS Guideline for the Diagnosis and the Management of Patients With Stable Ischemic Heart Disease: Executive Summary: A Report of the American College of Cardiology Foundation/American Heart Association Task Force on Practice Guidelines, and the American College of Physicians, American Association for Thoracic Surgery, Preventive Cardiovascular Nurses Association, Society for Cardiovascular Angiography and Interventions, and Society of Thoracic Surgeons." J Am Coll Cardio 2012;60(24):2564-603.

Finh et al. "2014 ACC/AHA/AATS/PCNA/SCAI/STS focused update of the guideline for the diagnosis and management of patients with stable ischemic heart disease: a report of the American College of Cardiology/American Heart Association Task Force on Practice Guidelines, and the American Association for Thoracic Surgery, Preventive Cardiovascular Nurses Association, Society for Cardiovascular Angiography and Interventions, and Society of Thoracic Surgeons." Journal of the American College of Cardiology 2014;64 (18): 1929-49. doi: 10.1016/j.jacc.2014.07.017.

Friedman et al., "Additive logistic regression: a statistical view of boosting (With discussion and a rejoinder by the authors)." Ann Statist 2000; 28(2) pp. 337-407.

Funama, Yoshinori, et al. "Improved estimation of coronary plaque and luminal attenuation using a vendor-specific model-based iterative reconstruction algorithm in contrast-enhanced CT coronary angiography." Academic radiology 24.9.

Gaemperli et al. "Cardiac hybrid imaging." Eur Heart J 2011; 32(17): 2100-8.

Gaur et al., "Coronary plaque quantification and fractional flow reserve by coronary computed tomography angiography identify ischaemia-causing lesions", European Heart Journal, 2016 pp. 1220-1227.

Goff, et al. "2013 ACC/AHA Guidelines on the Assessment of Cardiovascular Risk: a Report of the American College of Cardiology/American Heart Association Task Force on Practice Guidelines." J Am Coll Cardiol. 2014;63: 2935-59.

Gogas, et al. "Assessment of Coronary Atherosclerosis by IVUS and IVUS-based Imaging Modalities: Profession and Regression Studies, Tissue Composition and Beyond." Int J Cardiovasc Imaging. 2011;27: 225-37.

Goldstein et al., "Moving beyond regression techniques in cardiovascular risk prediction: applying machine learning to address analytic challenges." Eur Heart J. 2017; 38(23) pp. 1805-1814.

Greenwood et al. "Effect of Care Guided by Cardiovascular Magnetic Resonance, Myocardial Perfusion Scintigraphy, or NICE Guidelines on Subsequent Unnecessary Angiography Rates: The CE-MARC 2 Randomized Clinical Trial." JAMA 2016; 316(10): 1051-60. doi: 10.1001/jama.2016.12680 [published Online First: Aug. 30, 2016.

Gupta et al., Apr. 8, 2015, Moving beyond luminal stenosis: imaging strategies for stroke prevention in asymptomatic carotid stenosis, Cerebrovascular Diseases, 39:253-261.

Guyon et al., "An introduction to variable and feature selection." J Mach Learn Res. 2003; 3:1157-1182.

Hadamitzky et al., "Optimized Progostic Score for Coronary Computed Tomographic Angiography", Journal of the American College of Cardiology, vol. 62, No. 5, 2013, pp. 468-476.

Hall et al., "Benchmarking attribute selection techniques for discrete clas data mining." IEEE Transaction on Knowledge and Data Engineering 2003; 15(6): pp. 1437-1447.

Hall et al., "The WEKA data mining software: an update." SIGKDD Explor Newsl. 2009; 11(1) pp. 10-18.

Hampe, N., Van Velzen, S. G., Aben, J., Collet, C., & Isgum, I. (2023). Deep Learning-Based Prediction of Fractional Flow Reserve along the Coronary Artery. ArXiv. /abs/2308.04923.

Han et al. "Incremental role of resting myocardial computed tomography perfusion for predicting physiologically significant coronary artery disease: A machine learning approach." J Nucl Cardiol. 2018; 25(1) pp. 223-233.

Han et al., "Quantitative measurement of lipid rich plaque by coronary computed tomography angiography: A correlation of histology in sudden cardiac death", Atherosclerosis, 2018 pp. 426-433.

Hausleiter et al. "Estimated radiation dose associated with cardiac CT angiography." JAMA 2009; 301(5): 500-7.

Heo et al., "Optimal boundary detection method and window settings for coronary atherosclerotic plaque volume analysis in coronary computed tomography angiography: comparison with intravascular ultrasound", Eur Radiol, (2016) 26:31, pp. 3190-3198.

Hesse et al. "EANM/ESC procedural guidelines for myocardial perfusion imaging in nuclear cardiology." Eur J Nucl Med Mol Imaging 2005; 32 (7): 855-97. doi: 10.1007/s00259-005-1779-y.

Howard G. et al. "Cigarette smoking and progression of atherosclerosis: The Atherosclerosis Risk in Communities (AIRC) Study." JAMA 1998; 279(2) pp. 119-124.

Hundley WG et al. "Society for Cardiovascular Magnetic Resonance guidelines for reporting cardiovascular magnetic resonance examinations." J Cardiovasc Magn Reson 2009; 11:5.

Job, Mark, Section 510(k) premarket notification of intent to market device "Plaque View, Model No. CSPV-001 A" as filed and Review, K043111, Department of Health & Human Services, Food and Drug Administration, Nov. 18, 2004, 5 pages, Silver Springs, Maryland.

Kanamori et al. "Robust Loss Functions for Boosting" Neural Computation. 2007; 19(8) pp. 2183-2244.

(56) References Cited

OTHER PUBLICATIONS

Kang, et al. "Structured Learning Algorithm for Detection of Nonobstructive and Obstructive Coronary Plaque Lesions from Computed Tomography Angiography", Journal of Medical Imaging, (2015).
Kang, et al. Automated Knowledge-Based Detection of Nonobstructive and Obstructive Arterial Lesions from Coronary CT Angiography. Med Phys. 40(4): 041912-1-041912-10.
Kanitsar et al., 2002, CPR—curved planar reformation, IEEE Visualization, DOI: 10.1109/VISUAL.2002.1183754, 8 pp.
Karlof et al , 2019, Correlation of computed tomography with carotid plaque transcriptomes associates calcification with lesion-stabilization, atherosclerosis, 288 175-185.
Karlof et al , 2021, Carotid plaque phenotyping by correlating plaque morphology from computed tomography angiography with transcriptional profiling, Eur J Vas Endovas Surg , 62 716-726.
Kim et al , "Natural History of Diabetic Coronary Atherosclerosis by Quantitative Measurement of Serial Coronary Computed Tomographic Angiography", JACC Cardiovascular Imaging, vol. 11, No. 10, 2018 pp. 1461-1471.
Klass O, et al. "Coronary plaque imaging with 256-slice multidetector computed tomography: interobserver ariability of volumetric lesion parameters with semiautomatic plaque analysis software", Int J Cardiovasc Imaging, (2010). 26; pp. 711-720.
Klein et al. :Diagnostic quality of time-averaged ECG-Gated CT data, SPIE medical imaging, 2019.
Knuiman et al "An Empirical comparison of multivariable methods for estimating risk of death from coronary heart disease" J Cardiovasc Risk 1997, 4(2) pp. 127-134.
Kolossvary, et al "Radiomic Features Are Superior to Conventional Quantitative Computed Tomographic Metrics to Identify Coronary Plaques with Napkin-Ring Sign" Circ Cardiovasc Imaging 2017,10.
Koo BK, et al. "Diagnosis of ischemia-causing coronary stenoses by noninvasive fractional flow reserve computed from coronary computed tomographic angiograms. Results from the prospective multicenter Discovery-Flow (Diagnosis of Ischemia-Causes Stenoses Obtained via Noninvasive Fractional Flow Reserve) study." J Am Coll Cardiol 2011; 58 (19): 1989-97. doi: 10.1016/j.jacc.2011.06.066 [published Online First: Oct. 29, 2011].
Kramer et al. "Standardized cardiovascular magnetic resonance imaging (CMR) protocols, society for cardiovascular magnetic resonance: board of trustees task force on standardized protocols." J Cardiovasc Magn Reson 2008; 10:35. doi: 10.1186/1532-429X-10-35.
Kwan et al , "Bridging the gap for lipid lowering therapy plaque regression, coronary computed tomographic angiography, and imaging-guided personalized medicine" Expert Rev Cardiovasc Ther 2017, 15(7) pp. 547-558.
Kwee et al., Apr. 2010, Systematic review on the association between calcification in carotid plaques and clinical ischemic symptoms, Journal of Vascular Surgery, 51(4):1015-1025.
Lee et al., "Differences in Progression to Obstructive Lesions per High-Risk Plaque Features and Plaque Volumes With CCTA", JACC: Cardiovascular Imaging, 2019 in 9 pages.
Lee et al., "Effects of Statins on Coronary Atherosclerotic Plaques—The PARADIGM (Progession of AtheRosclerotic PlAque Determined by Computed TomoGraphic Angiography Imaging) Study", JACC: Cardiovascular Imaging, 2018.
Lee et al., "Identification of High-Risk Plaques Destined to Cause Acute Coronary Syndrome Using Coronary Computed Tomographic Angiography and Computational Fluid Dynamics", JACC: Cardiovascular Imaqini:t vol. ■12, No. 6, Jun. 2019. pp. 1032-1043.
Lee et al., "Quantification of Coronary Atherosclerosis in the Assessment of Coronary Artery Disease." Circ Cardiovasc Imaging. 2018; 11(7): e007562.
Tomey MI, et al. "Advances in the understanding of plaque composition and treatment options: year in review." J Am Coll Cardio. 2014; 63(16) pp. 1604-1616.
Tonino et al., "Angiographic versus functional severity of coronary artery stenoses in the FAME study fractional flow reserve versus angiography in multivessel evaluation." Journal of the American College of Cardiology 201O; 55 (25): 2816-21. doi: 10.1016/j.jacc.2009.11-096 [published Online First:2010/06/291.
Tonino et al., Jan. 15, 2009, Fractional flow reserve versus angiography for guiding percutaneous coronary interventions, The New England Journal of Medicine, 360(3):213-224.
U.S. Food and Drug Administration, Nov. 5, 2010, K100868 501(k) Summary, 10 pp.
U.S. Food and Drug Administration, Oct. 2, 2020, K202280 501(k) Summary, 9 pp.
Van Ooijen, et al. "Coronary Artery Imaging with Multidetector CT: Visualization Issues" RadioGraphics, vol. 23. (2003).
Van Rosendael et al., "Maximization of the usage of coronary CTA derived plaque information using a machine learning based algorithm to improve risk stratification; insights from the CONFIRM registry", Journal of Cardiovascular Computed Tomography 12, 2018, pp. 204-209.
Van Rosendael et al., "Quantitative Evaluation of High-Risk Coronary Plaque by Coronary CTA and Subsequent Acute Coronary Events", JACC: Cardiovascular Imaging, vol. 12, No. 8, Aug. 2019. pp. 1568-1571.
Velivelli, S. L.S., et al., "Antifungal symbiotic peptide NCR044 exhibits unique structure and multifaceted mechanisms of action that confer plant protection.", Proceedings of the National Academy of Sciences, vol. 117, Issue. 27, 2020, pp. 16043-16054.
Versteylen MO, et al. "Additive value of semiautomated quantification of coronary artery disease using cardiac computed tomographic angiography to predict future acute coronary syndrome." J Am Coll Cardiol. 2013; 61(22): pp. 2296-2305.
Virmani, et al. "Atherosclerotic plaque progression and vulnerability to rupture: angiogenesis as a source of intraplaque hemorrage." Arterioscler Thromb Vasc Biol. 2005; 25: 2054-61.
Virmani, et al. "Lessons from sudden coronary death: a comprehensive morphological classification scheme for atherosclerotic lesions." Arterioscler Thromb Vasc Biol. 2000;20: 1262-75.
Virmani, et al. "Pathology of the Vulnerable Plaque." J Am Coll Cardiol. 2006; 47: C13-8.
Wei, et al. "Computerized Detection of Noncalcified Plaques in Coronary CT Angiography: Evaluation of Topological Soft Gradient Prescreening Method and Luminal Analysis" Med Phys, (2014).
Weir-MacCall et al., "Impact of Non-obstructive left main disease on the progression of coronary artery disease: A PARADIGM substudy", Journal of Cardiovascular Computed Tomography 12, 2018, pp. 231-237.
Weisenfeld et al. "Automatic Segmentation of Newborn Brain MRI", NIH PA Author Manuscript 2010.
Williams et al. "Use of Coronary Computed Tomographic Angiography to Guide Management of Patients with Coronary Disease." Journal of American College of Cardiology 2016; 67 (15) : 1759-68. doi: 10.1016/J.Jacc.2016.02.026 [published Online First: Apr. 16, 2016].
Williams et al., "Coronary Artery Plaque Characteristics Associated With Adverse Outcomes in the SCOT-HEART Study", Journal of the American College of Cardiology, vol. 73, No. 3, Jan. 29, 2019.DD. 291-301.
Wilson et al. "Prediction of coronary heart disease using risk factor categories" Circulation 1998; 97(18) pp. 1837-1847.
Wintermark et al., May 2008, High-resolution CT imaging of carotid artery atheroscierotic plaques, Am J Neuroradiol, 29:875-882.
Won et al., "Longitudinal assessment of coronary plaque volume change related to glycemic status using serial coronary computed tomography angiography: A Computed TomoGraphic Angiography Imaging) substudy", Journal of Cardiovascular Computed Tomography 13, 2019 pp. 142-147.
Won et al., "Longitudinal quanititive assessment of coronary plaque progression related to body mass index using serial coronary computed tomography angiography", European Heart Journal—Cardiovascular Imaging, 2019 pp. 591-599.
Won, Philip, Section 510(k) premarket notification of intent to market device "Medical image management and processing system" as filed and Review, K212758, Department of Health & Human Services, Food and Drug Administration, May 19, 2023, 9 pages, Silver Springs, Maryland.

(56) References Cited

OTHER PUBLICATIONS

Wu et al., Jun. 11, 2018. Group normalization, arXiv:1803.08494v3, [cs.CV], 10 pp.
Xu et al., Aug. 2023, ELIXR: Towards a general purpose X-ray artificial intelligence system through alignment of large language models and radiology vision encoders, arXiv.2308.01317 [cs.CV], 54 pp.
Yang et al., "Prognostic Implications of Comprehensive Whole Vessel Plaque Quantification Using Coronary Computed Tomography Angiography", Jun. 2021 JACC Asia vol. 1 No. 1:37-48 (Year 2021), Elsevier on behalf of the American College of Cardiology Foundation.
Yang, et al. "Automatic centerline extraction of coronary arteries in coronary computed tomographic angiography" The International Journal of Cardiocascular Imaging, 28, pp. 921-933. (2012).
Yokoya K, et al. "Process of progression of coronary artery lesions from mild or moderate stenosis to moderate or severe stenosis: A study based on four serial coronary arteriograms per year." Circulation 1999; 100(9); pp. 903-909.
Zeb I et al. "Effect of statin treatment on coronary plaque progression—a serial coronary CT angiography study." Atherosclerosis. 2013; 231(2) pp. 198-204.
Zhao Z., et al. "Dynamic nature of nonculprit coronary artery lesion morphology in STEMI: a serial IVUS analysis from HORIZONS-AMI trial." JACC Cardiovasc Imaging, 2013; 6(1) pp. 86-95.
Zreik et al., Dec. 10, 2018, A recurrent CNN for automatic detection and classification of coronary artery plaque and stenosis in coronary CT angiography, arXiv:1803/04360v4, 11 pp.
Zreik, M., et al., "Deep Learning Analysis of Coronary Arteries in Cardiac CT Angiography for Detection of Patients Requiring Invasive Coronary Angiography," IEEE Transactions on Medical Imaging 39, 1545-1557 (2020).
Zreik, M., et al., "Deep learning analysis of the myocardium for identification of patients with functionally significant coronary artery stenosis with coronary CT angiography.", Medical Image Analysis, vol. 44, Nov. 16, 2017, 42 pages.
Okubo, Ryo, et al. "Pericoronary adipose tissue ratio is a stronger associated factor of plaque vulnerability than epicardial adipose tissue on coronary computed tomography angiography." Heart and vessels 32.7 (2017): 813-822. (Year: 2017).
Otsuka et al. "Napkin-ring sign on coronary CT angiography for the prediction of acute coronary syndrome." JACC Cardiovasc Imaging 2013; 6(4): 448-57.
Ovrehus et al., "CT-based total vessel plaque analyses improves prediction of hemodynamic significance lesions as assessed by fractional flow reserve in patients with stable angina pectoris", Journal of Cardiovascular Computed Tomography 12, 2018 pp. 344-349.
Ovrehus, et al. "Reproducibility of Semi-Automatic Coronary Plaque Quantification in Coronary CT Angiography with Sub-mSv Radiation Dose." J Cardiovasc Comput Tomogr, (2016).
Papadopoulou, et al. "Detection and Quantification of Coronary Atherosclerotic plaque by 64-slice multidetector CT: A systematic head-to-head comparison with intravascular ultrasound." Atherosclerosis. 2011;219: 163-70.
Papadopoulou, et al. Reproducibility of CT Angiography Data Analysis Using Semiautomated Plaque Quantification Software: Implications for the Design of Longitudinal Studies. Int J Cardiovasc Imaging.
Park et al., "Atherosclerotic Plaque Characteristics by CT Angiography Identify Coronary Lesions That Cause Ischemia", JACC: Cardiovascular Imaging, vol. 8, No. 1, 2015 in 10 pages.
Park, et al. "Clinical Feasibility of 3D Automated Coronary Atherosclerotic Plaque Quantification Algorithm on Coronary Computed Tomography Angiography: Comparison with Intravascular Ultrasound" European Radiology (2015), 25: 3073-3083.
Park, et al. "Visual-functional Mismatch between Coronary Angiography and Fractional Flow Reserve." JACC Cardiovasc Interv. 2012; 5: 1029-36.
Patel et al., 2019, 1-year impact on medical practice and clinical outcomes of FFRCT, JACC: Cardiovascular Imaging, https://doi.org/l0.,1016/j.jcmg.2019.03.003, 9 pp.
Pavlou et al., "A note on obtaining correct marginal predictions from a random intercepts model for binary outcomes." BMC Med Res Methodol 2015; 15:59. doi: 10.1186/s12874-015-004606 [published Online First: Aug. 6, 2015].
Pedregosa, et al. "Scikit-learn: Machine Learning in Python." Journal of Machine Learning Research, 2011;12: 2825-2830.
Picano et al. "The appropriate and justified use of medical radiation in cardiovascular imaging: a position document of the ESC Associations of Cardiovascular Imaging, Percutaneous Cardiovascular Interventions and Electrophysiology." Eur Heart J 2014; 35(10): 665-72.
Puchner et al., Mar. 2015, High-Risk Coronary Plaque at Coronary CT Angiography is Associated with NAFLD, Independent of Coronary Plaque and Stenosis Burden, ,J Cardiovasc Comput Tomogr., 27413):693-701.
Puchner, et al. "High-Risk Plaque Detected on Coronary CT Angiography Predicts Acute Coronary Syndrome independent of Significant Stenosis in Patients with Acute Chest Pain" J Am Coif Cardio/2014.
Raff, et al. "SCCT guidelines for the interpretation and reporting of coronary computed tomographic angiography" J Cardiovasc Comput Tomogr 2009: 3(2): 122-36.
Rehani et al. "ICRP Publication 117. Radiological protection in fluoroscopically guided procedures performed outside the imaging department." Ann ICRP 2010; 40(6): 1-102.
Rizvi et al , "Rationale and Design of the CREDENCE Trial computed Tomographic evaluation of atherosclerotic Determinants of myocardial Ischemia", BMC Cardiovascular Disorders, 2016, in 10 pages.
Rizvi et al., "Diffuse coronary artery disease among other atherosclerotic plaque characteristics by coronary computed tomography angiography for predicting coronary vessel-specific ischemia by fractional flow reserve", Atherosclerosis 258, 2017 pp. 145-151.
Rongero, Jeff D., Section 510(k) premarket notification of intent to market device "Vessel Analysis and Autoplaque for ORS Visual" as filed and Review, K122429, Department of Health & Human Services, Food and Drug Administration, Nov. 28, 2012, 11 pages, Silver Springs, Maryland.
Roy-Cardinal et al. "Intravascular Ultrasound Image Segmentation: A Three-Dimensional Fast-Marching Method Based on Grey Level Distributions", IEEE Transactions on Medical Imaging, vol. 25, No. 5, May 2006.
Rozie et al., 2009, Atherosclerotic plaque volume and composition in symptomatic carotid arteries assess with the multidetector CT angiography; relationship with severity of stenosis and cardiovascular risk factors, Eur Radiol, 19:2294-2301.
Sabir, A et al. Measuring Noncalcified Coronary Atherosclerotic Plaque Using Voxel Analysis with MDCT Angiography: Phantom Validation: American Journal of Roentgenology, Apr. 2008; vol. 190, No. 4, pp. 242-246.
Samady H. et ai. "Coronary artery wall shear is associated with progression and transformation of atherosclerotic plaque and arterial remodeling in patients with coronary artery disease." American Heart Association Circulation, vol. 124, Issue 7, Aug. 16, 2011, pp. 779-788.
Schinkel et al "Noninvasive evaluation of ischaemic heart disease myocardial perfusion imaging or stress echocardiography?" European Heart Journal (2003) 24, 789-800.
Schlett et al. "How to assess non-calcified plaque in CT angiography: delineation methods affect diagnostic accuracy of low-attenuation plaque by CT for lipid-core plaque in history." Euro Heart J Cardiovasc Imaging 2013; 14(11): 1099-105.
Schuurman, et al. "Prognostic Value of intravascular Ultrasound in Patients with Coronary Artery Disease." J Am Coll Cardioi. 2018;72: 2003-2011.
Seghier et al , "Lesion identification using unified segmentation-normalisation models and fuzzy clustering" NeuroImage 40(2008) 1253-1266.

(56) References Cited

OTHER PUBLICATIONS

Seifarth, et al. "Histopathological Correlates of the Napkin-Ring Sign Plaque in Coronary CT Angiography." Send to Atherosclerosis. 2012;224: 90-6.
Sharma et al., "Stress Testing Versus CT Angiography in Patients With Diabetes and Suspected Coronary Artery Disease", Journal of the American College of Cardiology, vol. 73, No. 8, 2019 pp. 893-902.
Shaw et al "Optimal medical therapy with or without percutaneous coronary intervention to reduce ischemic burden results from the Clinical Outcomes Utilizing Revascularization and Aggressive Drug Evaluation (COURAGE) trail nuclear substudy" Circulation 2008, 117 (10) 1283-91 doi 10 116/CIRCULATIONAHA 107 743963.
Shaw et al. "Why all the focus on cardiac imaging?" JAAC Cardiovasc Imaging 2010; 3(7): 789-94 doi: 10.16/j.jcmg.2010.05.004.
Sheahan et al., Feb. 2018, Atheroscierotic plaque tissue: noninvasive quantitative assessment of characteristics with software-aided measurements from conventional CT angiography, Radiology, 286(2):622-631.
Shin S et al., "Impact of Intensive LDL Cholesterol Lowering on Coronary Artery Atherosclerosis Progression: A Serial CT Angiography Study." JACC Cardiovasc Imaging. 2017; 10(4) pp. 437-446.
Siasos, et al. "Local Low Shear Stress and Endotheliai Dysfunction in Patients with Nonobstructive Coronary Atherosclerosis." J Arn Coll Cardiol. 2018;71: 2092-2102.
Smith, John, Section 5 IO(k) premarket notification of intent to market device "Picture archiving and communications system" as filed and Review, K190868, Department of Health & Human Services, Food and Drug Administration, Nov. 5, 2019, 10 pages, Silver Springs, Maryland.
Smith, John, Section 5 IO(k) premarket notification of intent to market device "Picture archiving and communications system" as filed and Review, K202280, Department of Health & Human Services, Food and Drug Administration, Oct. 2, 2020, 9 pages, Silver Springs, Maryland.
Smith, John, Section 510(k) premarket notification of intent to market device "Adjunctive cardiovascular status indicator" as filed and Review, K231335, Department of Health & Human Services, Food and Drug Administration, Sep. 8, 2023, 9 pages, Silver Springs, Maryland.
Song et al. "Comparison of machine learning techniques with classical statistical models in predicting health outcomes." Stud Health Technol Inform. 2004; 107(Pt 1) pp. 736-740.
Staruch, et al. "Automated Quantitative Plaque Analysis for Discrimination of Coronary Chronic Total Occlusion and Subtotal Occlusion in Computed Tomography Angiography", J Thoracic Imaging, (2016).
Stone, et al. "A prospective natural-history stucy of coronary atherosclerosis." N Engl J Med 2011; 364(3): 226-35.
Stuijfzand, et al. "Stress Myocardial Perfusion Imaging vs Coronary Computed Tomographic Angiography for Diagnosis of Invasive Vessel-Specific Coronary Physiology Predictive Modeling Results From the Computed Tomographic Evaluation of Atherosclerotic Determinants of Myocardial Ischemia (CREDENCE) Trial", JAMA Cardiology, doi:10.1001/jamacardio.2020.3409, Aug. 19, 2020.
Sun et al., Mar. 2017, Carotid plaque lipid content and fibrous cap status predict systemic cv outcomes, JACC: Cardiovascular Imaging, 10(3):241-249.
Sun, et al. "Diagnostic Value of Multislice Computed Tomography Angiography in Coronary Artery Disease: a Meta-Analysis." Eur J Radial. 2006;60: 279-86.
Taylor et al., "Patient-Specific Modeling of Cardiovascular Mechanics", Annu. Rev. Biomed. Eng. Nov. 2009:109-139.
The Copenhagen Wheel, https://senseable.mit.edu/copenhagenwheel/, website pages, 2 pages, printed on Oct. 2, 2023 (origination date unknown).
Thim, et al. "Unreliable Assessment of Necrotic Core by Virtual Histology Intravascular Ultrasound in Porcine Coronary Artery Disease." Circ Cardiovasc Imaging. 2010;3: 384-91.
Thygesen, et al. "Third Universal Definition of Myocardial Infarction." Glob Heart. 2013;7: 275-95.
Tian, et al. "Distinct Morphological Features of Ruptured Culprit Plaque for Acute Coronary Events Compared to those with Silent Rupture and Thin-Cap Fibroatheroma: a Combined Optical Coherence Tomography and Intravascular Ultrasound Study." J Am Coll Cardiol. 2014;63: 2209-16.
Tilkemeier et al., "American Society of Nuclear Cardiology information statement: Standardized reporting matrix for radionuclide myocardial perfusion imaging." J Nucl Cardiol 2006; 13 (6): e157-71. doi: 10.1016/j.nuclcard.2006.08.014.
Abbara et al., "SCCT Guidelines for the performance and acquisition of coronary computed tomographic angiography: A report of the society of Cardiovascular Computed Tomography Guidelines Committee: Endorsed by the North American Society for Cardiovascular Imaging (NASCI)." Journal of cardiovascular computed tomography 2016; 10(6) pp. 435-449.
Abdelrahman et al., Sep. 8, 2020, Coronary computed tomography angiography from clinical uses to emerging technologies, Journal of the American College of Cardiology, 76(10): 1226-1243.
Achenbach et al. "Detection of calcified and noncalcified coronary atherosclerotic plaque by contrast-enhanced, submillimeter multidetector spiral computed tomography: a segment-based comparison with intravascular ultrasound." Circulation 2004; 109(1) pp. 14-17.
Ahmadi A. et al. "Do Plaques rapidly progress prior to myocardial infarction? The interplay between plaque vulnerability and progression." Circ Res. 2015; 117(1):99-104.
Ahmadi et al., "Lesion-Specific and Vessel-Related Determinants of Fractional Flow Reserve Beyond Coronary Artery Stenosis", JACCL Cardiovascular Imaging, vol. 11, No. 4. 2018 pp. 521-530.
Ahmadi et al., "Association of Coronary Stenosis and Plaque Morphology with Fractional Flow Reserve and Outcomes." JAMA cardiology 2016; 1 (3): 350-7. doi: 10.1001/jamacardio.2016.0263 [published Online First: Jul. 22, 2016].
Al'Aref et al., "High-risk atherosclerotic plaque features for cardiovascular risk assessment in the Prospective Multicenter Imaging Study for Evaluation of Chest Pain trial", Cardiovascular Diagnosis and Therapy, vol. 9, No. 1, Feb. 2019. pp. 89-93.
Al'Aref et al. "Clinical Applications of machine learning in cardiovascular disease and its relevance to cardiac imaging." Eur Heart J. Jul. 27, 2018. [Epub ahead of print].
Anjana, P.S. et al., "Study on Self Balancing Motorcycle Using the Concept of Reinforcement Learning," International Research Journal of Engineering and Technology (IRJET), vol. 7, Issue 4, Apr. 2020, pp. 6524-6531.
Antonopoulos et al., "Detecting Human coronary inflammation by imaging perivascular fat", Sci. Transl. Med. 9, eaal2658 (2017) Jul. 12, 2017.
Arbab-Zadeh et al., "Contemporary Reviews in Cardiovascular Medicine, Acute Coronary Events", Amercan Heart Assocation, Inc., Circulation. 2012;125:1147-1156, Mar. 6, 2012, pp. 1147-1156.
Arbab-Zadeh, et al. "the myth of the vulnerable plaque: transitioning from a focus on individual lesions to atherosclerotic disease burden for coronaiy artery disease risk assessment." J Arn Coll Cardiol.2015;65: 846-855.
Arthur S Agatston et al., Quantification ofcoronary artery calcium using ultrafast computed tomography, Journal of the American College of Cardiology, Mar. 15, 1990 , vol. 15, No. 4, pp. 827-832.
Bakhasi, et al. "Comparative Effectiveness of CT-Derived Atherosclerotic Plaque Metrics for Predicting Myocardial Ischemia." JACC Cardiovasc Imaging. Jul. 13, 2018. doi: 10.2013/j.jcmg.2018.05.019. [Epubahead of print].
Baskaran et al., "Dense calcium and lesion-specific ischemia: A comparison of CCTA with fractional flow reserve", Atherosclerosis 260, 2017 pp. 163-168.
Bax, Maxim et al., "Comparative differences in the atherosclerotic disease burden between the epicardial coronary arteries: quantitative plaque analysis on coronary computed tomography angiography", European Society of Cardiology, European Heart Journal—Cardiovascular Imaging (2021) 22, 322-330, published ahead-of-print online Nov. 11, 2020, 9 pages total.

(56) References Cited

OTHER PUBLICATIONS

Benjamin, et al. "Heart Disease and Stroke Statistics—2018 Update: A Report From the American Heart Association." Circulation. 2018;137: e67-e492.
Benjamin, Mina M, Rabbat, Mark G., "Machine learning-based advances in coronary computed tomography angiography," Editorial, Quantitative imaging in Medicine and Sugery, vol. 11, No. 6 Jun. 2021, http://dx.doi.org/10.21037/qims-21-99.
Bergman "Using Multicoloured Halftsone Screens for Offset Print Quality Monitoring", Linkdping Studies in Science and Technology; LiU-TEK-LIC-2005:02.
Blankstein R. et al. "Coronary CTA in the Evaluation of Stable Chest Pain: Clear Benefits, But Not for All." J Am Coll Cardiol 2017; 69 (14): 1771-73. doi: 10.1016/j.jacc.2017.02.011 [published Online First: Apr. 8, 2017].
Boogers, et al. "Automated Quantification of Coronary Plaque with Computed Tomography: Comparison with Intravascular Ultrasound using a Dedicated Registration Algorithm for Fusion-Based Quantification", Epub, (2012).
Boussoussou et al., 2023, The effect of patient and imaging characteristics on coronary CT angiography assessed perocoronary adipose tissue attenuation and gradient, Journal of Cardiovascular Computed Tomoaraphv, 17:34-42.
Budde et al., Sep. 15, 2021, CT-derived fractional flow reserve (FFRct) for functional coronary artery evaluation in the follow-up of patients after heart transplantation, European Radiology, https://doi.org/1 0/1007/s00330-0921-08246-5.
Budoff MJ, et al. "Diagnostic performance of 64-multidetector row coronary computed tomographic angiography for evaluation of coronary artery stenosis in individuals without know coronary artery disease: results from the prospective multicenter ACCURACY (Assessment by Coronary Computed Tomography of Individuals Undergoing Invasive Coronary Angiography) trial." J Am Coll Cardiol 2008; 52(21): 1724-32.
Bzdok "Classical Statistics and Statistical Learning in Imaging Neuroscience." Front Neurosci. 2017; 11:543.
Calvert, et al. "Association between IVUS Findings and Adverse Outcomes in Patients with Coronary Artery Disease: the VIVA (VH-IVUS in Vulnerable Atherosclerosis) Study." JACC Cardiovasc Imaging. 2011;4: 894-901.
Celeng, et aL"Non-invasive and Invasive Imaging of Vulnerable Coronary Plaque." trends Cardiovasc Med. 2016;26-538-47.
Cerqueira et al. "Standardized myocardial segmentation and nomenclature for tomographic imaging of the heart. A statement for healthcare professinals from the Cardiac Imaging Committee of the Council on Clinical Cardiology of the American Heart Association." Int J Cardiovasc Imaging 2002; 18(1): 539-42.
Chang et al., "Coronary Atherosclerotic Precursors of Acute Coronary Syndromes", Journal of the American College of Cardiology, vol. 71, No. 22, Jun. 5, 2018. pp. 2511-2522.
Chang et al., "Selective Referral Using CCTA Versus Direct Referral for Individuals Referred to Invasive Coronary Angiography for Suspected CAD", JACC: Cardiovascular Imaging, vol. 12, No. 7, Jul. 2019. pp. 1303-1312.
Chrencik et al., Sep. 2019, Quantitative assessment of carotid plaque morphology (geometry and tissue comoosition) using computed tomography angiography, Journal of Vascular Surgery, 70(3):858-868.
Chung et al. "Image Segmentation Methods for Detecting Blood Vessels in Angiography", 2006 9th Int. Conf. Control, Automation, Robotics and Vision, Singapore, Dec. 5-8, 2006, ICARCV 2006, pp. 1424-1429.
Costopoulos, et al "Intravascular Ultrasound and Optical Coherence Tomography Imaging of Coronary Atherosclerosis" Int J Cardiovasc Imaging 2016,32 189-200.
Cury et al., 2022, CAD-RADSTM 2.0-2022 coronary artery disease-reporting and data system an expert consensus document of the Society of Cardiovascular Computed Tomography (SCCT), the American College of Cardiology (ACC), the American College of Radiology (ACR) and the North America Society of Cardiovascular Imaging (NASCI), Journal of Cardiovascular Computed Tomography, https://doi.org/10.1016/j.jcct.2022.07.002.
Cury, et al. "CAD-RADS TM Coronary Artery Disease-Reporting and Data System. An Expert consensus documents of the Society of Cardiovascular Computed Tomography (SCCT), the American College of Radiology (ACR) and the North American Society for Cardiovascular Imaging (NASCI)." Endorsed by the American College of Cardiology. J Cardiovasc Compute Tomoqr. 2016;10: 269-81.
Danad et al. "Comparison of Coronary CT Angiography, SPECT, PET, and Hybrid Imaging for Diagnosis of Ischemic Heart Disease Determined by Fractional Flow Reserve." JAMA Cardiol 2017; 2 (10): 1100-07. doi 10.1001/jamacardio.2017.2471 [published Online First: Aug. 17, 2017].
De Bruyne B. et al. "Fractional flow reserve-guided PCI for stable coronary artery disease." The New England journal of medicine 2014; 371 (13): 1208-17. doi: 10.1056/NEJMoa1408758 [published Online First: 2014/0902].
De Bruyne et al , Sep. 13, 2012, Fractional flow reserve-guided PCA versus medical therapy in stable coronary disease, The New England Journal of Medicine, 367(11) 991-1001.
De Graaf, et al. "Automatic Quantification and Characterization of Coronary Atherosclerosis with Computed Tomography Coronary Angiography: Cross-Correlation with Intravascular Ultrasound Virtual Histology", Int J Cardiovasc, pp. 1177-1190, (2013).
De Graaf, et al. "Feasibility of an Automated Quantitative Computed Tomography Angiography-Derived Risk Stratification of Patients with Suspected CAD." Am J Cardiol (2014).
Delong ER, et al. "Comparing the areas under two or more correlated receiver operating characteristic curves: a nonparametric approach." Biometrics 1988; 44 (3): 837-45. [published Online First: Sep. 1, 1988 1.
Dey et al., "Direct Quantatitive In Vivo Comparison of Calcified Atherosclerotic Plaque on Vascular MRI and CT by Multimodality Image Registration" Journal of Magnetic Resonance Imaging 23:345-354 (2006).
Dey et al., 2018, Integrated prediction of lesion-specific ischemia from quantitative coronary CT Angiography using machine learning: a multicenter study, European Radiology, 28(6):2655-2664.
Dey, et al. "Comparison of Quantitative Atherosclerotic Plaque Burden from Coronary CT Angiography in Patients with First Acute Coronary Syndrome and Stable CAD" J Cardiovasc Comput tomogr (2014).
Dey, et al. "Non-Invasive Measurement of Coronary Plaque from Coronary CT Angiography and its Clinical Implication", Experl Review of Cardiovascular Therapy (2013).
Diaz-Zamudio, et al. "Automated Quantitative Plaque Burden from Coronary CT Angiography Non-Invasively Predicts Hemodynamic Significance by Using Fractional Flow Reserve in Intermediate Coronary Lesions." Radiology (2015).
Douglas et al., "Outcomes of Anatomical versus Functional Testing for Coronary Artery Disease", N Engl J Med. Apr. 2, 2015, p. 1291-1300.
Douglas et al., Aug. 2, 2016, 1-year outcomes of FFRCT-guided care in patients with suspected coronary disease, Journal of the American College of Cardiology, 68(5):435-445.
Driessen et al., "Adverse Plaque Characteristic Relate More Strongly With Hyperemic Fractional Flow Reserve and Instantaneous Wave-Free Ratio Than With Resting Instantaneous Wave-Free Ratio", JACC: Cardiovascular Imaging, 2019, in 11 pages.
Driessen et al., "Effect of Plaque Burden and Morphology on Myocardial Blood Flow and Fractional Flow Reserve", Journal of the American College of Cardiology, vol. 71, No. 5, 2018 p. 499-509.
Lee et al., Rationale and design of the Coronary Computed Tomographic Angiography for Selective Cardiac Catheterization: Relation to Cardiovascular Outcomes, Cost Effectiveness and Quality of Life (CONSERVE) trial:, Am Heart J, 2017; vol. 186, pp. 48-55.
Lee et al., "Rationale and design of the Progession of AtheRosclerotic PlAque Determined by Computed TomoGraphic Angiography Imaging (PARADIGM) registry: A comprehensive exploration of plaque progression and its impact on clinical outcomes from a multicenter

(56) References Cited

OTHER PUBLICATIONS serial coronary computed tomographic angiography study", American Heart Journal, vol. 182. 2016 pp. 72-79.
Lee et al., "Reproducibility in the assessment of noncalcified coronary plaque with 256-slice multi-detector CT and automated plaque analysis software", Int J Cardiovasc Imaging; 2010; 26:237-244.
Leipsic et al. "SCCT guidelines for the interpretation and reporting of coronary CT angiography: a report of the Society of Cardiovascular Computed Tomography Guidelines Committee" J Cardiovasc Comput Tomogr 2014; 8(5): 342-58.
Libby P. "Mechanisms of acute coronary syndromes and their implications for therapy." N Engl J Med. 2013; 368: 2004-13.
Lu et al., "Central Core Laboratory versus Site Interpretation of Coronary CT Angiography: Agreement and Association with Cardiovascular Events in tlie PROMISE Trial", Radiology: vol. 287, No. 1, Apr. 2018, pp. 87-95.
Lundberg, et al. "A Unified Approach to Interpreting Model Predictions." 31st Conference on Neural Information Processing Systems (NIPS 2017).
MacAlpin, Feb. 1980, Contribution of dynamic vascular wall thickening to luminal narrowing during coronary arterial constriction, Circulation, 60(2) 296-301.
Mancio, Jennifer, et al "Perivascular adipose tissue and coronary atherosclerosis" Hear 104 20 (2018) 1654-1662 (Year 2018).
Maurovich-Horvat et al., 2014, Comprehensive plaque assessment by coronary CT angiography, Nature Reviews Cardiology, 11 (7):390-402.
Maurovich-Horvat, et al. "The napkin-ring sign indicates advanced atherosclerotic lesions in coronary CT angiography.", JACC Cardiovasc Imaging 2012; 5(12): 1243-52.
Meijboom et al. "Diagnostic accuracy of 64-slice computed tomography coronary angiography: a prospective, multicenter, multivendor study." J Am Coll Cardiol 2008; 52 (25): 2135-44. doi: 10.1016/j.jacc.2008.08.058.
Melikian et al. "Fractional flow reserve and myocardial perfusion imaging in patients with angiographic multivessel coronary artery disease." JACC Cardiovasc Interv 2010; 3 (3): 307-14. doi: 10.1016/'.'cin.2009.12.010 [published Online First: Mar. 20, 2010].
Mettler et al. "Effective doses in radiology and diagnostic nuclear medicine: a catalog." Radiology 2008; 248(1): 254-63.
Michail et al., Jan. 2021, Feasibility and validity of computed tomography-derived fractional flow reserve in patients with severe aortic stenosis, Circ. Cardiovasc., Interv. 14:e009586.
Miller et al. "Diagnostic performance of coronary angiography by 61-row CT." N Engel J Med 2008; 359 (22): 2324-36. doi: 10.1056/NEJMoa0806576 [published Online First: Nov. 29, 2008].
Min et al "Prognostic value of multidetector coronary computed tomographic angiography for predication of all-cause mortality" J Am Coll Cardio 2007, 50(12) 1161-70.
Min et al , "Atherosclerosis, Stenosis, and Ischemia", JACC Cardiovascular Imaging, vol. 11, No. 4, Apr. 2018 pp. 531-533.
Min et al., "Diagnostic accuracy of fractional flow reserve from anatomic CT angiography." JAMA 2012; 038 (12): 1237-45. doi: 10.1001/2012.jama.11274 [published Online First: Aug. 28, 2012].
Min et al., "The Immediate Effects of Statins on Coronary Atherosclerosis", JACC: Cardiovascular Imaging, vol. 11, No. 6, Jun. 2018. pp. 839-841.
Min et al., 2022, Coronary CTA plaque volume severity stages according to invasive coronary angiography and FFR, Journal of Cardiovascular Computed Tomography, https://doi.org/10.1016/j.jcct.2002.03.001.
Min, "Atherosclerotic plaque characterization: a need for a paradigm shift for prediction of risk", European Heart Journal—Cardiovascular Imaging, Oct. 2017. pp. 1340-1341.
Min, "Chess and Coronary Artery Ischemia: Clinical Implication of Machine-Learning Applications", Circulation: Cardiovascular Imaging, 2018 in 4 pages.
Min, et al. "Rationale and Design of the CONFIRM (Coronary CT Angiography Evaluation for Clinical Outcomes: An International Multicenter) Registry." J Cardiovasc Comput Tomogr. 2011;5: 84-92.
Mintz GS. "Intravascular Imaging of Coronary Calcification and its Clinical Implications." JACC Cardiovasc Imaging. 2015;8: 461-471.
Montalescot et al. "2013 ESC guidelines on the management of stable coronary artery disease: the Task Force on the management of stable coronary artery disease of the European Society of Cardiology." Eur Heart J 2013;34(35: 2949-3003. doi: 10.1093/eurheartj/eht296 [published Online First:Sep. 3, 2013].
Motoyama et al. "Atherosclerotic plaque characterization by 0.5-mm-slice multislice computed tomographic imaging." Circ J 2009; 71(3): 363-6.
Motoyama et al. "Computed tomographic angiography characteristics of atherosclerotic plaques subsequently resulting in acute coronary syndrome." J Am Coll Cardiol 2009; 54(1): 49-57.
Motoyama et al. "Multislice computed tomographic characteristics of coronary lesions in acute coronary syndromes." J Am Coll Cardiol 2007; 50(4): 319-26.
Motwani et al., "Machine learning for prediction of all-cause mortality in patients with suspected coronary artery disease: a 5-year multicentre prospective registry analysis", European Heart Journal, 2017, pp. 500-507.
Murgia et al., Aug. 2020, Plaque imaging volume analysis: technique and application, Cardiovasc Diagn Ther, 10(4):1032-1047.
Naghavi, et al. From Vulnerable Plaque to Vulnerable Patient: a call for new definitions and risk assessment strategies: Part 1. Circulation. 2003; 108: 1664-72.
Nair, et al. "Automated Coronary Plaque Characterisation with intravascular ultrasound backscatter: ex vivo validation." EuroIntervention. 2007; 3: 113-20.
Nakanishi R. et al. "Plaque progression assessed by a novel semi-automated quantitative plaque software on coronary computed tomography angiography between diabetes and non-diabetes patients: A propensity-score matching study." Atherosclerosis 2016; 255 pp. 73-79.
Nakazato et al., "Additive diagnostic value of atherosclerotic plaque characteristics to non-invasive FFR for identification of lesions causing ischaemia: results from a prospective international multicentre trial", http://www.pcronline.com/eurointervention/aheadof print/201509-02/ in 9 pages.
Nakazato et al., "Aggregate Plaque Volume by Coronary Computed Tomography Angiography Is Superior and Incremental to Luminal Narrowing for Diagnosis of Ischemic Lesions of Intermediate Stenosis Severity", Journal of the American College of Cardiology, vol. 62, No. 5, 2013 pp. 460-467.
Nakazato et al., "Atherosclerotic plaque characterization by CT angiography for identification of high-risk coronary artery lesions: a comparison to optical coherence tomography", European Heart Journal—Cardiovascular Imaging, vol. 16, 2015. pp. 373-379.
Nakazato et al., "Relationship of low- and high-density lipoproteins to coronary artery plaque composition by CT angiography", Journal of Cardiovascular Computed Tomography 7, 2013, pp. 83-90.
Nakazato et al., "Quantification and characterisation of coronary artery plaque vol. and adverse plaque features by coronary computed tomographic angiography: a direct comparison to intravascular ultrasound", Eur Radiol (2013) 23, pp. 2109-2117.
Narula et al., 2021, SCCT 2021 expert consensus document of coronary computed tomographic angiography: a report of the Society of Cardiovascular Computed Tomography, Journal of Cardiovascular Computed Tomography.
Neglia et al "Detection of significant coronary artery disease by noninvasive anatomical and functional imaging" Circ Cardiovasc Imaging 2015, 8 (3) doi 10 1161/CIRCIMAGING 114 002179 [published Online First Feb. 26, 2015].
Newby et al., "Coronary CT Angiography and 5-Year Risk of Myocardial Infarction", The New England Journal of Medicine, Aug. 25, 2018, pp. 924-933.
Newby et al., "CT coronary angiography in patients with suspected angina due to coronary heart disease (SCOT-HEART): an open-

(56) References Cited

OTHER PUBLICATIONS label, parallel-group, multicentre trial", www.thelancet.com, vol. 385.Jun. 13, 2015, pp. 2383-2391.

Nicholls et al. "Intravascular ultrasound-derived measures of coronary atherosclerotic plaque burden and clinical outcome." J Am Coll Cardiol. 2010; 55(21): pp. 2399-2407.

Nicholls, et al. "Effect of Evolocumab on Coronary Plaque Composition." J Am Coll Cardiol. 2018;72: 2012-2021.

Norgaard et al., 2020, Clinical outcomes following real-world computed tomography angiography-derived factional flow reserve testing in chronic coronary syndrome patients with calcification, European Heart Journal—Cardiovascular Imaging, doi:10.1093/ehic/jeaa173.

Norgaard et al., Apr. 1, 2014, Diagnostic performance of noninvasive fractional flow reserve derived from coronary computed tomography angiography in suspected coronary artery disease, Journal of the American Colleae of Cardioloav, 63(12):1145-1155.

Obaid, D.R., et al. "Atherosclerotic Plaque Composition and Classification Identified by Coronary Computed Tomography: Assessment of CT-Generated Plaque Maps Compared with Virtual Histology Intravascular Ultrasound and Histology." Circulation: Cardiovascular Imaging 6.5 (2013): 655-664.(Year: 2013).

Obaid, Daniel R., et al. "Coronary CT angiography features of ruptured and high-risk atherosclerotic plaques: correlation with intra-vascular ultrasound." Journal of Cardiovascular Computed Tomography 11.6 (2017): 455-461. (Year: 2017).

Oikonomou et al., Aug. 28, 2018, Non-invasive detection of coronary inflammation using computed tomography7 and prediction of residual cardiovascular risk (the CRIPS CT Study): a post-hoc analysis of prospective outcome data, The Lancet, 382(10151):929-393.

* cited by examiner

SYSTEMS, DEVICES, AND METHODS FOR NON-INVASIVE IMAGE-BASED PLAQUE ANALYSIS AND RISK DETERMINATION

PRIORITY AND RELATED APPLICATIONS

This application is a continuation of U.S. application Ser. No. 18/390,555 (Dec. 20, 2023, which is a continuation in part of U.S. application Ser. No. 18/508,098 (Nov. 13, 2023, which is a continuation in part of U.S. application Ser. No. 18/179,921 (Mar. 7, 2023. U.S. application Ser. No. 18/390,555 also claims the benefit of priority to U.S. Provisional Application Nos. 63/476,577 (Dec. 21, 2022), 63/476,522 (Dec. 21, 2022), 63/477,661 (Dec. 29, 2022), 63/477,650) (Dec. 29, 2022), 63/477,643 (Dec. 29, 2022), 63/477,632 (Dec. 29, 2022), 63/477,947 (Dec. 30, 2022), 63/478,124 (Dec. 31, 2022), 63/478,126 (Dec. 31, 2022), 63/478,127 (Dec. 31, 2022), 63/478,128 (Dec. 31, 2022), and 63/501,490 (May 11, 2023). U.S. application Ser. No. 18/508,098 also claims the benefit of priority to U.S. Provisional Application Nos. 63/383,632 (Nov. 14, 2022), 63/383,904 (Nov. 15, 2022), 63/385,179 (Nov. 28, 2022), 63/385,472 (Nov. 30, 2022), 63/386,297 (Dec. 6, 2022), 63/386,376 (Dec. 7, 2022). 63/476,251 (Dec. 20, 2022), 63/476,245 (Dec. 20, 2022), 63/476,255 (Dec. 20, 2022), 63/477,640) (Dec. 29, 2022), 63/477,638 (Dec. 29, 2022), 63/477,656 (Dec. 29, 2022), 63/477,985 (Dec. 30, 2022), 63/477,961 (Dec. 30, 2022), 63/478,076 (Dec. 30, 2022), and 63/478,084 (Dec. 30, 2022). U.S. application Ser. No. 18/179,921 also claims the benefit of priority to U.S. Provisional Application Nos. 63/269,136 (Mar. 10, 2022), 63/362,108 (Mar. 29, 2022), 63/362,856 (Apr. 12, 2022), 63/364,078 (May 3, 2022), 63/364,084 (May 3, 2022), 63/365,381 (May 26, 2022), 63/368,293 (Jul. 13, 2022), and 63/381,210 (Oct. 27, 2022).

This application is also related to U.S. Pat. No. 10,813,612, filed Jan. 23, 2020, U.S. Pat. No. 11,501,436, filed Jan. 5, 2021, and U.S. Pat. No. 11,302,001, filed Aug. 4, 2021, and U.S. application Ser. No. 17/820,439, filed Aug. 17, 2022, and U.S. application Ser. No. 18/179,921, filed Mar. 7, 2023, and each of the above-listed patents and applications is incorporated by reference herein in its entirety.

BACKGROUND

The present application relates to non-invasive image-based plaque analysis and risk determination.

SUMMARY

Various embodiments described herein relate to systems, devices, and methods for non-invasive image-based plaque analysis and risk determination. In particular, in some embodiments, the systems, devices, and methods described herein are related to analysis of one or more regions of plaque, such as for example coronary plaque, based on one or more distances, volumes, shapes, morphologies, embeddedness, and/or axes measurements. In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to generate a proposed treatment and/or graphical representation based on the determined risk of CAD and/or one or more plaque analyses described herein.

BRIEF DESCRIPTION OF THE DRAWINGS

A better understanding of the devices and methods described herein will be appreciated upon reference to the following description in conjunction with the accompanying drawings, wherein.

DETAILED DESCRIPTION

Figure 1:
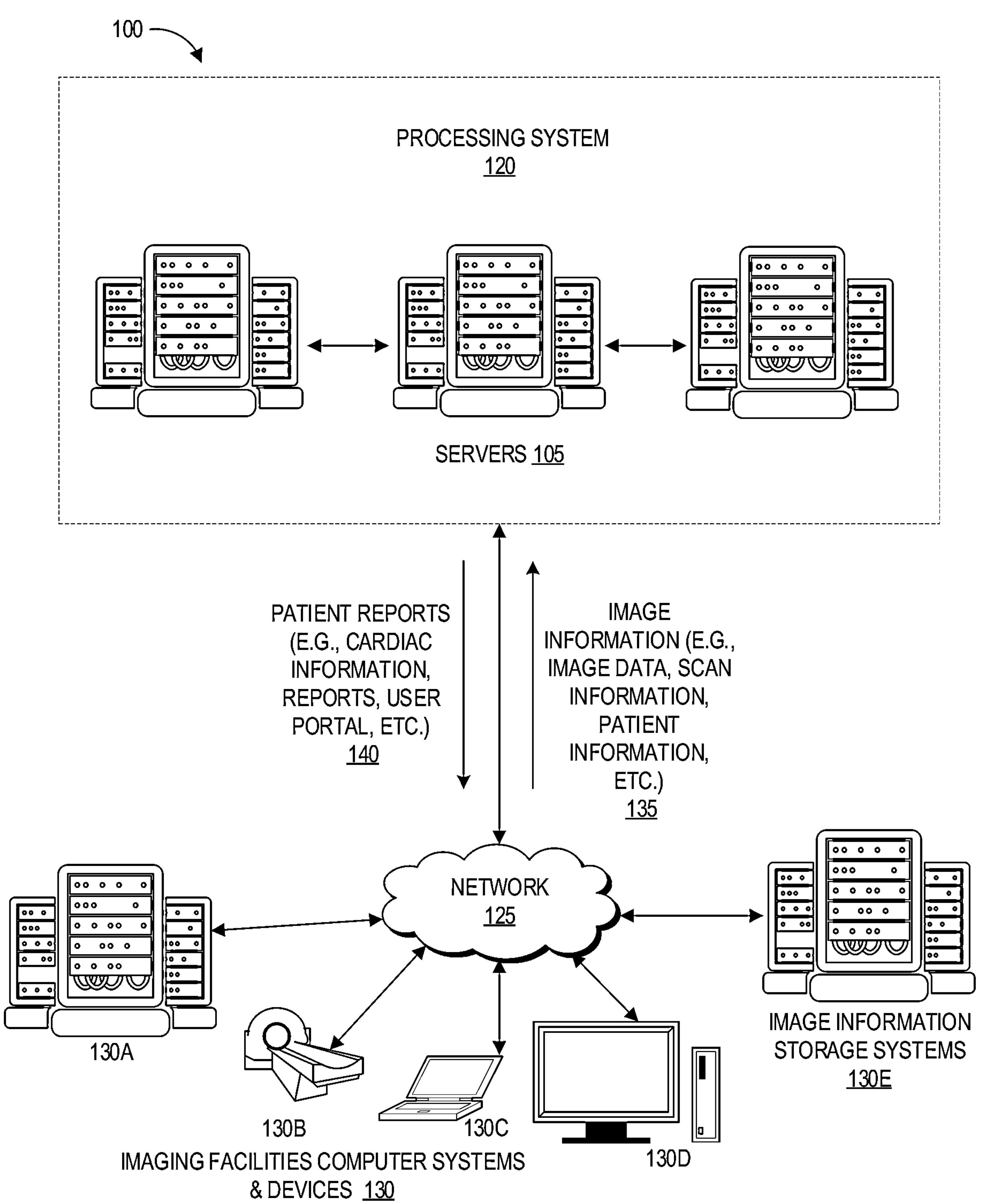
FIG. 1 depicts a schematic of an example of an embodiment of a system 100 that includes a processing system configured to characterize coronary plaque.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Disclosed herein are systems, devices, and methods for non-invasive image-based plaque analysis and risk determination. In particular, in some embodiments, the systems, devices, and methods described herein are related to analysis of one or more regions of plaque, such as for example coronary plaque, based on one or more distances, volumes, shapes, morphologies, embeddedness, and/or axes (or dimension) measurements. "Plaque" or "a region of plaque" or "one or more regions of plaque" may be referred to simply as "plaque" for ease of reference unless otherwise indicated, explicitly or by context. For example, in some embodiments, the systems, devices, and methods described herein are related to plaque analysis based on one or more of distance between plaque and a vessel wall, distance between plaque and a lumen wall, length along longitudinal axis of plaque, length along latitudinal axis of plaque, volume of low density non-calcified plaque, volume of total plaque, a ratio(s) between volume of low density non-calcified plaque and volume of total plaque, embeddedness of low density non-calcified plaque, and/or the like. In some embodiments, the systems, devices, and methods described herein are configured to determine a risk of coronary artery disease (CAD), such as for example myocardial infarction (MI), based on one or more plaque analyses described herein. In some embodiments, the systems, devices, and methods described herein are configured to generate a proposed treatment and/or graphical representation based on the determined risk of CAD and/or one or more plaque analyses described herein.

Also disclosed herein are systems, methods, and devices for cardiovascular risk and/or state assessment using image-based analyses. In particular, in some embodiments, the systems, devices, and methods are related to cardiovascular risk and/or disease state assessment using image-based analysis of vessel surface and/or coordinates of features. In some embodiments, assessment of cardiovascular risk and/or disease state generated using the systems, methods, and devices herein can be utilized to diagnose and/or generate a proposed treatment for a patient.

Also disclosed herein are systems, methods, and devices for cardiovascular risk and/or state assessment using image-based analyses, where in some embodiments, the systems, devices, and methods are related to cardiovascular risk and/or disease state assessment using image-based analysis of vessel surface and/or coordinates of features. In some embodiments, assessment of cardiovascular risk and/or disease state generated using the systems, methods, and devices herein can be utilized to diagnose and/or generate a proposed treatment for a patient.

Also disclosed herein are systems, methods, and devices for cardiovascular risk and/or state assessment using image-based analyses, where in some embodiments the systems, devices, and methods are related to cardiovascular risk and/or disease and/or state assessment using modified and/or normalized image analysis-based plaque parameters. In some embodiments, assessment of cardiovascular risk and/or disease and/or state generated using the systems, methods, and devices herein can be utilized to diagnose and/or generate a proposed treatment for a patient.

Also disclosed herein are systems, methods, and devices for generation of a patient-specific report on the risk and/or state assessment, diagnosis, and/or treatment of cardiovascular disease, including for example coronary artery disease (CAD). In particular, in some embodiments, the systems, devices, and methods are configured to generate an immersive patient-specific report on the patient's cardiovascular disease risk, state, diagnosis, and/or treatment. In some embodiments, the systems, devices, and methods are configured to generate an immersive patient-specific report based at least in part on image-based analysis, for example of one or more plaque and/or vessel parameters. In some embodiments, the systems, devices, and methods are configured to view the patient's cardiovascular disease state or risk from a point of view within one or more arteries of the patient. In some embodiments, the systems, devices, and methods are configured to graphically view and/or track actual or hypothetical progression of the patient's cardiovascular disease state or risk based on actual or proposed treatment from a point of view within one or more arteries of the patient.

Also disclosed herein are systems, methods, and devices for cardiovascular risk and/or state assessment using image-based analyses, wherein in some embodiments the systems, devices, and methods are related to cardiovascular risk and/or disease and/or state assessment using normalized image analysis-based plaque parameters. In some embodiments, assessment of cardiovascular risk and/or disease and/or state generated using the systems, methods, and devices herein can be utilized to diagnose and/or generate a proposed treatment for a patient.

Also disclosed herein are systems, devices, and methods for non-invasive image-based determination of fractional flow reserve (FFR) and/or ischemia. In particular, in some embodiments, the systems, devices, and methods are related to FFR and/or ischemia analysis of arteries, such as coronary, aortic, and/or carotid arteries using one or more image analysis techniques. For example, in some embodiments, the systems, methods, and devices can be configured to derive one or more stenosis and/or normal measurements from a medical image, which can be obtained non-invasively, and use the same to derive an assessment of FFR and/or ischemia. In some embodiments, the systems, methods, and devices can be configured to apply one or more allometric scaling laws to one or more stenosis and/or normal measurements to derive and/or generate an assessment of FFR and/or ischemia.

Coronary heart disease affects over 17.6 million Americans. The current trend in treating cardiovascular health issues is generally two-fold. First, physicians generally review a patient's cardiovascular health from a macro level, for example, by analyzing the biochemistry or blood content or biomarkers of a patient to determine whether there are high levels of cholesterol elements in the bloodstream of a patient. In response to high levels of cholesterol, some physicians will prescribe one or more drugs, such as statins, as part of a treatment plan in order to decrease what is perceived as high levels of cholesterol elements in the bloodstream of the patient.

The second general trend for currently treating cardiovascular health issues involves physicians evaluating a patient's cardiovascular health through the use of angiography to identify large blockages in various arteries of a patient. In response to finding large blockages in various arteries, physicians in some cases will perform an angioplasty procedure wherein a balloon catheter is guided to the point of narrowing in the vessel. After properly positioned, the balloon is inflated to compress or flatten the plaque or fatty matter into the artery wall and/or to stretch the artery open to increase the flow of blood through the vessel and/or to the heart. In some cases, the balloon is used to position and expand a stent within the vessel to compress the plaque and/or maintain the opening of the vessel to allow more blood to flow. About 500,000 heart stent procedures are performed each year in the United States.

However, a recent federally funded $100 million study calls into question whether the current trends in treating cardiovascular disease are the most effective treatment for all types of patients. The recent study involved over 5,000 patients with moderate to severe stable heart disease from 320 sites in 37 countries and provided new evidence showing that stents and bypass surgical procedures are likely no more effective than drugs combined with lifestyle changes for people with stable heart disease. Accordingly, it may be more advantageous for patients with stable heart disease to forgo invasive surgical procedures, such as angioplasty and/or heart bypass, and instead be prescribed heart medicines, such as statins, and certain lifestyle changes, such as regular exercise. This new treatment regimen could affect thousands of patients worldwide. Of the estimated 500,000 heart stent procedures performed annually in the United States, it is estimated that a fifth of those are for people with stable heart disease. It is further estimated that 25% of the estimated 100,000 people with stable heart disease, or roughly 23,000 people, are individuals that do not experience any chest pain. Accordingly, over 20,000 patients annually could potentially forgo invasive surgical procedures or the complications resulting from such procedures.

To determine whether a patient should forego invasive surgical procedures and opt instead for a drug regimen and/or to generate a more effective treatment plan, it can be important to more fully understand the cardiovascular disease of a patient. Specifically, it can be advantageous to better understand the arterial vessel health of a patient. For example, it is helpful to understand whether plaque build-up in a patient is mostly fatty matter build-up or mostly calcified matter build-up, because the former situation may warrant treatment with heart medicines, such as statins, whereas in the latter situation a patient should be subject to further periodic monitoring without prescribing heart medicine or implanting any stents. However, if the plaque build-up is significant enough to cause severe stenosis or narrowing of the arterial vessel such that blood flow to heart muscle might be blocked, then an invasive angioplasty procedure to implant a stent may likely be required because heart attack or sudden cardiac death (SCD) could occur in such patients without the implantation of a stent to enlarge the vessel opening. Sudden cardiac death is one of the largest causes of natural death in the United States, accounting for approximately 325,000 adult deaths per year and responsible for nearly half of all deaths from cardiovascular disease. For males, SCD is twice as common as compared to females. In general, SCD strikes people in the mid-30 to mid-40 age range. In over 50% of cases, sudden cardiac arrest occurs with no warning signs.

With respect to the millions suffering from heart disease, there is a need to better understand the overall health of the artery vessels within a patient beyond just knowing the blood chemistry or content of the blood flowing through such artery vessels. For example, in some embodiments of systems, devices, and methods disclosed herein, arteries with "good" or stable plaque or plaque comprising hardened calcified content are considered non-life threatening to patients whereas arteries containing "bad" or unstable plaque or plaque comprising fatty material are considered more life threatening because such bad plaque may rupture within arteries thereby releasing such fatty material into the arteries. Such a fatty material release in the blood stream can cause inflammation that may result in a blood clot. A blood clot within an artery can prevent blood from traveling to heart muscle thereby causing a heart attack or other cardiac event. Further, in some instances, it is generally more difficult for blood to flow through fatty plaque buildup than it is for blood to flow through calcified plaque build-up. Therefore, there is a need for better understanding and analysis of the arterial vessel walls of a patient.

Further, while blood tests and drug treatment regimens are helpful in reducing cardiovascular health issues and mitigating against cardiovascular events (for example, heart attacks), such treatment methodologies are not complete or perfect in that such treatments can misidentify and/or fail to pinpoint or diagnose significant cardiovascular risk areas. For example, the mere analysis of the blood chemistry of a patient will not likely identify that a patient has artery vessels having significant amounts of fatty deposit material bad plaque buildup along a vessel wall. Similarly, an angiogram, while helpful in identifying areas of stenosis or vessel narrowing, may not be able to clearly identify areas of the artery vessel wall where there is significant buildup of bad plaque. Such areas of buildup of bad plaque within an artery vessel wall can be indicators of a patient at high risk of suffering a cardiovascular event, such as a heart attack. In certain circumstances, areas where there exist areas of bad plaque can lead to a rupture wherein there is a release of the fatty materials into the bloodstream of the artery, which in turn can cause a clot to develop in the artery. A blood clot in the artery can cause a stoppage of blood flow to the heart tissue, which can result in a heart attack. Accordingly, there is a need for new technology for analyzing artery vessel walls and/or identifying areas within artery vessel walls that comprise a buildup of plaque whether it be bad or otherwise.

In some embodiments, the systems, devices, and methods described herein are configured to utilize non-invasive medical imaging technologies, such as a CT image or CCTA for example, which can be inputted into a computer system configured to automatically and/or dynamically analyze the medical image to identify one or more coronary arteries and/or plaque within the same. For example, in some embodiments, the system can be configured to utilize one or more machine learning and/or artificial intelligence algorithms to automatically and/or dynamically analyze a medical image to identify, quantify, and/or classify one or more coronary arteries and/or plaque. In some embodiments, the system can be further configured to utilize the identified, quantified, and/or classified one or more coronary arteries and/or plaque to generate a treatment plan, track disease progression, and/or a patient-specific medical report, for example using one or more artificial intelligence and/or machine learning algorithms. In some embodiments, the system can be further configured to dynamically and/or automatically generate a visualization of the identified, quantified, and/or classified one or more coronary arteries and/or plaque, for example in the form of a graphical user interface. Further, in some embodiments, to calibrate medical images obtained from different medical imaging scanners and/or different scan parameters or environments, the system can be configured to utilize a normalization device comprising one or more compartments of one or more materials.

As will be discussed in further detail, the systems, devices, and methods described herein allow for automatic and/or dynamic quantified analysis of various parameters relating to plaque, cardiovascular arteries, and/or other structures. More specifically, in some embodiments described herein, a medical image of a patient, such as a coronary CT image or CCTA, can be taken at a medical facility. Rather than having a physician eyeball or make a general assessment of the patient, the medical image is transmitted to a backend main server in some embodiments that is configured to conduct one or more analyses thereof in a reproducible manner. As such, in some embodiments, the systems, methods, and devices described herein can provide a quantified measurement of one or more features of a coronary CT image using automated and/or dynamic processes. For example, in some embodiments, the main server system can be configured to identify one or more vessels, plaque, fat, and/or one or more measurements thereof from a medical image. Based on the identified features, in some embodiments, the system can be configured to generate one or more quantified measurements from a raw medical image, such as for example radiodensity of one or more regions of plaque, identification of stable plaque and/or unstable plaque, volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like. Based on the identified features and/or quantified measurements, in some embodiments, the system can be configured to generate a risk and/or disease state assessment and/or track the progression of a plaque-based disease or condition, such as for example atherosclerosis, stenosis, and/or ischemia, using raw medical images. Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or non-response to medication. In particular, in some embodiments, the system can be configured to automatically and/or dynamically assess such health risk of a subject by analyzing only non-invasively obtained medical images. In some embodiments, one or more of the processes can be automated using an artificial intelligence (AI) and/or machine learning (ML) algorithm. In some embodiments, one or more of the processes described herein can be performed within minutes in a reproducible manner. This is stark contrast to existing measures today which do not produce reproducible prognosis or assessment, take extensive amounts of time, and/or require invasive procedures. In some embodiments, the systems, methods, and devices described herein comprise and/or are configured to utilize any one or more of such techniques described in US Patent Application Publication No. US 2021/0319558, which is incorporated herein by reference in its entirety.

As such, in some embodiments, the systems, devices, and methods described herein are able to provide physicians and/or patients specific quantified and/or measured data relating to a patient's plaque and/or ischemia that do not exist today. In some embodiments, such detailed level of quantified plaque parameters from image processing and downstream analytical results can provide more accurate and useful tools for assessing the health and/or risk of patients in completely novel ways.

Disclosed are methods for identification of high-risk plaques using volumetric characterization of coronary plaque and perivascular adipose tissue data by computed tomography (CT) scanning. The volumetric characterization of the coronary plaque and perivascular adipose tissue allows for determination of the inflammatory status of the plaque by CT scanning. This is of use in the diagnosis, prognosis and treatment of coronary artery disease. While certain example embodiments are shown by way of example in the drawings and will herein be described in detail, these embodiments are capable of various modifications and alternative forms. There is no intent to limit example embodiments to the particular forms disclosed, but on the contrary, example embodiments are to cover all modifications, equivalents, and alternatives falling within the scope of example embodiments.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes all combinations of one or more of the associated listed items.

The terminology used herein is for the purpose of describing embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof. In this specification, the term "and/or" picks out each individual item as well as all combinations of them.

Unless otherwise defined, all terms (including technical and scientific terms) used herein have the same meaning as commonly understood by one of ordinary skill in the art to which example embodiments belongs. It will be further understood that terms, such as those defined in commonly used dictionaries, should be interpreted as having a meaning that is consistent with their meaning in the context of the relevant art and should not be interpreted in an idealized or overly formal sense unless expressly so defined herein. It should also be noted that in some alternative implementations, the functions/acts noted may occur out of the order noted in the figures. For example, two figures shown in succession may in fact be executed concurrently or may sometimes be executed in the reverse order, depending upon the functionality/acts involved.

In the drawings, the dimensions of layers and regions are exaggerated for clarity of illustration. It will also be understood that when a layer (or tissue) is referred to as being "on" another layer or tissue, it can be directly on the other layer or substrate, or intervening layers may also be present. Further, it will be understood that when a layer is referred to as being "under" another layer, it can be directly under, and one or more intervening layers may also be present. In addition, it will also be understood that when a layer is referred to as being 'between' two layers, it can be the only layer between the two layers, or one or more intervening layers may also be present. Like reference numerals refer to like elements throughout.

Overview of Example Processing System to Characterize Coronary Plaque

This disclosure includes methods and systems of using data generated from images collected by scanning a patient's arteries to identify coronary artery plaques that are at higher risk of causing future heart attack or acute coronary syndrome. In particular, the characteristics of perivascular coronary fat, coronary plaque, and/or the coronary lumen, and the relationship of the characteristics of perivascular coronary fat, coronary plaque, and/or the coronary lumen are discussed to determine ways for identifying the coronary plaque that is more susceptible to implication in future ACS, heart attack and death. The images used to generate the image data may be CT images, CCTA images, or images generated using any applicable technology that can depict the relative densities of the coronary plaque, perivascular fat, and coronary lumen. For example, CCTA images may be used to generate two-dimensional (2D) or volumetric (three-dimensional (3-D)) image data, and this image data may be analyzed to determine certain characteristics that are associated with the radiodensities of the coronary plaque, perivascular fat, and/or coronary lumen. In some implementations, the Hounsfield scale is used to provide a measure of the radiodensity of these features. A Hounsfield unit, as is known, represents an arbitrary unit of x-ray attenuation used for CT scans. Each pixel (2D) or voxel (3D) of a feature in the image data may be assigned a radiodensity value on the Hounsfield scale, and then these values characterizing the features may be analyzed.

In various embodiments, processing of image information may include: (1) determining scan parameters (for example, mA (milliampere), kvP (peak kilovoltage)); (2) determining the scan image quality (e.g., noise, signal-to-noise ratio, contrast-to-noise ratio); (3) measuring scan-specific coronary artery lumen densities (e.g., from a point distal to a coronary artery wall to a point proximal to the coronary artery wall to distal to the coronary artery, and from a central location of the coronary artery to an outer location (e.g., outer relative to radial distance from the coronary artery): (4) measuring scan-specific plaque densities (e.g., from central to outer, abruptness of change within a plaque from high-to-low or low-to-high) as a function of their 3D shape; and (5) measuring scan-specific perivascular coronary fat densities (from close to the artery to far from the artery) as a function of its 3D shape.

From these measurements, which are agnostic to any commonly known features of ischemia-causing atherosclerosis, we can determine several characteristics, including but not limited to:

1. A ratio of lumen attenuation to plaque attenuation, wherein the volumetric model of scan-specific attenuation density gradients within the lumen adjusts for reduced luminal density across plaque lesions that are more functionally significant in terms of risk value
2. A ratio of plaque attenuation to fat attenuation, wherein plaques with high radiodensities are considered to present a lower risk, even within a subset of plaques considered "calcified," where there can be a gradation of densities (for example, 130 to 4000 HU) and risk is considered to be reduced as density increases.
3. A ratio of lumen attenuation/plaque attenuation/fat attenuation
4. A ratio of #1-3 as a function of 3D shape of atherosclerosis, which can include a 3D texture analysis of the plaque
5. The 3D volumetric shape and path of the lumen along with its attenuation density from the beginning to the end of the lumen.
6. The totality of plaque and plaque types before and after any given plaque to further inform its risk.

7. Determination of "higher plaque risks" by "subtracting" calcified (high-density) plaques to obtain a better absolute measure of high risk plaques (lower-density plaques). In other words, this particular embodiment involves identifying calcified plaque and excluding it from further analysis of plaque for the purpose of identifying high risk plaques.

Other characteristics can also be determined.

The above listed characteristics/metrics, and others, can be analyzed together to assess the risk of the plaque being implicated in future heart attack, ACS, ischemia or death. This can be done through development and/or validation of a traditional risk score or through machine learning methods. Factors for analysis from the metrics, that are likely to be associated with heart attack, ACS, ischemia or death, may include: (1) a ratio of [bright lumen:dark plaque]; (2) a ratio of [dark plaque:light fat]; (3) a ratio of [bright lumen:dark plaque:light fat]; and (4) a low ratio of [dark lumen:dark myocardium in 1 vessel area]/[lumen:myocardium in another vessel area]. Some improvements in the disclosed methods and systems include: (1) using numerical values from ratios of [lumen:plaque], [plaque:fat] and [lumen: plaque:fat] instead of using qualitative definitions of atherosclerotic features; (2) using a scan-specific [lumen:plaque attenuation] ratio to characterize plaque; (3) using a scan-specific [plaque:fat attenuation] ratio to characterize plaque; (4) using ratios of [lumen:plaque:fat circumferential] to characterize plaque; and (5) integration of plaque volume and type before and after as a contributor to risk for any given individual plaque.

Atherosclerotic plaque features may change over time with medical treatment (colchicine and statin medications) and while some of these medications may retard progression of plaque, they also have very important roles in promoting the change in plaque. While statin medications may have reduced the overall progression of plaque they may also have actually resulted in an increased progression of calcified plaque and a reduction of non-calcified plaque. This change will be associated with a reduction in heart attack or ACS or death, and the disclosed methods can be used to monitor the effects of medical therapy on plaque risk over time. Also, this method can also be used to identify individuals whose atherosclerotic plaque features or [lumen: plaque]/[plaque:fat]/[lumen:plaque:fat] ratios indicate that they are susceptible to rapid progression or malignant transformation of disease. In addition, these methods can be applied to single plaques or to a patient-basis wherein whole-heart atherosclerosis tracking can be used to monitor risk to the patient for experiencing heart attack (rather than trying to identify any specific plaque as being causal for future heart attack). Tracking can be done by automated co-registration processes of image data associated with a patient over a period of time.

FIG. 1 depicts a schematic of an example of an embodiment of a system 100 that includes a processing system 120 configured to characterize coronary plaque. The processing system 120 include one or more servers (or computers) 105 each configured with one or more processors. The processing system 120 includes non-transitory computer memory components for storing data and non-transitory computer memory components for storing instructions that are executed by the one or more processors data communication interfaces, the instructions configuring the one or more processors to perform methods of analyzing image information. A more detailed example of a server/computer 105 is described in reference to FIG. 9.

The system 100 also includes a network. The processing system 120 is in communication with the network 125. The network 125 may include, as at least a portion of the network 125, the Internet, a wide area network (WAN), a wireless network, or the like. In some embodiments, the processing system 120 is part of a "cloud" implementation, which can be located anywhere that is in communication with the network 125. In some embodiments, the processing system 120 is located in the same geographic proximity as an imaging facility that images and stores patient image data. In other embodiments, the processing system 120 is located remotely from where the patient image data is generated or stored.

FIG. 1 also illustrates in system 100 various computer systems and devices 130 (e.g., of an imaging facility) that are related to generating patient image data and that are also connected to the network 125. One or more of the devices 130 may be at an imaging facility that generates images of a patient's arteries, a medical facility (e.g., a hospital, doctor's office, etc.) or may be the personal computing device of a patient or care provider. For example, as illustrated in FIG. 1, an imaging facility server (or computer) 130A may be connected to the network 125. Also, in this example, a scanner 130B in an imaging facility maybe connected to the network 125. One or more other computer devices may also be connected to the network 125. For example, a laptop 130C, a personal computer 130D, and/or and an image information storage system 130E may also be connected to the network 125, and communicate with the processing system 120, and each other, via the network 125.

In some examples, the scanner 130B can be a computed tomography (CT) scanner that uses a rotating X-ray tube and a row of detectors to measure X-ray attenuations by different tissues in the body and form a corresponding image. In another example, a scanner 130B can use a spinning tube ("spiral CT") in which an entire X-ray tube and detectors are spun around a central axis of the area being scanned. In another example, the scanner 130B can utilize electron beam tomography (EBT). In another example, the scanner 130B can be a dual source CT scanner with a two X-ray tube system. The methods and systems described herein can also use images from other CT scanners. In some examples, the scanner 130B is a photon counting CT scanner, a spectral CT scanner, or a dual energy CT scanner. A photon counting CT scanner, a spectral CT scanner, or a dual energy CT scanner can help provide more detailed higher resolution images that better show small blood vessels, plaque, and other vascular pathologies, and allow for the determination of absolute material densities over relative densities. In general, a photon counting CT scanner uses an X-ray detector to count photons and quantifies the energy, determining the count of the number of photons in several discrete energy bins, resulting in higher contrast-to-noise ratio, and improved spatial resolution and spectral imaging compared to conventional CT scanners. Each registered photon is assigned to a specific bin depending on its energy, such that each pixel measures a histogram of the incident X-ray spectrum. This spectral information provides several advantages, First, it can be used to quantitatively determine the material composition of each pixel in the reconstructed CT image, as opposed to the estimated average linear attenuation coefficient obtained in a conventional CT scan. The spectral/energy information can be used to remove beam hardening artifacts that occur higher linear attenuation of many materials that shifts mean energy of the X-ray spectrum towards higher energies. Also, use of more than two energy bins allows discrimination between objects (bone, calcifications, contrast agents, tissue, etc.). In some embodiments, images generated using a photon counting CT scanner allows assessment of plaques at different monochromatic energies as well as different polychromatic spectra (e.g., 100 kvp, 120 kvp, 140 kvp, etc.), and this can change definition of non-calcified and calcified plaques compared to conventional CT scanners. A spectral CT scanner uses different X-ray wavelengths (or energies) to produce a CT scan. A dual energy CT scanner uses separate X-ray energies to detect two different energy ranges. In an example, a dual energy CT scanner (also known as spectral CT) can use an X-ray detector with separate layers to detect two different energy ranges ('dual layer'). In another example, a dual energy CT scanner can use a single scanner to scan twice using two different energy levels (e.g., electronic kVp switching). Images can be formed from combining the images detected at each different energy level, or the images may be used separately to assess a medical condition of a patient. In addition to providing absolute material densities, a photon counting CT scanner also allows for evaluation of images that are "monochromatic" as opposed to the typical CT, which is polychromatic spectra of light. As noted above, features (e.g., low density non-calcified plaque, calcified plaque, non-calcified plaque) that are depicted images formed using a photon counting CT scanner, a spectral CT scanner, or a dual energy CT scanner may have different radiodensities than those depicted in images formed from a conventional CT scanner, that is, such images may affect or change the definition of calcified and non-calcified plaque. However, radiodensities of calcified and non-calcified plaque, or other features depicted in images formed from a photon counting CT scanner, a spectral CT scanner, or a dual energy CT scanner, can be normalized to correspond to densities of conventional CT scanners and to the densities disclosed herein. Accordingly, the radiodensities disclosed herein can be directly correlated to radiodensities of images generated with a photon counting CT scanner, a spectral CT scanner, or a dual energy CT scanner such that the systems and methods, analysis, plaque densities etc. disclosed herein are directly applicable to images formed from a photon counting CT scanner, a spectral CT scanner, or a dual energy CT scanner, and are directly applicable to images formed from a photon counting CT scanner, a spectral CT scanner, or a dual energy CT scanner that are normalized to equivalent conventional CT scanner radiodensities.

The information communicated from the devices 130 to the processing system 120 via the network 125 may include image information 135. In various embodiments, the image information 135 may include 2D or 3D image data of a patient, scan information related to the image data, patient information, and other imagery or image related information that relates to a patient. For example, the image information may include patient information including (one or more) characteristics of a patient, for example, age, gender, body mass index (BMI), medication, blood pressure, heart rate, height, weight, race, whether the patient is a smoker or non-smoker, body habitus (for example, the "physique" or "body type" which may be based on a wide range of factors), medical history, diabetes, hypertension, prior coronary artery disease (CAD), dietary habits, drug history, family history of disease, information relating to other previously collected image information, exercise habits, drinking habits, lifestyle information, lab results and the like. In some embodiments, the image information includes identification information of the patient, for example, patient's name, patient's address, driver's license number, Social Security number, or indicia of another patient identification. Once the processing system 120 analyzes the image information 135, information relating to a patient 140 may be communicated from the processing system 120 to a device 130 via the network 125. The patient information 140 may include for example, a patient report. Also, the patient information 140 may include a variety of patient information which is available from a patient portal, which may be accessed by one of the devices 130.

In some embodiments, image information comprising a plurality of images of a patient's coronary arteries and patient information/characteristics may be provided from one or more of the devices 130 to the one or more servers 105 of the processing system 120 via a network 125. The processing system 120 is configured to generate coronary artery information using the plurality of images of the patient's coronary arteries to generate two-dimensional and/or three-dimensional data representations of the patient's coronary arteries. Then, the processing system 120 analyzes the data representations to generate patient reports documenting a patient's health conditions and risks related to coronary plaque. The patient reports may include images and graphical depictions of the patient's arteries in the types of coronary plaque in or near the coronary arteries. Using machine learning techniques or other artificial intelligent techniques, the data representations of the patient's coronary arteries may be compared to other patients' data representations (e.g., that are stored in a database) to determine additional information about the patient's health. For example, based on certain plaque conditions of the patient's coronary arteries, the likelihood of a patient having a heart attack or other adverse coronary effect can be determined. Also, for example, additional information about the patient's risk of CAD may also be determined.

Figure 2:
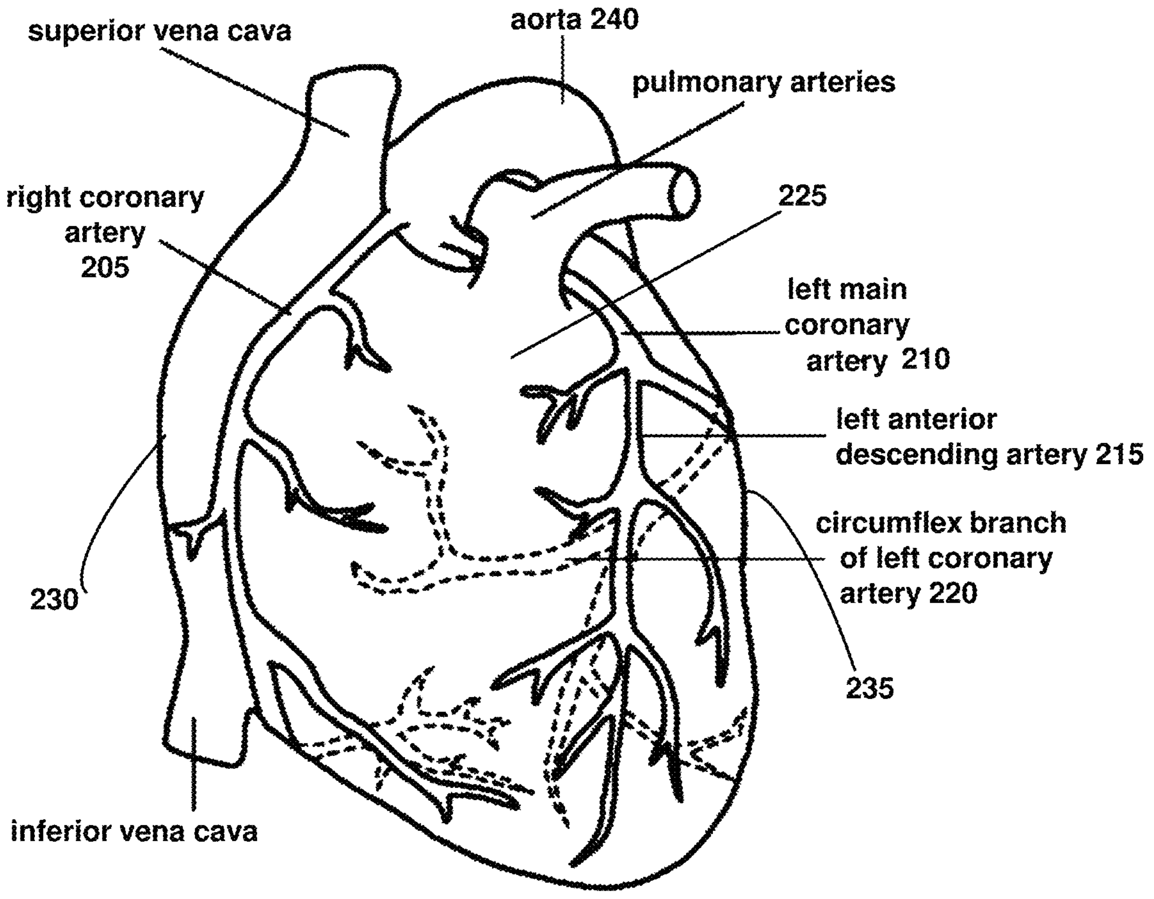
FIG. 2 is a schematic illustrating an example of a heart muscle and its coronary arteries.

FIG. 2 is a schematic illustrating an example of a heart muscle 225 and its coronary arteries. The coronary vasculature includes a complex network of vessels ranging from large arteries to arterioles, capillaries, venules, veins, etc. FIG. 1 depicts a model 220 of a portion of the coronary vasculature that circulates blood to and within the heart and includes an aorta 240 that supplies blood to a plurality of coronary arteries, for example, a left anterior descending (LAD) artery 215, a left circumflex (LCX) artery 220, and a right coronary (RCA) artery 230, described further below. Coronary arteries supply blood to the heart muscle 225. Like all other tissues in the body, the heart muscle 225 needs oxygen-rich blood to function. Also, oxygen-depleted blood must be carried away. The coronary arteries wrap around the outside of the heart muscle 225. Small branches dive into the heart muscle 225 to bring it blood. The examples of methods and systems described herein may be used to determine information relating to blood flowing through the coronary arteries in any vessels extending therefrom. In particular, the described examples of methods and systems may be used to determine various information relating to one or more portions of a coronary artery where plaque has formed which is then used to determine risks associated with such plaque, for example, whether a plaque formation is a risk to cause an adverse event to a patient.

The right side 230 of the heart 225 is depicted on the left side of FIG. 2 (relative to the page) and the left side 235 of the heart is depicted on the right side of FIG. 2. The coronary arteries include the right coronary artery (RCA) 205 which extends from the aorta 240 downward along the right side 230 of the heart 225, and the left main coronary artery (LMCA) 210 which extends from the aorta 240 downward on the left side 235 of the heart 225. The RCA 205 supplies blood to the right ventricle, the right atrium, and the SA (sinoatrial) and AV (atrioventricular) nodes, which regulate the heart rhythm. The RCA 205 divides into smaller branches, including the right posterior descending artery and the acute marginal artery. Together with the left anterior descending artery 215, the RCA 205 helps supply blood to the middle or septum of the heart.

The LMCA 210 branches into two arteries, the anterior interventricular branch of the left coronary artery, also known as the left anterior descending (LAD) artery 215 and the circumflex branch of the left coronary artery 220. The LAD artery 215 supplies blood to the front of the left side of the heart. Occlusion of the LAD artery 215 is often called the widow-maker infarction. The circumflex branch of the left coronary artery 220 encircles the heart muscle. The circumflex branch of the left coronary artery 220 supplies blood to the outer side and back of the heart, following the left part of the coronary sulcus, running first to the left and then to the right, reaching nearly as far as the posterior longitudinal sulcus.

Figure 3:
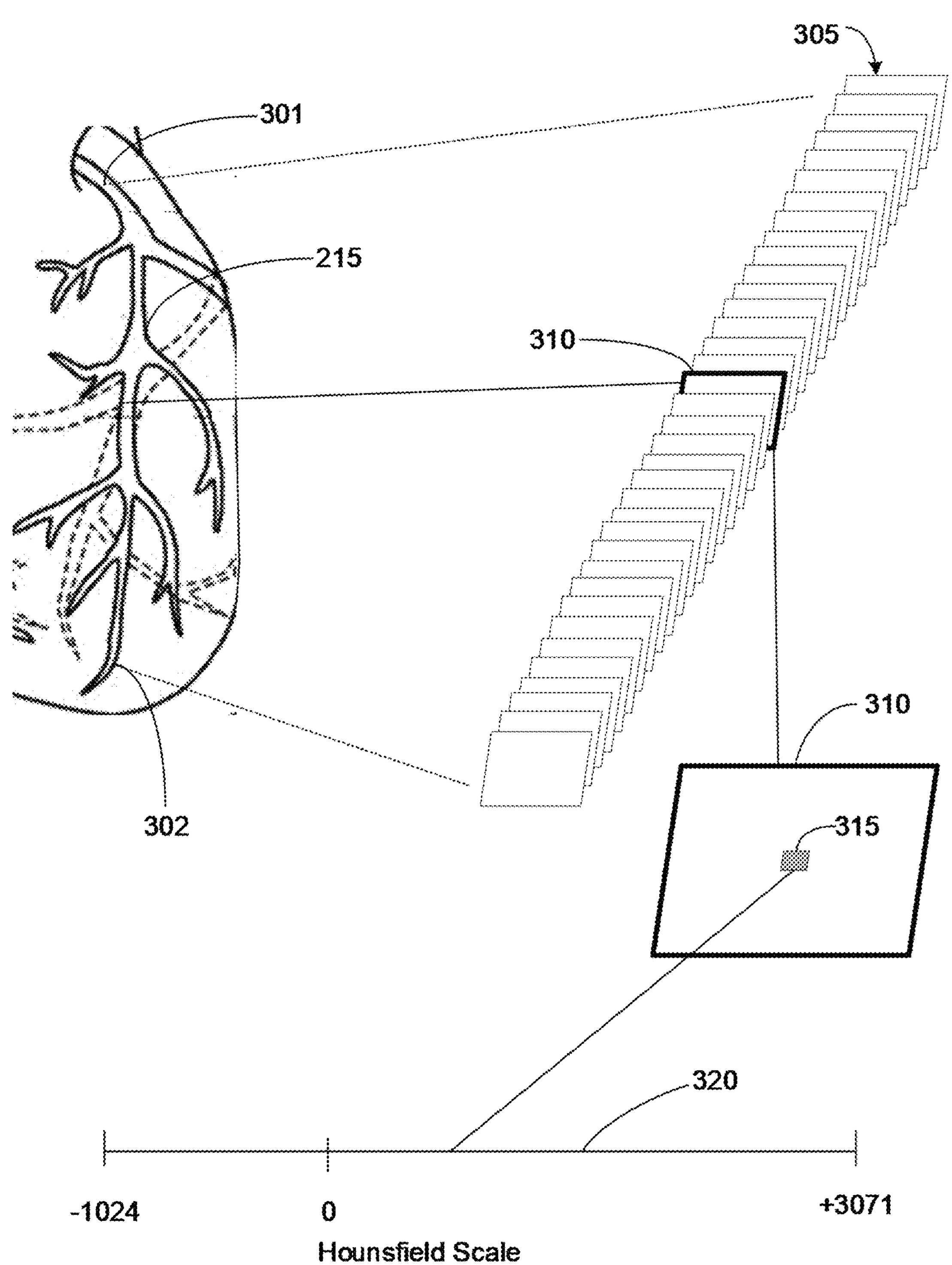
FIG. 3 illustrates an example of a set of images generated from scanning along a coronary artery, including a selected image of a portion of a coronary artery, and how image data may correspond to a value on the Hounsfield Scale.

FIG. 3 illustrates an example of a set of images generated from scanning along a coronary artery, including a selected image of a portion of a coronary artery, and how image data may correspond to a value on the Hounsfield Scale. As discussed in reference to FIG. 1, in addition to obtaining image data, scan information including metrics related to the image data, and patient information including characteristics of the patient may also be collected.

A portion of a heart 225, the LMCA 210, and the LAD artery 215 is illustrated in the example of FIG. 3. A set of images 305 can be collected along portions of the LMCA 210 and the LAD artery 215, in this example from a first point 301 on the LMCA 210 to a second point 302 on the LAD artery 215. In some examples, the image data may be obtained using noninvasive imaging methods. For example, CCTA image data can be generated using a scanner to create images of the heart in the coronary arteries and other vessels extending therefrom. Collected CCTA image data may be subsequently used to generate three-dimensional image models of the features contained in the CCTA image data (for example, the right coronary artery 205, the left main coronary artery 210, the left anterior descending artery 215, the circumflex branch of the left coronary artery 220, the aorta 240, and other vessels related to the heart that appear in the image data.

In various embodiments, different imaging methods may be used to collect the image data. For example, ultrasound or magnetic resonance imaging (MRI) may be used. In some embodiments, the imaging methods involve using a contrast agent to help identify structures of the coronary arteries, the contrast agent being injected into the patient prior to the imaging procedure. The various imaging methods may each have their own advantages and disadvantages of usage, including resolution and suitability of imaging the coronary arteries. Imaging methods which may be used to collect image data of the coronary arteries are constantly improving as improvements to the hardware (e.g., sensors and emitters) and software are made. The disclosed systems and methods contemplate using CCTA image data and/or any other type of image data that can provide or be converted into a representative 3D depiction of the coronary arteries, plaque contained within the coronary arteries, and perivascular fat located in proximity to the coronary arteries containing the plaque such that attenuation or radiodensity values of the coronary arteries, plaque, and/or perivascular fat can be obtained.

Referring still to FIG. 3, a particular image 310 of the image data 305 is shown, which represents an image of a portion of the left anterior descending artery 215. The image 310 includes image information, the smallest point of the information manipulated by a system referred to herein generally as a pixel, for example pixel 315 of image 310. The resolution of the imaging system used to capture the image data will affect the size of the smallest feature that can be discerned in an image. In addition, subsequent manipulation of the image may affect the dimensions of a pixel. As one example, the image 310 in a digital format, may contain 4000 pixels in each horizontal row, and 3000 pixels in each vertical column. Pixel 315, and each of the pixels in image data 310 and in the image data 305, can be associated with a radiodensity value that corresponds to the density of the pixel in the image. Illustratively shown in FIG. 3 is mapping pixel 315 to a point on the Hounsfield scale 320. The Hounsfield scale 320 is a quantitative scale for describing radiodensity. The Hounsfield unit scale linear transformation of the original linear attenuation coefficient measurement into one in which the radiodensity of distilled water at standard pressure and temperature is defined as zero Hounsfield units (HU), while the radiodensity of air at standard pressure and temperature is defined as −1000 HU. Although FIG. 3 illustrates an example of mapping pixel 315 of image 310 to a point on the Hounsfield scale 320, such an association of a pixel to a radiodensity value can also be done with 3D data. For example, after the image data 305 is used to generate a three-dimensional representation of the coronary arteries.

Once the data has been obtained and rendered into a three-dimensional representation, various processes can be performed on the data to identify areas of analysis. For example, a three-dimensional depiction of a coronary artery may be segmented to define a plurality of portions of the artery and identified as such in the data. In some embodiments, the data may be filtered (e.g., smoothed) by various methods to remove anomalies that are the result of scanning or other various errors. Various known methods for segmenting and smoothing the 3D data may be used, and therefore for brevity of the disclosure will not be discussed in any further detail herein.

Figure 4A:
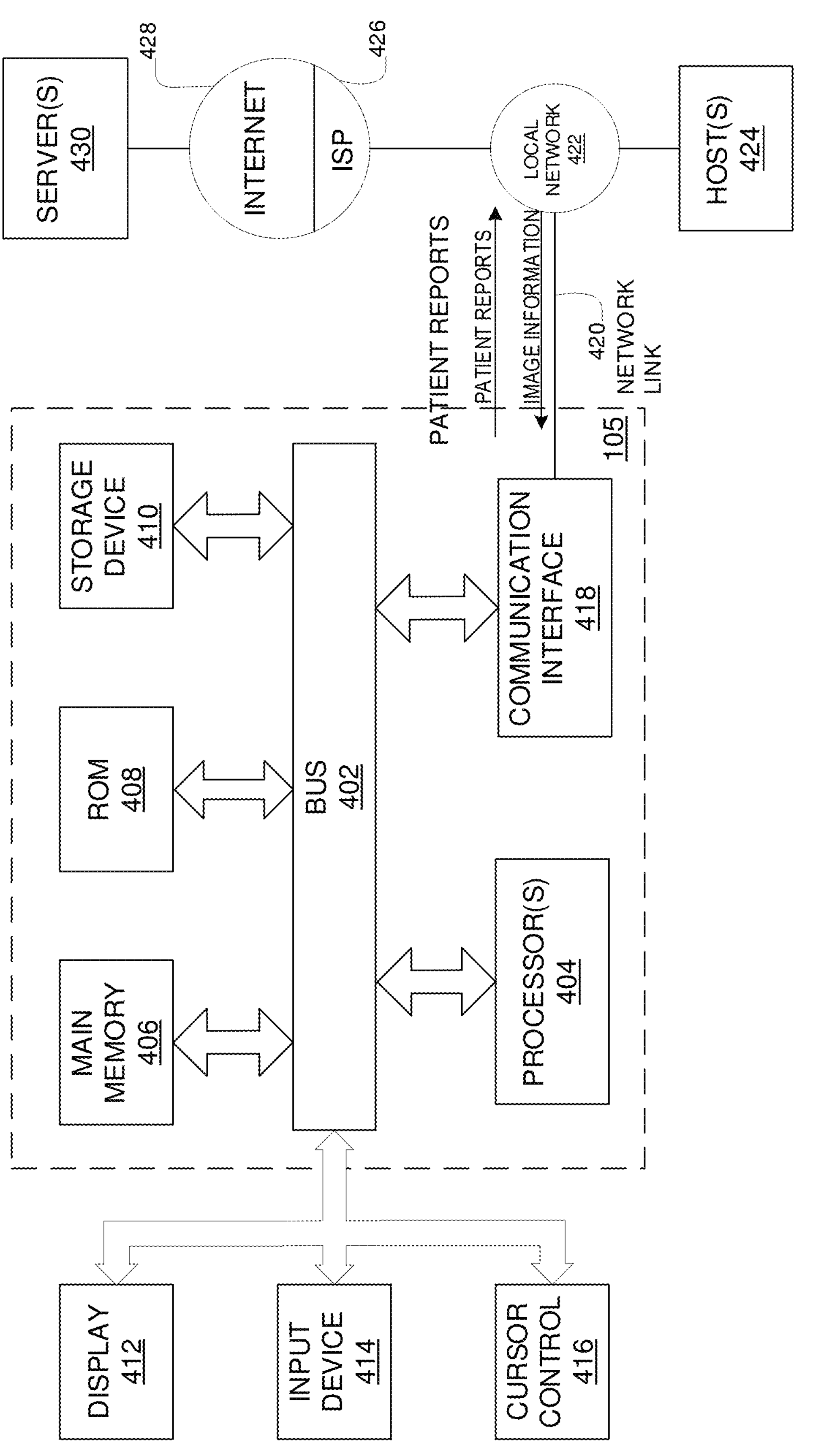
FIG. 4A is a block diagram that illustrates a computer system upon which various embodiments may be implemented.

FIG. 4A is a block diagram that illustrates a computer system 400 upon which various embodiments may be implemented. Computer system 400 includes a bus 402 or other communication mechanism for communicating information, and a hardware processor, or multiple processors, 404 coupled with bus 402 for processing information. Hardware processor(s) 404 may be, for example, one or more general purpose microprocessors.

Computer system 400 also includes a main memory 406, such as a random access memory (RAM), cache and/or other dynamic storage devices, coupled to bus 402 for storing information and instructions to be executed by processor 404. Main memory 406 also may be used for storing temporary variables or other intermediate information during execution of instructions to be executed by processor 404. Such instructions, when stored in storage media accessible to processor 404, render computer system 400 into a special-purpose machine that is customized to perform the operations specified in the instructions. The main memory 406 may, for example, include instructions that analyze image information to determine characteristics of coronary features (e.g., plaque, perivascular fat and coronary arteries) to produce patient reports containing information that characterizes aspects of the patient's health relating to their coronary arteries. For example, one or more metrics may be determined, the metrics including one or more of a slope/gradient of a feature, a maximum density, minimum density, a ratio of a slope of one feature to the slope of another feature, a ratio of a maximum density of one feature to the maximum density of another feature, a ratio of a minimum density of a feature to the minimum density of the same feature, or a ratio of the minimum density of a feature to the maximum density of another feature.

Computer system 400 further includes a read only memory (ROM) 408 or other static storage device coupled to bus 402 for storing static information and instructions for processor 404. A storage device 410, such as a magnetic disk, optical disk, or USB thumb drive (Flash drive), etc., is provided and coupled to bus 402 for storing information and instructions.

Computer system 400 may be coupled via bus 402 to a display 412, such as a cathode ray tube (CRT) or LCD display (or touch screen), for displaying information to a computer user. An input device 414, including alphanumeric and other keys, is coupled to bus 402 for communicating information and command selections to processor 404. Another type of user input device is cursor control 416, such as a mouse, a trackball, or cursor direction keys for communicating direction information and command selections to processor 404 and for controlling cursor movement on display 412. This input device typically has two degrees of freedom in two axes, a first axis (e.g., x) and a second axis (e.g., y), that allows the device to specify positions in a plane. In some embodiments, the same direction information and command selections as cursor control may be implemented via receiving touches on a touch screen without a cursor.

Computing system 400 may include a user interface module to implement a GUI that may be stored in a mass storage device as computer executable program instructions that are executed by the computing device(s). Computer system 400 may further, as described below, implement the techniques described herein using customized hard-wired logic, one or more ASICs or FPGAs, firmware and/or program logic which in combination with the computer system causes or programs computer system 400 to be a special-purpose machine. According to one embodiment, the techniques herein are performed by computer system 400 in response to processor(s) 404 executing one or more sequences of one or more computer readable program instructions contained in main memory 406. Such instructions may be read into main memory 406 from another storage medium, such as storage device 410. Execution of the sequences of instructions contained in main memory 406 causes processor(s) 404 to perform the process steps described herein. In alternative embodiments, hard-wired circuitry may be used in place of or in combination with software instructions.

Various forms of computer readable storage media may be involved in carrying one or more sequences of one or more computer readable program instructions to processor 404 for execution. For example, the instructions may initially be carried on a magnetic disk or solid state drive of a remote computer. The remote computer can load the instructions into its dynamic memory and send the instructions over a telephone line using a modem. A modem local to computer system 400 can receive the data on the telephone line and use an infra-red transmitter to convert the data to an infra-red signal. An infra-red detector can receive the data carried in the infra-red signal and appropriate circuitry can place the data on bus 402. Bus 402 carries the data to main memory 406, from which processor 404 retrieves and executes the instructions. The instructions received by main memory 406 may optionally be stored on storage device 410 either before or after execution by processor 404.

Computer system 400 also includes a communication interface 418 coupled to bus 402. Communication interface 418 provides a two-way data communication coupling to a network link 420 that is connected to a local network 422. For example, communication interface 418 may be an integrated services digital network (ISDN) card, cable modem, satellite modem, or a modem to provide a data communication connection to a corresponding type of telephone line. As another example, communication interface 418 may be a local area network (LAN) card to provide a data communication connection to a compatible LAN (or WAN component to communicate with a WAN). Wireless links may also be implemented. In any such implementation, communication interface 418 sends and receives electrical, electromagnetic or optical signals that carry digital data streams representing various types of information.

Network link 420 typically provides data communication through one or more networks to other data devices. For example, network link 420 may provide a connection through local network 422 to a host computer 424 or to data equipment operated by an Internet Service Provider (ISP) 426. ISP 426 in turn provides data communication services through the worldwide packet data communication network now commonly referred to as the "Internet" 428. Local network 422 and Internet 428 both use electrical, electromagnetic or optical signals that carry digital data streams. The signals through the various networks and the signals on network link 420 and through communication interface 418, which carry the digital data to and from computer system 400, are example forms of transmission media.

Computer system 400 can send messages and receive data, including program code, through the network(s), network link 420 and communication interface 418. In the Internet example, a server 430 might transmit a requested code for an application program through Internet 428, ISP 426, local network 422 and communication interface 418.

The received code may be executed by processor 404 as it is received, and/or stored in storage device 410, or other non-volatile storage for later execution.

Accordingly, in an embodiment, the computer system 105 comprises a non-transitory computer storage medium storage device 410 configured to at least store image information of patients. The computer system 105 can also include non-transitory computer storage medium storage that stores instructions for the one or more processors 404 to execute a process (e.g., a method) for characterization of coronary plaque tissue data and perivascular tissue data using image data gathered from a computed tomography (CT) scan along a blood vessel, the image information including radiodensity values of coronary plaque and perivascular tissue located adjacent to the coronary plaque. Executing the instructions, the one or more processors 404 can quantify, in the image data, the radiodensity in regions of coronary plaque, quantify in the image data, radiodensity in at least one region of corresponding perivascular tissue adjacent to the coronary plaque, determine gradients of the quantified radiodensity values within the coronary plaque and the quantified radiodensity values within the corresponding perivascular tissue, determine a ratio of the quantified radiodensity values within the coronary plaque and the corresponding perivascular tissue, and characterizing the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue.

Various embodiments of the present disclosure may be a system, a method, and/or a computer program product at any possible technical detail level of integration. The computer program product may include a computer readable storage medium (or mediums) having computer readable program instructions thereon for causing a processor to carry out aspects of the present disclosure. For example, the functionality described herein may be performed as software instructions are executed by, and/or in response to software instructions being executed by, one or more hardware processors and/or any other suitable computing devices. The software instructions and/or other executable code may be read from a computer readable storage medium (or mediums).

The computer readable storage medium can be a tangible device that can retain and store data and/or instructions for use by an instruction execution device. The computer readable storage medium may be, for example, but is not limited to, an electronic storage device (including any volatile and/or non-volatile electronic storage devices), a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a solid state drive, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions (as also referred to herein as, for example, "code," "instructions," "module," "application," "software application," and/or the like) for carrying out operations of the present disclosure may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. Computer readable program instructions may be callable from other instructions or from itself, and/or may be invoked in response to detected events or interrupts. Computer readable program instructions configured for execution on computing devices may be provided on a computer readable storage medium, and/or as a digital download (and may be originally stored in a compressed or installable format that requires installation, decompression or decryption prior to execution) that may then be stored on a computer readable storage medium. Such computer readable program instructions may be stored, partially or fully, on a memory device (e.g., a computer readable storage medium) of the executing computing device, for execution by the computing device. The computer readable program instructions may execute entirely on a user's computer (e.g., the executing computing device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present disclosure.

Aspects of the present disclosure are described herein with reference to flowchart illustrations and/or block diagrams of methods, apparatus (systems), and computer program products according to embodiments of the disclosure. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart(s) and/or block diagram(s) block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. For example, the instructions may initially be carried on a magnetic disk or solid state drive of a remote computer. The remote computer may load the instructions and/or modules into its dynamic memory and send the instructions over a telephone, cable, or optical line using a modem. A modem local to a server computing system may receive the data on the telephone/cable/optical line and use a converter device including the appropriate circuitry to place the data on a bus. The bus may carry the data to a memory, from which a processor may retrieve and execute the instructions. The instructions received by the memory may optionally be stored on a storage device (e.g., a solid state drive) either before or after execution by the computer processor.

The flowchart and block diagrams in the Figures illustrate the architecture, functionality, and operation of possible implementations of systems, methods, and computer program products according to various embodiments of the present disclosure. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. In addition, certain blocks may be omitted in some implementations. The methods and processes described herein are also not limited to any particular sequence, and the blocks or states relating thereto can be performed in other sequences that are appropriate.

Figure 4B:
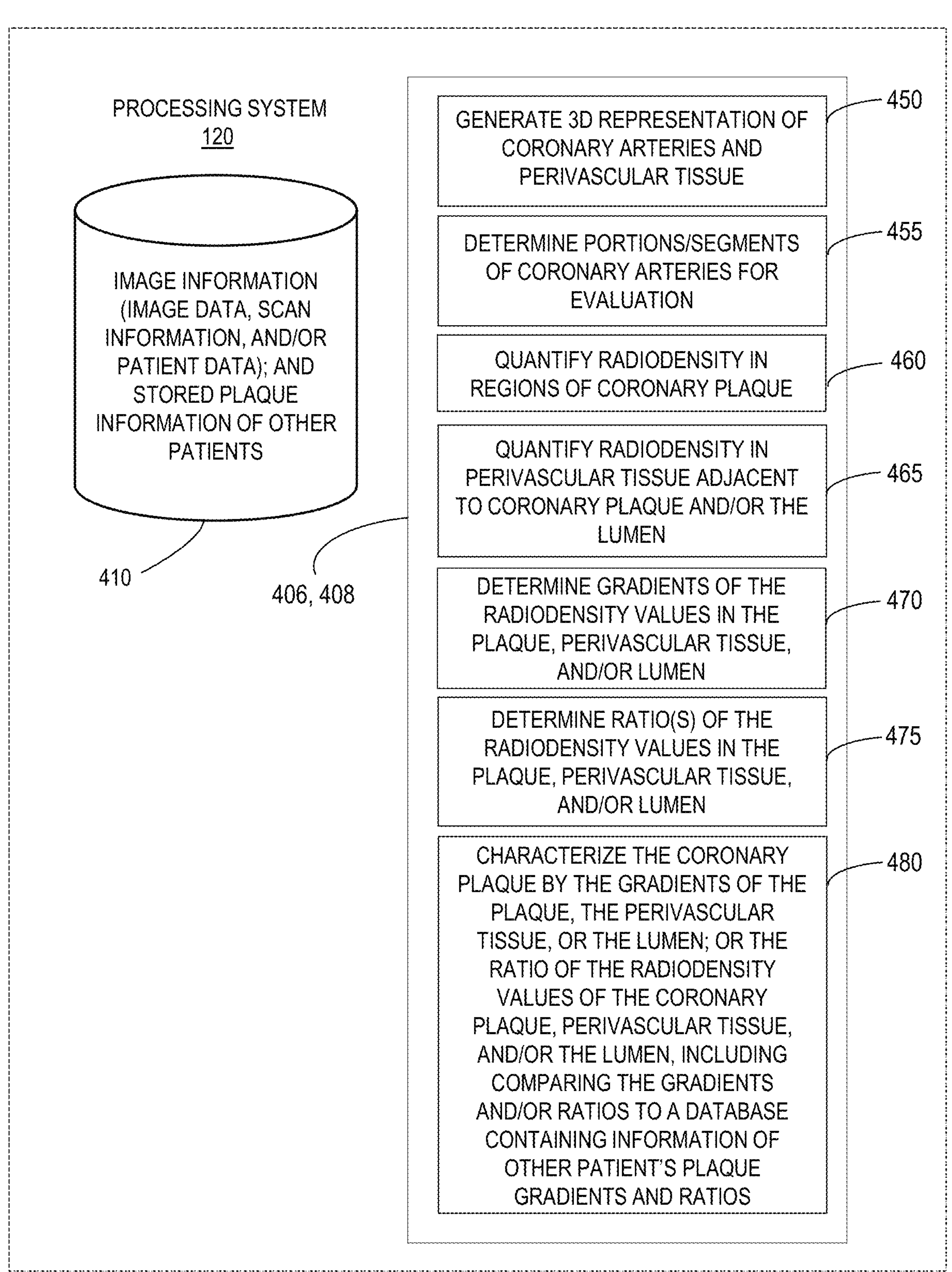
FIG. 4B is a block diagram that illustrates computer modules in a computer system 400 which may implement various embodiments.

FIG. 4B is a block diagram that illustrates examples of representative instructions which may be executed by one or more computer hardware processors in one or more computer modules in a representative processing system (computer system) 120 which may implement various embodiments described herein. As illustrated in FIG. 1, the processing system 120 can be implemented in one computer (for example, a server) or in 2 or more computers (two or more servers). Although the instructions are represented in FIG. 4B as being in seven modules 450, 455, 460, 465, 470, 475, 480, in various implementations the executable instructions may be in fewer modules, including a single module, or more modules.

The processing system 120 includes image information stored on a storage device 410, which may come from the network 125 illustrated in FIG. 1. The image information may include image data, scan information, and/or patient data. In this example, the storage device 410 also includes stored plaque information of other patients. For example, the stored plaque information of other patients may be stored in a database on the storage device 410. In other examples, stored plaque information of other patients is stored on a storage device that is in communication with processing system 120. The other patients' stored plaque information may be a collection of information from one, dozens, hundreds, thousands, tens of thousands, hundreds of thousands, or millions of patients, or more.

The information for each patient may include characterizations of that patient's plaque, such as densities and density gradients of the patient's plaque, and the location of the plaque relative to the perivascular tissue near or adjacent to the plaque. The information for each patient may include patient information. For example, the information may include one or more of sex, age, BMI (body mass index), medication, blood pressure, heart rate, weight, height, race, body habitus, smoking history, history or diagnosis of diabetes, history or diagnosis of hypertension, prior coronary artery disease, family history of coronary artery disease and/or other diseases, or one or more lab results (e.g., blood test results). The information for each patient may include scan information. For example, the information may include one or more of contrast-to-noise ratio, signal-to-noise ratio, tube current, tube voltage, contrast type, contrast volume, flow rate, flow duration, slice thickness, slice spacing, pitch, vasodilator, beta blockers, recon option whether it's iterative or filter back projection, recon type whether it's standard or high resolution, display field-of-view, rotation speed, gating whether it's perspective triggering or retrospective gating, stents, heart rate, or blood pressure. The information for each patient may also include cardiac information. For example, the information may include characterizations of plaque including one or more of density, volume, geometry (shape), location, remodeling, baseline anatomy (for diameter, length), compartments (inner, outer, within), stenosis (diameter, area), myocardial mass, plaque volume, and/or plaque composition, texture, or uniformity.

The processing system 120 also includes memory 406, 408, which may be main memory of the processing system or read only memory (ROM). The memory 406, 408 stores instructions executable by one or more computer hardware processors 404 (groups of which referred to herein as "modules") to characterize coronary plaque. The memory 406, 408 will be collectively referred to, in reference to this diagram, as memory 406 for the sake of brevity. Examples of the functionality that is performed by the executable instructions are described below.

Memory 406 includes module 450 that generates, from the image data stored on the storage device 410, 2-D or 3-D representations of the coronary arteries, including plaque, and perivascular tissue that is located adjacent to or in proximity of the coronary arteries in the plaque. The generation of the 2-D or 3-D representations of the coronary arteries may be done from a series of images 305 (e.g., CCTA images) is described above in reference to FIG. 3. Once the representation of the coronary arteries are generated, different portions or segments of the coronary arteries can be identified for evaluation. For example, portions of interest of the right coronary artery 205, the left anterior descending artery 215, or the circumflex branch of the left coronary artery 220 may be identified as areas of analysis (areas of interest) based on input from a user, or based on a feature determined from the representation of the coronary artery (plaque).

In module 460, the one or more computer hardware processors quantify radiodensity in regions of coronary plaque. For example, the radiodensity in regions of coronary plaque are set to a value on the Hounsfield scale. In module 465, the one or more computer hardware processors quantify radiodensity of perivascular tissue that is adjacent to the coronary plaque, and quantify radiodensity value of the lumen of the vessel of interest. In module 470, the one or more computer hardware processors determine gradients of the radiodensity values of the plaque the perivascular tissue and/or the lumen. In module 475, the one or more computer hardware processors determine one or more ratios of the radiodensity values in the plaque, perivascular tissue, and/or the lumen. Next, in module 480, the one or more computer hardware processors characterize the coronary plaque using the gradients of the plaque, the perivascular tissue, and/or the lumen, and/or characterize ratio of the radiodensity values of the coronary plaque to perivascular tissue and/or the lumen including comparing the gradients and or ratios to a database containing information of other patients' plaque gradients and ratios. For example, the gradients and/or the ratios are compared to patient data that stored on storage device 410. Determining gradients and ratios of the plaque the perivascular tissue and the lumen are described in more detail with reference to FIGS. 6-12.

Figure 5A:
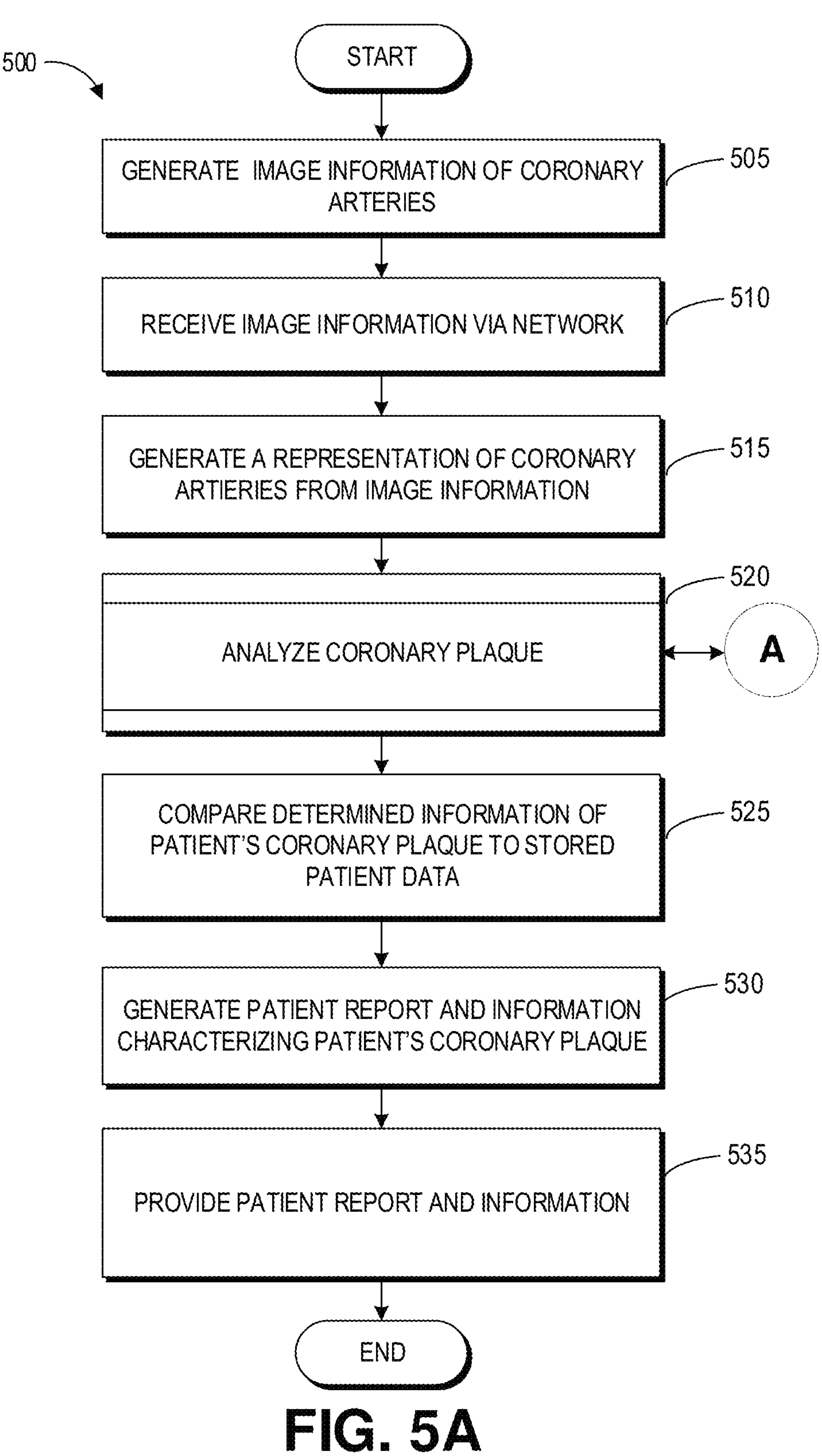
FIG. 5A illustrates an example of a flowchart of a process for analyzing coronary plaque.

FIG. 5A illustrates an example of a flowchart of a process 500 for analyzing coronary plaque. At block 505, the process 500 generates image information including image data relating to coronary arteries. In various embodiments, this may be done by a scanner 130B (FIG. 1). At block 510, a processing system may receive image information via a network 125 (FIG. 1), the image information including the image data. At block 515, the process 500 generates a 3D representation of the coronary arteries including perivascular fat and plaque on the processing system. The functionality of blocks 505, 510, and 515, can be performed, for example, using various scanning techniques (e.g., CCTA) to generate image data, communication techniques to transfer data over the network, and processing techniques to generate the 3D representation of the coronary arteries from the image data.

Figure 5B:
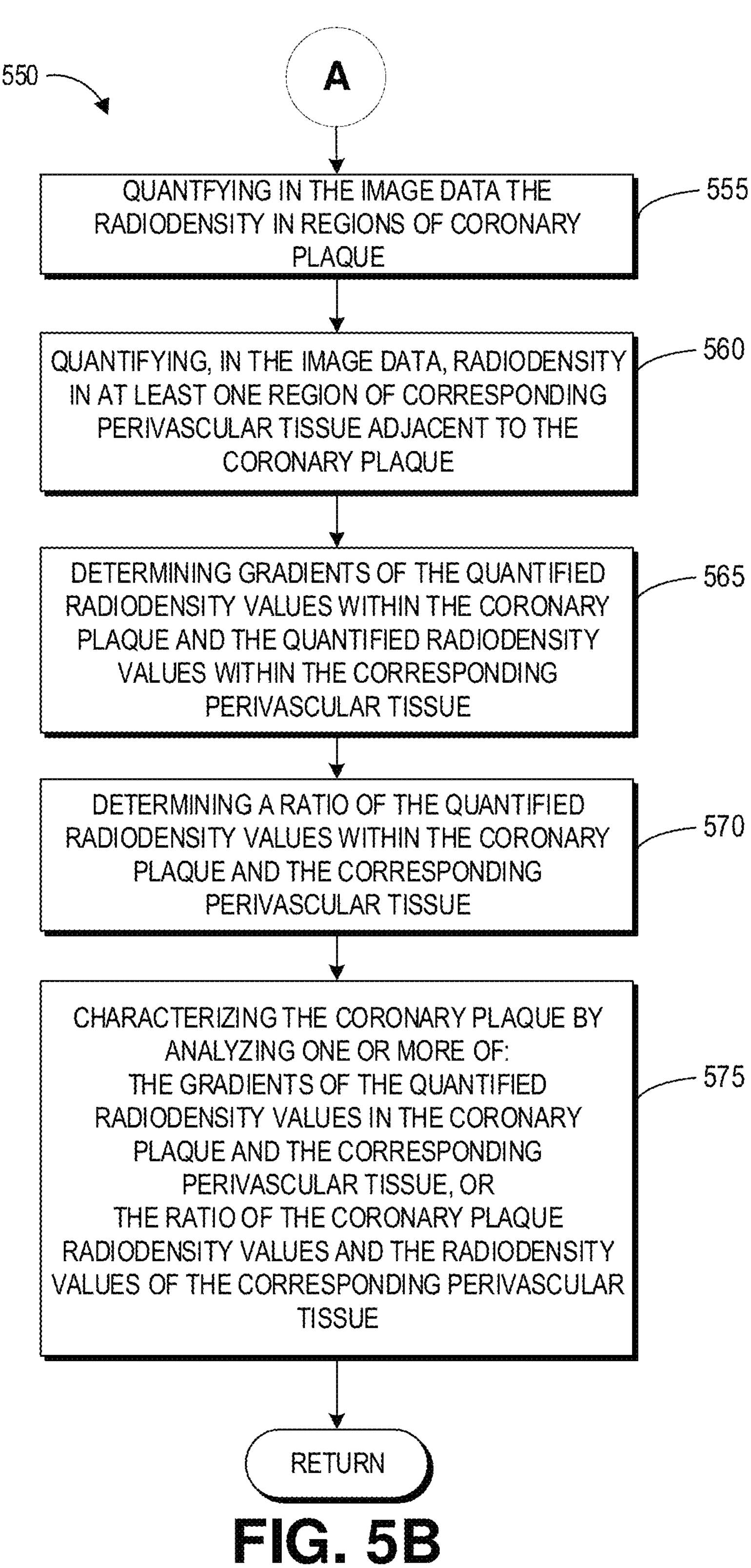
FIG. 5B illustrates an example of a flowchart that expands on a portion of the flowchart in FIG. 5A for determining characteristics of coronary plaque.

At block 520, the processing system performs a portion of the process 500 to analyze the coronary plaque, which is described in further detail in reference to process 550 of FIG. 5B. Additional details of this process to analyze the coronary plaque in reference to FIGS. 6-12.

FIG. 5B illustrates an example of a flowchart that expands on a portion of the flowchart in FIG. 5A for determining characteristics of coronary plaque. Referring now to FIG. 5B, at block 555, process 550 can utilize the one or more processors 404 to quantify the radiodensity in regions of coronary plaque. At block 560, the process 550 can utilize the one or more processors 404 to quantify, in the image data, radiodensity in at least one region of corresponding perivascular tissue, meaning perivascular tissue that is adjacent to the coronary plaque. At block 565, the process 550 determines gradients of the quantified radiodensity values within the coronary plaque and the quantified radiodensity values within the corresponding perivascular tissue. The one or more processors 404 can be the means to determine these gradients. At block 570, the process 550 may determine a ratio of the quantified radiodensity values within the coronary plaque and the corresponding perivascular tissue. For example, the perivascular tissue that is adjacent to the coronary plaque. The one or more processors 404 can determine these ratios. At block 575, process 550 can utilize the one or more processors 404 to characterize the coronary plaque by analyzing one or more of the gradients of the quantified radiodensity values in the coronary plaque and the corresponding perivascular tissue, or the ratio of the coronary plaque radiodensity values and the radiodensity values of the corresponding perivascular tissue. The process 550 can then return to process 500 as illustrated by the circle A.

Referring again to FIG. 5A, at block 525, the process 500 may compare determined information of a particular patient's coronary plaque to stored patient data, for example patient data stored on storage device 410. An example of the coronary plaque information of a particular patient that can be compared to stored patient data. To better understand the patient's coronary plaque information, and/or to help determine the particular patient's coronary plaque information, one or more of the scan information may be used. Also, when comparing a particular patient's coronary plaque information to previously stored coronary plaque information, one or more characteristics of the patient may be compared, including, for example, one or more of the characteristics of a patient. In some examples, the coronary plaque information of the patient being examined may be compared to or analyzed in reference to a patient who has one or more of the same or similar patient characteristics. For example, the patient being examined may be compared to a patient that has the same or similar characteristics of sex, age, BMI, medication, blood pressure, heart rate, weight, height, race, body habitus, smoking, diabetes, hypertension, prior coronary artery disease, family history, and lab results. Such comparisons can be done through various means, for example machine learning and/or artificial intelligence techniques. In some examples, neural network is used to compare a patient's coronary artery information to numerous (e.g., 10,000+) other patients' coronary artery information. For such patients that have similar patient information and similar cardiac information, risk assessments of the plaque of the patient being examined may be determined.

Figure 6:
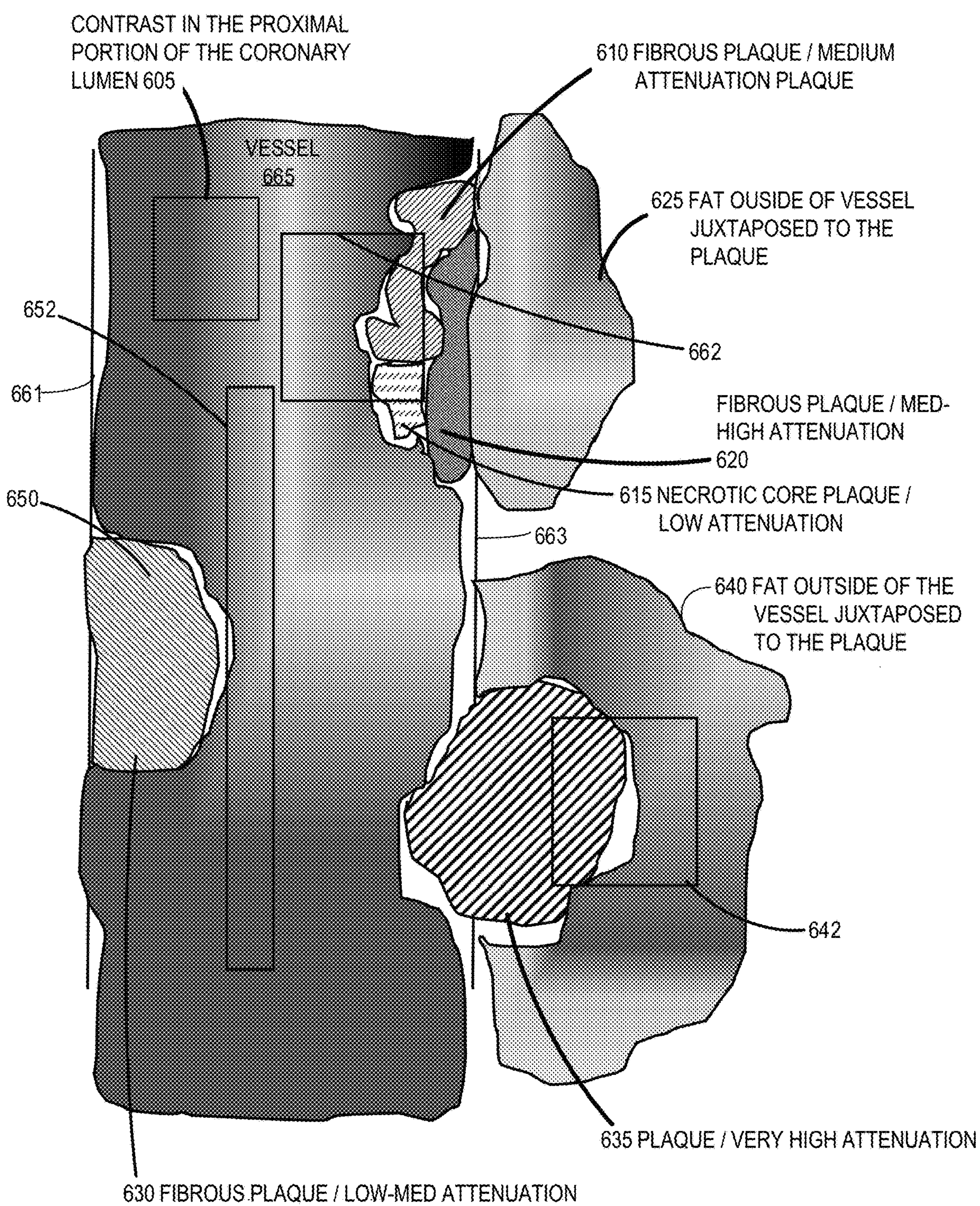
FIG. 6 illustrates a representation of image data depicting an example of a portion of a coronary artery (sometimes referred to herein as a “vessel” for ease of reference).

FIG. 6 illustrates an example of an area, indicated by box 605, where contrast attenuation patterns in a proximal portion of the coronary lumen can be analyzed, box 605 extending from a central area of the vessel 665 towards the vessel wall 661. FIG. 6 illustrates another example of an area, indicated by box 652, where contrast attenuation patterns in a portion of the coronary lumen of vessel 665 can be analyzed, box 652 extending longitudinally relative to vessel 665 from a central area of the vessel 665 towards the vessel wall 661. FIG. 6 further illustrates an example of an area, indicated by box 662, where contrast attenuation patterns of a portion of the lumen, a portion of fibrous plaque 610 and plaque 620 can be analyzed, box 662 thus covering a portion of the vessel 665 and a portion of fibrous plaque 610 and plaque 620. FIG. 6 further illustrates an example of an area indicated by box 642, where contrast attenuation patterns of a portion of plaque 635 and a portion of fat 640 positioned adjacent to plaque 635 can be analyzed, box 642 extending over a portion of plaque 635 and a portion of fat 640. Information determined by analyzing various aspects of the density of coronary artery features (e.g., the lumen, the plaque, and/or the perivascular fat) can be combined with other information to determine characteristics of a patient's arteries. In some examples, the determined information may include for any of the lumen, plaque or perivascular fat, one or more of a slope/gradient of a feature, a maximum density, a minimum density, a ratio of a slope of the density of one feature to the slope of the density of another feature, a ratio of a maximum density of one feature to the maximum density of another feature, a ratio of a minimum density of a feature to the minimum density of the same feature, a directionality of the density ratios, e.g., a density ratio between features facing one way or direction and features facing in an opposite direction (for example, the radiodensity ratio of features facing inwards towards the myocardium and features facing outwards toward the pericardium), or a ratio of the minimum density of a feature to the maximum density of another feature. Such determined information may indicate distinct differences in risks of plaque in a patient. In some examples, determined information (for example as listed above) may be used with a percentage diameter of stenosis to determine characteristics of a patient's arteries.

Still referring to FIG. 6, in an example of the directionality of radiodensity ratios, the density of a portion of the necrotic core plaque 615 to the density of a portion of the vessel 665 (e.g., plaque:vessel inward facing ratio) can be determined and may indicate a certain risk of plaque. In another example of the directionality of radiodensity ratios, the density of a portion of a portion of the vessel 665 to the density of the necrotic core plaque 615 (e.g., vessel:plaque outward facing) can be determined and may indicate a certain risk of plaque. In another example, the density ratio of the necrotic core plaque 615 to the density of a portion of the vessel 665 (e.g., plaque:vessel inward facing ratio) can be compared to the density ratio of the necrotic core plaque 615 to the fibrous plaque 620 (e.g., plaque:plaque outward facing) may indicate a certain risk of plaque. In other examples, features that are adjacently positioned can be used to determine inward and/or outward directional radiodensity values that may be used to indicate a risk associated with plaque. Such ratios may provide distinct differences in risk of plaque. Various embodiments of directional radiodensity values and/or directional radiodensity ratios can be included with any of the other information described herein to indicates plaque risk.

The size of a compartment may be used to also indicate a risk associated with plaque. For example, determination of risk associated with a plaque may be based at least partially on the size of the compartments, such that the ratio of the of the radiodensities affects the determination of risk and the function of the size of the compartments can also affect the determination of risk. While the presence of plaque in a patient where the ratio of plaque:fat may indicate a high risk plaque, if there is only a small amount of plaque (e.g., a small compartment of plaque), it would be of risk than if there was a larger compartment of the same plaque with the same radiodensity ratio of plaque to fat. In one implementation, the size (e.g., a volume) of the compartment a feature (e.g., of lumen, plaque, perivascular tissue (fat), and myocardium) can be determined, and a radiodensity ratio can also be determined, and then the ratio can be weighted based on the size of the compartment. For example, a large compartment can increase the weight of a ratio to make the ratio more indicative of a risk associated with the plaque. Similarly, a small compartment can decrease the weight of a ratio to make the ratio less indicative of a risk associated with the plaque. In an implementation, only the compartment size of the plaque is used to weight (or adjust) the ratio. In an implementation, the compartment size of both of the features that are used in the radiodensity ratio can be used to weight the ratio to determine a resulting risk. In an implementation, the compartment size of one of plaque, lumen, perivascular tissue, or myocardium is used to weight (or adjust) the risk associated with the radiodensity ratio. In an implementation, the compartment size of more than one of plaque, lumen, perivascular tissue, or myocardium is used to weight the risk associated with the radiodensity ratio. Various embodiments of determining plaque risk using compartment size can be included with any of the other information described herein to indicate plaque risk.

Figure 7:
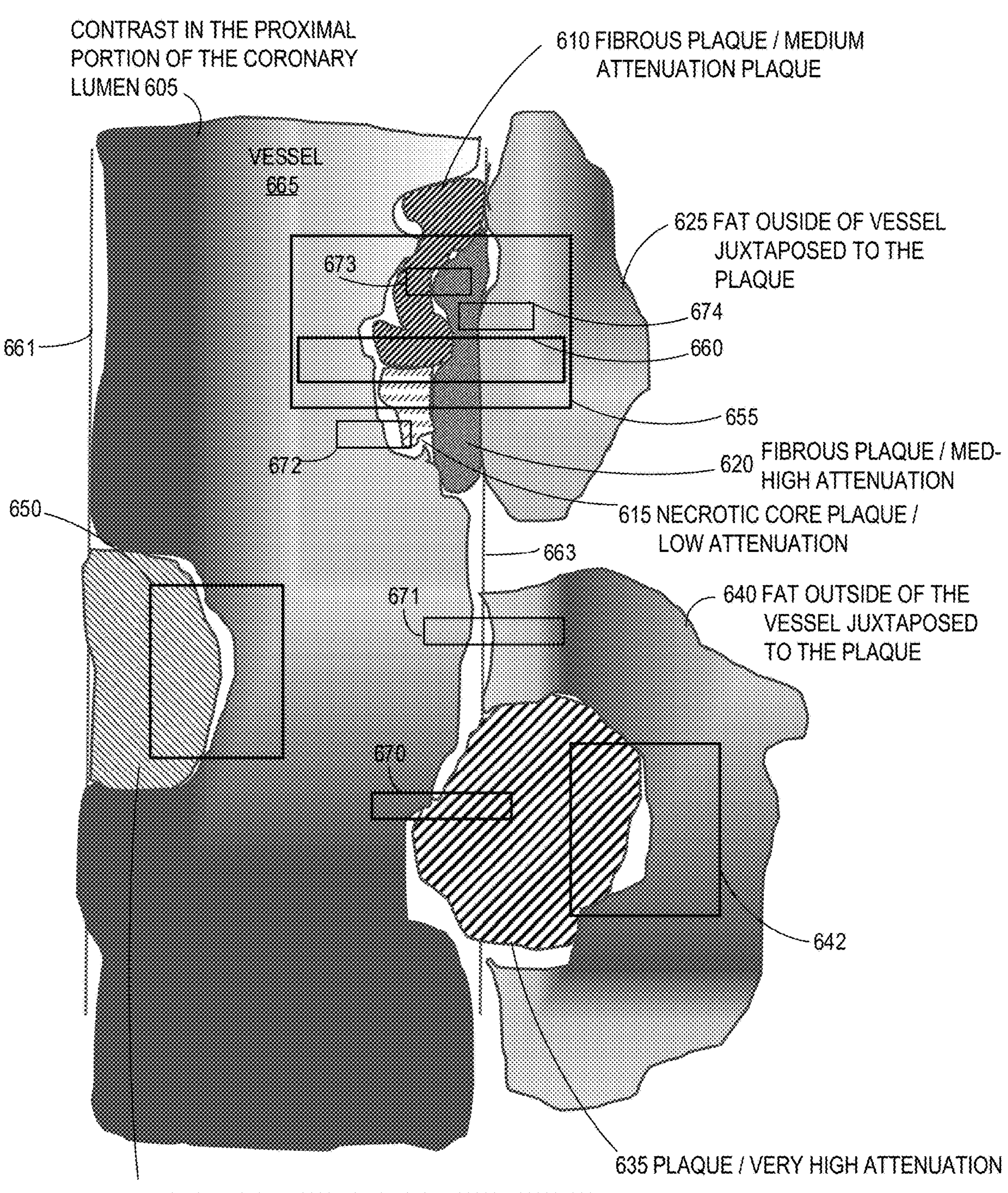
FIG. 7 illustrates the same vessel and features of plaque and fat as illustrated in FIG. 6 and further illustrates additional examples of areas of an artery, and the plaque and/or perivascular fat that is near an artery, that may be analyzed to determine characteristics of a patient’s arteries.

FIG. 7 illustrates the same vessel 665 and features of plaque and fat as illustrated in FIG. 6 and further illustrates additional examples of areas of an artery, and plaque and/or perivascular fat near the artery, that may be analyzed to determine characteristics of a patient's arteries. Such areas are indicated in FIG. 7 by rectangular boxes, similar to the illustrations in FIG. 6. Although particular locations of the rectangular boxes are illustrated in FIG. 6 and FIG. 7, these are only examples of areas that may be analyzed. In one example, FIG. 7 illustrates box 660 which includes a portion of the vessel 665, a portion of necrotic core plaque 615, a portion of fibrous plaque 610, a portion of plaque 620, and a portion of fat 625. In another example, FIG. 7 illustrates box 655 which includes a portion of the vessel 665, a portion of the fibers plaque 610 a portion of the plaque 620 the portion of the necrotic core plaque 615, and a portion of fat 625. Box 655 may, in some cases, illustrate the general area for analysis due to the existence of 3 different types of plaque 610, 615, 620, and adjacently disposed fat 625. Particular portions of a general area for analysis may be analyzed to better understand the characteristics formed by adjacent features. For example, FIG. 7 illustrates the general area 665 containing box 660 (described above), box 673, which extends across a portion of fibrous plaque 610 and plaque 620, and box 674 which extends across a portion of plaque 620 and perivascular fat 625. As another example, FIG. 7 also illustrates another box 672 that extends across a portion of the vessel 655 and necrotic core plaque 615. As a further example, FIG. 7 illustrates box 671 that extends across a portion of the vessel 665 and fat 640 juxtaposed to the vessel 665. As a further example, FIG. 7 illustrates box 670 that extends across a portion of the vessel 665 and plaque 635. As indicated above, characteristics of a patient's arteries that can be analyzed based on these features can include but are not limited to:

1. A ratio of lumen attenuation to plaque attenuation, wherein the volumetric model of scan-specific attenuation density gradients within the lumen adjusts for reduced luminal density across plaque lesions that are more functionally significant in terms of risk value.
2. A ratio of plaque attenuation to fat attenuation, wherein plaques with high radiodensities are considered to present a lower risk, even within a subset of plaques considered "calcified," where there can be a gradation of densities (for example, 130 to 4000 HU) and risk is considered to be reduced as density increases.
3. A ratio of lumen attenuation/plaque attenuation/fat attenuation.
4. A ratio of #1-3 as a function of 3D shape of atherosclerosis, which can include a 3D texture analysis of the plaque.
5. The 3D volumetric shape and path of the lumen along with its attenuation density from the beginning to the end of the lumen.
6. The totality of plaque and plaque types before and after any given plaque to further inform its risk.
7. Determination of "higher plaque risks" by "subtracting" calcified (high-density) plaques to obtain a better absolute measure of high risk plaques (lower-density plaques). In other words, this particular embodiment involves identifying calcified plaque and excluding it from further analysis of plaque for the purpose of identifying high risk plaques.

In some embodiments, the systems, devices, and methods described herein can automatically and/or dynamically perform quantified analysis of various parameters relating to plaque, cardiovascular arteries, and/or other structures. For example, rather than having a physician eyeball or make a general assessment of the patient, a medical image can be transmitted to a backend main server in some embodiments that is configured to conduct such analyses, which advantageously can be performed in a consistent, objective, and/or reproducible manner. In some embodiments, the systems, methods, and devices described herein can provide a quantified measurement of one or more features of a coronary CT image using automated and/or dynamic processes. For example, in some embodiments, the main server system can be configured to identify one or more vessels, plaque, and/or fat from a medical image. Based on the identified features, in some embodiments, the system can be configured to generate one or more quantified measurements from a raw medical image, such as for example density and/or radiodensity of one or more regions of plaque, identification of stable plaque and/or unstable plaque, perivascular fat, pericoronary adipose tissue (PCAT), fat attenuation index (FAI), volumes thereof, surface areas thereof, geometric shapes, heterogeneity thereof, and/or the like. In some embodiments, the system can also generate one or more quantified measurements of vessels from the raw medical image, such as for example diameter, volume, morphology, and/or the like.

Based on the identified features and/or quantified measurements, in some embodiments, the system can be configured to generate a risk assessment and/or track the progression of a plaque-based disease or condition, such as for example atherosclerosis, stenosis, ischemia, myocardial infarction, and/or major adverse cardiovascular event (MACE), using raw medical images. As described further herein, in some embodiments the system can perform risk assessment and/or tracking the progression of a plaque-based disease based on other patients' information. For example, by comparing or evaluating features in a patient's medical images and patient information (e.g., age, gender, BMI, medication, blood pressure, heart rate, height, weight, race, whether the patient is a smoker or non-smoker, medical history, family history of disease, etc.) to features in other patients' medical images and their associated patient information including their outcome after a period of time.

Further, in some embodiments, the system can be configured to generate a visualization of GUI of one or more identified features and/or quantified measurements, such as a quantized color mapping of different features. In some embodiments, the systems, devices, and methods described herein are configured to utilize medical image-based processing to assess for a subject his or her risk of a cardiovascular event, major adverse cardiovascular event (MACE), rapid plaque progression, and/or response to non-response to medication and/or lifestyle change and/or other treatment and/or invasive procedure. In particular, in some embodiments, the system can be configured to automatically and/or dynamically assess such health risk of a subject by analyzing only non-invasively obtained medical images. In some embodiments, one or more of the processes can be automated using an artificial intelligence (AI) and/or machine learning (ML) algorithm. In some embodiments, one or more of the processes described herein can be performed within minutes in a reproducible manner. This is stark contrast to existing measures today which do not produce reproducible prognosis or assessment, take extensive amounts of time, and/or require invasive procedures.

In some embodiments, image information comprising a plurality of images of a patient's coronary arteries and patient information/characteristics may be provided from one or more of the devices to the one or more servers of the processing system via a network. The processing system is configured to generate coronary artery information using the plurality of images of the patient's coronary arteries to generate two-dimensional and/or three-dimensional data representations of the patient's coronary arteries. Then, the processing system analyzes the data representations to generate patient reports documenting a patient's health conditions and risks related to coronary plaque. The patient reports may include images and graphical depictions of the patient's arteries in the types of coronary plaque in or near the coronary arteries. Using machine learning techniques or other artificial intelligent techniques, the data representations of the patient's coronary arteries may be compared to other patients' data representations (e.g., that are stored in a database) to determine additional information about the patient's health. In some embodiments, the artificial intelligence can be trained using a dataset of other patients' data representations to identify correlations in data. For example, based on certain plaque conditions of the patient's coronary arteries, the likelihood of a patient having a heart attack or other adverse coronary effect can be determined. Also, for example, additional information about the patient's risk of CAD may also be determined.

In some embodiments, the coronary plaque information of a patient being examined may be compared to or analyzed in reference to a patient who has one or more of the same or similar patient characteristics. For example, the patient being examined may be compared to a patient that has the same or similar characteristics of sex, age, BMI, medication, blood pressure, heart rate, weight, height, race, body habitus, smoking, diabetes, hypertension, prior coronary artery disease, family history, and lab results. Such comparisons can be done through various means, for example machine learning and/or artificial intelligence techniques. In some examples, neural network is used to compare a patient's coronary artery information to numerous (e.g., 10,000+) other patients' coronary artery information. For such patients that have similar patient information and similar cardiac information, risk assessments of the plaque of the patient being examined may be determined.

In some embodiments, Deep Learning (DL) methods, machine learning (ML) methods, and artificial intelligence (AI) methods can be used to analyze image information. In an example, this analysis can comprise image segmentation, feature extraction, and classification. In some embodiments, ML methods can comprise image feature extraction and image-based learning from raw data. In some embodiments, the ML method can receive an input of a large training set to learn to ignore variations that could otherwise skew the results of the method. In some embodiments, DL can comprise a Neural Network (NN) with three or more layers that can improve the accuracy of determinations. Advantageously, in some embodiments, DL can obviate the need for pre-processing data and, instead, process raw data. For example, while a human may input a hierarchy of important features of coronary image information for a ML algorithm to make determinations, DL algorithms can determine which features are important and use these features to make determinations. Advantageously, in some embodiments, a DL algorithm can adjust itself for accuracy and precision. In some embodiments, ML and DL algorithms can perform supervised learning, unsupervised learning, and reinforcement learning.

In some embodiments, NN approaches, including convolutional neural networks (CNN) and recurrent convolutional neural networks (RCNN), among others, can be used to analyze information in a manner similar to high-level cognitive functions of a human mind. In some embodiments, a NN approach can comprise training an object recognition system numerous medical images in order to teach it patterns in the images that correlate with particular labels. In some embodiments, a CNN can comprise a NN where the nodes of each layer are clustered, the clusters overlap, and each cluster feeds data to multiple nodes of the next layer. In some embodiments, a RCNN can comprise a CNN where recurrent connections are incorporated in each convolutional layer. Advantageously, in some embodiments, the recurrent connections can make object recognition a dynamic process despite the fact that the input is static.

In some embodiments, the vessel identification algorithm, coronary artery identification algorithm, and/or plaque identification algorithm can be trained on a plurality of medical images wherein one or more vessels, coronary arteries, and/or regions of plaque are pre-identified. Based on such training, for example by use of a CNN in some embodiments, the system can be configured to automatically and/or dynamically identify from raw medical images the presence and/or parameters of vessels, coronary arteries, and/or plaque. In some embodiments, the system can be configured to utilize one or more AI and/or ML algorithms to identify and/or analyze vessels or plaque, derive one or more quantification metrics and/or classifications, and/or generate a treatment plan. In some embodiments, the system can be configured to utilize an AI and/or ML algorithm to identify areas in an artery that exhibit plaque buildup within, along, inside and/or outside the arteries. In some embodiments, input to the AI and/or ML algorithms can include images of a patient and patient information (or characteristics), for example, one or more of age, gender, body mass index (BMI), medication, blood pressure, heart rate, height, weight, race, whether the patient is a smoker or non-smoker, body habitus (for example, the "physique" or "body type" which may be based on a wide range of factors), medical history, diabetes, hypertension, prior coronary artery disease (CAD), dietary habits, drug history, family history of disease, information relating to other previously collected image information, exercise habits, drinking habits, lifestyle information, or lab results, and the like. In an example where a NN is used, the NN can be trained using information from a plurality of patients, where the information for each patient can include medical images and one or more patient characteristics.

In some embodiments, the system can be configured to utilize one or more AI and/or ML algorithms to automatically and/or dynamically identify one or more regions of plaque using image processing. For example, in some embodiments, the one or more AI and/or ML algorithms can be trained using a CNN on a set of medical images on which regions of plaque have been identified, thereby allowing the AI and/or ML algorithm automatically identify regions of plaque directly from a medical image. In some embodiments, the system can be configured to identify a vessel wall and a lumen wall for each of the identified coronary arteries in the medical image. In some embodiments, the system is then configured to determine the volume in between the vessel wall and the lumen wall as plaque. In some embodiments, the system can be configured to identify regions of plaque based on the radiodensity values typically associated with plaque, for example by setting a predetermined threshold or range of radiodensity values that are typically associated with plaque with or without normalizing using a normalization device.

In some embodiments, the one or more vascular morphology parameters and/or plaque parameters can comprise quantified parameters derived from the medical image. For example, in some embodiments, the system can be configured to utilize an AI and/or ML algorithm or other algorithm to determine one or more vascular morphology parameters and/or plaque parameters. As another example, in some embodiments, the system can be configured to determine one or more vascular morphology parameters, such as classification of arterial remodeling due to plaque, which can further include positive arterial remodeling, negative arterial remodeling, and/or intermediate arterial remodeling. In some embodiments, the classification of arterial remodeling is determined based on a ratio of the largest vessel diameter at a region of plaque to a normal reference vessel diameter of the same region which can be retrieved from a normal database. In some embodiments, the system can be configured to classify arterial remodeling as positive when the ratio of the largest vessel diameter at a region of plaque to a normal reference vessel diameter of the same region is more than 1.1. In some embodiments, the system can be configured to classify arterial remodeling as negative when the ratio of the largest vessel diameter at a region of plaque to a normal reference vessel diameter is less than 0.95. In some embodiments, the system can be configured to classify arterial remodeling as intermediate when the ratio of the largest vessel diameter at a region of plaque to a normal reference vessel diameter is between 0.95 and 1.1.

In some embodiments, the system is configured to classify atherosclerosis of a subject based on the quantified atherosclerosis as one or more of high risk, medium risk, or low risk. In some embodiments, the system is configured to classify atherosclerosis of a subject based on the quantified atherosclerosis using an AI, ML, and/or other algorithm. In some embodiments, the system is configured to classify atherosclerosis of a subject by combining and/or weighting one or more of a ratio of volume of surface area, volume, heterogeneity index, and radiodensity of the one or more regions of plaque.

In some embodiments, the system can be configured to identify one or more regions of fat, such as epicardial fat, in the medical image, for example using one or more AI and/or ML algorithms to automatically and/or dynamically identify one or more regions of fat. In some embodiments, the one or more AI and/or ML algorithms can be trained using a CNN on a set of medical images on which regions of fat have been identified, thereby allowing the AI and/or ML algorithm automatically identify regions of fat directly from a medical image. In some embodiments, the system can be configured to identify regions of fat based on the radiodensity values typically associated with fat, for example by setting a predetermined threshold or range of radiodensity values that are typically associated with fat with or without normalizing using a normalization device.

In some embodiments, the system is configured to utilize an AI, ML, and/or other algorithm to characterize the change in calcium score based on one or more plaque parameters derived from a medical image. For example, in some embodiments, the system can be configured to utilize an AI and/or ML algorithm that is trained using a CNN and/or using a dataset of known medical images with identified plaque parameters combined with calcium scores. In some embodiments, the system can be configured to characterize a change in calcium score by accessing known datasets of the same stored in a database. For example, the known dataset may include datasets of changes in calcium scores and/or medical images and/or plaque parameters derived therefrom of other subjects in the past. In some embodiments, the system can be configured to characterize a change in calcium score and/or determine a cause thereof on a vessel-by-vessel basis, segment-by-segment basis, plaque-by-plaque basis, and/or a subject basis.

In some embodiments, the systems disclosed herein can be used to dynamically and automatically determine a necessary stent type, length, diameter, gauge, strength, and/or any other stent parameter for a particular patient based on processing of the medical image data, for example using AI, ML, and/or other algorithms.

In some embodiments, the system can be configured to utilize an AI and/or ML algorithm to generate the patient-specific report. In some embodiments, the patient-specific report can include a document, AR experience, VR experience, video, and/or audio component.

Figure 8A:
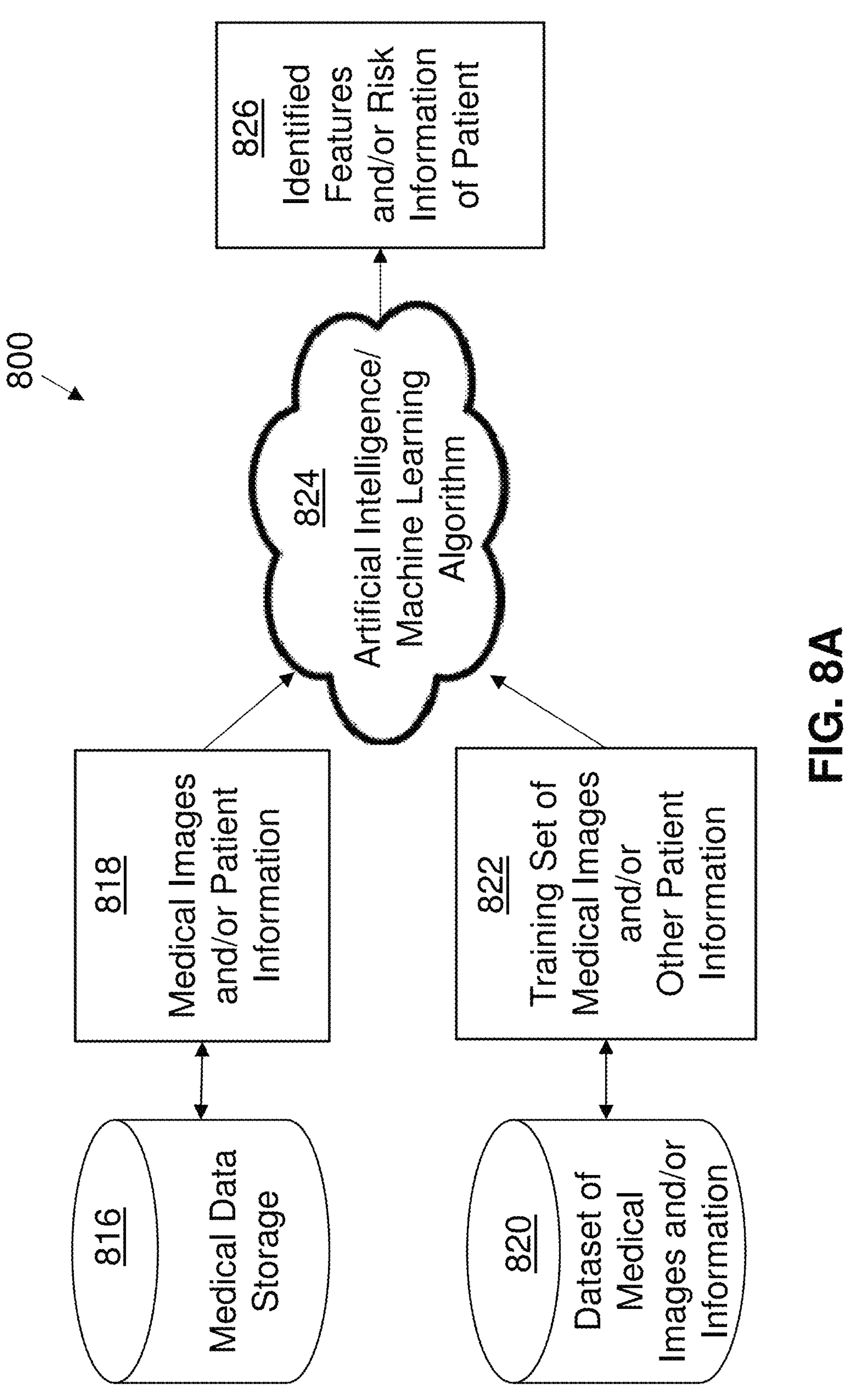
FIG. 8A is a block diagram that illustrates an example process of identifying features of medical images using artificial intelligence or machine learning.

FIG. 8A is a block diagram that illustrates an example of a system and/or process 800 (both referred to here as a "system" for ease of reference) for identifying features and/or risk information of a patient using AI/ML based on non-invasively obtained medical images of the patient and/or patient information. A current patient's medical data including images and/or patient information is first obtained and electronically stored on medical data storage 816 (e.g., cloud storage, hard disk, etc.). The system 800 obtains medical images and/or patient information 818 from the medical data storage 816 and preprocess it, if necessary, for example to re-format it as necessary for further processing. The system 800 can also obtain a training set of medical images and/or patient information 822 from a stored dataset 820 of medical images and/or information of other patients (e.g., hundreds, thousands, tens of thousands, or hundreds of thousands or more of other patients). The medical images and information of other patients can be used to train the AI/ML algorithm 824 prior to processing the medical images and/or patient information 818 of the current patient, as described in further detail in reference to FIGS. 8C and 8D. In some embodiments, the AI/ML algorithm 824 can include one or more NN's, for example, as described in reference to the example NN illustrated in FIG. 8B. The ML/AI 824 processes the medical images and/or patient information 818 of the current patient and generates outputs of identified features and/or risk information 826 of the current patient.

Figure 8B:
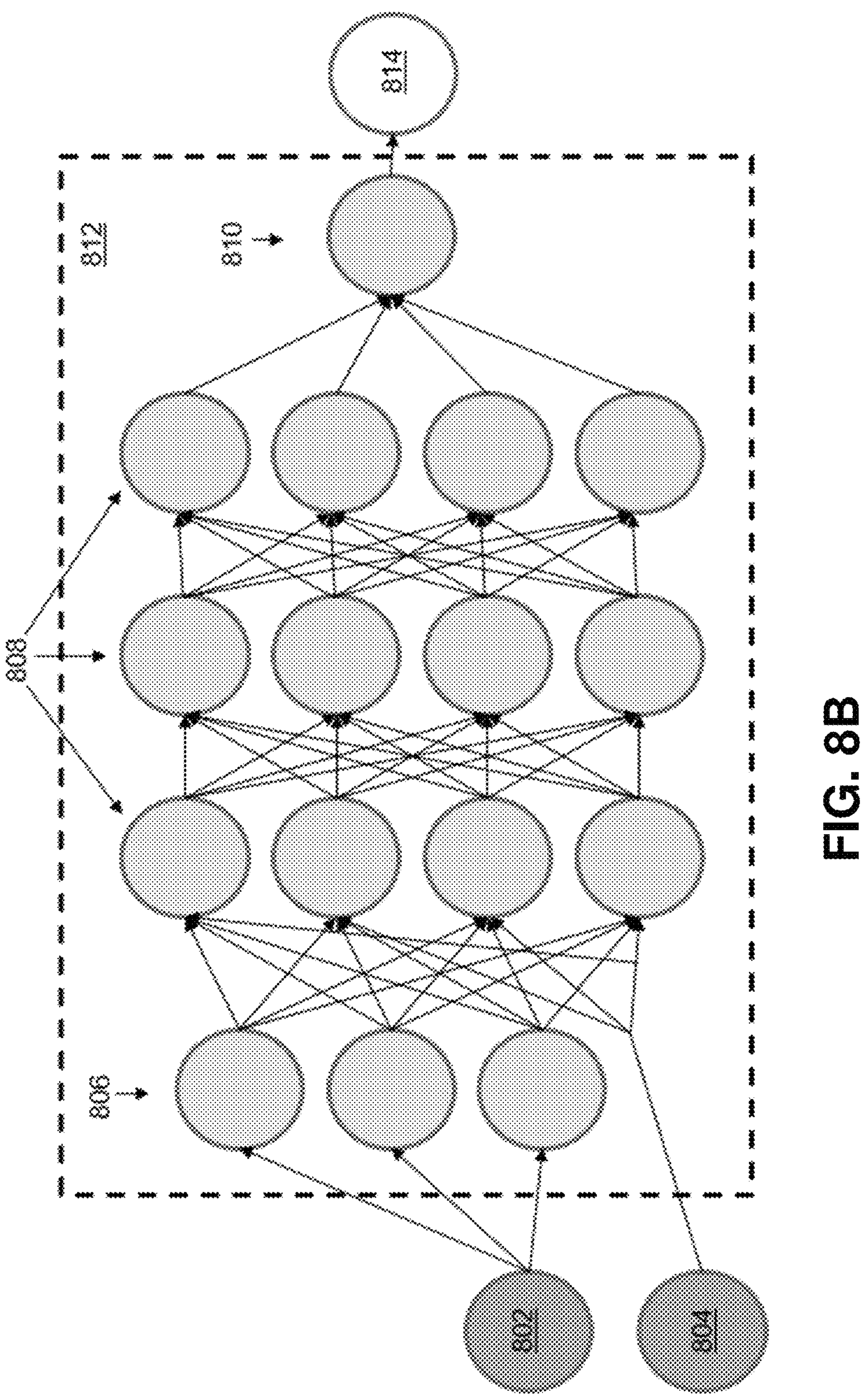
FIG. 8B is a schematic illustrating an example neural network that makes determinations about characteristics of a patient based on medical images.

FIG. 8B is a schematic illustrating an example of a NN 812 that makes determinations 814 about characteristics of a (current) patient based on inputs that include medical images 802. In some embodiments, the NN 812 can be configured to receive other inputs 804. In some embodiments, the other inputs 804 can be medical images of other patients. In some embodiments, the other inputs 804 can be medical history of other patients. In some embodiments, the other inputs 804 can be medical history of the (current) patient. The NN 812 can include an input layer 806. In some embodiments, the NN 812 can be configured to present the training pattern to the input layer 806. In some embodiments, the NN 812 can include one or more hidden layers 808. In some embodiments, the input layer 806 can provide signals to the hidden layers 808, and the hidden layers 808 can receive signals from the input layer 806. In some embodiments, the hidden layers 808 can pass signals to the output layer 810. In some embodiments, one or more hidden layers 808 may be configured as convolutional layers (comprising neurons/nodes connected by weights, the weights corresponding to the strength of the connection between neurons), pooling layers, fully connected layers and/or normalization layers. In some embodiments, the NN 812 may be configured with pooling layers that combine outputs of neuron clusters at one layer into a single neuron in the next layer. In some embodiments, max pooling and/or average pooling may be utilized. In some embodiments, max pooling may utilize the maximum value from each of a cluster of neurons at the prior layer. In some embodiments, back propagation may be utilized, and the corresponding neural network weights may be adjusted to minimize or reduce the error. In some embodiments, the loss function may comprise the Binary Cross Entropy loss function.

In some embodiments, the NN 812 can include an output layer 810. In some embodiments, the output layer 810 can receive signals from the hidden layers 808. In some embodiments, the output layer can generate determinations 814. In some embodiments, the NN 812 can make determinations 814 about characteristics of the patient. In some embodiments, the determinations 814 can include a characterized set of plaque. In some embodiments, the determinations 814 can include a patient's risk of CAD.

Figure 8C:
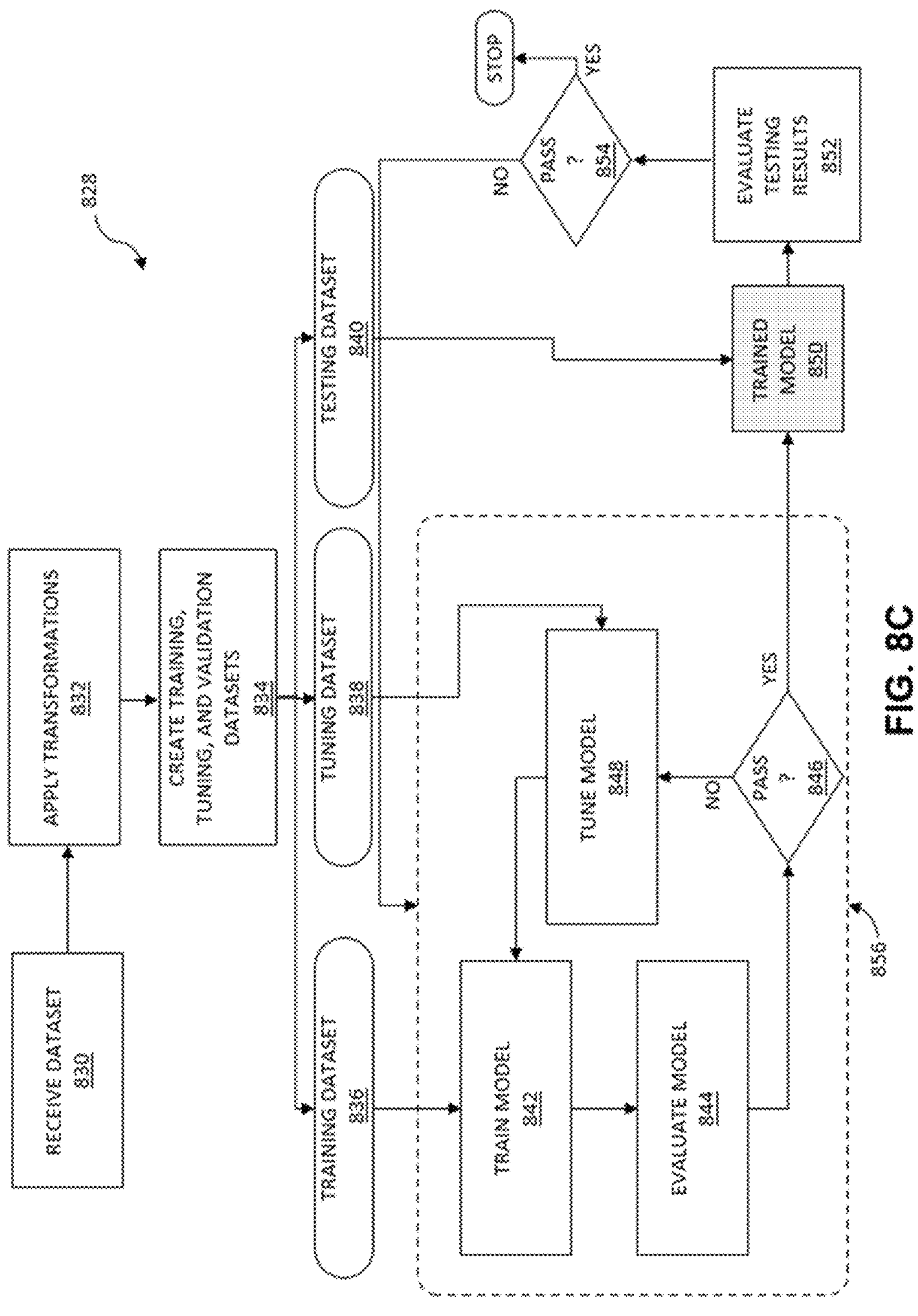
FIG. 8C depicts a flow chart for training an artificial intelligence or machine learning model according to some embodiments.

FIG. 8C depicts an example of a process in a flow diagram for training an artificial intelligence or machine learning model. The process 828 can be performed on a computing system. Various embodiments of such a process for training an AI or ML model may include additional features, and/or may exclude certain illustrated features (for example, when a transformed dataset is accessed such that "apply transformations" in block 832 does not need to be performed.)

As illustrated in the example of FIG. 8C, at block 830 the system receives a dataset that includes patient health information which can include medical images, user surveys, historical test results, genetic information, and/or other patient information (e.g., height, weight, age, etc.). The dataset can also include non-health information, for example, employment information, income information, transportation information, housing information, distances to pharmacies, and/or distances to healthcare providers.

At block 832, one or more transformations may be performed on the data. In an example, data may require transformations to conform to expected input formats to conform with expected formatting, e.g., date formatting, units (e.g., pounds vs kilograms, Celsius vs Fahrenheit, inches vs centimeters, etc.), address conventions, be of a consistent format, and the like. In some embodiments, addresses can be converted, or altered, to be of a consistent format and/or to conform to standards published by the United States Postal Service or a similar postal authority. In some embodiments, the data may undergo conversions to prepare it for use in training an AI or ML algorithm, for example, categorical data may be encoded in a particular manner. In some embodiments, nominal data may be encoded using one-hot encoding, binary encoding, feature hashing, or other suitable encoding methods. In some embodiments, ordinal data may be encoded using ordinal encoding, polynomial encoding, Helmert encoding, and so forth. In some embodiments, numerical data may be normalized, for example by scaling data to a maximum of 1 and a minimum of 0 or −1. These are merely examples, and the skilled artisan will readily appreciate that other transformations are possible.

At block 834, the system may create, from the received dataset, training, tuning, and testing/validation datasets. In some embodiments, the training dataset 836 may be used during training to determine features for forming a predictive model. In some embodiments, the tuning dataset 838 may be used to select final models and to prevent or correct overfitting that may occur during training with the training dataset 836, as the trained model should be generally applicable to a broad spectrum of patients. In some embodiments, the testing dataset 840 may be used after training and tuning to evaluate the model. For example, in some embodiments, the testing dataset 840 may be used to check if the model is overfitted to the training dataset. In some embodiments, the system, in training loop 856, may train the model at block 842 using the training dataset 836. In some embodiments, training may be conducted in a supervised, unsupervised, or partially supervised manner. At 844, in some embodiments, the system may evaluate the model according to one or more evaluation criteria. For example, in some embodiments, the evaluation may include determining how often the model determines reasonable scores for a patient's risk of CAD. At 846, in some embodiments, the system may determine if the model meets the one or more evaluation criteria. In some embodiments, if the model fails evaluation, the system may, at 848, tune the model using the tuning dataset 838, repeating the training 842 and evaluation 844 until the model passes the evaluation at 846. In some embodiments, once the model passes the evaluation at 846, the system may exit the model training loop 856. In some embodiments, the testing dataset 836 may be run through the trained model 842 and, at block 844, the system may evaluate the results. In some embodiments, if the evaluation fails, at block 846, the system may reenter training loop 856 for additional training and tuning. If the model passes, the system may stop the training process, resulting in a trained model 850. In some embodiments, the training process may be modified. For example, in some embodiments, the system may not use a tuning dataset 838. In some embodiments, the model may not use a testing dataset 840.

While described above with respect to determining risk scores for CAD, a model can be trained for use in a wide variety of problems.

Figure 8D:
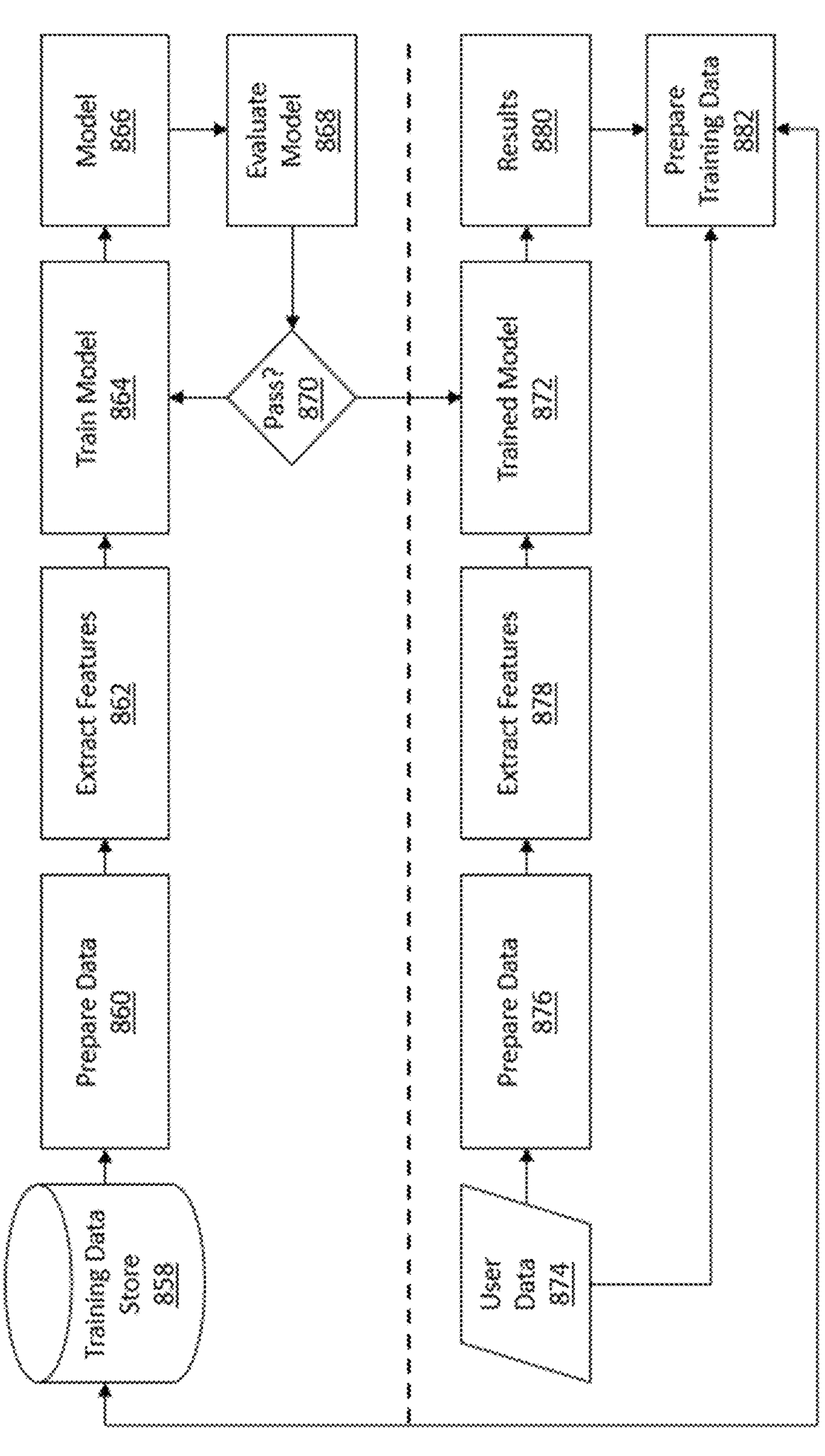
FIG. 8D illustrates an example of training and using an AI/ML model according to some embodiments.

FIG. 8D illustrates an example of a process for training and using an AI/ML model. In some embodiments, the process of FIG. 8D can be used for various purposes, e.g., to determine risk scores of CAD for a patient or to characterize plaque. In some embodiments, training data store 858 can store data for training a model. For example, in some embodiments, training data store 858 can store a patient's medical images, as well as information about patient's health, age, socioeconomic status, employment status, housing arrangements, transportation, and so forth. In some embodiments, the training data can be annotated to include information about user outcomes. For example, in some embodiments, the user outcomes can indicate whether a user had to miss work due to illness, was hospitalized, visited an emergency room, visited an urgent care facility, and so forth. In some embodiments, the training data can indicate whether a user received medication to treat an illness at home, treatments delivered at a hospital or other healthcare facility, did not receive any treatment, and so forth. At block 860, in some embodiments, a system can be configured to prepare the training data if it was not previously prepared for use in training a model. In some embodiments, as described briefly above, preparing the training data can include performing one or more normalization procedures, standardization procedures, and so forth, such as converting units (e.g., between Fahrenheit and Celsius, between inches and centimeters, between pounds and kilograms), converting dates to a standard format, converting times to a standard format, and so forth. In some embodiments, similar treatments or symptoms may be described or coded differently by different healthcare providers. In some embodiments, different providers may use different coding schemes. In some embodiments, even within a particular coding scheme, providers may select different codes to indicate similar information. In some embodiments, a large number of similar codes can lead to variances in coding. Thus, in some embodiments, a code can be changed to another related code. In some embodiments, certain codes can be excluded if they are not relevant to the issue that the model is intended to address. In some embodiments, it can be desirable to exclude certain data as additional data can consume additional computing resources and it can take longer to train a model. However, in some embodiments, exclusions may not be desirable as there can be a risk of excluding a factor that actually is relevant to the patient's risk. In some embodiments, data preparation at block 860 can include modifying or removing coding data, treatment data, and so forth. At block 862, the system can extract features from the training data and, at block 864, can train the model using the training data to produce model 866. At block 868, in some embodiments, the system can evaluate the model to determine if it passes one or more criteria. In some embodiments, at decision point 870, if the model fails, the system can perform additional training. In some embodiments, if, at decision point 870, the model passes, the system can make available trained model 872, which can be the model 872 after training is complete.

In some embodiments, the trained model 872 can be used to evaluate a particular user. The user data 874 can relate to a specific user for whom the outputs of the trained model 872 are desired. At block 876, the system can prepare the data, for example as described above in relations to the stored training data. In some embodiments, at block 878, the system can extract features from the prepared user data. In some embodiments, the system can be configured to feed the extracted features to the trained model 872 to produce results 880. The results 880 can be used to, for example, to determine a risk level associated with the user and/or to determine one or more risk sub-scores for the user.

In some embodiments, the user data 874, the results 880, and other information about the user (e.g., information about the user's outcomes after either receiving or not receiving treatment for plaque-based disease) can be used to train the model. At block 882, in some embodiments, the system can user prepare the user data 874 and the results 880 for use in training. In some embodiments, preparing the data can include, for example, anonymizing the data. For example, in some embodiments, any information about the patient's name, social security number, or other information that could personally identify the patient can be removed. In some embodiments, the system can anonymize the user data 874 in part by altering the user's birthday, for example retaining only the year the user was born (as age is often an important factor in evaluating ask) or the year and month the user was born. In some embodiments, the system can store the prepared data in training data store 858. In some embodiments, the prepared data can be stored, additionally or alternatively, in another database or data store. In some embodiments, the system can retrain the model on periodically, continuously, or whenever an operator indicates to the system that the model should be retrained. Thus, in some embodiments, the trained model 872 can evolve over time, which can result in, for example, improved risk evaluation over time as the model is trained on additional data.

Figure 9:
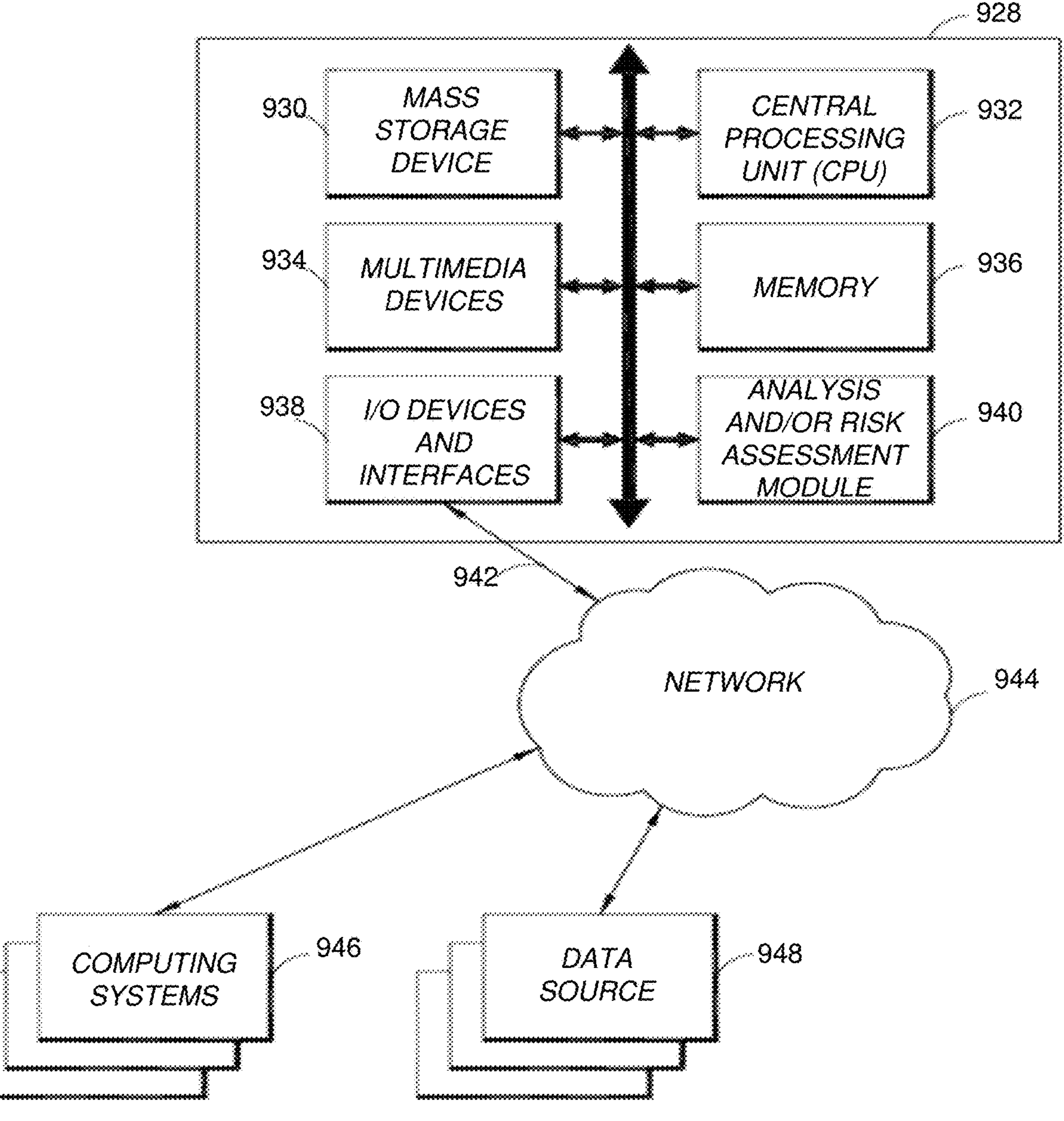
FIG. 9 is a block diagram depicting an embodiment(s) of a computer hardware system configured to run software for implementing one or more embodiments of systems, devices, and methods described herein.

In some embodiments, the systems, processes, and methods described herein are implemented using a computing system, such as the one illustrated in FIG. 9. The example computer system 928 is in communication with one or more computing systems 946 and/or one or more data sources 948 via one or more networks 944. While FIG. 9 illustrates an embodiment of a computing system 928, it is recognized that the functionality provided for in the components and modules of computer system 928 can be combined into fewer components and modules, or further separated into additional components and modules.

The computer system 928 can comprise a plaque analysis and/or risk assessment module 940 that carries out the functions, methods, acts, and/or processes described herein. The plaque analysis and/or risk assessment module 940 executed on the computer system 928 by a central processing unit 932 discussed further below.

In general the word "module," as used herein, refers to logic embodied in hardware or firmware or to a collection of software instructions, having entry and exit points. Modules are written in a program language, such as JAVA, C, or C++, or the like. Software modules can be compiled or linked into an executable program, installed in a dynamic link library, or can be written in an interpreted language such as BASIC, PERL, LAU, PHP or Python and any such languages. Software modules can be called from other modules or from themselves, and/or can be invoked in response to detected events or interruptions. Modules implemented in hardware include connected logic units such as gates and flip-flops, and/or can include programmable units, such as programmable gate arrays or processors.

Generally, the modules described herein refer to logical modules that can be combined with other modules or divided into sub-modules despite their physical organization or storage. The modules are executed by one or more computing systems, and can be stored on or within any suitable computer readable medium, or implemented in-whole or in-part within special designed hardware or firmware. Not all calculations, analysis, and/or optimization require the use of computer systems, though any of the above-described methods, calculations, processes, or analyses can be facilitated through the use of computers. Further, in some embodiments, process blocks described herein can be altered, rearranged, combined, and/or omitted.

The computer system 928 includes one or more processing units (CPU) 932, which can comprise a microprocessor. The computer system 928 further includes a physical memory 936, such as random access memory (RAM) for temporary storage of information, a read only memory (ROM) for permanent storage of information, and a mass storage device 930, such as a backing store, hard drive, rotating magnetic disks, solid state disks (SSD), flash memory, phase-change memory (PCM), 3D XPoint memory, diskette, or optical media storage device. Alternatively, the mass storage device can be implemented in an array of servers. Typically, the components of the computer system 928 are connected to the computer using a standards based bus system. The bus system can be implemented using various protocols, such as Peripheral Component Interconnect (PCI), Micro Channel, SCSI, Industrial Standard Architecture (ISA) and Extended ISA (EISA) architectures.

The computer system 928 includes one or more input/output (I/O) devices and interfaces 938, such as a keyboard, mouse, touch pad, and printer. The I/O devices and interfaces 938 can include one or more display devices, such as a monitor, which allows the visual presentation of data to a user. More particularly, a display device provides for the presentation of GUIs as application software data, and multi-media presentations, for example. The I/O devices and interfaces 938 can also provide a communications interface to various external devices. The computer system 928 can comprise one or more multi-media devices 934, such as speakers, video cards, graphics accelerators, and microphones, for example.

The computer system 928 can run on a variety of computing devices, such as a server, a Windows server, a Structure Query Language server, a Unix Server, a personal computer, a laptop computer, and so forth. In other embodiments, the computer system 928 can run on a cluster computer system, a mainframe computer system and/or other computing system suitable for controlling and/or communicating with large databases, performing high volume transaction processing, and generating reports from large databases. The computing system 928 is generally controlled and coordinated by an operating system software, such as z/OS, Windows, Linux, UNIX, BSD, PHP, SunOS, Solaris, MacOS, ICloud services or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 928 illustrated in FIG. 9 is coupled to a network 944, such as a LAN, WAN, or the Internet via a communication link 942 (wired, wireless, or a combination thereof). Network 944 communicates with various computing devices and/or other electronic devices. Network 944 is communicating with one or more computing systems 946 and one or more data sources 948. The plaque analysis and/or risk assessment module 940 can access or can be accessed by computing systems 946 and/or data sources 948 through a web-enabled user access point. Connections can be a direct physical connection, a virtual connection, and other connection type. The web-enabled user access point can comprise a browser module that uses text, graphics, audio, video, and other media to present data and to allow interaction with data via the network 944.

The output module can be implemented as a combination of an all-points addressable display such as a cathode ray tube (CRT), a liquid crystal display (LCD), a plasma display, or other types and/or combinations of displays. The output module can be implemented to communicate with input devices 938 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module can communicate with a set of input and output devices to receive signals from the user.

The computing system 928 can include one or more internal and/or external data sources (for example, data sources 948). In some embodiments, one or more of the data repositories and the data sources described above can be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 928 can also access one or more databases 948. The databases 948 can be stored in a database or data repository. The computer system 928 can access the one or more databases 948 through a network 944 or can directly access the database or data repository through I/O devices and interfaces 938. The data repository storing the one or more databases 948 can reside within the computer system 928.

In some embodiments including any of the embodiments disclosed herein (above or below) one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

Cardiovascular Risk Determination Based on Image-Based Analysis of Cardiovascular Structures Disclosed herein are systems, devices, and methods for cardiovascular risk determination based on image-based analysis of cardiovascular structures. In particular, in some embodiments, the systems, devices, and methods described herein are related to facilitating determination of a cardiovascular risk assessment of a subject based at least in part on image-based analysis of cardiovascular structural dimensions. For example, in some embodiments, the systems, devices, and methods are related to accessing a medical image comprising a representation of a myocardium and analyzing the medical image to identify one or more cardiovascular structures. The cardiovascular structures can be identified based at least in part on image segmentation. The one or more cardiovascular structures can include one or more of aorta, superior vena cava, pulmonary artery, pulmonary veins, right atrium, right ventricle, left atrium, left ventricle, inferior vena cava, left coronary artery, circumflex artery, left anterior descending artery, right coronary artery, pericardium, septum, pulmonary valve, tricuspid valve, aortic valve, or mitral valve, among others cardiovascular structures. In some embodiments, the systems, devices, and methods are further related to quantifying one or more dimensions of the identified cardiovascular structures, including, for example, mass, volume, length, area, or diameter, and comparing the quantified dimensions of the identified cardiovascular structures with one or more reference dimensions. In some embodiments, the systems, devices, and methods are related to causing generation of a graphical display of the comparison of the one or more quantified dimensions, wherein the graphical display of the comparison is configured to be used to determine a cardiovascular risk assessment of the subject.

In some embodiments, the systems, devices, and methods described herein relate to cardiovascular risk determination based on image-based analysis of cardiovascular structures. Cardiovascular structures may refer to structures within the cardiovascular or circulatory system. Specifically, cardiovascular structures may include the aorta, superior vena cava, pulmonary artery, pulmonary veins, right atrium, right ventricle, left atrium, left ventricle, inferior vena cava, left coronary artery, circumflex artery, left anterior descending artery, right coronary artery, pericardium, septum, pulmonary valve, tricuspid valve, aortic valve, or mitral valve, among other structures. Dimensions of said cardiovascular structures may be indicative of a healthy or unhealthy cardiovascular system. For example, a subject with enlarged structures may be at higher risk of heart failure. Therefore, it would be advantageous to quantify the dimensions of various cardiovascular structures in determining the risk of disease. It would be further advantageous to compare the dimensions of a subject's cardiovascular structures with a database of other dimensions, for example, with a database of other dimensions of related structures sampled from a large populations of patient's with differing levels of cardiovascular disease states.

Figure 10:
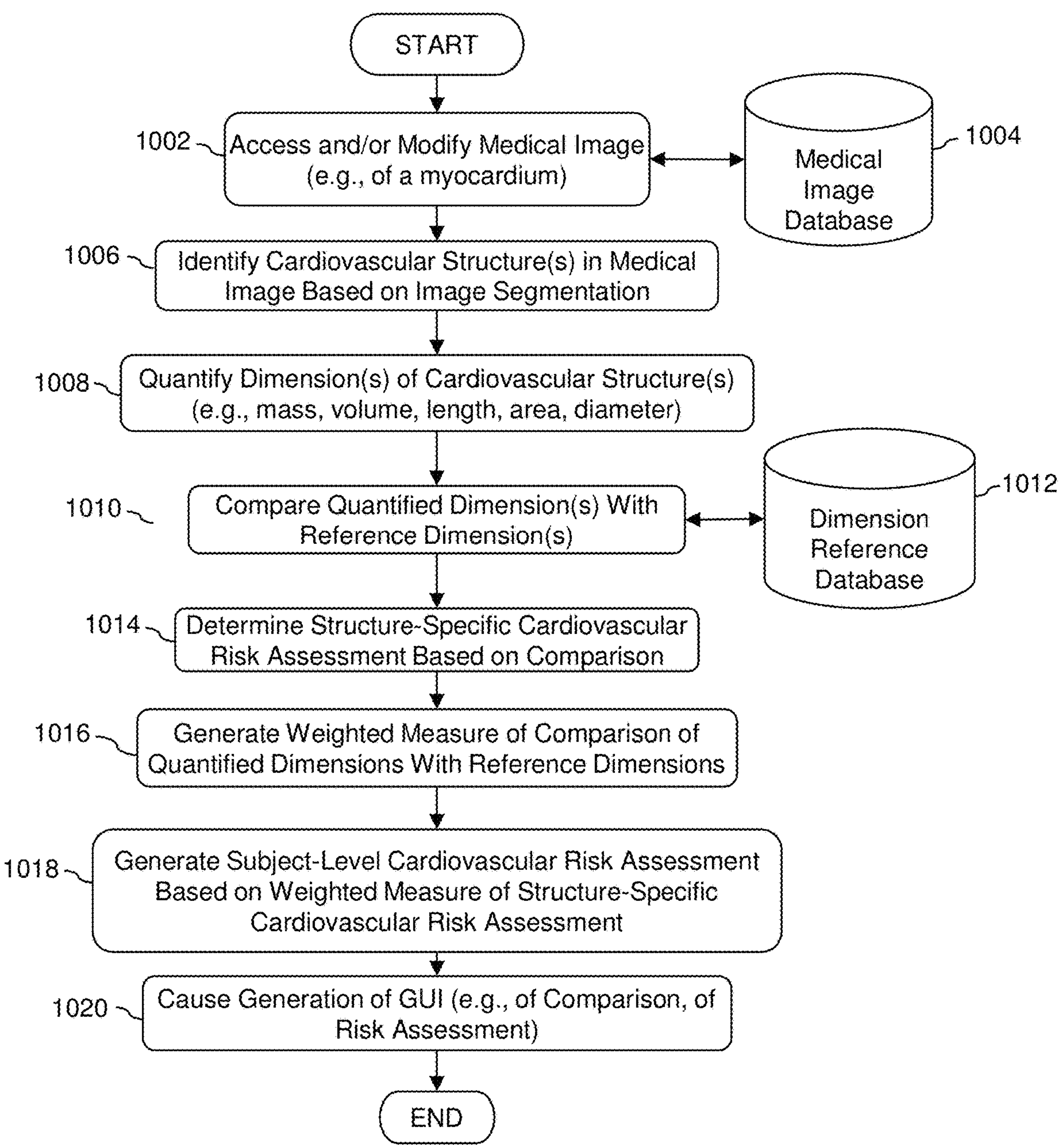
FIG. 10 is a flowchart illustrating an example embodiment(s) of systems, devices, and methods for cardiovascular risk determination based on image-based analysis of cardiovascular structures.

FIG. 10 is a flowchart illustrating an example embodiment(s) of systems, devices, and methods for facilitating determination of a cardiovascular risk assessment of a subject based at least in part on image-based analysis of cardiovascular structural dimensions. In some embodiments, at block 1002, the systems can be configured to access a medical image of a subject, the medical image comprising a representation of a myocardium of the subject, although images of other portions or regions of the patient are also useable. In some embodiments, the medical image can be stored in a medical image database 1004. In some embodiments, the medical image database 1004 can be locally accessible by the system and/or can be located remotely and accessible through a network connection. In some embodiments, the medical image is obtained using computed tomography (CT). In some embodiments, the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

In some embodiments, at block 1006, the system can be configured to analyze the medical image to identify one or more cardiovascular structures in the image. In some instances, the identification is based at least in part on image segmentation although other image processing techniques such as various other computer vision or machine learning techniques may also be used. In some embodiments, the one or more cardiovascular structures can include one or more of aorta, superior vena cava, pulmonary artery, pulmonary veins, right atrium, right ventricle, left atrium, left ventricle, inferior vena cava, left coronary artery, circumflex artery, left anterior descending artery, right coronary artery, pericardium, septum, pulmonary valve, tricuspid valve, aortic valve, or mitral valve, or other structures. In some embodiments, the image segmentation is performed using one or more of an artificial intelligence (AI) or machine learning (ML) algorithm.

In some embodiments, at block 1008, the system can be configured to quantify one or more dimensions of the one or more identified cardiovascular structures, the one or more dimensions comprising one or more of mass, volume, length, area, or diameter. For example, one or more of an artificial intelligence (AI) or machine learning (ML) algorithm that has been trained using one or more data sets with labeled dimensions and/or other image recognition and quantification techniques can be used. The quantified dimensions can be stored, for example, in a database associated with the patient.

In some embodiments, at block 1110, the system can be configured to compare the one or more quantified dimensions of the one or more identified cardiovascular structures with one or more reference dimensions of one or more cardiovascular structures generated from a plurality of other subjects, the plurality of other subjects comprising a population with no known cardiovascular disease and/or with differing levels on known cardiovascular disease. In some embodiments, reference dimensions may be stored in a dimension reference database 1012.

At block 1014, the system may be configured to determine a structure-specific cardiovascular risk assessment for the one or more identified cardiovascular structures based at least in part on the comparison of the one or more quantified dimensions of the one or more identified cardiovascular structures with the one or more reference dimensions of one or more cardiovascular structures generated from the plurality of other subjects. For example, upon comparison of the dimensions of the patient with the reference dimensions of the reference database, the system can determine whether the patient is likely to experience cardiovascular disease. In making this comparison, various other patient characteristics can also be considered, such as age, weight, height, sex, family history, diet, exercise habits, and others.

In some embodiments, the structure-specific cardiovascular risk assessment is determined as one or more of low, medium, or high based at least in part on predetermined thresholds of differences between the one or more quantified dimensions of the one or more identified cardiovascular structures and the one or more reference dimensions of one or more cardiovascular structures generated from the plurality of other subjects. In some embodiments, the structure-specific cardiovascular risk assessment is determined as a percentile based at least in part on differences between the one or more quantified dimensions of the one or more identified cardiovascular structures and the one or more reference dimensions of one or more cardiovascular structures generated from the plurality of other subjects.

In some embodiments, the system may be further configured to generate one or more proposed treatments for the subject based at least in part on the structure-specific cardiovascular risk assessment for the one or more identified cardiovascular structures.

At block 1016, the system may be configured to generate a weighted measure of the comparison of the one or more quantified dimensions of the one or more identified cardiovascular structures with the one or more reference dimensions of one or more cardiovascular structures generated from the plurality of other subjects. In some embodiments, the weighted measure is generated by assigning a different weight to one or more comparisons of the one or more quantified dimensions of the one or more identified cardiovascular structures with the one or more reference dimensions of one or more cardiovascular structures generated from the plurality of other subjects, wherein the weight is assigned based at least in part on a predetermined risk factor for the one or more identified cardiovascular structures. In some embodiments, the weighted measure is generated using one or more of an artificial intelligence (AI) or machine learning (ML) algorithm configured to assign a weight to one or more comparisons of the one or more quantified dimensions of the one or more identified cardiovascular structures with the one or more reference dimensions of one or more cardiovascular structures generated from the plurality of other subjects. The weighted measure can include consideration of various other patient characteristics can also be considered, such as age, weight, height, sex, family history, diet, exercise habits, and others.

At block 1018, the system may be configured to generate a subject-level cardiovascular risk assessment by generating a weighted measure of the determined structure-specific cardiovascular risk assessment for the one or more identified cardiovascular structures. In some embodiments, the subject-level cardiovascular risk assessment is determined as one or more of low, medium, or high based at least in part on predetermined thresholds of differences between the one or more quantified dimensions of the one or more identified cardiovascular structures and the one or more reference dimensions of one or more cardiovascular structures generated from the plurality of other subjects. In some embodiments, the subject-level cardiovascular risk assessment is determined as a percentile based at least in part on differences between the one or more quantified dimensions of the one or more identified cardiovascular structures and the one or more reference dimensions of one or more cardiovascular structures generated from the plurality of other subjects. In some embodiments, the weighted measure is generated by assigning a different weight to one or more of the determined structure-specific cardiovascular risk assessment for the one or more identified cardiovascular structures, wherein the weight is assigned based at least in part on a predetermined risk factor for the one or more identified cardiovascular structures. In some embodiments, the weighted measure is generated using an artificial intelligence (AI) or machine learning (ML) algorithm configured to assign a weight to one or more of the determined structure-specific cardiovascular risk assessment for the one or more identified cardiovascular structures. The subject-level risk can be determined based in part on various other patient characteristics can also be considered, such as age, weight, height, sex, family history, diet, exercise habits, and others.

In some embodiments, the system may be further configured to generate one or more proposed treatments for the subject based at least in part on the subject-level cardiovascular risk assessment.

In some embodiments, at block 1020, the system can cause generation of a graphical display. In some embodiments, the system can be configured to cause generation of a graphical display of the comparison of the one or more quantified dimensions of the one or more identified cardiovascular structures with the one or more reference dimensions of one or more cardiovascular structures generated from the plurality of other subjects, wherein the graphical display of the comparison is configured to be used to determine a cardiovascular risk assessment of the subject.

In some embodiments, the graphical display comprises the determined structure-specific cardiovascular risk assessment for the one or more identified cardiovascular structures. In some embodiments, the graphical display comprises color-coding of the one or more identified cardiovascular structures, wherein the color-coding is assigned based at least in part on the determined structure-specific cardiovascular risk assessment for the one or more identified cardiovascular structures.

In some embodiments, the graphical display comprises the generated subject-level cardiovascular risk assessment.

The computer system 902 of FIG. 9, and in some instances, the analysis and/or risk assessment module 940, can be configured to carry out the functions, methods, acts, and/or processes for cardiovascular risk determination based on image-based analysis of cardiovascular structures described herein, such as those described above with reference to FIG. 10

The following are non-limiting examples of certain embodiments of systems and methods for cardiovascular risk determination based on image-based analysis of cardiovascular structures. Other embodiments may include one or more other features, or different features, that are discussed herein.

Embodiment 1: A computer-implemented method of facilitating determination of a cardiovascular risk assessment of a subject based at least in part on image-based analysis of cardiovascular structural dimensions, the method comprising: accessing, by a computer system, a medical image of a subject, the medical image comprising a representation of a myocardium of the subject; analyzing, by the computer system, the medical image to identify one or more cardiovascular structures based at least in part on image segmentation, the one or more cardiovascular structures comprising one or more of aorta, superior vena cava, pulmonary artery, pulmonary veins, right atrium, right ventricle, left atrium, left ventricle, inferior vena cava, left coronary artery, circumflex artery, left anterior descending artery, right coronary artery, pericardium, septum, pulmonary valve, tricuspid valve, aortic valve, or mitral valve; quantifying, by the computer system, one or more dimensions of the one or more identified cardiovascular structures, the one or more dimensions comprising one or more of mass, volume, length, area, or diameter; comparing, by the computer system, the one or more quantified dimensions of the one or more identified cardiovascular structures with one or more reference dimensions of one or more cardiovascular structures generated from a plurality of other subjects, the plurality of other subjects comprising a population with no known cardiovascular disease; causing, by the computer system, generation of a graphical display of the comparison of the one or more quantified dimensions of the one or more identified cardiovascular structures with the one or more reference dimensions of one or more cardiovascular structures generated from the plurality of other subjects, wherein the graphical display of the comparison is configured to be used to determine a cardiovascular risk assessment of the subject, wherein the computer system comprises a computer processor and an electronic storage medium.

Embodiment 2: The computer-implemented method of Embodiment 1, further comprising: determining, by the computer system, a structure-specific cardiovascular risk assessment for the one or more identified cardiovascular structures based at least in part on the comparison of the one or more quantified dimensions of the one or more identified cardiovascular structures with the one or more reference dimensions of one or more cardiovascular structures generated from the plurality of other subjects, wherein the graphical display comprises the determined structure-specific cardiovascular risk assessment for the one or more identified cardiovascular structures.

Embodiment 3: The computer-implemented method of Embodiment 2, wherein the structure-specific cardiovascular risk assessment is determined as one or more of low, medium, or high based at least in part on predetermined thresholds of differences between the one or more quantified dimensions of the one or more identified cardiovascular structures and the one or more reference dimensions of one or more cardiovascular structures generated from the plurality of other subjects.

Embodiment 4: The computer-implemented method of Embodiment 2, wherein the structure-specific cardiovascular risk assessment is determined as a percentile based at least in part on differences between the one or more quantified dimensions of the one or more identified cardiovascular structures and the one or more reference dimensions of one or more cardiovascular structures generated from the plurality of other subjects.

Embodiment 5: The computer-implemented method of Embodiment 2, wherein the graphical display comprises color-coding of the one or more identified cardiovascular structures, wherein the color-coding is assigned based at least in part on the determined structure-specific cardiovascular risk assessment for the one or more identified cardiovascular structures.

Embodiment 6: The computer-implemented method of Embodiment 2, further comprising generating, by the computer system, one or more proposed treatments for the subject based at least in part on the structure-specific cardiovascular risk assessment for the one or more identified cardiovascular structures.

Embodiment 7: The computer-implemented method of Embodiment 1, further comprising: determining, by the computer system, a structure-specific cardiovascular risk assessment for the one or more identified cardiovascular structures based at least in part on the comparison of the one or more quantified dimensions of the one or more identified cardiovascular structures with the one or more reference dimensions of one or more cardiovascular structures generated from the plurality of other subjects; and generating, by the computer system, a subject-level cardiovascular risk assessment by generating a weighted measure of the determined structure-specific cardiovascular risk assessment for the one or more identified cardiovascular structures, wherein the graphical display comprises the generated subject-level cardiovascular risk assessment.

Embodiment 8: The computer-implemented method of Embodiment 7, wherein the subject-level cardiovascular risk assessment is determined as one or more of low, medium, or high based at least in part on predetermined thresholds of differences between the one or more quantified dimensions of the one or more identified cardiovascular structures and the one or more reference dimensions of one or more cardiovascular structures generated from the plurality of other subjects.

Embodiment 9: The computer-implemented method of Embodiment 7, wherein the subject-level cardiovascular risk assessment is determined as a percentile based at least in part on differences between the one or more quantified dimensions of the one or more identified cardiovascular structures and the one or more reference dimensions of one or more cardiovascular structures generated from the plurality of other subjects.

Embodiment 10: The computer-implemented method of Embodiment 7, wherein the weighted measure is generated by assigning a different weight to one or more of the determined structure-specific cardiovascular risk assessment for the one or more identified cardiovascular structures, wherein the weight is assigned based at least in part on a predetermined risk factor for the one or more identified cardiovascular structures.

Embodiment 11: The computer-implemented method of Embodiment 7, wherein the weighted measure is generated using an artificial intelligence (AI) or machine learning (ML) algorithm configured to assign a weight to one or more of the determined structure-specific cardiovascular risk assessment for the one or more identified cardiovascular structures.

Embodiment 12: The computer-implemented method of Embodiment 7, further comprising generating, by the computer system, one or more proposed treatments for the subject based at least in part on the subject-level cardiovascular risk assessment.

Embodiment 13: The computer-implemented method of Embodiment 1, further comprising: generating, by the computer system, a weighted measure of the comparison of the one or more quantified dimensions of the one or more identified cardiovascular structures with the one or more reference dimensions of one or more cardiovascular structures generated from the plurality of other subjects.

Embodiment 14: The computer-implemented method of Embodiment 13, wherein the weighted measure is generated by assigning a different weight to one or more comparisons of the one or more quantified dimensions of the one or more identified cardiovascular structures with the one or more reference dimensions of one or more cardiovascular structures generated from the plurality of other subjects, wherein the weight is assigned based at least in part on a predetermined risk factor for the one or more identified cardiovascular structures.

Embodiment 15: The computer-implemented method of Embodiment 13, wherein the weighted measure is generated using one or more of an artificial intelligence (AI) or machine learning (ML) algorithm configured to assign a weight to one or more comparisons of the one or more quantified dimensions of the one or more identified cardiovascular structures with the one or more reference dimensions of one or more cardiovascular structures generated from the plurality of other subjects.

Embodiment 16: The computer-implemented method of Embodiment 13, further comprising: generating, by the computer system, a subject-level cardiovascular risk assessment based at least in part on the generated weighted measure of the comparison of the one or more quantified dimensions of the one or more identified cardiovascular structures with the one or more reference dimensions of one or more cardiovascular structures generated from the plurality of other subjects, wherein the graphical display comprises the generated subject-level cardiovascular risk assessment.

Embodiment 17: The computer-implemented method of Embodiment 16, wherein the subject-level cardiovascular risk assessment is determined as one or more of low, medium, or high based at least in part on predetermined thresholds of the generated weighted measure of the comparison of the one or more quantified dimensions of the one or more identified cardiovascular structures with the one or more reference dimensions of one or more cardiovascular structures generated from the plurality of other subjects.

Embodiment 18: The computer-implemented method of Embodiment 16, wherein the subject-level cardiovascular risk assessment is determined as a percentile based at least in part on the generated weighted measure of the comparison of the one or more quantified dimensions of the one or more identified cardiovascular structures with the one or more reference dimensions of one or more cardiovascular structures generated from the plurality of other subjects.

Embodiment 19: The computer-implemented method of Embodiment 16, further comprising generating, by the computer system, one or more proposed treatments for the subject based at least in part on the subject-level cardiovascular risk assessment.

Embodiment 20: The computer-implemented method of Embodiment 1, wherein the image segmentation is performed using one or more of an artificial intelligence (AI) or machine learning (ML) algorithm.

Embodiment 21: The computer-implemented method of Embodiment 1, wherein the medical image is obtained using computed tomography (CT).

Embodiment 22: The computer-implemented method of Embodiment 1, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 23: A system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a medical image of a subject, the medical image comprising a representation of a myocardium of the subject; analyze the medical image to identify one or more cardiovascular structures based at least in part on image segmentation, the one or more cardiovascular structures comprising one or more of aorta, superior vena cava, pulmonary artery, pulmonary veins, right atrium, right ventricle, left atrium, left ventricle, inferior vena cava, left coronary artery, circumflex artery, left anterior descending artery, right coronary artery, pericardium, septum, pulmonary valve, tricuspid valve, aortic valve, or mitral valve; quantify one or more dimensions of the one or more identified cardiovascular structures, the one or more dimensions comprising one or more of mass, volume, length, area, or diameter; compare the one or more quantified dimensions of the one or more identified cardiovascular structures with one or more reference dimensions of one or more cardiovascular structures generated from a plurality of other subjects, the plurality of other subjects comprising a population with no known cardiovascular disease; cause generation of a graphical display of the comparison of the one or more quantified dimensions of the one or more identified cardiovascular structures with the one or more reference dimensions of one or more cardiovascular structures generated from the plurality of other subjects, wherein the graphical display of the comparison is configured to be used to determine a cardiovascular risk assessment of the subject.

Embodiment 24: The system of Embodiment 23, wherein the one or more hardware processors are further configured to: determine a structure-specific cardiovascular risk assessment for the one or more identified cardiovascular structures based at least in part on the comparison of the one or more quantified dimensions of the one or more identified cardiovascular structures with the one or more reference dimensions of one or more cardiovascular structures generated from the plurality of other subjects, wherein the graphical display comprises the determined structure-specific cardiovascular risk assessment for the one or more identified cardiovascular structures.

Embodiment 25: The system of Embodiment 24, wherein the structure-specific cardiovascular risk assessment is determined as one or more of low, medium, or high based at least in part on predetermined thresholds of differences between the one or more quantified dimensions of the one or more identified cardiovascular structures and the one or more reference dimensions of one or more cardiovascular structures generated from the plurality of other subjects.

Embodiment 26: The system of Embodiment 24, wherein the structure-specific cardiovascular risk assessment is determined as a percentile based at least in part on differences between the one or more quantified dimensions of the one or more identified cardiovascular structures and the one or more reference dimensions of one or more cardiovascular structures generated from the plurality of other subjects.

Embodiment 27: The system of Embodiment 24, wherein the graphical display comprises color-coding of the one or more identified cardiovascular structures, wherein the color-coding is assigned based at least in part on the determined structure-specific cardiovascular risk assessment for the one or more identified cardiovascular structures.

Embodiment 28: The system of Embodiment 24, wherein the one or more hardware processors are further configured to generate one or more proposed treatments for the subject based at least in part on the structure-specific cardiovascular risk assessment for the one or more identified cardiovascular structures.

Embodiment 29: The system of Embodiment 23, wherein the one or more hardware processors are further configured to: determine a structure-specific cardiovascular risk assessment for the one or more identified cardiovascular structures based at least in part on the comparison of the one or more quantified dimensions of the one or more identified cardiovascular structures with the one or more reference dimensions of one or more cardiovascular structures generated from the plurality of other subjects; and generate a subject-level cardiovascular risk assessment by generating a weighted measure of the determined structure-specific cardiovascular risk assessment for the one or more identified cardiovascular structures, wherein the graphical display comprises the generated subject-level cardiovascular risk assessment.

Embodiment 30: The system of Embodiment 29, wherein the subject-level cardiovascular risk assessment is determined as one or more of low, medium, or high based at least in part on predetermined thresholds of differences between the one or more quantified dimensions of the one or more identified cardiovascular structures and the one or more reference dimensions of one or more cardiovascular structures generated from the plurality of other subjects.

Embodiment 31: The system of Embodiment 29, wherein the subject-level cardiovascular risk assessment is determined as a percentile based at least in part on differences between the one or more quantified dimensions of the one or more identified cardiovascular structures and the one or more reference dimensions of one or more cardiovascular structures generated from the plurality of other subjects.

Embodiment 32: The system of Embodiment 29, wherein the weighted measure is generated by assigning a different weight to one or more of the determined structure-specific cardiovascular risk assessment for the one or more identified cardiovascular structures, wherein the weight is assigned based at least in part on a predetermined risk factor for the one or more identified cardiovascular structures.

Embodiment 33: The system of Embodiment 29, wherein the weighted measure is generated using an artificial intelligence (AI) or machine learning (ML) algorithm configured to assign a weight to one or more of the determined structure-specific cardiovascular risk assessment for the one or more identified cardiovascular structures.

Embodiment 34: The system of Embodiment 29, wherein the one or more hardware processors are further configured to generate one or more proposed treatments for the subject based at least in part on the subject-level cardiovascular risk assessment.

Embodiment 35: The system of Embodiment 23, wherein the one or more hardware processors are further configured to: generate a weighted measure of the comparison of the one or more quantified dimensions of the one or more identified cardiovascular structures with the one or more reference dimensions of one or more cardiovascular structures generated from the plurality of other subjects.

Embodiment 36: The computer-implemented method of Embodiment 35, wherein the weighted measure is generated by assigning a different weight to one or more comparisons of the one or more quantified dimensions of the one or more identified cardiovascular structures with the one or more reference dimensions of one or more cardiovascular structures generated from the plurality of other subjects, wherein the weight is assigned based at least in part on a predetermined risk factor for the one or more identified cardiovascular structures.

Embodiment 37: The computer-implemented method of Embodiment 35, wherein the weighted measure is generated using one or more of an artificial intelligence (AI) or machine learning (ML) algorithm configured to assign a weight to one or more comparisons of the one or more quantified dimensions of the one or more identified cardiovascular structures with the one or more reference dimensions of one or more cardiovascular structures generated from the plurality of other subjects.

Embodiment 38: The computer-implemented method of Embodiment 35, wherein the one or more hardware processors are further configured to: generate a subject-level cardiovascular risk assessment based at least in part on the generated weighted measure of the comparison of the one or more quantified dimensions of the one or more identified cardiovascular structures with the one or more reference dimensions of one or more cardiovascular structures generated from the plurality of other subjects, wherein the graphical display comprises the generated subject-level cardiovascular risk assessment.

Embodiment 39: The system of Embodiment 38, wherein the subject-level cardiovascular risk assessment is determined as one or more of low, medium, or high based at least in part on predetermined thresholds of the generated weighted measure of the comparison of the one or more quantified dimensions of the one or more identified cardiovascular structures with the one or more reference dimensions of one or more cardiovascular structures generated from the plurality of other subjects.

Embodiment 40: The system of Embodiment 38, wherein the subject-level cardiovascular risk assessment is determined as a percentile based at least in part on the generated weighted measure of the comparison of the one or more quantified dimensions of the one or more identified cardiovascular structures with the one or more reference dimensions of one or more cardiovascular structures generated from the plurality of other subjects.

Embodiment 41: The system of Embodiment 38, wherein the one or more hardware processors are further configured to: generate one or more proposed treatments for the subject based at least in part on the subject-level cardiovascular risk assessment.

Embodiment 42: The system of Embodiment 23, wherein the image segmentation is performed using one or more of an artificial intelligence (AI) or machine learning (ML) algorithm.

Embodiment 43: The system of Embodiment 23, wherein the medical image is obtained using computed tomography (CT).

Embodiment 44: The system of Embodiment 23, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 45: A non-transitory computer readable medium configured for facilitating determination of a cardiovascular risk assessment of a subject based at least in part on image-based analysis of cardiovascular structural dimensions, the computer readable medium having program instructions for causing a hardware processor to perform a method of: accessing a medical image of a subject, the medical image comprising a representation of a myocardium of the subject; analyzing the medical image to identify one or more cardiovascular structures based at least in part on image segmentation, the one or more cardiovascular structures comprising one or more of aorta, superior vena cava, pulmonary artery, pulmonary veins, right atrium, right ventricle, left atrium, left ventricle, inferior vena cava, left coronary artery, circumflex artery, left anterior descending artery, right coronary artery, pericardium, septum, pulmonary valve, tricuspid valve, aortic valve, or mitral valve; quantifying one or more dimensions of the one or more identified cardiovascular structures, the one or more dimensions comprising one or more of mass, volume, length, area, or diameter; comparing the one or more quantified dimensions of the one or more identified cardiovascular structures with one or more reference dimensions of one or more cardiovascular structures generated from a plurality of other subjects, the plurality of other subjects comprising a population with no known cardiovascular disease; causing generation of a graphical display of the comparison of the one or more quantified dimensions of the one or more identified cardiovascular structures with the one or more reference dimensions of one or more cardiovascular structures generated from the plurality of other subjects, wherein the graphical display of the comparison is configured to be used to determine a cardiovascular risk assessment of the subject.

Embodiment 46: The non-transitory computer readable medium of Embodiment 45, wherein the method performed by the hardware processor further comprises: determining a structure-specific cardiovascular risk assessment for the one or more identified cardiovascular structures based at least in part on the comparison of the one or more quantified dimensions of the one or more identified cardiovascular structures with the one or more reference dimensions of one or more cardiovascular structures generated from the plurality of other subjects, wherein the graphical display comprises the determined structure-specific cardiovascular risk assessment for the one or more identified cardiovascular structures.

Embodiment 47: The non-transitory computer readable medium of Embodiment 46, wherein the structure-specific cardiovascular risk assessment is determined as one or more of low, medium, or high based at least in part on predetermined thresholds of differences between the one or more quantified dimensions of the one or more identified cardiovascular structures and the one or more reference dimensions of one or more cardiovascular structures generated from the plurality of other subjects.

Embodiment 48: The non-transitory computer readable medium of Embodiment 46, wherein the structure-specific cardiovascular risk assessment is determined as a percentile based at least in part on differences between the one or more quantified dimensions of the one or more identified cardiovascular structures and the one or more reference dimensions of one or more cardiovascular structures generated from the plurality of other subjects.

Embodiment 49: The non-transitory computer readable medium of Embodiment 46, wherein the graphical display comprises color-coding of the one or more identified cardiovascular structures, wherein the color-coding is assigned based at least in part on the determined structure-specific cardiovascular risk assessment for the one or more identified cardiovascular structures.

Embodiment 50: The non-transitory computer readable medium of Embodiment 46, wherein the method performed by the hardware processor further comprises generating one or more proposed treatments for the subject based at least in part on the structure-specific cardiovascular risk assessment for the one or more identified cardiovascular structures.

Embodiment 51: The non-transitory computer readable medium of Embodiment 45, wherein the method performed by the hardware processor further comprises: determining a structure-specific cardiovascular risk assessment for the one or more identified cardiovascular structures based at least in part on the comparison of the one or more quantified dimensions of the one or more identified cardiovascular structures with the one or more reference dimensions of one or more cardiovascular structures generated from the plurality of other subjects; and generating a subject-level cardiovascular risk assessment by generating a weighted measure of the determined structure-specific cardiovascular risk assessment for the one or more identified cardiovascular structures, wherein the graphical display comprises the generated subject-level cardiovascular risk assessment.

Embodiment 52: The non-transitory computer readable medium of Embodiment 51, wherein the subject-level cardiovascular risk assessment is determined as one or more of low, medium, or high based at least in part on predetermined thresholds of differences between the one or more quantified dimensions of the one or more identified cardiovascular structures and the one or more reference dimensions of one or more cardiovascular structures generated from the plurality of other subjects.

Embodiment 53: The non-transitory computer readable medium of Embodiment 51, wherein the subject-level cardiovascular risk assessment is determined as a percentile based at least in part on differences between the one or more quantified dimensions of the one or more identified cardiovascular structures and the one or more reference dimensions of one or more cardiovascular structures generated from the plurality of other subjects.

Embodiment 54: The non-transitory computer readable medium of Embodiment 51, wherein the weighted measure is generated by assigning a different weight to one or more of the determined structure-specific cardiovascular risk assessment for the one or more identified cardiovascular structures, wherein the weight is assigned based at least in part on a predetermined risk factor for the one or more identified cardiovascular structures.

Embodiment 55: The non-transitory computer readable medium of Embodiment 51, wherein the weighted measure is generated using an artificial intelligence (AI) or machine learning (ML) algorithm configured to assign a weight to one or more of the determined structure-specific cardiovascular risk assessment for the one or more identified cardiovascular structures.

Embodiment 56: The non-transitory computer readable medium of Embodiment 51, wherein the method performed by the hardware processor further comprises generating one or more proposed treatments for the subject based at least in part on the subject-level cardiovascular risk assessment.

Embodiment 57: The non-transitory computer readable medium of Embodiment 45, wherein the method performed by the hardware processor further comprises:

generating a weighted measure of the comparison of the one or more quantified dimensions of the one or more identified cardiovascular structures with the one or more reference dimensions of one or more cardiovascular structures generated from the plurality of other subjects.

Embodiment 58: The non-transitory computer readable medium of Embodiment 57, wherein the weighted measure is generated by assigning a different weight to one or more comparisons of the one or more quantified dimensions of the one or more identified cardiovascular structures with the one or more reference dimensions of one or more cardiovascular structures generated from the plurality of other subjects, wherein the weight is assigned based at least in part on a predetermined risk factor for the one or more identified cardiovascular structures.

Embodiment 59: The non-transitory computer readable medium of Embodiment 57, wherein the weighted measure is generated using one or more of an artificial intelligence (AI) or machine learning (ML) algorithm configured to assign a weight to one or more comparisons of the one or more quantified dimensions of the one or more identified cardiovascular structures with the one or more reference dimensions of one or more cardiovascular structures generated from the plurality of other subjects.

Embodiment 60: The non-transitory computer readable medium of Embodiment 57, wherein the method performed by the hardware processor further comprises: generating a subject-level cardiovascular risk assessment based at least in part on the generated weighted measure of the comparison of the one or more quantified dimensions of the one or more identified cardiovascular structures with the one or more reference dimensions of one or more cardiovascular structures generated from the plurality of other subjects, wherein the graphical display comprises the generated subject-level cardiovascular risk assessment.

Embodiment 61: The non-transitory computer readable medium of Embodiment 60, wherein the subject-level cardiovascular risk assessment is determined as one or more of low, medium, or high based at least in part on predetermined thresholds of the generated weighted measure of the comparison of the one or more quantified dimensions of the one or more identified cardiovascular structures with the one or more reference dimensions of one or more cardiovascular structures generated from the plurality of other subjects.

Embodiment 62: The non-transitory computer readable medium of Embodiment 60, wherein the subject-level cardiovascular risk assessment is determined as a percentile based at least in part on the generated weighted measure of the comparison of the one or more quantified dimensions of the one or more identified cardiovascular structures with the one or more reference dimensions of one or more cardiovascular structures generated from the plurality of other subjects.

Embodiment 63: The non-transitory computer readable medium of Embodiment 60, wherein the method performed by the hardware processor further comprises generating one or more proposed treatments for the subject based at least in part on the subject-level cardiovascular risk assessment.

Embodiment 64: The non-transitory computer readable medium of Embodiment 45, wherein the image segmentation is performed using one or more of an artificial intelligence (AI) or machine learning (ML) algorithm.

Embodiment 65: The non-transitory computer readable medium of Embodiment 45, wherein the medical image is obtained using computed tomography (CT).

Embodiment 66: The non-transitory computer readable medium of Embodiment 45, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Multivariable Image-Based Analysis of Vulnerable Plaque Features

Disclosed herein are systems, devices, and methods for multivariable image-based analysis of vulnerable plaque features. In particular, in some embodiments, the systems, devices, and methods described herein are related to analysis (e.g., image-based analysis) of a medical image or medical images to determine one or more coronary artery disease (CAD)-related variables or plaque parameters from which the presence of vulnerable plaque features, which themselves may not be easily recognizable within the image, can be determined or estimated. For example, in some embodiments, the variables can include one or more of distance between plaque and vessel wall, distance between plaque and lumen wall, length along longitudinal axis, length along latitudinal axis, volume of low density non-calcified plaque, volume of total plaque, a ratio(s) between volume of low density non-calcified plaque and volume of total plaque, embeddedness of low density non-calcified plaque, and/or the like. In some embodiments, the plaque analyses are based on plaque parameters generated by medical imaging and are compared to known vulnerable plaque indicators to determine or estimate the presence of vulnerable plaque features and risk of CAD. For example, a machine learning algorithm can be trained to determine or estimate the presence of vulnerable plaque features based on the CAD-related variables and/or plaque parameters determined from an image-based analysis. In some embodiments, the vulnerable plaque features can include presence of thin-cap fibroatheroma (TCFA). In some embodiments, the systems, devices, and methods described herein are configured to determine a risk of coronary artery disease (CAD), such as for example, myocardial infarction (MI), based on one or more plaque or vulnerable plaque features analyses described herein. In some embodiments, the systems, devices, and methods described herein are configured to generate a proposed treatment and/or graphical representation based on the determined risk of CAD and/or one or more plaque analyses described herein.

As discussed herein, disclosed herein are systems, methods, and devices for determining a likelihood of vulnerable plaque features based at least in part on a plurality of variables derived from non-invasive medical image analysis, such as for example a CT image. In some embodiments, the system devices, and methods described herein are configured to determine a risk of CAD based on vulnerable plaque features as determined by one or more plaque and/or vascular analyses described herein. In some embodiments, the plaque and/or vascular analyses are based on plaque and/or vascular parameters generated by medical imaging and are compared to plaque and/or vascular parameters derived from known cases with or without vulnerable plaque features to determine vulnerable plaque features or risk of CAD. In some embodiments, the systems, devices, and methods are configured to generate a proposed treatment based on the determined risk of vulnerable plaque features and/or one or more plaque and/or vascular analyses described herein.

In some instances, plaque can be determined to be "vulnerable plaque," which, as used herein, can be plaque that is more likely to cause a heart attack. Features of vulnerable plaque that can be useful in determining vulnerability can include necrotic core, non-calcified plaque, low-density non-calcified plaque, positive arterial remodeling, inflammation, macrophage infiltration, and/or thin-cap fibroatheroma (TCFA). TCFA can be a fibrous, thin layer that stretches across a lipid pool. The lipid pool can be filled with a necrotic core and/or noncalcified plaque. If the layer of TCFA breaks, the lipid pool escapes into the vessel potentially causing a cardiac event. The presence of TCFA indicates that a patient is more at risk of cardiac events such as MI. The presence of TCFA is a feature of vulnerable plaque. Positive arterial remodeling can be an increase in vessel size in response to the presence of plaque. Inflammation can be the presence of inflamed vessel. Inflammation can be inflamed tissue near the vessel. Macrophage infiltration can be accumulation of macrophages in the vessel wall. Macrophage infiltration can be accumulation of macrophages into plaque.

If features of vulnerable plaque are detectable, patients and physicians could better analyze a patient's CAD based at least in part on the detected features, and more accurately prescribe a course of treatment. While certain invasive imaging capabilities, such as integrated intravascular ultrasound (IVUS), and/or high-resolution imaging capabilities, such as optical coherence tomography (OCT), may allow for visualization of some vulnerable plaque features, such as TCFA, more commonly available imaging capabilities, such as CT, have limitations on spatial resolution, with the resolution being around 500 microns. TCFA can have a spatial resolution at around 10 microns and can be essentially undetectable by the limits of CT imaging.

Without more readily adequate imaging existing to detect vulnerable plaque features, there is a need for vulnerable plaque features to be discovered through other methods, systems, and devices. Vulnerable plaque and TCFA can be associated with indicators that suggest the presence of vulnerable plaque features. Because certain vulnerable plaque features, such as TCFA, are undetectable by imaging methods such as CT, additional methods are needed to identify vulnerable plaque features to aid in detecting at-risk patients.

Some embodiments of the systems, devices, and methods described herein address this technical shortcoming by providing a way to diagnose, detect, and/or determine the presence or likelihood of presence of vulnerable plaque features by utilizing one or more variables that can derived from a medical image without directly identifying vulnerable plaque features from the medical image. That is, in some embodiments, an analysis can generate an estimate or determination of vulnerable plaque features indirectly by analyzing one or more other variables or plaque parameters determined from an image-based analysis, even when vulnerable plaque features itself is not directly determinable within the medical image.

The one or more variables derived from the medical image can be one or more of around 60 variables (or more) of which some or all can be used to determine the presence or likelihood of vulnerable plaque features. Some embodiments may include a machine learning algorithm that can compare the variables with a database of variables derived from known cases with or without vulnerable plaque features, for example verified through IVUS and/or OCT and/or other techniques. A database can be created by using a collection of cases and for each case in the collection, determining through IVUS and/or OCT if there is vulnerable plaque features in the case. The database, after each case has been checked for vulnerable plaque features, can be used as a training set for a machine learning algorithm. In some embodiments, the algorithm can provide a physician the percent chance of having vulnerable plaque features based on the variables and the database. In some examples, the variables include percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, presence of TCFA, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, inflammation, macrophage infiltration, number of severe stenosis excluding CTO, vessel area, lumen area, diameter stenosis percentage, presence of ischemia, number of stents, reference lumen diameter before stenosis, perivascular fat attenuation, or reference lumen diameter after stenosis. In various embodiments, one or more of the variables can be used. In some embodiments, low-density non-calcified plaque can be defined as a region of plaque with a radiodensity value less than or equal to about 30 Hounsfield units, non-calcified plaque can be defined as a region of plaque with a radiodensity value greater than about 30 Hounsfield units and/or less than or equal to about 350 Hounsfield units, calcified plaque can be defined as a region of plaque with a radiodensity value greater than about 350 Hounsfield units, low-density calcified plaque can be defined as a region of plaque with a radiodensity value greater than about 350 Hounsfield units and/or less than or equal to about 700 Hounsfield units, medium-density calcified plaque can be defined as a region of plaque with a radiodensity value greater than about 700 Hounsfield units and/or less than or equal to about 1000 Hounsfield units, and/or high-density calcified plaque can be defined as a region of plaque with a radiodensity value greater than about 1000 Hounsfield units. It is noted that based on changing/improving imaging techniques, some of the examples of Hounsfield units indicated above (30, 350, 700, and 1000) and throughout this disclosure, may also change over time based on the imaging technique/system. In various embodiments, calibration between previously generated images and images generated with new imaging techniques can be done to account for such differences, for example, in AI and/or ML processes.

As an example, a medical image can be obtained and analyzed to determine one or more vascular parameters or variable and/or one or more plaque parameters or variables based on an image-based analysis of the image. A machine learning algorithm can be applied to these variables in conjunction with a database of vulnerable plaque indicators to determine the presence of vulnerable plaque features or to estimate a percent chance of vulnerable plaque features. In some embodiments, the machine learning algorithm, using testing and imaging outputs, can provide an analysis that determines a likelihood of the presence or absence of vulnerable plaque features or a binary yes or no which could include data that indicates if it is more or less probable there is vulnerable plaque.

In some embodiments, the systems, methods, and devices can be configured to analyze a medical image to perform one or more analyses of plaque and/or types of plaque, such as for example low density non-calcified plaque, calcified plaque, non-calcified plaque, and/or the like. In particular, in some embodiments, low density non-calcified plaque can be a focus due to the high-risk generally associated with low density non-calcified plaque. For example, low density non-calcified plaque can have a higher risk of potential rupture compared to other types of plaque, such as regular non-calcified plaque or calcified plaque. A plaque rupture can, in some instances, clog or block a vessel, thereby causing a heart attack or MI. As such, it can be advantageous to analyze one or more features of low density non-calcified plaque, and/or non-calcified plaque and/or calcified plaque, which may correspond to high or low risk of CAD and/or stability or instability of plaque. In some embodiments, the systems, devices, and methods are configured to analyze a medical image, such as a CT or CCTA image, to derive one or more features, measures, and/or characterizations of plaque, such as low density non-calcified plaque, non-calcified plaque, and/or calcified plaque, and use the same to facilitate an assessment or and/or generate an assessment of risk of CAD and/or stability or instability of plaque. Thus, in some embodiments, the systems, devices, and methods can provide an efficient and/or non-invasive method of assessing risk of CAD and/or plaque.

Additionally, to prevent a rupture or to assess risk of CAD, in some embodiments, the systems, methods, and devices can be configured to use the analysis of plaque and other variables provided by the CT to create a risk assessment of vulnerable plaque features. In some embodiments, the risk assessment is created by comparing the variables to a database of known vulnerable plaque indicators. Vulnerable plaque indicators can include but are not limited to total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, inflammation, macrophage infiltration, presence of TCFA, number of severe stenosis excluding CTO, vessel area, lumen area, diameter stenosis percentage, presence of ischemia, number of stents, reference lumen diameter before stenosis, perivascular fat attenuation, or reference lumen diameter after stenosis. In some embodiments, low-density non-calcified plaque can be defined as a region of plaque with a radiodensity value less than or equal to about 30 Hounsfield units, non-calcified plaque can be defined as a region of plaque with a radiodensity value greater than about 30 Hounsfield units and/or less than or equal to about 350 Hounsfield units, calcified plaque can be defined as a region of plaque with a radiodensity value greater than about 350 Hounsfield units, low-density calcified plaque can be defined as a region of plaque with a radiodensity value greater than about 350 Hounsfield units and/or less than or equal to about 700 Hounsfield units, medium-density calcified plaque can be defined as a region of plaque with a radiodensity value greater than about 700 Hounsfield units and/or less than or equal to about 1000 Hounsfield units, and/or high-density calcified plaque can be defined as a region of plaque with a radiodensity value greater than about 1000 Hounsfield units.

In some embodiments, the systems, methods, and devices can be configured to identify vulnerable plaque indicators and calculate a percentage risk of having vulnerable plaque features. The percentage risk of vulnerable plaque features, in some embodiments, could be included in an overall diagnosis for CAD and can be included in a general risk assessment for CAD and MI. In some embodiments, the systems, methods, and devices can be configured to indicate positively or negatively of a diagnosis of vulnerable plaque features.

In some embodiments, the systems, methods, and devices can be configured to assess risk of vulnerable plaque features and provide, from a risk/treatment database, a treatment option or plan for the physician to advise to the patient. In some embodiments, a diagnostic plan may include aiding the medical provider in step-by-step treatment options and provide analysis at different stages of the treatment.

Figure 11:
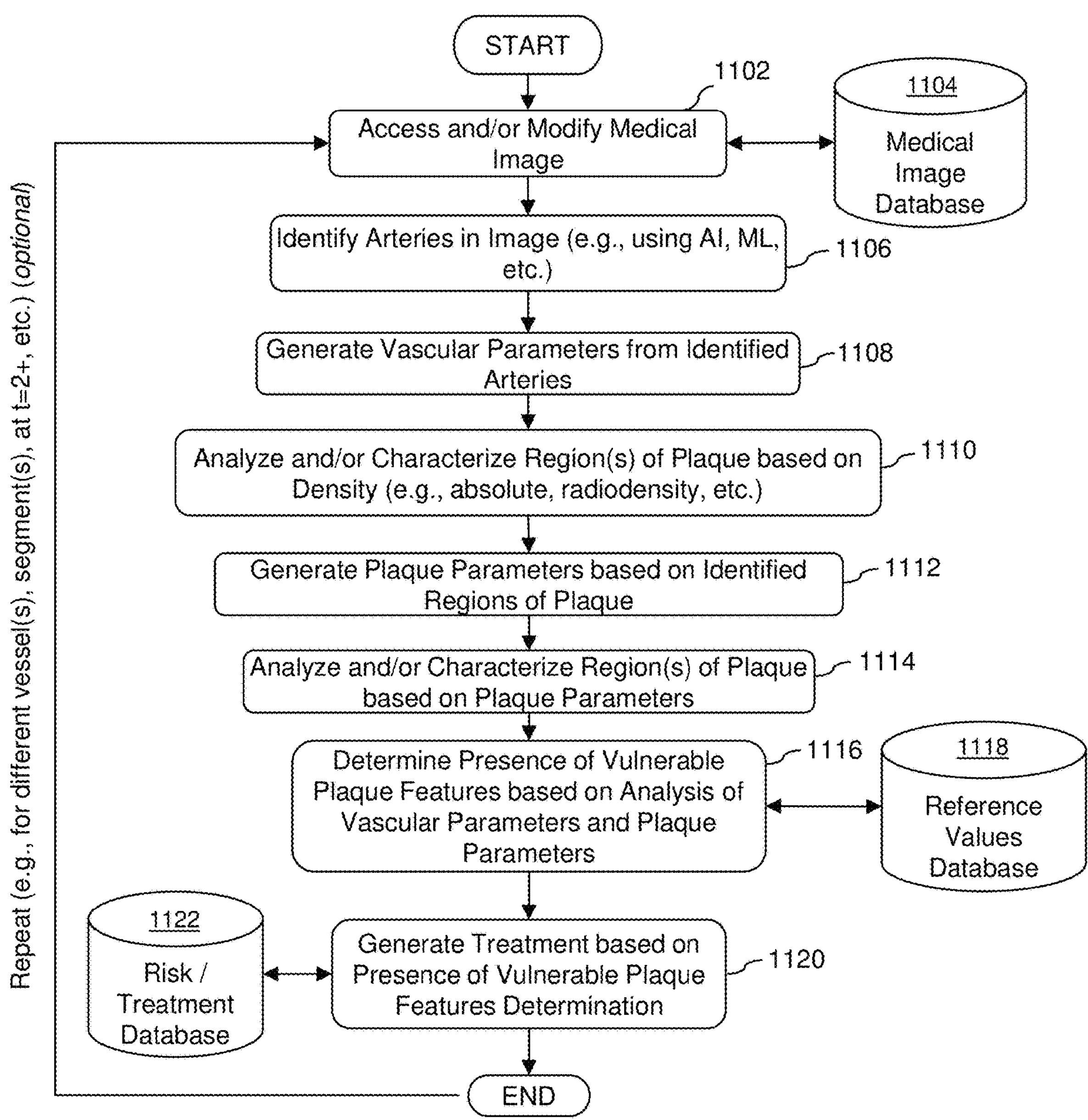
FIG. 11 is a flowchart illustrating an example embodiment (s) of systems, devices, and methods for multivariable image-based analysis of vulnerable plaque features.

FIG. 11 is a flowchart illustrating an example embodiment(s) of systems, devices, and methods for multivariable image-based analysis of vulnerable plaque features. As illustrated in FIG. 11, in some embodiments, the system can be configured to access and/or modify one or more medical images at block 1102. In some embodiments, the medical image can include one or more arteries, such as coronary, carotid, and/or other arteries of a subject. In some embodiments, the medical image can be stored in a medical image database 1104. In some embodiments, the medical image database 1104 can be locally accessible by the system and/or can be located remotely and accessible through a network connection. The medical image can comprise an image obtain using one or more modalities such as for example, Computed Tomography (CT), Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1106, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1108, the system can be configured to identify one or more quantified vascular parameters. In some embodiments, the system can be configured to utilize one or more AI and/or ML algorithms to automatically and/or dynamically identify the one or more quantified vascular parameters. For example, in some embodiments, the one or more AI and/or ML algorithms can be trained using a Convolutional Neural Network (CNN) on a set of medical images on which quantified vascular parameters have been identified, thereby allowing the AI and/or ML algorithm automatically identify quantified vascular parameters from a medical image. In some embodiments, quantified vascular parameters can be one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, presence of thin-cap fibroatheroma (TCFA), low-density calcium percentage, medium-density calcified percentage, high-density calcified percentage, presence of two-feature positive plaques, or number of two-feature positive plaques. In some embodiments, the one or more quantified vascular parameters may further comprise one or more of wherein the one or more quantified vascular parameters comprises one or more of vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, inflammation, macrophage infiltration, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

In some embodiments, at block 1110, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density non-calcified plaque, non-calcified plaque, and calcified plaque, using any one or more processes and/or features described herein. In some embodiments, the one or more regions of plaque can include one or more low density non-calcified plaque and/or non-calcified plaque. In some embodiments, the regions of plaque can be identified as low density non-calcified plaque when it has a radiodensity value between about −189 and about 30 Hounsfield units. In some embodiments, the regions of plaque can be identified as non-calcified plaque when it has a radiodensity value between about 31 and about 350 Hounsfield units. In some embodiments, the regions of plaque can be identified as calcified plaque when it has a radiodensity value between about 351 and about 2500 Hounsfield units. In some embodiments, the lower and/or upper Hounsfield unit boundary threshold for determining whether a plaque corresponds to one or more of low density non-calcified plaque, non-calcified plaque, and/or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU. Other factors can also be considered. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque. In some embodiments, the one or more regions of plaque can include a necrotic core and/or non-calcified plaque.

Based on the analysis or characterization of the regions of plaque, in some embodiments, at block 1112, the system can generate plaque parameters. These include, in some instances, plaque parameters that are derivable from the generated vascular parameters, but which may be not be derivable directly from the medical image itself. For example, in some embodiments, the system can identify, from the medical image of block 1102, additional parameters related to plaque, coronary artery disease, and/or artery anatomy that are located in the identified regions of plaque of block 1110. In some embodiments, the system can be configured to provide quantified plaque parameters based on one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, or number of two-feature positive plaques.

In some embodiments, the system can be configured to analyze and/or characterize regions of plaque based on vulnerable plaque variables. In some embodiments, for example, at block 1114, the system can be configured to use the quantified plaque parameters of block 1112 compared with known vulnerable plaque variables analyze and/or characterize regions of plaque based on the vulnerable plaque variables. In some examples, the variables include percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, inflammation, macrophage infiltration, presence of TCFA, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

In some embodiments, the system can be configured to determine risk of vulnerable plaque features based on a vulnerable plaque variable analysis. For example, in some embodiments, at block 1116, the system can be configured to determine the risk of vulnerable plaque features. In some embodiments, based on the analysis and/or characterization of the regions of plaque of block 1114, the system can use the reference values found in the reference values database of block 1118 to determine the risk and/or likelihood of vulnerable plaque features found in the identified regions of plaque. In some embodiments, the likelihood of the presence of vulnerable plaque features is determined on a subject basis. In some embodiments, the determined likelihood of the presence of vulnerable plaque features provides a percentage of likelihood of the presence of vulnerable plaque features. In some embodiments, the system provides a binary output, for example "yes" or "no," to identify if there are vulnerable plaque features detected and/or suspected by the system.

In some embodiments, at block 1116, the system can use recognizable parameters (e.g., parameters that are determinable directly from an analysis of a medical image) to predict features that are otherwise unrecognizable (e.g., from an initial analysis of the medical image). For example, in some embodiments, the system can find one pixel of necrotic core and determine, using machine learning (ML), that there is likely more necrotic core that is not visible at the resolution of the image. In this example, in some embodiments, the system may predict additional necrotic core as a vulnerable plaque feature based on the recognizable volume of necrotic core as a plaque parameter, either alone or in combination with other parameters. In another example, the system can determine the presence of inflammation based on the stenosis percentage alone or in combination with other parameters. In some embodiments, in this example, the ML algorithm can determine the presence of inflammation based on the stenosis despite the inflammation not being recognizable from the image. In some embodiments, the ML algorithm can make this determination based on images and results from the reference value database of block 1118. In some embodiments, at block 1116, the system can perform an iterative process, where one pass (e.g., a first analysis based on a medical image) determines plaque parameters and vascular parameters that are recognizable, and the second pass (e.g., a second analysis based on the results of the first analysis) uses ML to determine vulnerable plaque features that were not initially recognizable. In some embodiments, the ML algorithm can be trained on values from the reference values database of block 1118.

In some embodiments, for example, at block 1120, the system is configured to generate treatment based on the vulnerable plaque features risk determination of block 1116. In some embodiments, the system uses a risk/treatment database as depicted in block 1122, in conjunction with the determined risk of block 1116 to provide a treatment for the suspected and/or detected vulnerable plaque features. In some embodiments, the treatment can include advising a known regiment, crafting a personalized plan for the individual, and/or providing treatment plan options. In some embodiments, the treatment may include follow up scans at designated points which can allow the system to make changes to the treatment plan based on the scans.

In some embodiments, the system can be further configured to determine a risk of artery disease for the subject, based at least in part on the determined likelihood of the presence of vulnerable plaque features. In such embodiments, the artery disease may be coronary artery disease and/or peripheral artery disease. In some embodiments, the determination of artery disease is determined, in part, by comparing the determined likelihood of vulnerable plaque features against a dataset of various risks of artery disease from a reference population. In such embodiments, the system can use the determined likelihood of vulnerable plaque features and the vulnerable plaque variables to determine, using a dataset from a reference population, what variables are most often found with artery disease and/or which carry the most risk associated with artery disease.

In some embodiments, the system can further be configured to propose a treatment for the subject based, at least in part, on the determined risk of artery disease. In some embodiments, the system uses a risk/treatment database to provide a treatment for the suspected and/or detected artery disease determine by the likelihood of vulnerable plaque. In some embodiments, the treatment can include advising a known regiment, crafting a personalized plan for the individual, and/or providing treatment plan options. In some embodiments, the treatment may include follow up scans at designated points which can allow the system to make changes to the treatment plan based on the scans.

The computer system 902 of FIG. 9, and in some instances, the analysis and/or risk assessment module 940, can be configured to carry out the functions, methods, acts, and/or processes for multivariable image-based analysis of vulnerable plaque features described herein, such as those described above with reference to FIG. 11.

The following are non-limiting examples of certain embodiments of systems and methods for multivariable image-based analysis of vulnerable plaque features. Other embodiments may include one or more other features, or different features, that are discussed herein.

Embodiment 1: A computer-implemented method of determining a likelihood of vulnerable plaque features based at least in part on a plurality of variables derived from non-invasive medical image analysis, the method comprising: accessing, by a computer system, a medical image of a subject, wherein the medical image of the subject is obtained non-invasively; analyzing, by the computer system, the medical image of the subject to identify one or more arteries; generating, by the computer system, one or more quantified vascular parameters based at least in part on the identified one or more arteries; analyzing, by the computer system, the identified one or more arteries to identify one or more regions of plaque based at least in part on density; generating, by the computer system, one or more quantified plaque parameters based at least in part on the identified one or more regions of plaque; determining, by the computer system, a likelihood of presence of vulnerable plaque features for the one or more regions of plaque without direct identification of vulnerable plaque features from the medical image, wherein the likelihood of presence of vulnerable plaque features is determined by applying a machine learning algorithm to the one or more quantified vascular parameters and the one or more quantified plaque parameters, wherein the machine learning algorithm is trained by a dataset comprising one or more quantified vascular parameters and one or more quantified plaque parameters derived from a plurality of other medical images with known presence or absence of vulnerable plaque features for a region of plaque, and wherein the vulnerable plaque features comprise one or more of necrotic core, non-calcified plaque, low-density non-calcified plaque, positive arterial remodeling, inflammation, macrophage infiltration, or thin-cap fibroatheroma (TCFA), wherein the computer system comprises a computer processor and an electronic storage medium.

Embodiment 2: The computer-implemented method of Embodiment 1, wherein the one or more quantified plaque parameters comprises one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, presence of thin-cap fibroatheroma (TCFA), low-density calcium percentage, medium-density calcified percentage, high-density calcified percentage, presence of two-feature positive plaques, or number of two-feature positive plaques.

Embodiment 3: The computer-implemented method of Embodiment 1, wherein the one or more quantified vascular parameters comprises one or more of vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, inflammation, macrophage infiltration, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 4: The computer-implemented method of Embodiment 1, wherein the likelihood of presence of vulnerable plaque features is determined on a subject basis.

Embodiment 5: The computer-implemented method of Embodiment 1, wherein the determined likelihood of presence of vulnerable plaque features comprises a percentage of likelihood of presence of vulnerable plaque features.

Embodiment 6: The computer-implemented method of Embodiment 1, wherein the determined likelihood of presence of vulnerable plaque features comprises a binary output of likelihood or unlikelihood of presence of vulnerable plaque features.

Embodiment 7: The computer-implemented method of Embodiment 1, further comprising determining a risk of artery disease for the subject based at least in part on the determined likelihood of presence of vulnerable plaque features.

Embodiment 8: The computer-implemented method of Embodiment 7, wherein the artery disease comprises coronary artery disease (CAD).

Embodiment 9: The computer-implemented method of Embodiment 7, wherein the artery disease comprises peripheral artery disease (PAD).

Embodiment 10: The computer-implemented method of Embodiment 7, wherein the risk of artery disease for the subject is determined based at least in part on comparing the determined likelihood of presence of vulnerable plaque features against dataset comprising varying risks of artery disease and known presence or absence of vulnerable plaque features derived from a reference population.

Embodiment 11: The computer-implemented method of Embodiment 7, further comprising determining a proposed treatment for the subject based at least in part on the determined risk of artery disease.

Embodiment 12: The computer-implemented method of Embodiment 11, wherein the proposed treatment comprises one or more of a lifestyle treatment, interventive treatment, or medication treatment.

Embodiment 13: The computer-implemented method of Embodiment 1, wherein the one or more regions of plaque comprises a necrotic core and non-calcified plaque.

Embodiment 14: The computer-implemented method of Embodiment 1, wherein the one or more regions of plaque comprises one or more of low density non-calcified plaque or non-calcified plaque.

Embodiment 15: The computer-implemented method of Embodiment 1, wherein the one or more arteries comprises one or more coronary arteries.

Embodiment 16: The computer-implemented method of Embodiment 1, wherein the one or more arteries comprises one or more coronary arteries, carotid arteries, lower extremity arteries, upper extremity arteries, or aorta.

Embodiment 17: The computer-implemented method of Embodiment 1, wherein the density comprises absolute density.

Embodiment 18: The computer-implemented method of Embodiment 1, wherein the density comprises radiodensity.

Embodiment 19: The computer-implemented method of Embodiment 1, wherein the one or more regions of plaque are identified as low density non-calcified plaque when a radiodensity value is between about −189 and about 30 Hounsfield units.

Embodiment 20: The computer-implemented method of Embodiment 1, wherein the one or more regions of plaque are identified as non-calcified plaque when a radiodensity value is between about 31 and about 350 Hounsfield units.

Embodiment 21: The computer-implemented method of Embodiment 1, wherein the one or more regions of plaque are identified as calcified plaque when a radiodensity value is between about 351 and 2500 Hounsfield units.

Embodiment 22: The computer-implemented method of Embodiment 1, wherein the medical image comprises a Computed Tomography (CT) image.

Embodiment 23: The computer-implemented method of Embodiment 1, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 24: A system for determining a likelihood of vulnerable plaque features based at least in part on a plurality of variables derived from non-invasive medical image analysis, the system comprising:

Embodiment 25: a non-transitory computer storage medium configured to at least store computer-executable instructions; and one or more computer hardware processors in communication with the non-transitory computer storage medium, the one or more computer hardware processors configured to execute the computer-executable instructions to at least: access a medical image of a subject, wherein the medical image of the subject is obtained non-invasively; analyze the medical image of the subject to identify one or more arteries; generate one or more quantified vascular parameters based at least in part on the identified one or more arteries; analyze the identified one or more arteries to identify one or more regions of plaque based at least in part on density; generate one or more quantified plaque parameters based at least in part on the identified one or more regions of plaque; determine a likelihood of presence of vulnerable plaque features for the one or more regions of plaque without direct identification of vulnerable plaque features from the medical image, wherein the likelihood of presence of vulnerable plaque features is determined by applying a machine learning algorithm to the one or more quantified vascular parameters and the one or more quantified plaque parameters, wherein the machine learning algorithm is trained by a dataset comprising one or more quantified vascular parameters and one or more quantified plaque parameters derived from a plurality of other medical images with known presence or absence of vulnerable plaque features for a region of plaque, and wherein the vulnerable plaque features comprise one or more of necrotic core, non-calcified plaque, low-density non-calcified plaque, positive arterial remodeling, inflammation, macrophage infiltration, or thin-cap fibroatheroma (TCFA).

Embodiment 26: The system of Embodiment 24, wherein the one or more quantified plaque parameters comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, or medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, presence of thin-cap fibroatheroma (TCFA), low-density calcium percentage, medium-density calcified percentage, high-density calcified percentage, presence of two-feature positive plaques, or number of two-feature positive plaques.

Embodiment 27: The system of Embodiment 24, wherein the one or more quantified vascular parameters comprising one or more of vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, inflammation, macrophage infiltration, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 28: The system of Embodiment 24, wherein the one or more computer hardware processors are further configured to execute the computer-executable instructions to at least determine the likelihood of presence of vulnerable plaque features on a subject basis.

Embodiment 29: The system of Embodiment 24, wherein the determined likelihood of presence of vulnerable plaque features comprises a percentage of likelihood of presence of vulnerable plaque features.

Embodiment 30: The system of Embodiment 24, wherein the determined likelihood of presence of vulnerable plaque features comprises a binary output of likelihood or unlikelihood of presence of vulnerable plaque features.

Embodiment 31: The system of Embodiment 24, wherein the one or more computer hardware processors are further configured to execute the computer-executable instructions to at least determine a risk of artery disease for the subject based at least in part on the determined likelihood of presence of vulnerable plaque features.

Embodiment 32: The system of Embodiment 30, wherein at least the artery disease comprises coronary artery disease (CAD).

Embodiment 33: The system of Embodiment 30, wherein the artery disease comprises peripheral artery disease (PAD).

Embodiment 34: The system of Embodiment 30, wherein the risk of artery disease for the subject is determined based at least in part on comparing the determined likelihood of presence of vulnerable plaque features against dataset comprising varying risks of artery disease and known presence or absence of vulnerable plaque features derived from a reference population.

Embodiment 35: The system of Embodiment 30, wherein the one or more computer hardware processors are further configured to execute the computer-executable instructions to at least determine a proposed treatment for the subject based at least in part on the determined risk of artery disease.

Embodiment 36: The system of Embodiment 34, wherein the proposed treatment comprises one or more of a lifestyle treatment, interventive treatment, or medication treatment.

Embodiment 37: The system of Embodiment 30, wherein the one or more regions of plaque comprises a necrotic core and non-calcified plaque.

Embodiment 38: The system of Embodiment 30, wherein the one or more regions of plaque comprises one or more of low density non-calcified plaque or non-calcified plaque.

Embodiment 39: The system of Embodiment 30, wherein the one or more arteries comprises one or more coronary arteries.

Embodiment 40: The system of Embodiment 30, wherein the one or more arteries comprises one or more coronary arteries, carotid arteries, lower extremity arteries, upper extremity arteries, or aorta.

Embodiment 41: The system of Embodiment 30, wherein the density comprises absolute density.

Embodiment 42: The system of Embodiment 30, wherein the density comprises radiodensity.

Embodiment 43: The system of Embodiment 24, wherein the one or more regions of plaque are identified as low density non-calcified plaque when a radiodensity value is between about −189 and about 30 Hounsfield units.

Embodiment 44: The system of Embodiment 24, wherein the one or more regions of plaque are identified as non-calcified plaque when a radiodensity value is between about 31 and about 350 Hounsfield units.

Embodiment 45: The system of Embodiment 24, wherein the one or more regions of plaque are identified as calcified plaque when a radiodensity value is between about 351 and 2500 Hounsfield units.

Embodiment 46: The system of Embodiment 30, wherein the medical image comprises a Computed Tomography (CT) image.

Embodiment 47: The system of Embodiment 30, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 48: A non-transitory computer readable medium configured for determining a likelihood of vulnerable plaque features based at least in part on a plurality of variables derived from non-invasive medical image analysis, the computer readable medium having program instructions for causing a hardware processor to perform a method of: accessing a medical image of a subject, wherein the medical image of the subject is obtained non-invasively; analyzing the medical image of the subject to identify one or more arteries; generating one or more quantified vascular parameters based at least in part on the identified one or more arteries; analyzing the identified one or more arteries to identify one or more regions of plaque based at least in part on density; generating one or more quantified plaque parameters based at least in part on the identified one or more regions of plaque;

Embodiment 49: determining a likelihood of presence of vulnerable plaque features for the one or more regions of plaque without direct identification of vulnerable plaque features from the medical image, wherein the likelihood of presence of vulnerable plaque features is determined by applying a machine learning algorithm to the one or more quantified vascular parameters and the one or more quantified plaque parameters, wherein the machine learning algorithm is trained by a dataset comprising one or more quantified vascular parameters and one or more quantified plaque parameters derived from a plurality of other medical images with known presence or absence of vulnerable plaque features for a region of plaque, and wherein the vulnerable plaque features comprise one or more of necrotic core, non-calcified plaque, low-density non-calcified plaque, positive arterial remodeling, inflammation, macrophage infiltration, or thin-cap fibroatheroma (TCFA).

Embodiment 50: The non-transitory computer readable medium of Embodiment 47, wherein the one or more quantified plaque parameters comprises one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, or medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, presence of thin-cap fibroatheroma (TCFA), low-density calcium percentage, medium-density calcified percentage, high-density calcified percentage, presence of two-feature positive plaques, or number of two-feature positive plaques.

Embodiment 51: The non-transitory computer readable medium of Embodiment 47, wherein the one or more quantified vascular parameters comprises one or more of vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, inflammation, macrophage infiltration, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 52: The non-transitory computer readable medium of Embodiment 47, wherein the likelihood of presence of vulnerable plaque features is determined on a subject basis.

Embodiment 53: The non-transitory computer readable medium Embodiment 47, wherein the determined likelihood of presence of vulnerable plaque features comprises a percentage of likelihood of presence of vulnerable plaque features.

Embodiment 54: The non-transitory computer readable medium of Embodiment 47, wherein the determined likelihood of presence of vulnerable plaque features comprises a binary output of likelihood or unlikelihood of presence of vulnerable plaque features.

Embodiment 55: The non-transitory computer readable medium of Embodiment 47, the method further comprising determining a risk of artery disease for the subject based at least in part on the determined likelihood of presence of vulnerable plaque features.

Embodiment 56: The non-transitory computer readable medium of Embodiment 53, wherein the artery disease comprises coronary artery disease (CAD).

Embodiment 57: The non-transitory computer readable medium of Embodiment 53, wherein the artery disease comprises peripheral artery disease (PAD).

Embodiment 58: The non-transitory computer readable medium of Embodiment 53, wherein the risk of artery disease for the subject is determined based at least in part on comparing the determined likelihood of presence of vulnerable plaque features against dataset comprising varying risks of artery disease and known presence or absence of vulnerable plaque features derived from a reference population.

Embodiment 59: The non-transitory computer readable medium of Embodiment 53, the method further comprising determining a proposed treatment for the subject based at least in part on the determined risk of artery disease.

Embodiment 60: The non-transitory computer readable medium of Embodiment 57, wherein the proposed treatment comprises one or more of a lifestyle treatment, interventive treatment, or medication treatment.

Embodiment 61: The non-transitory computer readable medium of Embodiment 47, wherein the one or more regions of plaque comprises a necrotic core and non-calcified plaque.

Embodiment 62: The non-transitory computer readable medium of Embodiment 47, wherein the one or more regions of plaque comprises one or more of low density non-calcified plaque or non-calcified plaque.

Embodiment 63: The non-transitory computer readable medium of Embodiment 47, wherein the one or more arteries comprises one or more coronary arteries.

Embodiment 64: The non-transitory computer readable medium of Embodiment 47, wherein the one or more arteries comprises one or more coronary arteries, carotid arteries, lower extremity arteries, upper extremity arteries, or aorta.

Embodiment 65: The non-transitory computer readable medium of Embodiment 47, wherein the density comprises absolute density.

Embodiment 66: The non-transitory computer readable medium of Embodiment 47, wherein the density comprises radiodensity.

Embodiment 67: The non-transitory computer readable medium of Embodiment 47, wherein the one or more regions of plaque are identified as low density non-calcfied plaque when a radiodensity value is between about −189 and about 30 Hounsfield units.

Embodiment 68: The non-transitory computer readable medium of Embodiment 47, wherein the one or more regions of plaque are identified as non-calcified plaque when a radiodensity value is between about 31 and about 350 Hounsfield units.

Embodiment 69: The non-transitory computer readable medium of Embodiment 47, wherein the one or more regions of plaque are identified as calcified plaque when a radiodensity value is between about 351 and 2500 Hounsfield units.

Embodiment 70: The non-transitory computer readable medium of Embodiment 47, wherein the medical image comprises a Computed Tomography (CT) image.

Embodiment 71: The non-transitory computer readable medium of Embodiment 47, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Image-Based Assessment of Microcirculatory Resistance

Various embodiments described herein relate to systems, devices, and methods for image-based assessment of microcirculatory resistance. In particular, in some embodiments, the systems, devices, and methods described herein can be configured to access a first medical image of a subject obtained at a first point in time after injection of a contrast dye to the subject and a second medical image of a subject obtained at a second point in time after injection of the contrast dye to the subject. For example, the second time point can be after dye washout in some embodiments. The systems, devices, and methods can further be configured to analyze the first medical image and the second medical image to identify a coronary artery and map myocardium subtended by the coronary artery in the first medical image and the second medical image. Based on a difference in radiodensity between the myocardium subtended by the coronary artery in the first medical image and the second medical image, the difference in radiodensity arising from flow of the contrast dye through microvasculature of the myocardium subtended by the coronary artery, the systems, methods, and devices can further be configured to generate a measure of per-artery microcirculatory resistance of the coronary artery by relating the difference in radiodensity between the myocardium subtended by the coronary artery in the first medical image and the second medical image to a difference in time between the first point in time and the second point in time.

Additionally, for some embodiments, the systems, methods, and devices can be configured to determine an assessment of microcirculatory resistance of the coronary artery based at least in part on comparing the generated measure of the per-artery microcirculatory resistance of the coronary artery to a plurality of reference measures of per-artery microcirculatory resistance, the plurality of reference measures of per-artery microcirculatory resistance derived from a plurality of other subjects, wherein the determined assessment of microcirculatory resistance of the coronary artery is configured to be utilized to determine a treatment for the subject. The devices, systems, and methods can further include applying a machine learning algorithm to determine risk of coronary artery disease (CAD) or major adverse cardiovascular event (MACE) for the patient based at least in part on the plurality of variables. In some embodiments, the machine learning algorithm is trained based at least in part on the variables derived from medical images of other subjects with known risk of CAD or MACE. The devices, systems, and methods can then further include determining a need for cardiac catheterization for the patient based at least in part on the determined risk of CAD or MACE.

Various embodiments described herein relate to systems, devices, and methods for image-based assessment of microcirculatory resistance. In particular, in some embodiments, the systems, devices, and methods described herein can be configured to access a first medical image of a subject obtained at a first point in time after injection of a contrast dye to the subject and a second medical image of a subject obtained at a second point in time after injection of the contrast dye to the subject. For example, the second time point can be after dye washout in some embodiments. The systems, devices, and methods can further be configured to analyze the first medical image and the second medical image to identify a coronary artery and map myocardium subtended by the coronary artery in the first medical image and the second medical image. Based on a difference in radiodensity between the myocardium subtended by the coronary artery in the first medical image and the second medical image, the difference in radiodensity arising from flow of the contrast dye through microvasculature of the myocardium subtended by the coronary artery, the systems, methods, and devices can further be configured to generate a measure of per-artery microcirculatory resistance of the coronary artery by relating the difference in radiodensity between the myocardium subtended by the coronary artery in the first medical image and the second medical image to a difference in time between the first point in time and the second point in time. Finally, the systems, methods, and devices can be configured to determine an assessment of microcirculatory resistance of the coronary artery based at least in part on comparing the generated measure of the per-artery microcirculatory resistance of the coronary artery to a plurality of reference measures of per-artery microcirculatory resistance, the plurality of reference measures of per-artery microcirculatory resistance derived from a plurality of other subjects, wherein the determined assessment of microcirculatory resistance of the coronary artery is configured to be utilized to determine a treatment for the subject.

The devices, systems, and methods can further include applying a machine learning algorithm to determine risk of coronary artery disease (CAD) or major adverse cardiovascular event (MACE) for the patient based at least in part on the plurality of variables. In some embodiments, the machine learning algorithm is trained based at least in part on the variables derived from medical images of other subjects with known risk of CAD or MACE. The devices, systems, and methods can then further include determining a need for cardiac catheterization for the patient based at least in part on the determined risk of CAD or MACE.

Microcirculatory resistance within the microvasculature can affect blood flow to the myocardium and cause myocardial disfunction or infarction. Microcirculatory resistance can be caused by plaque buildup within the microvasculature. Plaque build up within the microvasculature can be difficult or impossible to visualize with conventional imaging techniques, and accordingly can be very difficult to diagnose.

Figure 12A:
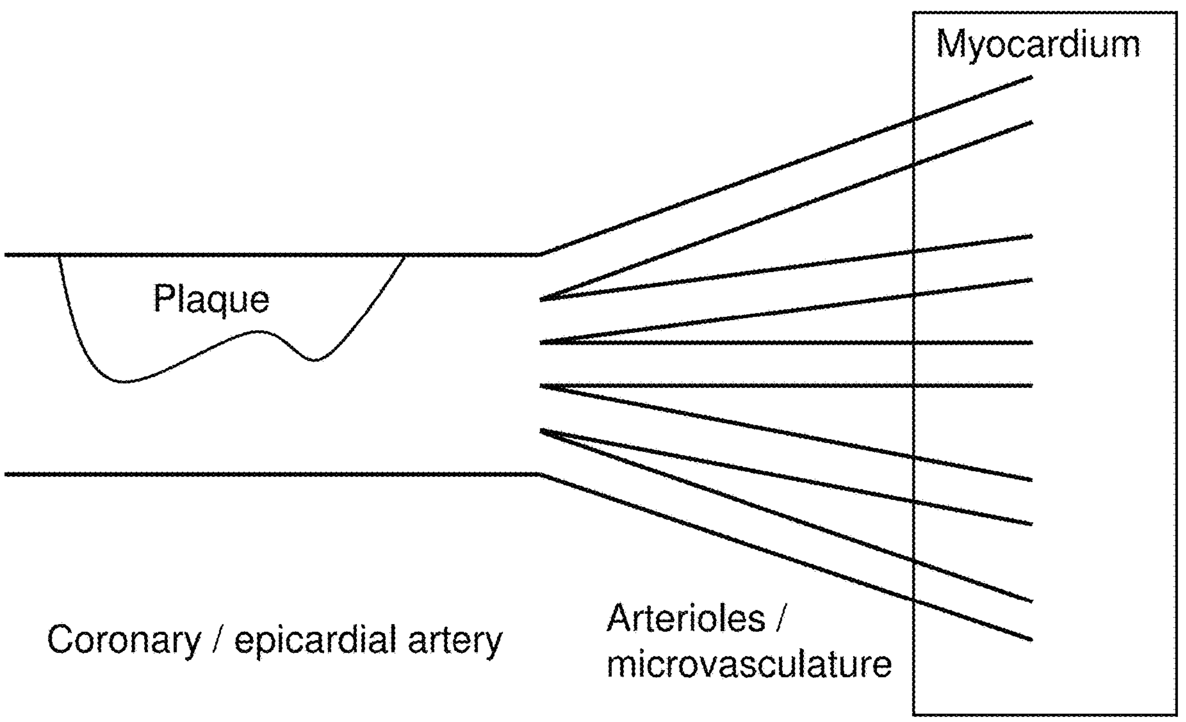
FIGS. 12A and 12B illustrate examples of microcirculatory resistance.
Figure 12B:
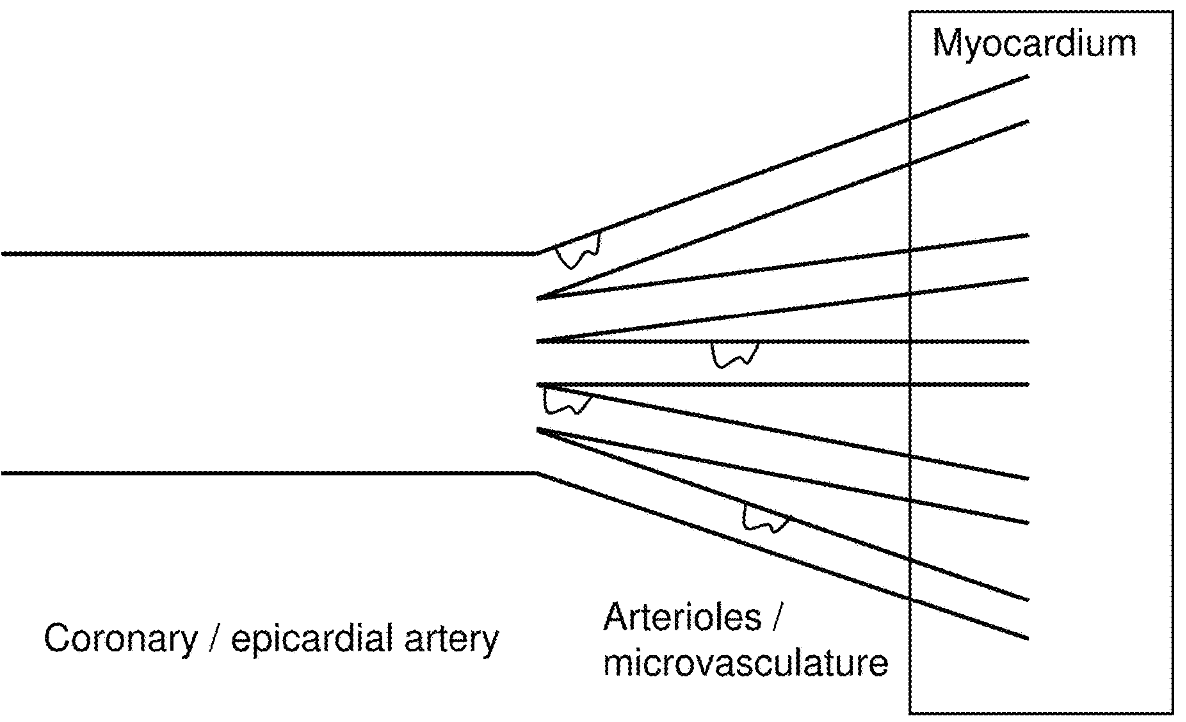

FIGS. 12A and 12B illustrate examples of microcirculatory resistance. In FIG. 12A, plaque buildup in a coronary artery can cause a pressure drop that occurs prior to the microvasculature. Blood flow through the microvasculature to the myocardium can be even. However, as shown in FIG. 12B, plaque buildup in the microvasculature can be cause uneven blood flow to the myocardium.

Blood flow can be visualized with the injection of a contrast material. For example, in a coronary CT angiogram, as contrast is injected, the contrast material is visible. However, the contrast material dissipates after a period of time due to blood flow. In some instances, the contrast material is visible within the microvasculature of the patient. Microcirculation within the microvasculature can be important because, if the microvasculature is diseased blood pressure and resistance increases.

By analyzing the dissipation of contrast through the microvasculature it can be possible determine or calculate an Index of Microcirculatory Resistance (IMR). This can be accomplished with an image-based analysis. This can be useful for diagnoses where a patient's arteries appear normal, for example, where the problem is within the microvasculature.

Figure 12C:
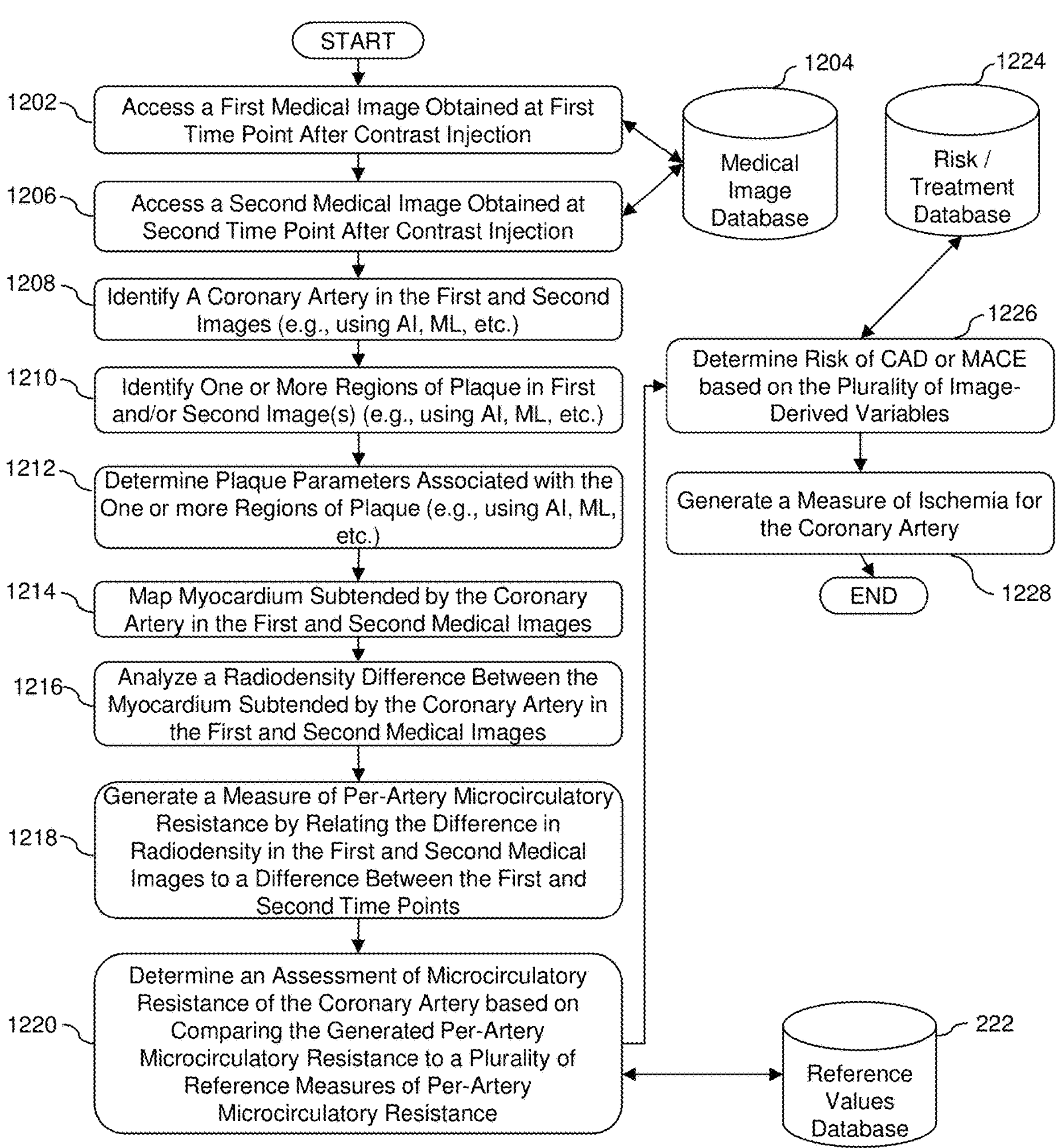
FIG. 12C is a flowchart illustrating an example embodiment(s) of systems, devices, and methods for image-based assessment of microcirculatory resistance.

FIG. 12C is a flowchart illustrating an example embodiment(s) of systems, devices, and methods for image-based assessment of microcirculatory resistance. As illustrated in FIG. 12C, in some embodiments, the system can be configured to capture or access a first medical image at block 1202. In some embodiments, the first medical image can include one or more arteries, such as coronary, carotid, and/or other arteries as well as a myocardium of a subject. In some embodiments, the first medical image can be obtained at a first time point after injection of a contrast material (e.g., a dye). For example, such that the contrast material is apparent in the image. The contrast material can be visible within the first medical image. In some embodiments, the first medical image can be stored in a medical image database 1204. In some embodiments, the medical image database 104 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

With continued reference to FIG. 12C, at block 1202, the system can be configured to capture access a second medical image. In some embodiments, the second medical image can include the same region of portion of the patient, for example, showing the same one or more arteries, such as coronary, carotid, and/or other arteries as well as the myocardium of a subject. In some embodiments, the second medical image can be obtained at a second time point after injection of the contrast material (e.g., the dye). The contrast material can be visible within the second medical image. However, because the second medical image is taken at a second time point after injection of the contrast material, the contrast material may have moved to a new region within the anatomy of the patient and/or have dissipated. In some embodiments, the second point in time is when washout of the contrast dye is complete. The second time point can be later in time than the first time point. In some embodiments, the second time point is about, at least, or at most 0.01 seconds, 0.025 seconds, 0.05 seconds, 0.075 seconds, 0.1 seconds, 0.125 seconds, 0.15 seconds, 0.175 seconds, 0.2 seconds, 0.225 seconds, 0.25 seconds, 0.275 seconds, 0.3 seconds, 0.325 seconds, 0.35 seconds, 0.375 seconds, 0.4 seconds, 0.425 seconds, 0.45 seconds, 0.475 seconds, 0.5 seconds, 0.525 seconds, 0.55 seconds, 0.575 seconds, 0.6 seconds, 0.625 seconds, 0.65 seconds, 0.675 seconds, 0.7 seconds, 0.725 seconds, 0.75 seconds, 0.775 seconds, 0.8 seconds, 0.825 seconds, 0.85 seconds, 0.875 seconds, 0.9 seconds, 0.925 seconds, 0.95 seconds, 0.975 seconds, 1 second, 1.25 seconds, 1.5 seconds, 1.75 seconds, 2 seconds, 2.25 seconds, 2.5 seconds, 2.75 seconds, 3 seconds, 3.25 seconds, 3.5 seconds, 3.75 seconds, 4 seconds, 4.25 seconds, 4.5 seconds, 4.75 seconds, 5 seconds, or more later than the first time points, although other time intervals smaller, greater, and in between the listed time intervals may also be used in some embodiments. In some embodiments, the second medical image can be stored in a medical image database 1204.

With reference to blocks 1202 and 1206, in some embodiments, the first medical image and the second medical image comprise a resolution that does not allow for image segmentation of plaque within the microvasculature. For example, the first medical image and the second medical image comprise a resolution of about 0.3 $mm^3$. In some embodiments, the first medical image and the second medical image comprise a resolution of about 0.5 $mm^3$.

In some embodiments, the system can be configured to automatically and/or dynamically perform one or more analyses of the first and second medical images as discussed herein. For example, in some embodiments, at block 1208, the system can be configured to identify one or more vessels, such as a coronary artery, within each of the first and second medical images. The one or more vessels can include coronary arteries, carotid arteries, aorta, renal artery, lower extremity artery, upper extremity artery, and/or cerebral artery, amongst others. In some embodiments, the one or more coronary arteries comprise one or more of left main (LM), ramus intermedius (RI), left anterior descending (LAD), diagonal 1 (D1), diagonal 2 (D2), left circumflex (Cx), obtuse marginal 1 (OM1), obtuse marginal 2 (OM2), left posterior descending artery (L-PDA), left posterolateral branch (L-PLB), right coronary artery (RCA), right posterior descending artery (R-PDA), or right posterolateral branch (R-PLB).

In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1210, the system can be configured to identify one or more regions of plaque in the vessels (e.g., the coronary artery) previously identified in the first and second medical images. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque. In some embodiments, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density non-calcified plaque, non-calcified plaque, and calcified plaque, using any one or more processes and/or features described herein.

In some embodiments, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque.

In some embodiments, the system can be configured to analyze and/or characterize one or more regions of plaque based on morphology or shape and/or one or more axes measurements of low density non-calcified plaque. In some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, the system can be configured to analyze and/or characterize plaque based on embeddedness. For example, in some embodiments, the system can be configured to determined how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees or more by non-calcified plaque can be associated with high risk of CAD. In some embodiments, the system can be configured to utilize one or more image processing algorithms to automatically and/or dynamically determine the embeddedness of one or more regions of plaque.

In some embodiments, microvasculature comprises one or more regions of plaque, but the one or more regions of plaque comprise a size that is not recognizable on the first medical image and the second medical image. This can be because of the image resolution, for example.

In some embodiments, at block 1212, the system can be configured to analyze the identified vessels (e.g., the coronary artery) and the one or more regions of plaque to determine a plurality of plaque parameters associated therewith. In some embodiments, analysis can be performed on or using the first and/or second medical image(s). In some embodiments, the plaque parameters can be quantified. In some embodiments, the quantified plaque parameters associated with the one or more regions of plaque can include one or more of volume of low-density non-calcified plaque, volume of non-calcified plaque, or volume of calcified plaque. In some embodiments, the volume of plaque comprises one or more of volume of total plaque, volume of low density non-calcified plaque, volume of non-calcified plaque, or volume of calcified plaque. In some embodiments, the volume of plaque is determined based at least in part on analyzing density of one or more pixels corresponding to plaque in the medical image. In some embodiments, the density comprises material density. In some embodiments, the density comprises radiodensity. For example, in some embodiments, the system can be configured to characterize a particular region of plaque as low density non-calcified plaque when the radiodensity of an image pixel or voxel corresponding to that region of plaque is between about −189 and about 30 Hounsfield units (HU). In some embodiments, the system can be configured to characterize a particular region of plaque as non-calcified plaque when the radiodensity of an image pixel or voxel corresponding to that region of plaque is between about 31 and about 350 HU. In some embodiments, the system can be configured to characterize a particular region of plaque as calcified plaque when the radiodensity of an image pixel or voxel corresponding to that region of plaque is between about 351 and about 2500 HU. In some embodiments, the lower and/or upper Hounsfield unit boundary threshold for determining whether a plaque corresponds to one or more of low density non-calcified plaque, non-calcified plaque, and/or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 310 HU, about 320 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 3100 HU, about 3200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU.

With continued reference to FIG. 12C, at block 1214, the system can further be configured to map myocardium subtended by the identified vessels (e.g., the identified coronary artery) in each of the first and second medical images. In some embodiments, one or more AI and/or ML algorithms can be used to map the myocardium subtended by the coronary artery in the first and second images. For example, in some embodiments, the one or more AI and/or ML algorithms can be trained using a Convolutional Neural Network (CNN) on a set of medical images on which subtended myocardium has been identified, thereby allowing the AI and/or ML algorithm automatically map subtended myocardium directly from a medical image.

At block 1216, the system can further be configured to analyze a radiodensity difference between the myocardium subtended by the coronary artery between the first medical image and the second medical image. For example, one or more AI and/or ML algorithms can determine, from the first and second medical images, radiodensities associated with the subtended myocardium and determine a difference therebetween. In some embodiments, the difference in radiodensity between the first and second medical images arises from flow of the contrast dye through microvasculature of the myocardium subtended by the coronary artery.

At block 1218, the system can further be configured to generate a measure of per-artery microcirculatory resistance of the coronary artery by relating the difference in radiodensity between the myocardium subtended by the coronary artery in the first medical image and the second medical image to a difference in time between the first point in time and the second point in time.

With continued reference to FIG. 12C, at block 1220, the system can further be configured to determine an assessment of microcirculatory resistance of the coronary artery based at least in part on comparing the generated measure of the per-artery microcirculatory resistance of the coronary artery to a plurality of reference measures of per-artery microcirculatory resistance. In some embodiments, the determined assessment of microcirculatory resistance of the coronary artery is configured to be utilized to determine a treatment for the subject. In some embodiments, the plurality of reference measures of per-artery microcirculatory resistance are derived from a plurality of other subjects. The plurality of reference values can be stored in a reference values database 1222. In some embodiments, the reference values database 1222 can be locally accessible by the system and/or can be located remotely and accessible through a network connection.

In some embodiments, the assessment of microcirculatory resistance of the coronary artery is determined utilizing a machine learning algorithm trained based at least in part on the plurality of reference measures of per-artery microcirculatory resistance. In some embodiments, the assessment of microcirculatory resistance of the coronary artery is determined utilizing a machine learning algorithm trained based at least in part on the plurality of reference measures of per-artery microcirculatory resistance and known index of microcirculatory resistance (IMR) values. In some embodiments, the assessment of microcirculatory resistance of the coronary artery is determined as normal or abnormal. In some embodiments, the assessment of microcirculatory resistance of the coronary artery is determined as one of low, medium, or high.

In some embodiments, the plurality of reference measures of per-artery microcirculatory resistance is derived from the plurality of other subjects with known IMR values for one or more coronary arteries. In some embodiments, determining the assessment of microcirculatory resistance comprises determining an IMR value for the coronary artery utilizing a machine learning algorithm trained based at least in part on the plurality of reference measures of per-artery microcirculatory resistance and known IMR values. In some embodiments, the determined assessment of microcirculatory resistance comprises an IMR value. In some embodiments, the measure of per-artery microcirculatory resistance comprises an IMR value. In some embodiments, the index of microcirculatory resistance comprises $P_d \times T_{mn}$ at maximal hyperemia, wherein Pa comprises distal coronary pressure, and wherein $T_{mn}$ comprises mean transit time.

In some embodiments, the microvasculature comprises one or more arterioles, capillaries, or venules. In some embodiments, wherein the microvasculature comprises vessels with a diameter less than about 500 μm. In some embodiments, the microvasculature comprises vessels with a diameter less than about 200 μm.

In some embodiments, at block 1226, the system can further be configured to determine a risk of CAD or MI based on one or more plaque analyses described herein, for example in relation to one or more of blocks 1202-1210. In some embodiments, the system can be configured to utilize some or all of the plaque analyses results. In some embodiments, the system can be configured to generate a weighted measure of some or all of the plaque analyses described herein in determining a risk of CAD. In some embodiments, the system can be configured to refer to one or more reference values of one or more plaque analyses results in determining risk of CAD. For example, in some embodiments, the one or more reference values can comprise one or more values derived from a population with varying states of risks of CAD, wherein the one or more values can comprise one or more of one or more distances to and/or from a low density non-calcified plaque, one or more axes measurements, morphology classification, size and/or volume, and/or embeddedness of low density non-calcified plaque. In some embodiments, the one or more reference values can be stored on a reference values database 118, which can be locally accessible by the system and/or can be located remotely and accessible through a network connection. In some embodiments, the risk of CAD or MACE is determined as one of low, medium, or high.

In some embodiments, the system can be configured to generate a graphical representation of the analyses results, determined risk of CAD, and/or proposed treatment for the subject. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1224, which can be locally accessible by the system and/or can be located remotely and accessible through a network connection. In some embodiments, the plaque risk/treatment database 1224 can include reference points or data that relate one or more treatment to cardiovascular disease risk or state determined based on one or more reference plaque analyses values.

With continued reference to FIG. 12C, at block 1228, in some embodiments, the system can further be configured to generate a measure of ischemia for the coronary artery. In some embodiments, a combination of the determined assessment of microcirculatory resistance of the coronary artery and the generated measure of ischemia for the coronary artery is configured to be used to determine a treatment for the subject. In some embodiments, the measure of ischemia comprises fractional flow reserve. In some embodiments, the measure of ischemia is generated utilizing a machine learning algorithm trained based at least in part on data of a plurality of medical images and known measures of ischemia of a plurality of subjects.

In some embodiments, the system can be configured to repeat one or more processes described in relation to blocks 1202-1228, for example for one or more other vessels, segment, regions of plaque, different subjects, and/or for the same subject at a different time.

The computer system 902 of FIG. 9, and in some instances, the analysis and/or risk assessment module 940, can be configured to carry out the functions, methods, acts, and/or processes for image-based assessment of microcirculatory resistance described herein, such as those described above with reference to FIG. 12.

The following are non-limiting examples of certain embodiments of systems and methods for image-based assessment of microcirculatory resistance. Other embodiments may include one or more other features, or different features, that are discussed herein.

Embodiment 1: A computer-implemented method of assessing microcirculatory resistance of coronary microvasculature based on non-invasive medical image analysis, the method comprising: accessing, by a computer system, a first medical image of a subject, wherein the first medical image of the subject is obtained at a first point in time after injection of a contrast dye to the subject; accessing, by the computer system, a second medical image of a subject, wherein the second medical image of the subject is obtained at a second point in time after injection of the contrast dye to the subject; analyzing, by the computer system, the first medical image and the second medical image to identify a coronary artery; mapping, by the computer system, myocardium subtended by the coronary artery in the first medical image and the second medical image; analyzing, by the computer system, a difference in radiodensity between the myocardium subtended by the coronary artery in the first medical image and the second medical image, the difference in radiodensity arising from flow of the contrast dye through microvasculature of the myocardium subtended by the coronary artery; generating, by the computer system, a measure of per-artery microcirculatory resistance of the coronary artery by relating the difference in radiodensity between the myocardium subtended by the coronary artery in the first medical image and the second medical image to a difference in time between the first point in time and the second point in time; and determining, by the computer system, an assessment of microcirculatory resistance of the coronary artery based at least in part on comparing the generated measure of the per-artery microcirculatory resistance of the coronary artery to a plurality of reference measures of per-artery microcirculatory resistance, the plurality of reference measures of per-artery microcirculatory resistance derived from a plurality of other subjects, wherein the determined assessment of microcirculatory resistance of the coronary artery is configured to be utilized to determine a treatment for the subject, wherein the computer system comprises a computer processor and an electronic storage medium.

Embodiment 2: The computer-implemented method of Embodiment 1, wherein the assessment of microcirculatory resistance of the coronary artery is determined utilizing a machine learning algorithm trained based at least in part on the plurality of reference measures of per-artery microcirculatory resistance.

Embodiment 3: The computer-implemented method of Embodiment 1, wherein the assessment of microcirculatory resistance of the coronary artery is determined utilizing a machine learning algorithm trained based at least in part on the plurality of reference measures of per-artery microcirculatory resistance and known index of microcirculatory resistance (IMR) values.

Embodiment 4: The computer-implemented method of Embodiment 1, wherein the assessment of microcirculatory resistance of the coronary artery is determined as normal or abnormal.

Embodiment 5: The computer-implemented method of Embodiment 1, wherein the assessment of microcirculatory resistance of the coronary artery is determined as one of low, medium, or high.

Embodiment 6: The computer-implemented method of Embodiment 1, wherein the plurality of reference measures of per-artery microcirculatory resistance is derived from the plurality of other subjects with known IMR values for one or more coronary arteries.

Embodiment 7: The computer-implemented method of Embodiment 1, wherein determining the assessment of microcirculatory resistance comprises determining an IMR value for the coronary artery utilizing a machine learning algorithm trained based at least in part on the plurality of reference measures of per-artery microcirculatory resistance and known IMR values.

Embodiment 8: The computer-implemented method of Embodiment 1, wherein the determined assessment of microcirculatory resistance comprises an IMR value.

Embodiment 9: The computer-implemented method of Embodiment 1, wherein the measure of per-artery microcirculatory resistance comprises an IMR value.

Embodiment 10: The computer-implemented method of Embodiment 9, wherein the index of microcirculatory resistance comprises Pd×Tmn at maximal hyperemia, wherein Pd comprises distal coronary pressure, and wherein Tmn comprises mean transit time.

Embodiment 11: The computer-implemented method of Embodiment 1, wherein the microvasculature comprises one or more arterioles, capillaries, or venules.

Embodiment 12: The computer-implemented method of Embodiment 1, wherein the microvasculature comprises vessels with a diameter less than about 500 μm.

Embodiment 13: The computer-implemented method of Embodiment 1, wherein the microvasculature comprises vessels with a diameter less than about 200 μm.

Embodiment 14: The computer-implemented method of Embodiment 1, wherein the first medical image and the second medical image comprise a resolution of about 0.3 $mm^3$.

Embodiment 15: The computer-implemented method of Embodiment 1, wherein the first medical image and the second medical image comprise a resolution of about 0.5 $mm^3$.

Embodiment 16: The computer-implemented method of Embodiment 1, wherein the first medical image and the second medical image comprise a resolution that does not allow for image segmentation of plaque within the microvasculature.

Embodiment 17: The computer-implemented method of Embodiment 1, wherein the microvasculature comprises one or more regions of plaque, and wherein the one or more regions of plaque comprise a size that is not recognizable on the first medical image and the second medical image.

Embodiment 18: The computer-implemented method of Embodiment 1, further comprising: identifying, by the computer system, one or more regions of plaque on one or more of the first medical image or the second medical image; and generating, by the computer system, one or more quantified plaque parameters associated with the one or more regions of plaque, the one or more quantified plaque parameters comprising one or more of volume of low-density non-calcified plaque, volume of non-calcified plaque, or volume of calcified plaque, wherein a combination of the generated one or more quantified plaque parameters and the determined assessment of microcirculatory resistance of the coronary artery is configured to be used to determine a risk of major adverse cardiovascular event (MACE) for the subject.

Embodiment 19: The computer-implemented method of Embodiment 18, wherein the combination of the generated one or more quantified plaque parameters and the determined assessment of microcirculatory resistance of the coronary artery is configured to be used to determine a treatment for the subject.

Embodiment 20: The computer-implemented method of Embodiment 18, low density non-calcified plaque comprises a region of plaque comprising a radiodensity value between about −189 and about 30 Hounsfield units.

Embodiment 21: The computer-implemented method of Embodiment 18, wherein non-calcified plaque comprises a region of plaque comprising a radiodensity value between about 31 and about 350 Hounsfield units.

Embodiment 22: The computer-implemented method of Embodiment 18, wherein calcified plaque comprises a region of plaque comprising a radiodensity value between about 351 and 2500 Hounsfield units.

Embodiment 23: The computer-implemented method of Embodiment 1, wherein the determined assessment of microcirculatory resistance of the coronary artery is further configured to be used to generate a risk assessment of MACE of the subject.

Embodiment 24: The computer-implemented method of Embodiment 23, wherein a higher measure of per-artery microcirculatory resistance is indicative of higher risk of MACE.

Embodiment 25: The computer-implemented method of Embodiment 1, wherein the difference in radiodensity between the myocardium subtended by the coronary artery in the first medical image and the second medical image is due to washout of the contrast dye.

Embodiment 26: The computer-implemented method of Embodiment 25, wherein the second point in time is when washout of the contrast dye is complete.

Embodiment 27: The computer-implemented method of Embodiment 1, wherein the difference in radiodensity between the myocardium subtended by the coronary artery in the first medical image and the second medical image is due to washout of the contrast dye.

Embodiment 28: The computer-implemented method of Embodiment 1, wherein the first medical image and the second medical image comprise a Computed Tomography (CT) image.

Embodiment 29: The computer-implemented method of Embodiment 1, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 30: The computer-implemented method of Embodiment 1, further comprising: generating, by the computer system, a measure of ischemia for the coronary artery, wherein a combination of the determined assessment of microcirculatory resistance of the coronary artery and the generated measure of ischemia for the coronary artery is configured to be used to determine a treatment for the subject.

Embodiment 31: The computer-implemented method of Embodiment 30, wherein the measure of ischemia comprises fractional flow reserve.

Embodiment 32: The computer-implemented method of Embodiment 30, wherein the measure of ischemia is generated utilizing a machine learning algorithm trained based at least in part on data of a plurality of medical images and known measures of ischemia of a plurality of subjects.

Embodiment 33: A system for image-based assessment of microcirculatory resistance, the system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a first medical image of a subject, wherein the first medical image of the subject is obtained at a first point in time after injection of a contrast dye to the subject; access a second medical image of a subject, wherein the second medical image of the subject is obtained at a second point in time after injection of the contrast dye to the subject; analyze the first medical image and the second medical image to identify a coronary artery; map myocardium subtended by the coronary artery in the first medical image and the second medical image; analyze a difference in radiodensity between the myocardium subtended by the coronary artery in the first medical image and the second medical image, the difference in radiodensity arising from flow of the contrast dye through microvasculature of the myocardium subtended by the coronary artery; generate a measure of per-artery microcirculatory resistance of the coronary artery by relating the difference in radiodensity between the myocardium subtended by the coronary artery in the first medical image and the second medical image to a difference in time between the first point in time and the second point in time; and determine an assessment of microcirculatory resistance of the coronary artery based at least in part on comparing the generated measure of the per-artery microcirculatory resistance of the coronary artery to a plurality of reference measures of per-artery microcirculatory resistance, the plurality of reference measures of per-artery microcirculatory resistance derived from a plurality of other subjects, wherein the determined assessment of microcirculatory resistance of the coronary artery is configured to be utilized to determine a treatment for the subject.

Embodiment 34: The system of Embodiment 33, wherein the assessment of microcirculatory resistance of the coronary artery is determined utilizing a machine learning algorithm trained based at least in part on the plurality of reference measures of per-artery microcirculatory resistance.

Embodiment 35: The system of Embodiment 33, wherein the assessment of microcirculatory resistance of the coronary artery is determined utilizing a machine learning algorithm trained based at least in part on the plurality of reference measures of per-artery microcirculatory resistance and known index of microcirculatory resistance (IMR) values.

Embodiment 36: The system of Embodiment 33, wherein the assessment of microcirculatory resistance of the coronary artery is determined as normal or abnormal.

Embodiment 37: The system of Embodiment 33, wherein the assessment of microcirculatory resistance of the coronary artery is determined as one of low, medium, or high.

Embodiment 38: The system of Embodiment 33, wherein the plurality of reference measures of per-artery microcirculatory resistance is derived from the plurality of other subjects with known IMR values for one or more coronary arteries.

Embodiment 39: The system of Embodiment 33, wherein determining the assessment of microcirculatory resistance comprises determining an IMR value for the coronary artery utilizing a machine learning algorithm trained based at least in part on the plurality of reference measures of per-artery microcirculatory resistance and known IMR values.

Embodiment 40: The system of Embodiment 33, wherein the determined assessment of microcirculatory resistance comprises an IMR value.

Embodiment 41: The system of Embodiment 33, wherein the measure of per-artery microcirculatory resistance comprises an IMR value.

Embodiment 42: The system of Embodiment 41, wherein the index of microcirculatory resistance comprises Pd×Tmn at maximal hyperemia, wherein Pd comprises distal coronary pressure, and wherein Tmn comprises mean transit time.

Embodiment 43: The system of Embodiment 33, wherein the microvasculature comprises one or more arterioles, capillaries, or venules.

Embodiment 44: The system of Embodiment 33, wherein the microvasculature comprises vessels with a diameter less than about 500 μm.

Embodiment 45: The system of Embodiment 33, wherein the microvasculature comprises vessels with a diameter less than about 200 μm.

Embodiment 46: The system of Embodiment 33, wherein the first medical image and the second medical image comprise a resolution of about 0.3 $mm^3$.

Embodiment 47: The system of Embodiment 33, wherein the first medical image and the second medical image comprise a resolution of about 0.5 $mm^3$.

Embodiment 48: The system of Embodiment 33, wherein the first medical image and the second medical image comprise a resolution that does not allow for image segmentation of plaque within the microvasculature.

Embodiment 49: The system of Embodiment 33, wherein the microvasculature comprises one or more regions of plaque, and wherein the one or more regions of plaque comprise a size that is not recognizable on the first medical image and the second medical image.

Embodiment 50: The system of Embodiment 33, wherein the processor is further configured to: identify one or more regions of plaque on one or more of the first medical image or the second medical image; and generate one or more quantified plaque parameters associated with the one or more regions of plaque, the one or more quantified plaque parameters comprising one or more of volume of low-density non-calcified plaque, volume of non-calcified plaque, or volume of calcified plaque, wherein a combination of the generated one or more quantified plaque parameters and the determined assessment of microcirculatory resistance of the coronary artery is configured to be used to determine a risk of major adverse cardiovascular event (MACE) for the subject.

Embodiment 51: The system of Embodiment 50, wherein the combination of the generated one or more quantified plaque parameters and the determined assessment of microcirculatory resistance of the coronary artery is configured to be used to determine a treatment for the subject.

Embodiment 52: The system of Embodiment 50, low density non-calcified plaque comprises a region of plaque comprising a radiodensity value between about −189 and about 30 Hounsfield units.

Embodiment 53: The computer-implemented method of Embodiment 18, wherein non-calcified plaque comprises a region of plaque comprising a radiodensity value between about 31 and about 350 Hounsfield units.

Embodiment 54: The system of Embodiment 50, wherein calcified plaque comprises a region of plaque comprising a radiodensity value between about 351 and 2500 Hounsfield units.

Embodiment 55: The system of Embodiment 33, wherein the determined assessment of microcirculatory resistance of the coronary artery is further configured to be used to generate a risk assessment of MACE of the subject.

Embodiment 56: The system of Embodiment 55, wherein a higher measure of per-artery microcirculatory resistance is indicative of higher risk of MACE.

Embodiment 57: The system of Embodiment 33, wherein the difference in radiodensity between the myocardium subtended by the coronary artery in the first medical image and the second medical image is due to washout of the contrast dye.

Embodiment 58: The system of Embodiment 57, wherein the second point in time is when washout of the contrast dye is complete.

Embodiment 59: The system of Embodiment 33, wherein the difference in radiodensity between the myocardium subtended by the coronary artery in the first medical image and the second medical image is due to washout of the contrast dye.

Embodiment 60: The system of Embodiment 33, wherein the first medical image and the second medical image comprise a Computed Tomography (CT) image.

Embodiment 61: The system of Embodiment 33, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 62: The system of Embodiment 33, wherein the processor is further configured to: generate a measure of ischemia for the coronary artery, wherein a combination of the determined assessment of microcirculatory resistance of the coronary artery and the generated measure of ischemia for the coronary artery is configured to be used to determine a treatment for the subject.

Embodiment 63: The system of Embodiment 62, wherein the measure of ischemia comprises fractional flow reserve.

Embodiment 64: The system of Embodiment 62, wherein the measure of ischemia is generated utilizing a machine learning algorithm trained based at least in part on data of a plurality of medical images and known measures of ischemia of a plurality of subjects.

Embodiment 65: A non-transitory computer readable medium configured for image-based assessment of microcirculatory resistance, the computer readable medium having program instructions for causing a hardware processor to perform a method of: accessing a first medical image of a subject, wherein the first medical image of the subject is obtained at a first point in time after injection of a contrast dye to the subject; accessing a second medical image of a subject, wherein the second medical image of the subject is obtained at a second point in time after injection of the contrast dye to the subject; analyzing the first medical image and the second medical image to identify a coronary artery; mapping myocardium subtended by the coronary artery in the first medical image and the second medical image; analyzing a difference in radiodensity between the myocardium subtended by the coronary artery in the first medical image and the second medical image, the difference in radiodensity arising from flow of the contrast dye through microvasculature of the myocardium subtended by the coronary artery; generating a measure of per-artery microcirculatory resistance of the coronary artery by relating the difference in radiodensity between the myocardium subtended by the coronary artery in the first medical image and the second medical image to a difference in time between the first point in time and the second point in time; and determining an assessment of microcirculatory resistance of the coronary artery based at least in part on comparing the generated measure of the per-artery microcirculatory resistance of the coronary artery to a plurality of reference measures of per-artery microcirculatory resistance, the plurality of reference measures of per-artery microcirculatory resistance derived from a plurality of other subjects, wherein the determined assessment of microcirculatory resistance of the coronary artery is configured to be utilized to determine a treatment for the subject.

Embodiment 66: The computer readable medium of Embodiment 65, wherein the assessment of microcirculatory resistance of the coronary artery is determined utilizing a machine learning algorithm trained based at least in part on the plurality of reference measures of per-artery microcirculatory resistance.

Embodiment 67: The computer readable medium of Embodiment 65, wherein the assessment of microcirculatory resistance of the coronary artery is determined utilizing a machine learning algorithm trained based at least in part on the plurality of reference measures of per-artery microcirculatory resistance and known index of microcirculatory resistance (IMR) values.

Embodiment 68: The computer readable medium of Embodiment 65, wherein the assessment of microcirculatory resistance of the coronary artery is determined as normal or abnormal.

Embodiment 69: The computer readable medium of Embodiment 65, wherein the assessment of microcirculatory resistance of the coronary artery is determined as one of low, medium, or high.

Embodiment 70: The computer readable medium of Embodiment 65, wherein the plurality of reference measures of per-artery microcirculatory resistance is derived from the plurality of other subjects with known IMR values for one or more coronary arteries.

Embodiment 71: The computer readable medium of Embodiment 65, wherein determining the assessment of microcirculatory resistance comprises determining an IMR value for the coronary artery utilizing a machine learning algorithm trained based at least in part on the plurality of reference measures of per-artery microcirculatory resistance and known IMR values.

Embodiment 72: The computer readable medium of Embodiment 65, wherein the determined assessment of microcirculatory resistance comprises an IMR value.

Embodiment 73: The computer readable medium of Embodiment 65, wherein the measure of per-artery microcirculatory resistance comprises an IMR value.

Embodiment 74: The computer readable medium of Embodiment 73, wherein the index of microcirculatory resistance comprises Pd×Tmn at maximal hyperemia, wherein Pd comprises distal coronary pressure, and wherein Tmn comprises mean transit time.

Embodiment 75: The computer readable medium of Embodiment 65, wherein the microvasculature comprises one or more arterioles, capillaries, or venules.

Embodiment 76: The computer readable medium of Embodiment 65, wherein the microvasculature comprises vessels with a diameter less than about 500 μm.

Embodiment 77: The computer readable medium of Embodiment 65, wherein the microvasculature comprises vessels with a diameter less than about 200 μm.

Embodiment 78: The computer readable medium of Embodiment 65, wherein the first medical image and the second medical image comprise a resolution of about 0.3 $mm^3$.

Embodiment 79: The computer readable medium of Embodiment 65, wherein the first medical image and the second medical image comprise a resolution of about 0.5 $mm^3$.

Embodiment 80: The computer readable medium of Embodiment 65, wherein the first medical image and the second medical image comprise a resolution that does not allow for image segmentation of plaque within the microvasculature.

Embodiment 81: The computer readable medium of Embodiment 65, wherein the microvasculature comprises one or more regions of plaque, and wherein the one or more regions of plaque comprise a size that is not recognizable on the first medical image and the second medical image.

Embodiment 82: The computer readable medium of Embodiment 65, wherein the method further comprises: identifying one or more regions of plaque on one or more of the first medical image or the second medical image; and generating one or more quantified plaque parameters associated with the one or more regions of plaque, the one or more quantified plaque parameters comprising one or more of volume of low-density non-calcified plaque, volume of non-calcified plaque, or volume of calcified plaque, wherein a combination of the generated one or more quantified plaque parameters and the determined assessment of microcirculatory resistance of the coronary artery is configured to be used to determine a risk of major adverse cardiovascular event (MACE) for the subject.

Embodiment 83: The computer readable medium of Embodiment 82, wherein the combination of the generated one or more quantified plaque parameters and the determined assessment of microcirculatory resistance of the coronary artery is configured to be used to determine a treatment for the subject.

Embodiment 84: The computer readable medium of Embodiment 82, low density non-calcified plaque comprises a region of plaque comprising a radiodensity value between about −189 and about 30 Hounsfield units.

Embodiment 85: The computer readable medium of Embodiment 82, wherein non-calcified plaque comprises a region of plaque comprising a radiodensity value between about 31 and about 350 Hounsfield units.

Embodiment 86: The computer readable medium of Embodiment 82, wherein calcified plaque comprises a region of plaque comprising a radiodensity value between about 351 and 2500 Hounsfield units.

Embodiment 87: The computer readable medium of Embodiment 65, wherein the determined assessment of microcirculatory resistance of the coronary artery is further configured to be used to generate a risk assessment of MACE of the subject.

Embodiment 88: The computer readable medium of Embodiment 82, wherein a higher measure of per-artery microcirculatory resistance is indicative of higher risk of MACE.

Embodiment 89: The computer readable medium of Embodiment 65, wherein the difference in radiodensity between the myocardium subtended by the coronary artery in the first medical image and the second medical image is due to washout of the contrast dye.

Embodiment 90: The computer readable medium of Embodiment 89, wherein the second point in time is when washout of the contrast dye is complete.

Embodiment 91: The computer readable medium of Embodiment 65, wherein the difference in radiodensity between the myocardium subtended by the coronary artery in the first medical image and the second medical image is due to washout of the contrast dye.

Embodiment 92: The computer readable medium of Embodiment 65, wherein the first medical image and the second medical image comprise a Computed Tomography (CT) image.

Embodiment 93: The computer readable medium of Embodiment 65, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 94: The computer readable medium of Embodiment 65, wherein the method further comprises: generating, by the computer system, a measure of ischemia for the coronary artery, wherein a combination of the determined assessment of microcirculatory resistance of the coronary artery and the generated measure of ischemia for the coronary artery is configured to be used to determine a treatment for the subject.

Embodiment 95: The computer readable medium of Embodiment 94, wherein the measure of ischemia comprises fractional flow reserve.

Embodiment 96: The computer readable medium of Embodiment 94, wherein the measure of ischemia is generated utilizing a machine learning algorithm trained based at least in part on data of a plurality of medical images and known measures of ischemia of a plurality of subjects.

Image-Based Plaque and Adiposity Prediction, Estimation, and/or Risk Determination As discussed herein, disclosed herein are systems, methods, and devices for image-based plaque and/or adiposity prediction, estimation, analysis, and/or risk determination. In particular, in some embodiments, the systems, devices, and methods described herein are related to analysis of one or more regions of visceral adiposity, which can be used to predict and/or estimate an amount of arterial plaque, such as coronary plaque, which in turn can be used to determine risk of arterial disease. As such, in some embodiments, the systems, methods, and devices described herein can be configured to determine risk of arterial disease, such as coronary artery disease (CAD) and/or MACE, based on analysis visceral adiposity or visceral fat of a subject. In some embodiments, the systems, devices, and methods described herein are related to analysis of one or more regions of visceral adiposity and/or arterial plaque to determine risk of arterial disease. For example, in some embodiments, the systems, devices, and methods described herein are related to visceral adiposity analysis based on one or more of volume of low-density non-calcified plaque, volume of non-calcified plaque, and calcified plaque, and/or the like. In some embodiments, the systems, devices, and methods described herein identify and analyze one or more regions of arterial plaque and/or one or more of a volume of low-density non-calcified plaque, volume of non-calcified plaque, and volume of calcified plaque to estimate an amount of visceral adiposity of a subject, for example using reference values. In some embodiments, the systems, devices, and methods described herein are configured to determine a risk of coronary artery disease (CAD), such as for example myocardial infarction (MI), based on one or more plaque analyses and/or visceral adiposity analyses described herein. In some embodiments, the systems, devices, and methods described herein are configured to generate a proposed treatment and/or graphical representation based on the determined risk of CAD and/or one or more plaque analyses and/or visceral adiposity analyses described herein.

More specifically, in some embodiments, the systems, methods, and devices can be configured to analyze a medical image to perform one or more analyses of arterial plaque and/or visceral adiposity, such as, for example, low density non-calcified plaque, calcified plaque, non-calcified plaque, and/or the like. In particular, in some embodiments, visceral adiposity can be a focus due to the high-risk of artery disease associated with visceral adiposity. For example, in some embodiments, imaging of an umbilicus region can show visceral adiposity which can, in turn, be used to determine a risk for CAD, for example through prediction and/or estimation of coronary plaque based on the amount of visceral adiposity. Also, it can be advantageous to analyze one or more features of low density non-calcified plaque, and/or non-calcified plaque and/or calcified plaque to estimate visceral adiposity. In some embodiments, the systems, devices, and methods are configured to analyze a medical image, such as a CT or CCTA image, to derive one or more features, measures, and/or characterizations of plaque, such as low density non-calcified plaque, non-calcified plaque, and/or calcified plaque, and use the same to facilitate an assessment of and/or generate an assessment of risk of CAD and/or stability or instability of plaque based on volume of arterial plaque and/or visceral adiposity. Thus, in some embodiments, the systems, devices, and methods can provide an efficient and/or non-invasive method of assessing risk of CAD and/or plaque.

Figure 13A:
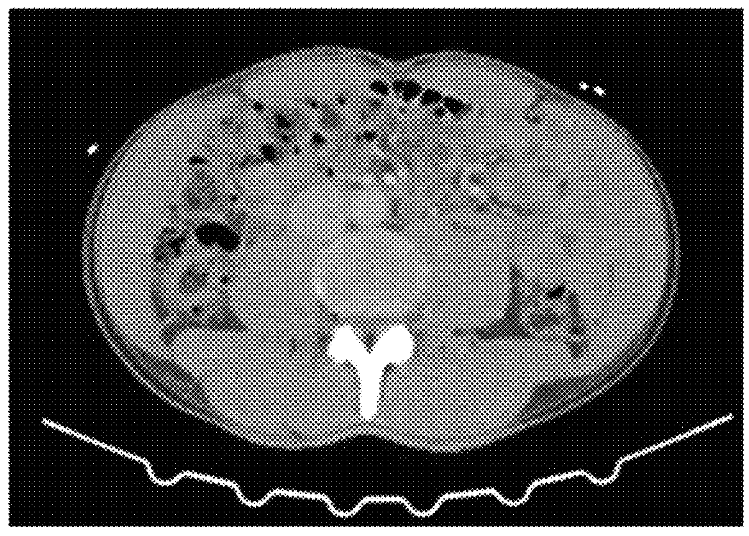
FIG. 13A illustrates a sample medical image for analysis to facilitate risk assessment of arterial plaque disease for a subject.
Figure 13B:
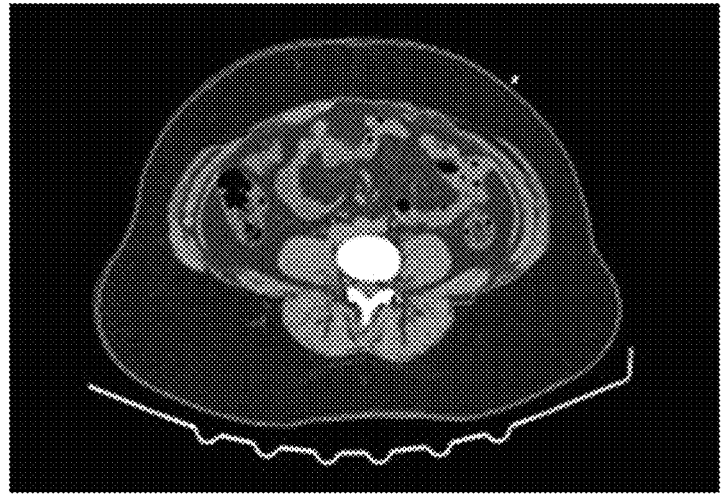
FIG. 13B illustrates a sample medical image for analysis to facilitate risk assessment of arterial plaque disease for a subject.

FIGS. 13A and 13B illustrate a sample medical images for analysis to facilitate risk assessment of arterial plaque disease for a subject. In some embodiments, the system can be configured to utilize medical images, examples being illustrated in FIGS. 13A and 13B. The medical image can comprise a CT or CCTA image that includes a visceral fat representation taken around the umbilicus region. In this example, subcutaneous fat is highlighted by purple color overlay while visceral fat is in green overlay. The image can be, for example, processed by the system and compared against reference standards in a database to identify portions of the image. In some embodiments, the identification may include identifying subcutaneous fat.

Figure 13C:
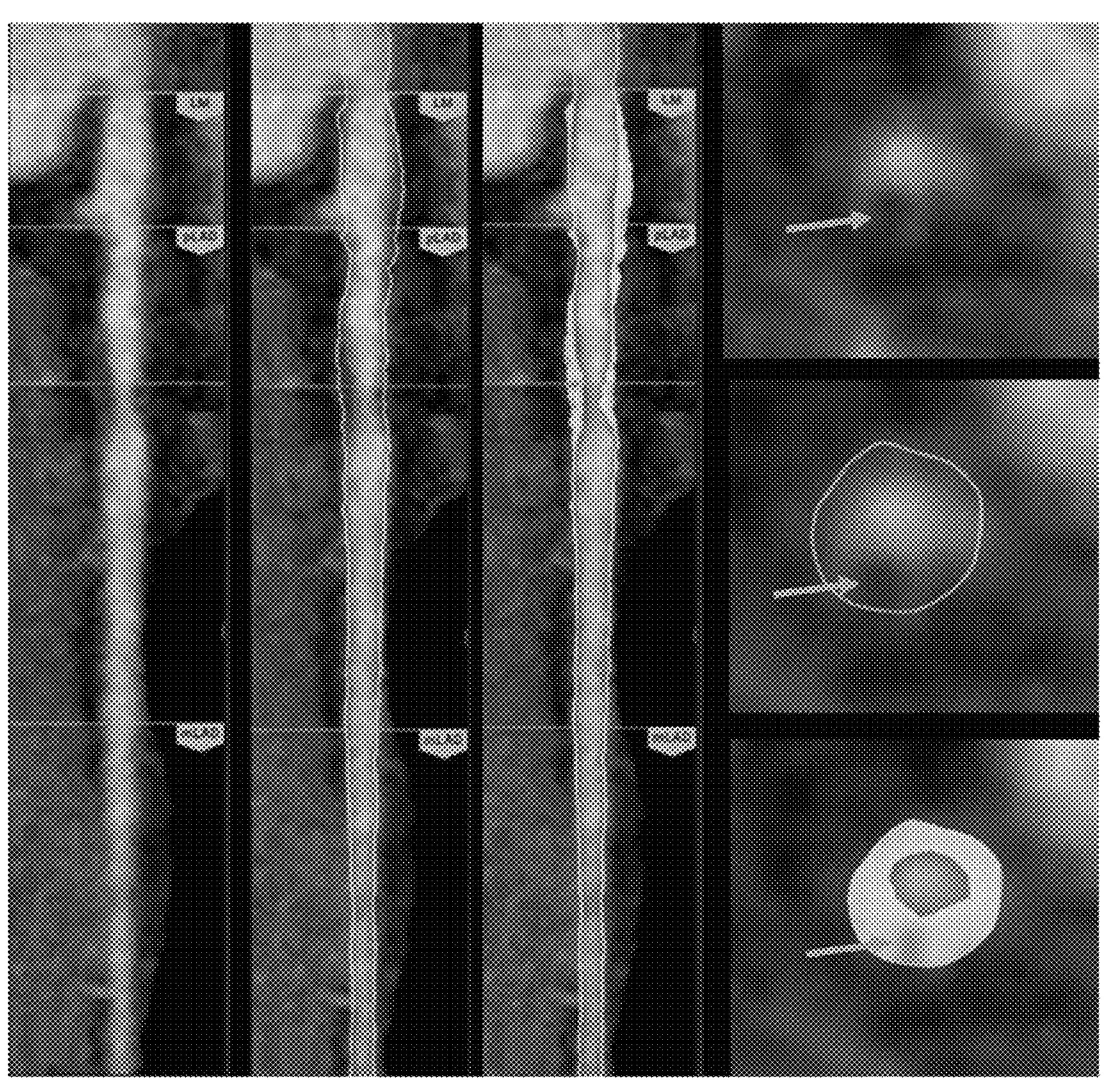
FIG. 13C is a sample reconstruction of a medical image for analysis to facilitate risk assessment of arterial plaque disease for a subject.

FIG. 13C is a sample reconstruction of a medical image for analysis to facilitate risk assessment of arterial plaque disease for a subject. In some embodiments as illustrated in FIG. 13C, a medical image can be used by the system to be manipulated to show alternative, reconstructed views of the medical image. For example, a CT or CCTA image can be taken of an artery which can then be reconstructed into a straightened view. The straightened view may have, for example, overlays that indicate areas of concern, or generally identify plaque and arteries. In some embodiments, the image can show visceral adiposity from a quartile, the image reconstructed. The overlay can, using a database of comparative images, determine areas of plaque and classify them as low-density non-calcified plaque, non-calcified plaque, and calcified plaque. In some embodiments, the system may indicate the classified plaques by a color scheme. In FIG. 13C, straightened multiplanar liner views of a vessel are sown as well as associated cross-sectional views.

In some embodiments, the system may use or generate a cross-sectional medical image. The system may, in some embodiments, be analyzed by the system using a machine learning or other artificial intelligence (e.g., computer vision algorithm). In some embodiments, an image or information derived from an image can be compared against a reference database. The reference database may be used to identify and classify areas of plaque within the cross-sectional medical image. The system may identify low-density non-calcified plaque, non-calcified plaque, and calcified plaque. In some embodiments, the system may indicate the classified plaques by a color scheme.

Figure 13D:
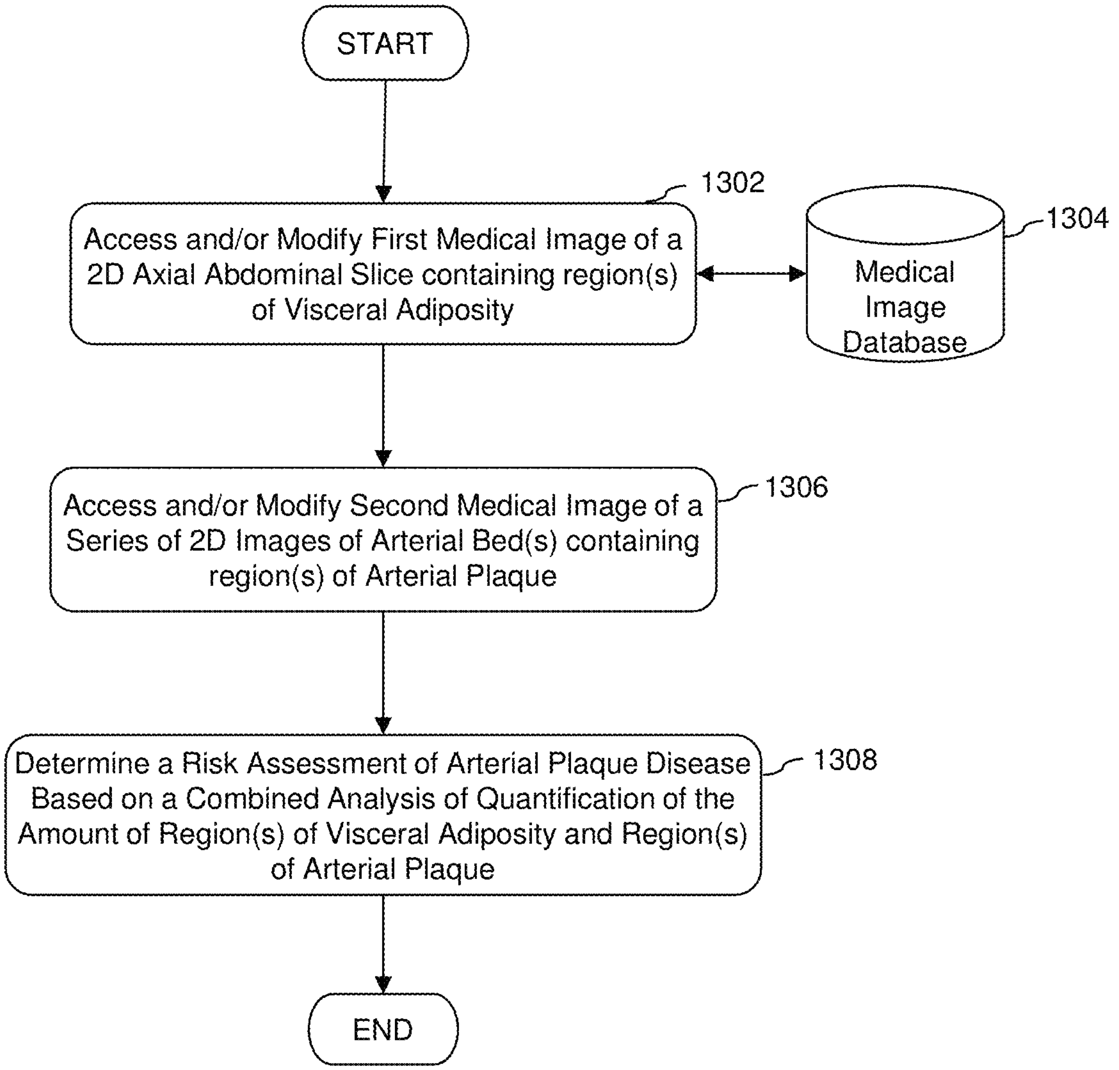
FIG. 13D is a flowchart illustrating an example embodiment(s) of systems, devices, and methods for acquisition of medical images for analysis to facilitate risk assessment of arterial plaque disease for a subject.

FIG. 13D is a flowchart illustrating an example embodiment(s) of image-based analysis for facilitating risk assessment and/or treatment of plaque disease. As illustrated in FIG. 13D, in some embodiments, at block 1302, the system can be configured to access and/or modify a first medical image. In some embodiments, the system can be configured to acquire the first medical image by a first computer system. In some embodiments, the medical image can be stored in a medical image database 1304. In some embodiments, the medical image database 1304 can be locally accessible by the system and/or can be located remotely and accessible through a network connection. In some embodiments, the first medical image comprises a two-dimensional axial slice image of an abdomen of the subject. In some embodiments, the medical image comprises a single axial computed tomography (CT) image acquired at or near a level of the umbilicus of the subject. In some embodiments, the medical image can be stored in a medical image database 1304. In some embodiments, the medical image database 1304 can be locally accessible by the system and/or can be located remotely and accessible through a network connection. The medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above. In some embodiments, the first medical image comprises a two-dimensional image.

In some embodiments, the first medical image comprises one or more regions of visceral adiposity. In some embodiments, the quantification of an amount of the one or more regions of visceral adiposity is indicative of volume of arterial plaque in one or more arterial beds of the subject.

In some embodiments, the system can be further configured to analyze the first medical image to quantify the amount of the one or more regions of visceral adiposity. In some embodiments, the system can be configured to determine whether the amount of the one or more regions of visceral adiposity is above a predetermined threshold. In some embodiments, if the amount of visceral adiposity is above a predetermined threshold, the system can be configured to access and/or obtain a second medical image of an arterial bed. In some embodiments, if the amount of visceral adiposity is below a predetermined threshold, the system can be configured to access and/or obtain a second medical image of an arterial bed. As such, in some embodiments, the system can be configured to utilize analysis of the first medical image as a gatekeeper for further analysis of a second medical image of an arterial bed. Thus, in some embodiments, the system can provide means for resource allocation and/or utilization, as the first medical image can be easier and/or cheaper to obtain than the second medical image.

At block 1306, the system can be configured to acquire, obtain, access and/or modify, by a second computer system, a second medical image. In some embodiments, the second medical image comprises a series of two-dimensional images of one or more arterial beds of the subject. In some embodiments, the series of two-dimensional images is configured to be reconstructed into a three-dimensional image of the one or more arterial beds of the subject. In some embodiments, the second medical image comprises a three-dimensional image of the one or more arterial beds of the subject. In some embodiments, the second medical image comprises one or more regions of arterial plaque, such as for example low-density non-calcified plaque, non-calcified plaque, and/or calcified plaque. In some embodiments, the second medical image comprises a single axial computed tomography (CT) image acquired at or near a level of the umbilicus of the subject. In some embodiments, the medical image can be stored in a medical image database 1304. In some embodiments, the medical image database 1304 can be locally accessible by the system and/or can be located remotely and accessible through a network connection. The medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above. In some embodiments, the second medical image comprises a two-dimensional image.

In some embodiments, the one or more arterial beds comprises one or more of a coronary artery, aorta, carotid artery, lower extremity artery, or upper extremity artery.

In some embodiments, the system is further configured to generate, by the computer system, a graphical representation indicating a need to acquire a second medical image when the amount of the one or more regions of visceral adiposity is above the predetermined threshold. In some embodiments, the system is configured to determine that a second medical image does not need to be acquired when the amount of the one or more regions of visceral adiposity is below the predetermined threshold.

In some embodiments, the first medical image and the second medical image are acquired simultaneously using a single image acquisition system. In some embodiments, the first medical image and the second medical image are acquired sequentially using a single image acquisition system. In some embodiments, the first medical image is acquired prior to the second medical image. In some embodiments, the first medical image is acquired subsequent to the second medical image. In some embodiments, the first medical image and the second medical image are acquired sequentially using a different image acquisition system. In some embodiments, the first computer system and the second computer system are part of a single computer system. In some embodiments, the first computer system and the second computer system are separate. In some embodiments, the first medical image and the second medical image comprises a computed tomography (CT) image. In some embodiments, one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

At block 1308, the system can be configured to determine a risk assessment of arterial plaque disease for the subject using one or both of quantification of the amount of the one or more regions of visceral adiposity and/or analysis of the one or more regions of arterial plaque. In some embodiments, the system is further configured to determine a risk of a major adverse cardiovascular event (MACE) for the subject based on one or both of the visceral adiposity analysis and/or arterial plaque analysis.

Figure 14A:
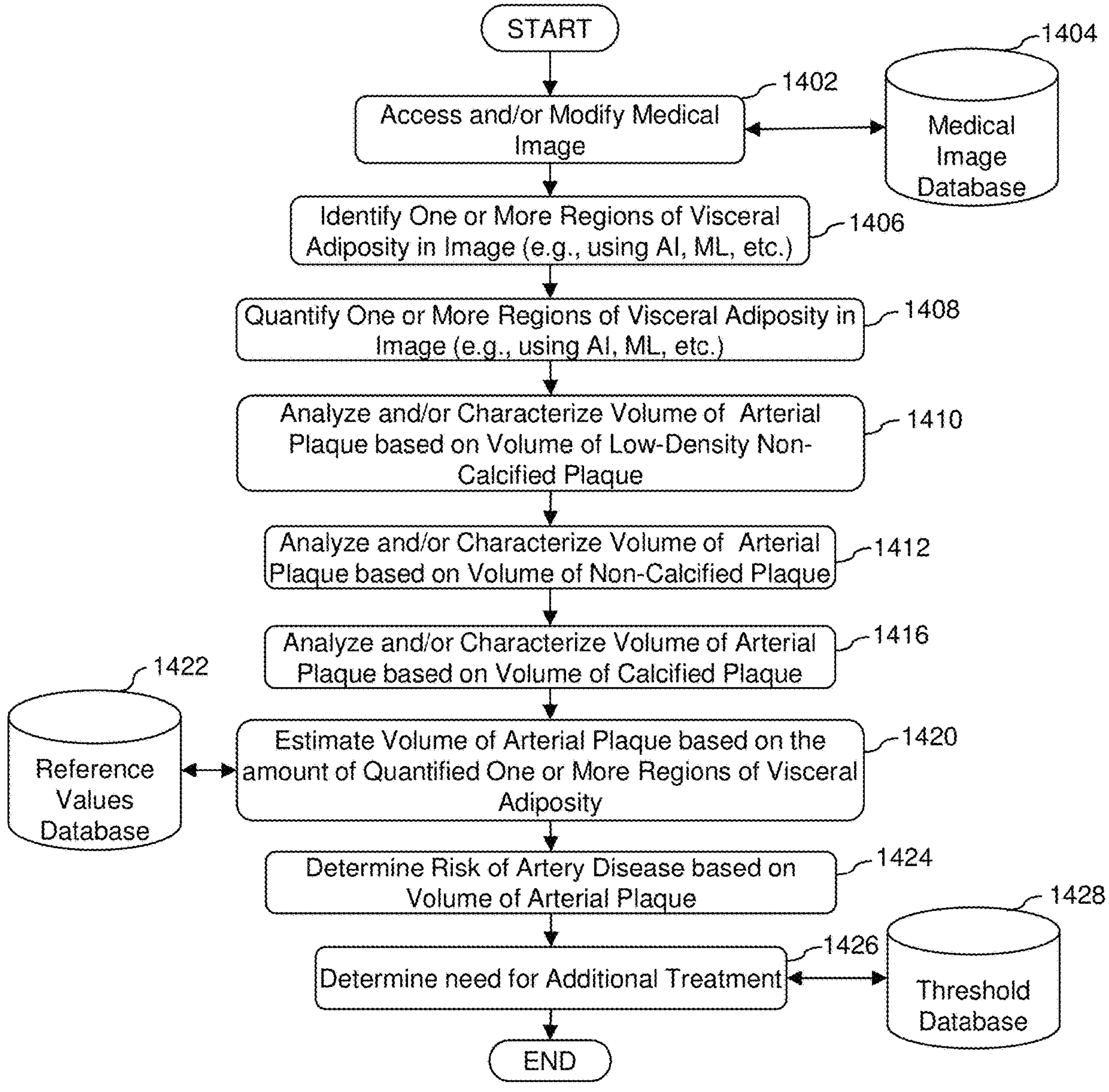
FIG. 14A is a flowchart illustrating an example embodiment(s) of systems, devices, and methods for image-based plaque prediction, estimation, analysis, and/or risk determination using visceral adiposity.

FIG. 14A is a flowchart illustrating an example embodiment(s) of systems, devices, and methods for image-based plaque prediction, estimation, analysis, and/or risk determination using visceral adiposity.

As illustrated in FIG. 14A, in some embodiments, the system can be configured to analyze, access, and/or modify a medical image to estimate volume of arterial plaque in an arterial bed region of a subject based at least in part on analysis of visceral adiposity on a medical image. The arterial bed region can be, for example, one or more of a coronary artery, aorta, carotid artery, lower extremity artery, or upper extremity artery. In some embodiments, at block 1402, a medical image is accessed. The medical image can comprise, for example, an axial slice of an abdomen of the subject. The medical image, or medical images, may be stored, in some embodiments at block 1404, in a medical image database. For example, the medical image can comprise a single axial computed tomography (CT) image acquired at or near a level of the umbilicus of the subject. The image can, in other embodiments, include x-ray, MRI, and/or the like.

Using a medical image or medical images, in some embodiments at block 1406, the system can analyze the medical image(s) to identify one or more regions of visceral adiposity. In some embodiments, the quantified amount of the one or more regions of visceral adiposity comprises a two-dimensional area of the one or more regions of visceral adiposity identified on the medical image. In some embodiments, the quantified amount of the one or more regions of visceral adiposity comprises volume of the one or more regions of visceral adiposity identified on the medical image. The identification of the one or more regions of visceral adiposity may comprise segmenting subcutaneous fat and/or visceral fat.

In some embodiments, at block 1408, the system quantifies an amount of the one or more regions of visceral adiposity identified on the medical image. Quantification can utilize AI or ML technology to increase speed and accuracy of quantification. Other embodiments can include using other technologies to aid the system in quantifying the regions of visceral adiposity. For example, an AI or ML algorithm can be trained on a data set of medical images that have been labeled with quantification of visceral adiposity.

The system can, in some embodiments, estimate the volume of arterial plaque in an arterial bed region based at least in part on the quantified amount of the one or more regions of visceral adiposity identified on the medical image. For example, in some embodiments, the system can be configured to use the quantified analysis of visceral adiposity to predict and/or estimate volume of low-density non-calcified plaque, volume of non-calcified plaque, and/or volume of calcified plaque. In some embodiments, the volume of arterial plaque in the arterial bed region is estimated using a plurality of reference values of volume of arterial plaque in the arterial bed and amount of visceral adiposity obtained from a plurality of reference subjects. In some embodiments, the volume of arterial plaque in the arterial bed region is estimated using an AI or ML algorithm. In some embodiments, the estimated volume of arterial plaque in the arterial bed region comprises one or more ranges of volume of arterial plaque. In some embodiments, the estimated volume of arterial plaque in the arterial bed region comprises a value of volume of arterial plaque.

In some embodiments, at block 1424, the volume of arterial plaque can be estimated using the quantified one or more regions of visceral adiposity. In some embodiments, the volume of arterial plaque is first analyzed and/or characterized by the volumes of low-density non-calcified plaque, non-calcified plaque, and/or calcified plaque. In some embodiments, the volume of arterial plaque is estimated based on the one or more regions of visceral adiposity. The estimation, at block 1422, can utilize reference values from a reference values database to make the estimation of the volume of arterial plaque based on collected or known values. The reference values database can contain data from a larger population having known values. The estimation, at block 1424, can be indicative of risk of artery disease for the subject.

In some embodiments, the system can be configured to estimate volume and/or amount of one or more types of arterial plaque of the subject based on analysis of visceral adiposity. For example, in some embodiments, the system can be configured to use visceral adiposity analysis to predict and/or estimate an amount of low density non-calcified plaque, non-calcified plaque, and/or calcified plaque. In some embodiments, calcified plaque can correspond to plaque having a highest density range, low density non-calcified plaque can correspond to plaque having a lowest density range, and non-calcified plaque can correspond to plaque having a density range between calcified plaque and low density non-calcified plaque. For example, in some embodiments, low density non-calcified plaque can correspond to a region of plaque with a radiodensity of an image pixel or voxel corresponding to that region of plaque between about −189 and about 30 Hounsfield units (HU). In some embodiments, non-calcified plaque can correspond to a region of plaque with a radiodensity of an image pixel or voxel corresponding to that region of plaque between about 31 and about 350 HU. In some embodiments, calcified plaque can correspond to a region of plaque with a radiodensity of an image pixel or voxel corresponding to that region of plaque between about 351 and about 2500 HU. In some embodiments, the lower and/or upper Hounsfield unit boundary threshold for defining one or more of low density non-calcified plaque, non-calcified plaque, and/or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU.

After the risk of artery disease is determined based on volume of arterial plaque, in some embodiments, at block 1426, the system can determine a need for additional treatment. The estimated volume of arterial plaque above a predetermined threshold is indicative of additional treatment or testing of the subject for artery disease. The threshold can be stored in a threshold database, at block 1428, from which the system can gain threshold data to compare against the determined risk to decide if additional treatment or testing needs to be performed. In some embodiments, the additional testing of the subject for artery disease comprises obtaining a computed tomography (CT) image of the arterial bed. In some embodiments, the CT image of the arterial bed comprises a coronary CT angiography (CCTA). In some embodiments, the additional testing of the subject for artery disease further comprises quantitative analysis of the CCTA. In some embodiments, the quantitative analysis of the CCTA is based at least in part on artificial intelligence (AI) or machine learning (ML). In some embodiments, the treatment comprises one or more of a medication treatment, lifestyle treatment, or revascularization treatment.

Figure 14B:
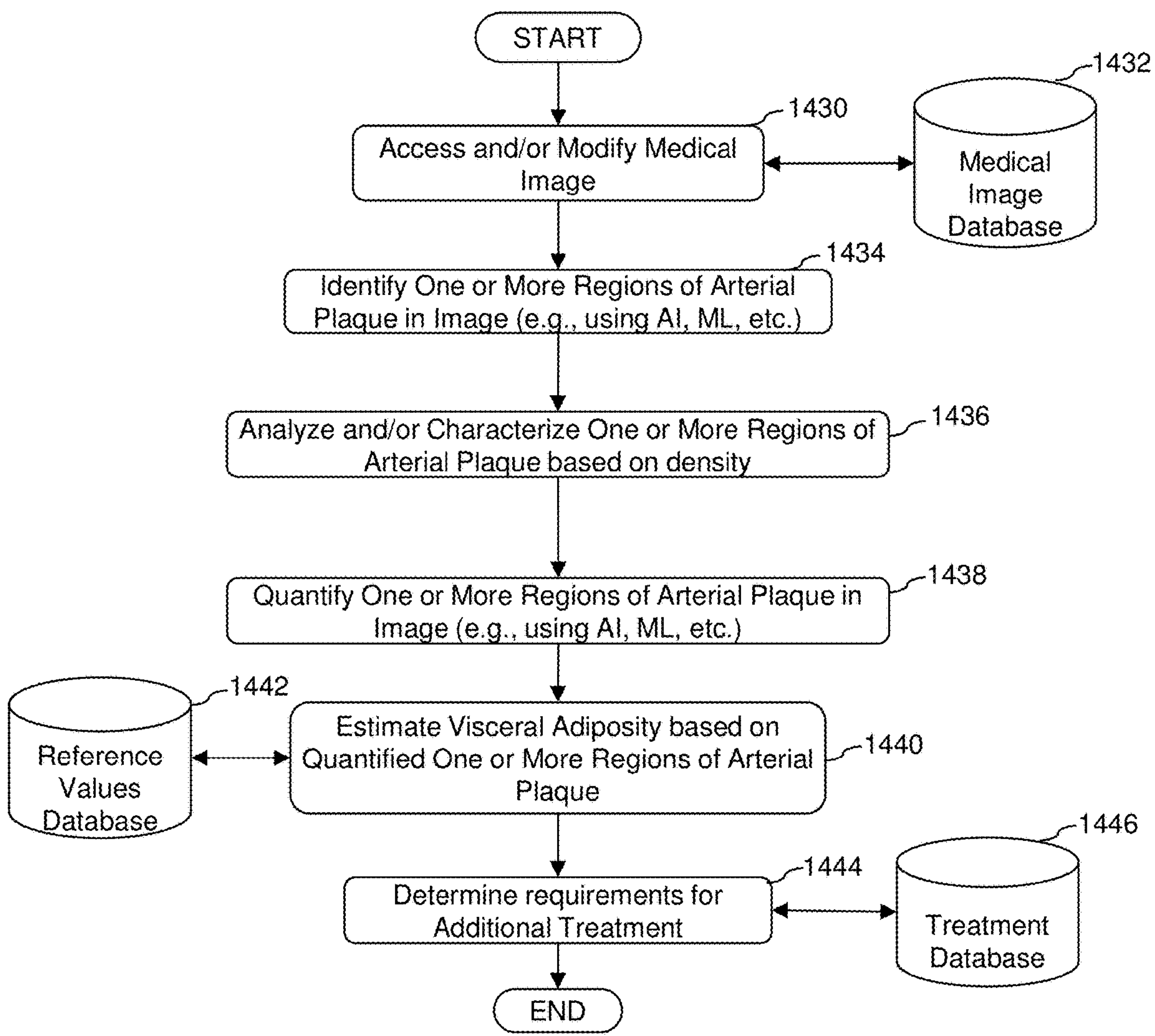
FIG. 14B is a flowchart illustrating an example embodiment(s) of systems, devices, and methods for image-based plaque prediction, estimation, analysis, and/or risk determination using arterial plaque and visceral adiposity.

FIG. 14B is a flowchart illustrating an example embodiment(s) of systems, devices, and methods for image-based plaque prediction, estimation, analysis, and/or risk determination using arterial plaque and visceral adiposity. As illustrated in FIG. 14B, in some embodiments, the system implements a method of estimating an amount of visceral adiposity of a subject based at least in part on analysis of arterial plaque in an arterial bed region of the subject using image analysis. In some embodiments, the arterial bed region comprises one or more of a coronary artery, aorta, carotid artery, lower extremity artery, or upper extremity artery. To analyze the arterial plaque in an arterial bed region, in some embodiments, at block 1430, the system accesses a medical image of the arterial bed region of the subject. In some embodiments, at block 1432, medical image can come from a medical image database. The medical image can, in some embodiments, comprise a Computed Tomography (CT) image. In some embodiments, the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

The system can, in some embodiments, at block 1434, identify one or more regions of arterial plaque in the medical image. The identification can be, for example, performed using AI, ML, or other such algorithms. In some embodiments, at block 1436, the system can analyze and/or characterize one or more regions of arterial plaque based on density. The arterial plaque can be, in some embodiments, characterized by analyzing volumes of low-density non-calcified plaque, non-calcified plaque, and calcified plaque. In some embodiments, calcified plaque can correspond to plaque having a highest density range, low density non-calcified plaque can correspond to plaque having a lowest density range, and non-calcified plaque can correspond to plaque having a density range between calcified plaque and low density non-calcified plaque. For example, in some embodiments, the system can be configured to characterize a particular region of plaque as low density non-calcified plaque when the radiodensity of an image pixel or voxel corresponding to that region of plaque is between about −189 and about 30 Hounsfield units (HU). In some embodiments, the system can be configured to characterize a particular region of plaque as non-calcified plaque when the radiodensity of an image pixel or voxel corresponding to that region of plaque is between about 31 and about 350 HU. In some embodiments, the system can be configured to characterize a particular region of plaque as calcified plaque when the radiodensity of an image pixel or voxel corresponding to that region of plaque is between about 351 and about 2500 HU. In some embodiments, the lower and/or upper Hounsfield unit boundary threshold for determining whether a plaque corresponds to one or more of low density non-calcified plaque, non-calcified plaque, and/or calcified plaque can be about −1000 HU, about −900 HU, about −800 HU, about −700 HU, about −600 HU, about −500 HU, about −400 HU, about −300 HU, about −200 HU, about −190 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30 HU, about −20 HU, about −10 HU, about 0 HU, about 10 HU, about 20 HU, about 30 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, about 350 HU, about 360 HU, about 370 HU, about 380 HU, about 390 HU, about 400 HU, about 410 HU, about 420 HU, about 430 HU, about 440 HU, about 450 HU, about 460 HU, about 470 HU, about 480 HU, about 490 HU, about 500 HU, about 510 HU, about 520 HU, about 530 HU, about 540 HU, about 550 HU, about 560 HU, about 570 HU, about 580 HU, about 590 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, about 2500 HU, about 2600 HU, about 2700 HU, about 2800 HU, about 2900 HU, about 3000 HU, about 3100 HU, about 3200 HU, about 3300 HU, about 3400 HU, about 3500 HU, and/or about 4000 HU.

In some embodiments, at block 1438, the system can quantify a volume of the characterized one or more regions of arterial plaque in the medical image. In some embodiments, at block 1440, the system can estimate the amount of visceral adiposity of the subject based at least in part on the quantified volume of the characterized one or more regions of arterial plaque. In some embodiments, the amount of visceral adiposity of the subject comprises a two-dimensional area of visceral adiposity on an axial slice medical image acquired at or near a level of the umbilicus of the subject. In some embodiments, the amount of visceral adiposity of the subject comprises volume of visceral adiposity in the abdomen of the subject.

In some embodiments, at block 1440, the amount of visceral adiposity of the subject is estimated using a plurality of reference values of volume of characterized arterial plaque in the arterial bed and amount of visceral adiposity obtained from a plurality of reference subjects in a reference values database. In some embodiments, at block 1444, the amount of visceral adiposity is configured to be used to determine a treatment for the subject. The treatment can be determined, for example at block 446, by using a treatment database of known or created treatments 1446.

As discussed herein, disclosed herein are systems, methods, and devices for image-based plaque prediction, estimation, analysis, and/or risk determination. In particular, in some embodiments, the systems, devices, and methods described herein are related to analysis of one or more regions of visceral adiposity, which can be used to predict and/or estimate an amount of arterial plaque, such as coronary plaque, which in turn can be used to determine risk of arterial disease. As such, in some embodiments, the systems, methods, and devices described herein can be configured to determine risk of arterial disease, such as coronary artery disease (CAD) and/or MACE, based on analysis visceral adiposity or visceral fat of a subject. In some embodiments, the systems, devices, and methods described herein are related to analysis of one or more regions of visceral adiposity and/or arterial plaque to determine risk of arterial disease. For example, in some embodiments, the systems, devices, and methods described herein are related to visceral adiposity analysis based on one or more of volume of low-density non-calcified plaque, volume of non-calcified plaque, and calcified plaque, and/or the like. In some embodiments, the systems, devices, and methods described herein identify and analyze one or more regions of arterial plaque and/or one or more of a volume of low-density non-calcified plaque, volume of non-calcified plaque, and volume of calcified plaque to estimate an amount of visceral adiposity of a subject, for example using reference values. In some embodiments, the systems, devices, and methods described herein are configured to determine a risk of coronary artery disease (CAD), such as for example myocardial infarction (MI), based on one or more plaque analyses and/or visceral adiposity analyses described herein. In some embodiments, the systems, devices, and methods described herein are configured to generate a proposed treatment and/or graphical representation based on the determined risk of CAD and/or one or more plaque analyses and/or visceral adiposity analyses described herein.

Figure 15:
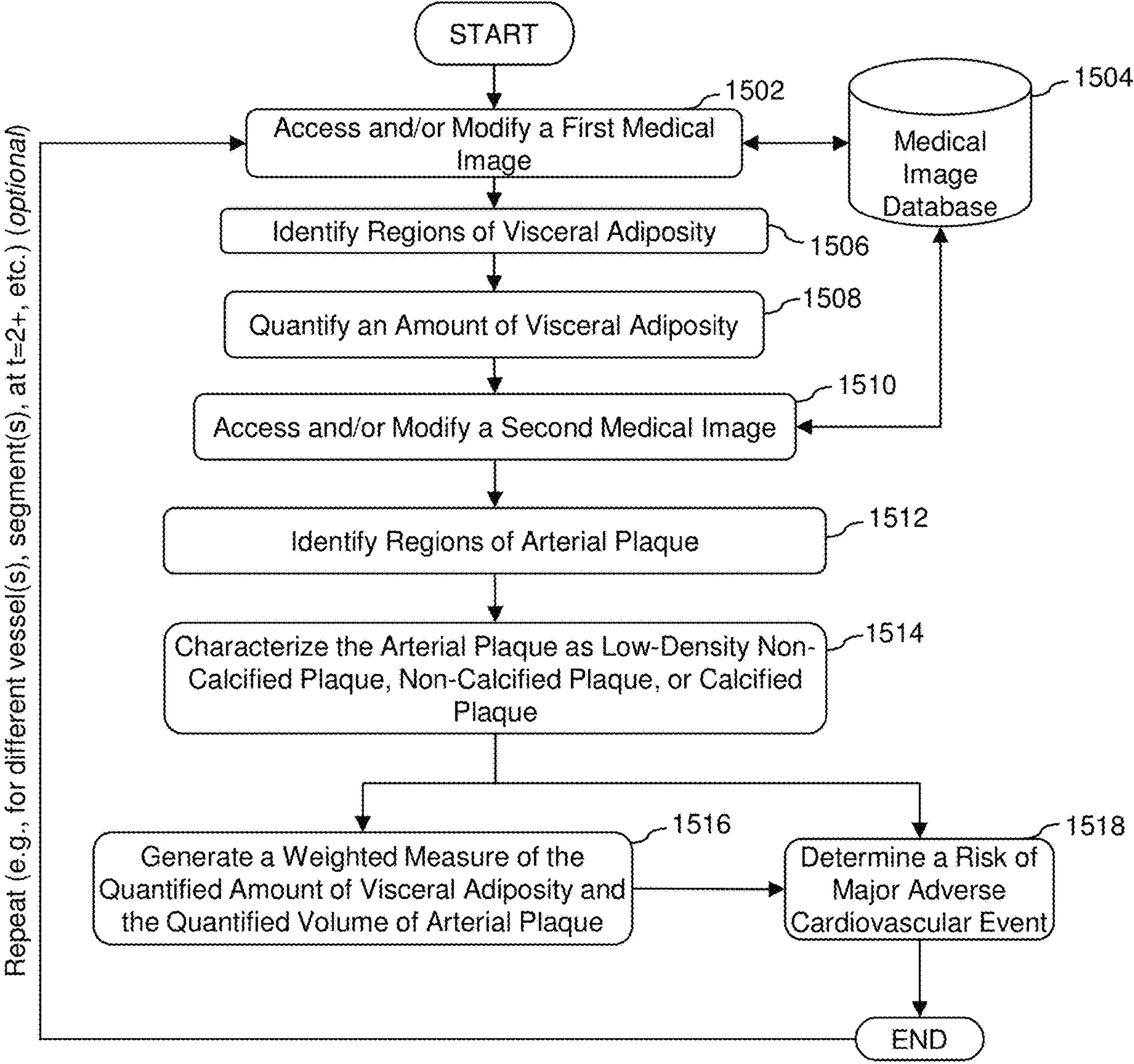
FIG. 15 is a flowchart illustrating an example embodiment(s) of systems, devices, and methods for non-invasive image-based plaque analysis and risk determination.

FIG. 15 is a flowchart illustrating an example embodiment(s) of systems, devices, and methods for image-based analysis for facilitating risk assessment and/or treatment of plaque disease. As illustrated in FIG. 15, in some embodiments, the system can be configured to access and/or modify one or more first medical images at block 1502. In some embodiments, the first medical image can include a first medical image comprising an axial slice of an abdomen of the subject. In some embodiments, the first medical image comprises a single axial computed tomography (CT) image acquired at or near a level of the umbilicus of the subject. In some embodiments, the medical image can be stored in a medical image database 1504. In some embodiments, the medical image database 1504 can be locally accessible by the system and/or can be located remotely and accessible through a network connection. The medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above. In some embodiments, the first medical image comprises a two-dimensional image.

In some embodiments, the system can be configured to automatically and/or dynamically perform one or more analyses of the medical image as discussed herein. For example, in some embodiments, at block 1506, the system can be configured to identify one or more regions of visceral adiposity. In some embodiments, the one or more regions of visceral adiposity are identified on the first medical image using an artificial intelligence (AI) or machine learning (ML) algorithm.

In some embodiments, at block 1508, the system can be configured to quantify an amount of visceral adiposity identified in the first medical image. In some embodiments, the volume of visceral adiposity is identified from the first medical image using an artificial intelligence (AI) or machine learning (ML) algorithm.

In some embodiments, the system can be configured to access and/or modify one or more second medical images at block 1510. In some embodiments, the second medical image can include the second medical image comprising an arterial bed of the subject. In some embodiments, the arterial bed region comprises one or more of a coronary artery, aorta, carotid artery, lower extremity artery, or upper extremity artery. In some embodiments, the medical image can be stored in a medical image database 1504. In some embodiments, the medical image database 1504 can be locally accessible by the system and/or can be located remotely and accessible through a network connection. The medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above. In some embodiments, the second medical image comprises a series of two-dimensional images configured to be reconstructed into a three-dimensional image.

In some embodiments, the system can be configured to automatically and/or dynamically perform one or more analyses of the medical image as discussed herein. For example, in some embodiments, at block 1512, the system can be configured to identify one or more regions of plaque in arteries. In some embodiments, the second medical image comprises a Computed Tomography (CT) image. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1512, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, at block 1514, the system can be configured to analyze and/or characterize one or more regions of plaque based on density. For example, in some embodiments, the system can be configured to analyze and/or characterize one or more regions of plaque based on absolute density and/or relative density and/or radiodensity. In some embodiments, the system can be configured to classify a region of plaque as one of low density non-calcified plaque, non-calcified plaque, and calcified plaque, using any one or more processes and/or features described herein.

In some embodiments, at block 1514, the system can be configured to analyze and/or characterize one or more regions of plaque based on one or more distances. For example, as described herein, in some embodiments, the system can be configured to determine a distance between a low density non-calcified plaque and lumen wall and/or vessel wall. In some embodiments, proximity of a low density non-calcified plaque to the lumen wall can be indicative of a high-risk plaque and/or CAD. Conversely, in some embodiments, a position of a low density non-calcified plaque far from the lumen wall can be indicative of less risk. In some embodiments, the system can be configured to utilize one or more predetermined thresholds in determining the risk factor associated with the proximity of low density non-calcified plaque with the vessel wall and/or lumen wall. In some embodiments, the system can be configured to utilize one or more image processing algorithms to automatically and/or dynamically determine one or more distances to and/or from one or more regions of plaque. In some embodiments, low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units. In some embodiments, the density comprises material density or radiodensity.

In some embodiments, at block 1514, the system can be configured to analyze and/or characterize one or more regions of plaque based on morphology or shape and/or one or more axes measurements of low density non-calcified plaque. As described herein, in some embodiments, the system can be configured to determine the length of one or more axes of a low density non-calcified plaque, such as for example a major axis of a longitudinal cross section and/or a major and/or minor axis of a latitudinal cross section of a low density non-calcified plaque. In some embodiments, the system can be configured to utilize the one more axes measurements to determine a morphology and/or shape of a low density non-calcified plaque. In some embodiments, the system can be configured to utilize one or more image processing algorithms to automatically and/or dynamically determine one or more axes measurements of one or more regions of plaque.

In some embodiments, the system can be configured to utilize one or more AI and/or ML algorithms to automatically and/or dynamically classify the shape of one or more regions of plaque using image processing. For example, in some embodiments, the one or more AI and/or ML algorithms can be trained using a Convolutional Neural Network (CNN) on a set of medical images on which the shape of regions of plaque have been identified, thereby allowing the AI and/or ML algorithm automatically identify the shape or morphology of a region of plaque directly from a medical image. In some embodiments, the system can be configured to classify the shape or morphology of a region of plaque as one or more of crescent, lobular, round, or bean-shaped. In some embodiments, round and/or bean-shaped plaques can be associated with high risk, while crescent and/or lobular-shaped plaques can be associated with low risk of CAD.

In some embodiments, at block 1514, the system can be configured to analyze and/or characterize one or more regions of plaque based on one or more sizes and/or volumes. For example, in some embodiments, the system can be configured to determine a size and/or volume of plaque based at least in part on one or more axes measurements described herein. In some embodiments, the system can be configured to determine the size and/or volume of a region of plaque directly from analysis of a three-dimensional image scan. In some embodiments, the system can be configured to determine the size and/or volume of total plaque, low-density non-calcified plaque, non-calcified plaque, calcified plaque, and/or a ratio between two of the aforementioned volumes or sizes. In some embodiments, a high total plaque volume and/or high low-density non-calcified plaque and/or non-calcified plaque volume can be associated with high risk of CAD. In some embodiments, a high ratio of low-density non-calcified plaque volume to total plaque volume and/or a high ratio of non-calcified plaque volume to total plaque volume can be associated with high risk of CAD. In some embodiments, a high calcified plaque volume and/or high ratio of calcified plaque volume to total plaque volume can be associated with low risk of CAD. In some embodiments, the system can be configured to utilize one or more predetermined threshold values for determining the risk of CAD based on plaque volume, size, or one or more ratios thereof. In some embodiments, the system can be configured to utilize one or more image processing algorithms to automatically and/or dynamically determine the size and/or volume of one or more regions of plaque.

In some embodiments, at block 1514, the system can be configured to analyze and/or characterize plaque based on embeddedness. For example, in some embodiments, the system can be configured to determine how embedded or surrounded a low density non-calcified plaque is by non-calcified plaque or calcified plaque. In some embodiments, the system can be configured to analyze the embeddedness of low density non-calcified plaque based on the degree by which it is surrounded by other types of plaque. In some embodiments, a higher embeddedness of a low density non-calcified plaque can be indicative of high risk of CAD. For example, in some embodiments, a low density non-calcified plaque that is surrounded by 270 degrees or more by non-calcified plaque can be associated with high risk of CAD. In some embodiments, the system can be configured to utilize one or more image processing algorithms to automatically and/or dynamically determine the embeddedness of one or more regions of plaque.

In some embodiments, at block 516, the system can be configured to generate a weighted measure of the quantified amount of the one or more regions of visceral adiposity identified on the first medical image and the quantified volume of the characterized one or more regions of arterial plaque. In some embodiments, the system can be configured to generate a weighted measure of some or all of the visceral adiposity analyses and plaque analyses described herein in determining a risk of CAD. In some embodiments, the system can be configured to refer to one or more reference values of one or more plaque analyses results in determining risk of CAD. For example, in some embodiments, the one or more reference values can comprise one or more values derived from a population with varying states of risks of CAD, wherein the one or more values can comprise one or more of one or more distances to and/or from a low density non-calcified plaque, one or more axes measurements, morphology classification, size and/or volume, and/or embeddedness of low density non-calcified plaque.

In some embodiments, at block 1518, the system can be configured to determine a risk of major adverse cardiovascular event (MACE) or arterial plaque disease for the subject based at least in part on the generated weighted measure. In some embodiments, the analysis results can be displayed on a vessel, lesion, and/or subject basis. In some embodiments, the system can be configured to determine a treatment for the subject based at least in part on the determined risk of MACE or arterial plaque disease, the treatment comprising one or more of lifestyle treatment, medication treatment, or invasive treatment. In some embodiments, the proposed treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 226, which can be locally accessible by the system and/or can be located remotely and accessible through a network connection. In some embodiments, the plaque risk/treatment database 226 can include reference points or data that relate one or more treatment to cardiovascular disease risk or state determined based on one or more reference plaque analysis values.

In some embodiments, the system can be configured to repeat one or more processes described in relation to blocks 1502-1518, for example for one or more other regions of visceral adiposity, vessels, segment, regions of plaque, different subjects, and/or for the same subject at a different time. As such, in some embodiments, the system can provide for longitudinal disease tracking and/or personalized treatment for a subject.

Figure 16A:
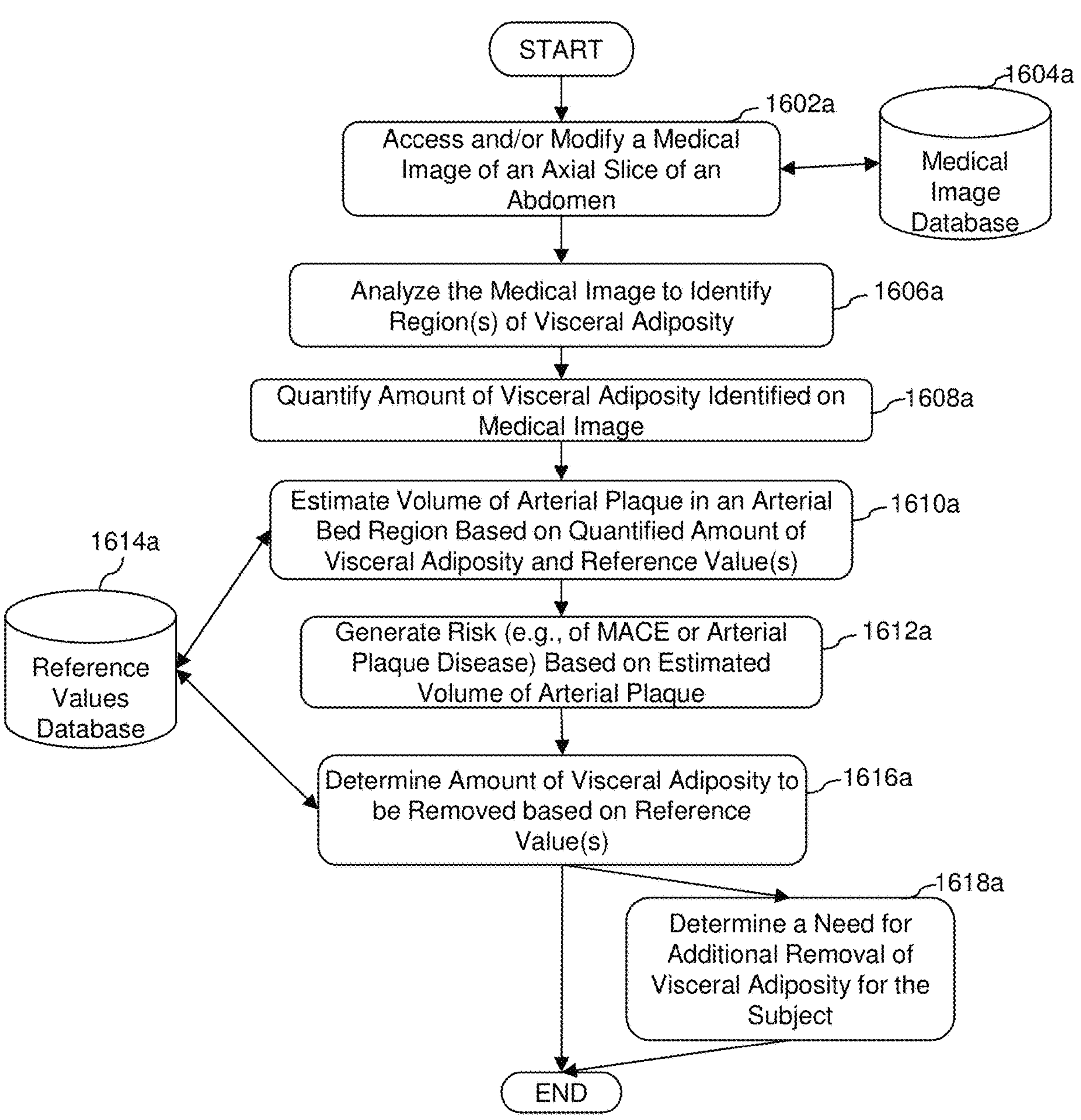
FIG. 16A is a flowchart illustrating an example embodiment(s) of systems, devices, and methods for facilitating treatment of arterial plaque disease through removal of visceral adiposity from an abdomen of a subject.

FIG. 16A is a flowchart illustrating an example embodiment(s) of systems, devices, and methods for facilitating treatment of arterial plaque disease through removal of visceral adiposity from an abdomen of a subject. As illustrated in FIG. 16A, in some embodiments, at block 1602*a*, the system can be configured to access and/or modify a first medical image. In some embodiments, the medical image can be stored in a medical image database 1604*a*. In some embodiments, the medical image database 1604*a* can be locally accessible by the system and/or can be located remotely and accessible through a network connection. In some embodiments, the first medical image comprises an axial slice of an abdomen of the subject. The computer-implemented method of claim 1, wherein the first medical image comprises a single axial computed tomography (CT) image acquired at or near a level of the umbilicus of the subject.

In some embodiments, at block 1606*a*, the system can be configured to analyze the first medical image to identify one or more regions of visceral adiposity, using for example, the methods previously described. In some embodiments, at block 1608*a*, the system can be configured to quantify an amount of the one or more regions of visceral adiposity identified on the first medical image. In some embodiments, the quantified amount of the one or more regions of visceral adiposity comprises a two-dimensional area of the one or more regions of visceral adiposity identified on the first medical image. In some embodiments, the quantified amount of the one or more regions of visceral adiposity comprises volume of the one or more regions of visceral adiposity identified on the first medical image. Quantification can be performed, in some embodiments, using an ML or AI algorithm as described previously.

In some embodiments, at block 1610*a*, the system can be configured to estimate a volume of arterial plaque in an arterial bed region based at least in part on the quantified amount of the one or more regions of visceral adiposity identified on the first medical image. In some embodiments, the volume of arterial plaque in the arterial bed region is estimated using a plurality of reference values of volume of arterial plaque in the arterial bed and amount of visceral adiposity obtained from a plurality of reference subjects. In some embodiments, in estimating the volume of arterial plaque, the system can access a reference values database 1614*a*, which can be locally accessible by the system and/or can be located remotely and accessible through a network connection.

In some embodiments, the volume of arterial plaque comprises one or more of volume of low-density non-calcified plaque, volume of non-calcified plaque, or volume of calcified plaque. In some embodiments, low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

In some embodiments, the low-density non-calcified plaque comprises a region of plaque on a CT image comprising a radiodensity value between about −189 and about 30 Hounsfield units. In some embodiments, the Hounsfield units in this range are, or between, two of about −189 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30, about −20, about −10, about 0, about 10, about 20, and about 30 HU.

In some embodiments, the non-calcified plaque comprises a region of plaque on a CT image comprising a radiodensity value between about 31 and about 350 Hounsfield units. In some embodiments, the Hounsfield units in this range are, or are between, two of about 31 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, and about 350 HU.

In some embodiments, the calcified plaque comprises a region of plaque on a CT image comprising a radiodensity value between about 351 and 2500 Hounsfield units. In some embodiments, the Hounsfield units in this range are, or are between, two of about 351 HU, about 400 HU, about 500 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, and about 2500 HU.

In some embodiments, the arterial bed region comprises one or more of a coronary artery, aorta, carotid artery, lower extremity artery, or upper extremity artery. In some embodiments, the volume of arterial plaque in the arterial bed region is estimated using an artificial intelligence (AI) or machine learning (ML) algorithm. In some embodiments, the estimated volume of arterial plaque in the arterial bed region comprises one or more ranges of volume of arterial plaque. In some embodiments, the estimated volume of arterial plaque in the arterial bed region comprises a value of volume of arterial plaque.

In some embodiments, at block 1612*a*, the system can be configured to generate a risk of major adverse cardiovascular event (MACE) or arterial plaque disease for the subject based at least in part on the estimated volume of arterial plaque in the arterial bed region.

In some embodiments, at block 1616*a*, the system can be configured to determine an amount of visceral adiposity to be removed from the abdomen of the subject to reduce the risk of MACE or arterial plaque disease for the subject below a predetermined threshold, wherein the amount of visceral adiposity to be removed is determined based at least in part on using the plurality of reference values of volume of arterial plaque in the arterial bed and amount of visceral adiposity obtained from the plurality of reference subjects. In some embodiments, in determining the amount of visceral adiposity to be removed, the system can access a reference values database 1614*a*, which can be locally accessible by the system and/or can be located remotely and accessible through a network connection.

In some embodiments, visceral adiposity is removed from the abdomen of the subject using cryolipolysis. In some embodiments, visceral adiposity is surgically removed from the abdomen of the subject. In some embodiments, visceral adiposity is removed from the abdomen of the subject using one or more of liposuction, radiofrequency treatment, or cauterization.

In some embodiments, at block 1618*a*, the system can be configured to determine a need for additional removal of visceral adiposity for the subject. In some embodiments, the system can be configured to access a second medical image, the second medical image comprising the arterial bed region of the subject, the second medical image obtained after removing from the abdomen of the subject at least a portion of the determined amount of visceral adiposity to be removed to reduce the risk of MACE or arterial plaque disease for the subject below the predetermined threshold. In some embodiments, the second medical image comprises a Computed Tomography (CT) image. In some embodiments, the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS). In some embodiments, the system can be configured to analyze the second medical image to identify one or more regions of arterial plaque. In some embodiments, the system can be configured to quantify a volume of the one or more regions of arterial plaque. In some embodiments, the system can be configured to determine an updated risk of MACE or arterial plaque disease for the subject based at least in part on the quantified volume of the one or more regions of arterial plaque. In some embodiments, the system can be configured to determine a need for additional removal of visceral adiposity for the subject based at least in part on the updated risk of MACE or arterial plaque disease.

In some embodiments, the system is further configured to treat the subject to reduce visceral adiposity to reduce the risk of MACE or arterial plaque disease for the subject below the predetermined threshold. In some embodiments, the treatment comprises one or more of lifestyle treatment, medication treatment, or surgical treatment.

Figure 16B:
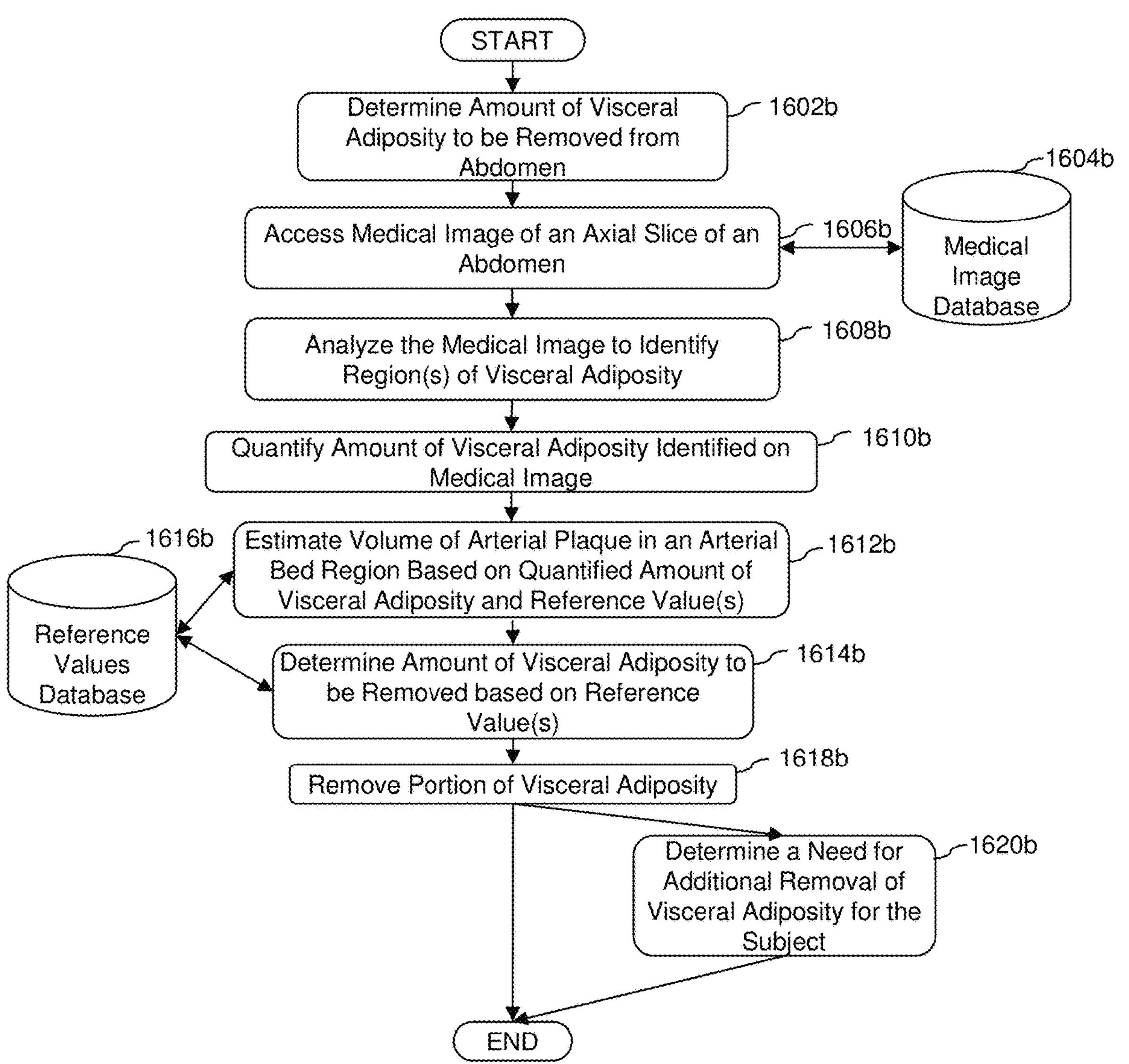
FIG. 16B is a flowchart illustrating an example embodiment(s) of systems, devices, and methods for removing visceral adiposity from an abdomen of a subject to treat arterial plaque disease.

FIG. 16B is a flowchart illustrating an example embodiment(s) of systems, devices, and methods for removing visceral adiposity from an abdomen of a subject to treat arterial plaque disease. As illustrated in FIG. 16B, in some embodiments, at block 1602*b*, the system can be configured to determine an amount of visceral adiposity to remove from an abdomen of a subject to reduce risk of major adverse cardiovascular event (MACE) or arterial plaque disease for the subject.

In some embodiments, the amount of visceral adiposity to remove is determined based at least in part on blocks 1606*b*-1614*b*. In some embodiments, at block 1606*b*, the system is configured to access a first medical image, the first medical image comprising an axial slice of the abdomen of the subject. In some embodiments, the first medical image comprises a single axial computed tomography (CT) image acquired at or near a level of the umbilicus of the subject. In some embodiments, the medical image can be stored in a medical image database 1604*b*.

In some embodiments, at block 1608*b*, the system is configured to analyze the first medical image to identify one or more regions of visceral adiposity. Identification of the regions of visceral adiposity can be accomplished, in some embodiments, using an ML or AI computer vision algorithm.

In some embodiments, at block 1610*b*, the system is configured to quantify an amount of the one or more regions of visceral adiposity identified on the first medical image. In some embodiments, the quantified amount of the one or more regions of visceral adiposity comprises a two-dimensional area of the one or more regions of visceral adiposity identified on the first medical image. In some embodiments, the quantified amount of the one or more regions of visceral adiposity comprises volume of the one or more regions of visceral adiposity identified on the first medical image. Quantification of the regions of visceral adiposity can be accomplished, in some embodiments, using an ML or AI computer vision algorithm.

In some embodiments, at block 1612*b*, the system is configured to estimate a volume of arterial plaque in an arterial bed region based at least in part on the quantified amount of the one or more regions of visceral adiposity identified on the first medical image. In some embodiments, the volume of arterial plaque in the arterial bed region is estimated using a plurality of reference values of volume of arterial plaque in the arterial bed and amount of visceral adiposity obtained from a plurality of reference subjects. In some embodiments, in estimating the volume of arterial plaque, the system can access a reference values database 1616*b*, which can be locally accessible by the system and/or can be located remotely and accessible through a network connection.

In some embodiments, the volume of arterial plaque comprises one or more of volume of low-density non-calcified plaque, volume of non-calcified plaque, or volume of calcified plaque.

In some embodiments, low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

In some embodiments, the low-density non-calcified plaque comprises a region of plaque on a CT image comprising a radiodensity value between about −189 and about 30 Hounsfield units. In some embodiments, the Hounsfield units in this range are, or between, two of about −189 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30, about −20, about −10, about 0, about 10, about 20, and about 30 HU.

In some embodiments, the non-calcified plaque comprises a region of plaque on a CT image comprising a radiodensity value between about 31 and about 350 Hounsfield units. In some embodiments, the Hounsfield units in this range are, or are between, two of about 31 HU, about 40 HU, about 50 HU, about 60 HU, about 70 HU, about 80 HU, about 90 HU, about 100 HU, about 110 HU, about 120 HU, about 130 HU, about 140 HU, about 150 HU, about 160 HU, about 170 HU, about 180 HU, about 190 HU, about 200 HU, about 210 HU, about 220 HU, about 230 HU, about 240 HU, about 250 HU, about 260 HU, about 270 HU, about 280 HU, about 290 HU, about 300 HU, about 310 HU, about 320 HU, about 330 HU, about 340 HU, and about 350 HU.

In some embodiments, the calcified plaque comprises a region of plaque on a CT image comprising a radiodensity value between about 351 and 2500 Hounsfield units. In some embodiments, the Hounsfield units in this range are, or are between, two of about 351 HU, about 400 HU, about 500 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, and about 2500 HU.

In some embodiments, the arterial bed region comprises one or more of a coronary artery, aorta, carotid artery, lower extremity artery, or upper extremity artery. In some embodiments, the volume of arterial plaque in the arterial bed region is estimated using an artificial intelligence (AI) or machine learning (ML) algorithm. In some embodiments, the estimated volume of arterial plaque in the arterial bed region comprises one or more ranges of volume of arterial plaque. In some embodiments, the estimated volume of arterial plaque in the arterial bed region comprises a value of volume of arterial plaque.

In some embodiments, at block 1614*b*, the system is configured to determine an amount of visceral adiposity to be removed from the abdomen of the subject to reduce the risk of MACE or arterial plaque disease for a patient below a predetermined threshold, wherein the amount of visceral adiposity to be removed is determined based at least in part on using the plurality of reference values of volume of arterial plaque in the arterial bed and amount of visceral adiposity obtained from the plurality of reference subjects. In some embodiments, in determining the amount of visceral adiposity to be removed, the system can access a reference values database 1616*b*, which can be locally accessible by the system and/or can be located remotely and accessible through a network connection.

In some embodiments, at block 1618*b*, the system is configured to provide a recommendation for removal of fat from the abdomen of the subject, wherein at least a portion of the amount of visceral adiposity to be removed to reduce the risk of MACE or arterial plaque disease for the subject below the predetermined threshold. In some embodiments, visceral adiposity is removed from the abdomen of the subject using cryolipolysis. In some embodiments, visceral adiposity is surgically removed from the abdomen of the subject. In some embodiments, visceral adiposity is removed from the abdomen of the subject using one or more of liposuction, radiofrequency treatment, or cauterization.

In some embodiments, at block 620*b*, the system is configured to determine a need for additional removal of visceral adiposity for the subject, wherein the need for additional removal of visceral adiposity is determined based at least in part on an updated risk of MACE or arterial plaque disease for the subject. In some embodiments, in determining the updated risk of MACE or arterial plaque disease, the system may be configured to access a second medical image, the second medical image comprising the arterial bed region of the subject, the second medical image obtained after removing from the abdomen of the subject at least a portion of the determined amount of visceral adiposity to be removed to reduce the risk of MACE or arterial plaque disease for the subject below the predetermined threshold. In some embodiments, the second medical image comprises a Computed Tomography (CT) image. In some embodiments, the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS). In some embodiments, the system may be configured to analyze the second medical image to identify one or more regions of arterial plaque. In some embodiments, the system may be configured to quantify a volume of the one or more regions of arterial plaque. In some embodiments, the system may be configured to determine an updated risk of MACE or arterial plaque disease for the subject based at least in part on the quantified volume of the one or more regions of arterial plaque.

In some embodiments, the system can be configured to characterize one or more regions of visceral adiposity and/or one or more regions of plaque or can be included in additional treatment determined by the system. In some embodiments, the system can generate a display of the same on a straightened multiplanar view or a multiplanar view of a vessel. In some embodiments, the systems, methods, and devices can be configured to perform one or more analyses on one or more regions of plaque, which can be a factor and/or indicator of the stability of plaque and/or risk of CAD or MI. For example, in some embodiments, the systems, methods, and devices can be configured to determine a distance from a region of low density non-calcified plaque to the vessel wall and/or lumen wall. In some embodiments, the systems, methods, and devices can be configured to determine one or more dimensions, such as for example major and/or minor axes, of a region of low density non-calcified plaque. In some embodiments, the systems, methods, and devices can be configured to determine the degree of embeddedness of a low density non-calcified plaque. In some embodiments, the systems, methods, and devices can be configured to determine a shape or morphology of low density non-calcified plaque. In some embodiments, the systems, methods, and devices can be configured to determine a volume or size of low density non-calcified plaque, total plaque, and/or a ratio thereof. In some embodiments, the systems, methods, and devices can be configured to take into account one or some or all of the aforementioned analyses in assessing the stability or instability of plaque and/or risk of CAD or MI on a patient or subject basis, vessel basis, lesion basis, and/or the like. In some embodiments, the systems, methods, and devices can be configured to generate a weighted measure of one or some or all of the aforementioned analyses in assessing the stability or instability of plaque and/or risk of CAD or MI on a patient or subject basis, vessel basis, lesion basis, and/or the like. In some embodiments, the systems, methods, and devices can be configured to utilize one or more artificial intelligence (AI) and/or machine learning (MI) algorithms in performing any one or more of the analyses described herein.

In particular, in some embodiments, the systems, methods, and devices can be configured to measure and/or determine a distance from a region of low density non-calcified plaque to the lumen and/or vessel walls. In some embodiments, the distance from a region of low density non-calcified plaque to the lumen and/or vessel walls can be indicative of the stability of the low density non-calcified plaque and hence be considered a factor in determining the risk of CAD arising from that low density non-calcified plaque. For example, in some embodiments, a low density non-calcified plaque that is closer to the lumen wall can be considered more susceptible to rupture and cause an MI.

In particular, in some embodiments, the system can be configured to determine the shortest distance between a point in the boundary of the region of low density non-calcified plaque and the vessel wall and/or lumen wall. In some embodiments, the system can be configured to determine the distance between a low density non-calcified plaque and the vessel wall and/or lumen wall based on a two-dimensional slice image and/or a three-dimensional rendering. In some embodiments, the system can be configured to automatically and/or semi-automatically determine a distance from a low density non-calcified plaque to the vessel and/or lumen wall. In some embodiments, the system can be configured to assist a user in determining a distance from a low density non-calcified plaque to the vessel and/or lumen wall. For example, in some embodiments, the system can be configured to generate a graphical user interface that allows a user to click on two points on the image, after which the system can automatically determine the distance between the two points.

For example, in some embodiments, the system can be configured to measure and/or determine the length of a major and/or minor axis of a region of low density noncalcified plaque. In some embodiments, the system can be configured to measure and/or determine the length of a major and/or minor axis of a region of low density non-calcified plaque automatically or semi-automatically, for example using an image processing algorithm. In some embodiments, the system can be configured to measure and/or determine the length of a major and/or minor axis of a region of low density non-calcified plaque based at least in part on user input, for example using a digital caliper. In some embodiments, the system can be configured to measure and/or determine the length of a major and/or minor axis of a region of low density non-calcified plaque based on a three-dimensional analysis and/or based on one or more two-dimensional images.

In some embodiments, the longitudinal slice can be taken such that it is parallel to a longitudinal axis of a multiplanar or straightened multiplanar view of a vessel. In some embodiments, the longitudinal slice can be taken such that it shows the longest possible longitudinal axis of the low density non-calcified plaque. In some embodiments, the system can be configured to take a latitudinal slice image of a region of plaque and measure the major and/or minor axis of low density non-calcified plaque. In some embodiments, the latitudinal slice can be taken such that is perpendicular or orthogonal to the longitudinal axis of a multiplanar or straightened multiplanar view of a vessel and/or longitudinal slice. In some embodiments, the longitudinal slice can be taken such that it shows the largest possible cross-sectional area of low density non-calcified plaque. In some embodiments, the system can be configured to determine measurements of one or more orthogonal axes of a low density non-calcified plaque.

In some embodiments, such measurements of one or more axes of a region of low density non-calcified plaque can be utilized by the system for further characterization and/or analysis. For example, in some embodiments, measurement (s) of one or more axes of a region of low density non-calcified plaque can be used as a factor in assessing the stability of plaque and/or risk of CAD or MI of the subject, either directly or indirectly. In some embodiments, the system can be configured to utilize one or more measurements of one or more axes of a region of low density non-calcified plaque to determine and/or estimate the size, volume, and/or shape of low density non-calcified plaque, which in turn can be correlated to an assessment of the stability of plaque and/or risk of CAD or MI. In some embodiments, the system can be configured to directly correlate one or more measurements of one or more axes of a region of low density non-calcified plaque to an assessment of the stability of plaque and/or risk of CAD or MI.

In some embodiments, the systems, methods, and devices can be configured to determine an embeddedness of low density non-calcified plaque, for example by regular non-calcified plaque and/or calcified plaque. In some embodiments, the embeddedness of low density non-calcified plaque can be a factor and/or indicator of the stability of plaque and/or risk of CAD or MI, as a more embedded a low-density non-calcified plaque can be more likely to rupture and/or have a thin fibrous cap or more likely to develop a thin fibrous cap. In some embodiments, the system can be configured to determine the embeddedness of low density non-calcified plaque based on the degree of encapsulation of the low density non-calcified plaque by non-calcified plaque or calcified plaque. For example, in some embodiments, the system can be configured to determine the embeddedness of low density non-calcified plaque as one or more of about 0°, about 30°, about 60°, about 90°, about 120°, about 150°, about 180°, about 210°, about 240°, about 270°, about 300°, about 330°, about 360°, and/or between a range defined by two of the aforementioned values. In the example illustrated in FIG. 13C, in some embodiments, the embeddedness of low density non-calcified plaque is determined to be about 90°, about 180°, about 270°, about 360° in each example. In some embodiments, an embeddedness of low density non-calcified plaque at or above about 270° can be considered a high-risk plaque. In some embodiments, the system can be configured to determine the embeddedness of a region of low density non-calcified plaque automatically or semi-automatically, for example using an image processing algorithm. In some embodiments, the system can be configured to determine the embeddedness of a region of low density non-calcified plaque based at least in part on user input. In some embodiments, the system can be configured to graphically overlay a protractor on a medical image to assist with and/or to display the embeddedness of a region of low density non-calcified plaque.

In some embodiments, the systems, methods, and devices can be configured to determine shape or morphology of a region of low density non-calcified plaque. In some embodiments, the system can be configured to determine and/or characterize the shape or morphology of a low density non-calcified plaque as one or more of a crescent, round, lobular, or bean shape. In some embodiments, the shape or morphology of a low density non-calcified plaque can be a factor and/or indicator of plaque stability and/or risk of CAD. For example, in some embodiments, a crescent-shaped low density non-calcified plaque can be associated with lower risk of CAD or MI. In some instances, this can be because what appears to be a crescent-shaped plaque due to image analysis can potentially correspond to perivascular fat rather than a true low density non-calcified plaque, especially for example if found around or near or adjacent to the vessel wall. In some embodiments, a round of bean-shaped low density non-calcified plaque can be associated with a higher risk of CAD or MI. In some embodiments, a lobular shaped low-density non-calcified plaque can be associated with higher risk of CAD compared to a crescent shape but lower risk of CAD compared to a bean or round-shaped low density non-calcified plaque. In some embodiments, a low density non-calcified plaque can be classified as lobular v. bean-shape depending on the number of lobes.

In some embodiments, the system can be configured to classify the shape or morphology of a region of low density non-calcified plaque automatically or semi-automatically, for example using an image processing algorithm. In some embodiments, the system can be configured to classify the shape or morphology of a region of low density non-calcified plaque based at least in part on user input. In some embodiments, the system can be configured to classify the shape or morphology of a region of low density non-calcified plaque based at least in part on the one or more measures of one or more axes of the low density non-calcified plaque. For example, in some embodiments, the system can be configured to compare the major longitudinal axis, major latitudinal axis, and/or minor latitudinal axis of a region of low density non-calcified plaque in determining the shape of the low density non-calcified plaque. In some embodiments, the system can be configured to take the standard deviation of one or more of the major longitudinal axis, major latitudinal axis, and/or minor latitudinal axis, and classify a low density non-calcified plaque as a round shape when the standard deviation is below a certain predetermined threshold. In some embodiments, a crescent, lobular, and/or bean-shaped low density non-calcified plaque can be associated with a higher standard deviation among axes measurements.

In some embodiments, the systems, devices, and methods can be configured to determine a volume or size of total plaque, low density non-calcified plaque, non-calcified plaque, and/or calcified plaque, and/or a ratio thereof. In some embodiments, the volume or size of total plaque, low density non-calcified plaque, non-calcified plaque, and/or calcified plaque can be a factor and/or indicator in determining the stability of plaque and/or assessing risk of CAD or MI. For example, in some embodiments, a higher volume of total plaque, low density non-calcified plaque, and/or non-calcified plaque can be indicative of a high-risk plaque and/or high risk of CAD. In some embodiments, a high ratio of low density non-calcified plaque to total plaque can be indicative of a high-risk plaque and/or high risk of CAD.

In some embodiments, the system can be configured to determine the size or volume of a region of low density non-calcified plaque automatically or semi-automatically, for example using an image processing algorithm. In some embodiments, the system can be configured to determine the size or volume of a region of low density non-calcified plaque based at least in part on user input. In some embodiments, the system can be configured to determine the size or volume of a region of low density non-calcified plaque based at least in part on the one or more measures of one or more axes of the low density non-calcified plaque.

In some embodiments, the use of coronary and visceral adiposity imaging, for example, as described above with respect to FIGS. 13A-16B can be used to guide the therapeutic benefit of various drugs, including, for example, weight loss drugs. For example, imaging can occur over time to determine a weight loss drug's effectiveness (e.g., showing a quantified reduction in visceral adiposity), but such treatment can also be guided to take into account other affects that the drug may have on other health metrics, such as coronary artery disease. In this way, it can be possible to increase the efficacy of a weight loss drug while also taking into account potential side effects of the drug, such as increasing CAD.

The computer system 902 of FIG. 9, and in some instances, the analysis and/or risk assessment module 940, can be configured to carry out the functions, methods, acts, and/or processes for image-based plaque and adiposity prediction, estimation, and/or risk determination described herein, such as those described above with reference to FIGS. 13A-16B.

The following are non-limiting examples of certain embodiments of systems and methods for image-based analysis for image-based plaque and adiposity prediction, estimation, and/or risk determination. Other embodiments may include one or more other features, or different features, that are discussed herein.

Embodiment 1: A computer-implemented method of acquisition of medical images for analysis to facilitate risk assessment of arterial plaque disease for a subject, the method comprising: acquiring, by a first computer system, a first medical image, the first medical image comprising a two-dimensional axial slice image of an abdomen of the subject, the first medical image comprising one or more regions of visceral adiposity, wherein quantification of an amount of the one or more regions of visceral adiposity is indicative of volume of arterial plaque in one or more arterial beds of the subject; and acquiring, by a second computer system, a second medical image, the second medical image comprising a series of two-dimensional images of one or more arterial beds of the subject, the series of two-dimensional images configured to be reconstructed into a three-dimensional image of the one or more arterial beds of the subject, wherein the second medical image comprises one or more regions of arterial plaque, the one or more regions of arterial plaque comprising one or more regions of low-density non-calcified plaque, non-calcified plaque, or calcified plaque, wherein a combination of analysis of quantification of the amount of the one or more regions of visceral adiposity and analysis of the one or more regions of arterial plaque is configured to be used to determine a risk assessment of arterial plaque disease for the subject, wherein each of the first computer system and the second computer system comprises a computer processor and an electronic storage medium.

Embodiment 2: The computer-implemented method of Embodiment 1, wherein the first medical image and the second medical image are acquired simultaneously using a single image acquisition system.

Embodiment 3: The computer-implemented method of Embodiment 1, wherein the first medical image and the second medical image are acquired sequentially using a single image acquisition system.

Embodiment 4: The computer-implemented method of Embodiment 3, wherein the first medical image is acquired prior to the second medical image.

Embodiment 5: The computer-implemented method of Embodiment 3, wherein the first medical image is acquired subsequent to the second medical image.

Embodiment 6: The computer-implemented method of Embodiment 1, wherein the first medical image and the second medical image are acquired sequentially using a different image acquisition system.

Embodiment 7: The computer-implemented method of Embodiment 1, wherein the first computer system and the second computer system are part of a single computer system.

Embodiment 8: The computer-implemented method of Embodiment 1, wherein the first computer system and the second computer system are separate.

Embodiment 9: The computer-implemented method of Embodiment 1, wherein the one or more arterial beds comprises one or more of a coronary artery, aorta, carotid artery, lower extremity artery, or upper extremity artery.

Embodiment 10: The computer-implemented method of Embodiment 1, wherein the first medical image and the second medical image comprises a computed tomography (CT) image.

Embodiment 11: The computer-implemented method of Embodiment 1, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 12: The computer-implemented method of Embodiment 1, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 13: The computer-implemented method of Embodiment 1, wherein determining the risk assessment of arterial plaque disease comprises determining a risk of a major adverse cardiovascular event (MACE) for the subject.

Embodiment 14: A computer-implemented method of acquisition of medical images for analysis to facilitate risk assessment of arterial plaque disease for a subject, the method comprising: acquiring, by a first computer system, a first medical image, the first medical image comprising a two-dimensional axial slice image of an abdomen of the subject, the first medical image comprising one or more regions of visceral adiposity, wherein quantification of an amount of the one or more regions of visceral adiposity is indicative of volume of arterial plaque in one or more arterial beds of the subject; analyzing the first medical image to quantify the amount of the one or more regions of visceral adiposity to determine whether the amount of the one or more regions of visceral adiposity is above a predetermined threshold; and acquiring, by a second computer system, a second medical image when the amount of the one or more regions of visceral adiposity is above the predetermined threshold, the second medical image comprising a series of two-dimensional images of one or more arterial beds of the subject, the series of two-dimensional images configured to be reconstructed into a three-dimensional image of the one or more arterial beds of the subject, wherein the second medical image comprises one or more regions of arterial plaque, the one or more regions of arterial plaque comprising one or more regions of low-density non-calcified plaque, non-calcified plaque, or calcified plaque, wherein each of the first computer system and the second computer system comprises a computer processor and an electronic storage medium.

Embodiment 15: The computer-implemented method of Embodiment 14, wherein the first medical image and the second medical image are acquired using a single image acquisition system.

Embodiment 16: The computer-implemented method of Embodiment 14, wherein the first medical image and the second medical image are acquired using a different image acquisition system.

Embodiment 17: The computer-implemented method of Embodiment 14, wherein the first computer system and the second computer system are part of a single computer system.

Embodiment 18: The computer-implemented method of Embodiment 14, wherein the first computer system and the second computer system are separate.

Embodiment 19: The computer-implemented method of Embodiment 14, wherein the one or more arterial beds comprises one or more of a coronary artery, aorta, carotid artery, lower extremity artery, or upper extremity artery.

Embodiment 20: The computer-implemented method of Embodiment 14, wherein the first medical image and the second medical image comprises a computed tomography (CT) image.

Embodiment 21: The computer-implemented method of Embodiment 14, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 22: The computer-implemented method of Embodiment 14, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 23: A computer-implemented method of acquisition of medical images for analysis to facilitate risk assessment of arterial plaque disease for a subject, the method comprising: accessing, by a computer system, a first medical image, the first medical image comprising a two-dimensional axial slice image of an abdomen of the subject, the first medical image comprising one or more regions of visceral adiposity, wherein quantification of an amount of the one or more regions of visceral adiposity is indicative of volume of arterial plaque in one or more arterial beds of the subject; analyzing, by the computer system, the first medical image to quantify the amount of the one or more regions of visceral adiposity to determine whether the amount of the one or more regions of visceral adiposity is above a predetermined threshold; and generating, by the computer system, a graphical representation indicating a need to acquire a second medical image when the amount of the one or more regions of visceral adiposity is above the predetermined threshold, the second medical image comprising a series of two-dimensional images of one or more arterial beds of the subject, the series of two-dimensional images configured to be reconstructed into a three-dimensional image of the one or more arterial beds of the subject, wherein the second medical image comprises one or more regions of arterial plaque, wherein the computer system comprises a computer processor and an electronic storage medium.

Embodiment 24: The computer-implemented method of Embodiment 23, wherein the first medical image and the second medical image are acquired using a single image acquisition system.

Embodiment 25: The computer-implemented method of Embodiment 23, wherein the first medical image and the second medical image are acquired using a different image acquisition system.

Embodiment 26: The computer-implemented method of Embodiment 23, wherein the one or more arterial beds comprises one or more of a coronary artery, aorta, carotid artery, lower extremity artery, or upper extremity artery.

Embodiment 27: The computer-implemented method of Embodiment 23, wherein the first medical image and the second medical image comprises a computed tomography (CT) image.

Embodiment 28: The computer-implemented method of Embodiment 23, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 29: The computer-implemented method of Embodiment 23, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 30: A system comprising: a first computer system and a second computer system; a non-transitory computer storage medium configured to at least store computer-executable instructions; and one or more computer hardware processors in communication with the first non-transitory computer storage medium, the one or more computer hardware processors configured to execute the computer-executable instructions to at least: acquire, by a first computer system, a first medical image, the first medical image comprising a two-dimensional axial slice image of an abdomen of the subject, the first medical image comprising one or more regions of visceral adiposity, wherein quantification of an amount of the one or more regions of visceral adiposity is indicative of volume of arterial plaque in one or more arterial beds of the subject; and acquire, by a second computer system, a second medical image, the second medical image comprising a series of two-dimensional images of one or more arterial beds of the subject, the series of two-dimensional images configured to be reconstructed into a three-dimensional image of the one or more arterial beds of the subject, wherein the second medical image comprises one or more regions of arterial plaque, the one or more regions of arterial plaque comprising one or more regions of low-density non-calcified plaque, non-calcified plaque, or calcified plaque, wherein a combination of analysis of quantification of the amount of the one or more regions of visceral adiposity and analysis of the one or more regions of arterial plaque is configured to be used to determine a risk assessment of arterial plaque disease for the subject.

Embodiment 31: The system of Embodiment 30, wherein the first medical image and the second medical image are acquired simultaneously using a single image acquisition system.

Embodiment 32: The system of Embodiment 30, wherein the first medical image and the second medical image are acquired sequentially using a single image acquisition system.

Embodiment 33: The system of Embodiment 32, wherein the first medical image is acquired prior to the second medical image.

Embodiment 34: The system of Embodiment 32, wherein the first medical image is acquired subsequent to the second medical image.

Embodiment 35: The system of Embodiment 30, wherein the first medical image and the second medical image are acquired sequentially using a different image acquisition system.

Embodiment 36: The system of Embodiment 30, wherein the first computer system and the second computer system are part of a single computer system.

Embodiment 37: The system of Embodiment 30, wherein the first computer system and the second computer system are separate.

Embodiment 38: The system of Embodiment 30, wherein the one or more arterial beds comprises one or more of a coronary artery, aorta, carotid artery, lower extremity artery, or upper extremity artery.

Embodiment 39: The system of Embodiment 30, wherein the first medical image and the second medical image comprises a computed tomography (CT) image.

Embodiment 40: The system of Embodiment 30, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 41: The system of Embodiment 30, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 42: The system of Embodiment 30, wherein determining the risk assessment of arterial plaque disease comprises determining a risk of a major adverse cardiovascular event (MACE) for the subject.

Embodiment 43: A system comprising: a first computer system and a second computer system; a non-transitory computer storage medium configured to at least store computer-executable instructions; and one or more computer hardware processors in communication with the first non-transitory computer storage medium, the one or more computer hardware processors configured to execute the computer-executable instructions to at least: acquire, by a first computer system, a first medical image, the first medical image comprising a two-dimensional axial slice image of an abdomen of the subject, the first medical image comprising one or more regions of visceral adiposity, wherein quantification of an amount of the one or more regions of visceral adiposity is indicative of volume of arterial plaque in one or more arterial beds of the subject; analyze the first medical image to quantify the amount of the one or more regions of visceral adiposity to determine whether the amount of the one or more regions of visceral adiposity is above a predetermined threshold; and acquire, by a second computer system, a second medical image when the amount of the one or more regions of visceral adiposity is above the predetermined threshold, the second medical image comprising a series of two-dimensional images of one or more arterial beds of the subject, the series of two-dimensional images configured to be reconstructed into a three-dimensional image of the one or more arterial beds of the subject, wherein the second medical image comprises one or more regions of arterial plaque, the one or more regions of arterial plaque comprising one or more regions of low-density non-calcified plaque, non-calcified plaque, or calcified plaque, wherein each of the first computer system and the second computer system comprises a computer processor and an electronic storage medium.

Embodiment 44: The system of Embodiment 43, wherein the first medical image and the second medical image are acquired using a single image acquisition system.

Embodiment 45: The system of Embodiment 43, wherein the first medical image and the second medical image are acquired using a different image acquisition system.

Embodiment 46: The system of Embodiment 43, wherein the first computer system and the second computer system are part of a single computer system.

Embodiment 47: The system of Embodiment 43, wherein the first computer system and the second computer system are separate.

Embodiment 48: The system of Embodiment 43, wherein the one or more arterial beds comprises one or more of a coronary artery, aorta, carotid artery, lower extremity artery, or upper extremity artery.

Embodiment 49: The system of Embodiment 43, wherein the first medical image and the second medical image comprises a computed tomography (CT) image.

Embodiment 50: The system of Embodiment 43, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 51: The system of Embodiment 43, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 52: A system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a first medical image, the first medical image comprising a two-dimensional axial slice image of an abdomen of the subject, the first medical image comprising one or more regions of visceral adiposity, wherein quantification of an amount of the one or more regions of visceral adiposity is indicative of volume of arterial plaque in one or more arterial beds of the subject; analyze the first medical image to quantify the amount of the one or more regions of visceral adiposity to determine whether the amount of the one or more regions of visceral adiposity is above a predetermined threshold; and generate a graphical representation indicating a need to acquire a second medical image when the amount of the one or more regions of visceral adiposity is above the predetermined threshold, the second medical image comprising a series of two-dimensional images of one or more arterial beds of the subject, the series of two-dimensional images configured to be reconstructed into a three-dimensional image of the one or more arterial beds of the subject, wherein the second medical image comprises one or more regions of arterial plaque.

Embodiment 53: The system of Embodiment 52, wherein the first medical image and the second medical image are acquired using a single image acquisition system.

Embodiment 54: The system of Embodiment 52, wherein the first medical image and the second medical image are acquired using a different image acquisition system.

Embodiment 55: The system of Embodiment 52, wherein the one or more arterial beds comprises one or more of a coronary artery, aorta, carotid artery, lower extremity artery, or upper extremity artery.

Embodiment 56: The system of Embodiment 52, wherein the first medical image and the second medical image comprises a computed tomography (CT) image.

Embodiment 57: The system of Embodiment 52, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 58: The system of Embodiment 52, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 59: A non-transitory computer readable medium configured for acquisition of medical images for analysis to facilitate risk assessment of arterial plaque disease for a subject, the computer readable medium having program instructions for causing a hardware processor to perform a method of: acquiring, by a first computer system, a first medical image, the first medical image comprising a two-dimensional axial slice image of an abdomen of the subject, the first medical image comprising one or more regions of visceral adiposity, wherein quantification of an amount of the one or more regions of visceral adiposity is indicative of volume of arterial plaque in one or more arterial beds of the subject; and acquiring, by a second computer system, a second medical image, the second medical image comprising a series of two-dimensional images of one or more arterial beds of the subject, the series of two-dimensional images configured to be reconstructed into a three-dimensional image of the one or more arterial beds of the subject, wherein the second medical image comprises one or more regions of arterial plaque, the one or more regions of arterial plaque comprising one or more regions of low-density non-calcified plaque, non-calcified plaque, or calcified plaque, wherein a combination of analysis of quantification of the amount of the one or more regions of visceral adiposity and analysis of the one or more regions of arterial plaque is configured to be used to determine a risk assessment of arterial plaque disease for the subject.

Embodiment 60: The non-transitory computer readable medium of Embodiment 59, wherein the first medical image and the second medical image are acquired simultaneously using a single image acquisition system.

Embodiment 61: The non-transitory computer readable medium of Embodiment 59, wherein the first medical image and the second medical image are acquired sequentially using a single image acquisition system.

Embodiment 62: The non-transitory computer readable medium of Embodiment 61, wherein the first medical image is acquired prior to the second medical image.

Embodiment 63: The non-transitory computer readable medium of Embodiment 61, wherein the first medical image is acquired subsequent to the second medical image.

Embodiment 64: The non-transitory computer readable medium of Embodiment 59, wherein the first medical image and the second medical image are acquired sequentially using a different image acquisition system.

Embodiment 65: The non-transitory computer readable medium of Embodiment 59, wherein the first computer system and the second computer system are part of a single computer system.

Embodiment 66: The non-transitory computer readable medium of Embodiment 59, wherein the first computer system and the second computer system are separate.

Embodiment 67: The non-transitory computer readable medium of Embodiment 59, wherein the one or more arterial beds comprises one or more of a coronary artery, aorta, carotid artery, lower extremity artery, or upper extremity artery.

Embodiment 68: The non-transitory computer readable medium of Embodiment 59, wherein the first medical image and the second medical image comprises a computed tomography (CT) image.

Embodiment 69: The non-transitory computer readable medium of Embodiment 59, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 70: The non-transitory computer readable medium of Embodiment 59, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 71: The non-transitory computer readable medium of Embodiment 59, wherein determining the risk assessment of arterial plaque disease comprises determining a risk of a major adverse cardiovascular event (MACE) for the subject.

Embodiment 72: A non-transitory computer readable medium configured for acquisition of medical images for analysis to facilitate risk assessment of arterial plaque disease for a subject, the computer readable medium having program instructions for causing a hardware processor to perform a method of: acquiring, by a first computer system, a first medical image, the first medical image comprising a two-dimensional axial slice image of an abdomen of the subject, the first medical image comprising one or more regions of visceral adiposity, wherein quantification of an amount of the one or more regions of visceral adiposity is indicative of volume of arterial plaque in one or more arterial beds of the subject; analyzing the first medical image to quantify the amount of the one or more regions of visceral adiposity to determine whether the amount of the one or more regions of visceral adiposity is above a predetermined threshold; and acquiring, by a second computer system, a second medical image when the amount of the one or more regions of visceral adiposity is above the predetermined threshold, the second medical image comprising a series of two-dimensional images of one or more arterial beds of the subject, the series of two-dimensional images configured to be reconstructed into a three-dimensional image of the one or more arterial beds of the subject, wherein the second medical image comprises one or more regions of arterial plaque, the one or more regions of arterial plaque comprising one or more regions of low-density non-calcified plaque, non-calcified plaque, or calcified plaque.

Embodiment 73: The non-transitory computer readable medium of Embodiment 72, wherein the first medical image and the second medical image are acquired using a single image acquisition system.

Embodiment 74: The non-transitory computer readable medium of Embodiment 72, wherein the first medical image and the second medical image are acquired using a different image acquisition system.

Embodiment 75: The non-transitory computer readable medium of Embodiment 72, wherein the first computer system and the second computer system are part of a single computer system.

Embodiment 76: The non-transitory computer readable medium of Embodiment 72, wherein the first computer system and the second computer system are separate.

Embodiment 77: The non-transitory computer readable medium of Embodiment 72, wherein the one or more arterial beds comprises one or more of a coronary artery, aorta, carotid artery, lower extremity artery, or upper extremity artery.

Embodiment 78: The non-transitory computer readable medium of Embodiment 72, wherein the first medical image and the second medical image comprises a computed tomography (CT) image.

Embodiment 79: The non-transitory computer readable medium of Embodiment 72, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 80: The non-transitory computer readable medium of Embodiment 72, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 81: A non-transitory computer readable medium configured for acquisition of medical images for analysis to facilitate risk assessment of arterial plaque disease for a subject, the computer readable medium having program instructions for causing a hardware processor to perform a method of: accessing, by a computer system, a first medical image, the first medical image comprising a two-dimensional axial slice image of an abdomen of the subject, the first medical image comprising one or more regions of visceral adiposity, wherein quantification of an amount of the one or more regions of visceral adiposity is indicative of volume of arterial plaque in one or more arterial beds of the subject; analyzing, by the computer system, the first medical image to quantify the amount of the one or more regions of visceral adiposity to determine whether the amount of the one or more regions of visceral adiposity is above a predetermined threshold; and generating, by the computer system, a graphical representation indicating a need to acquire a second medical image when the amount of the one or more regions of visceral adiposity is above the predetermined threshold, the second medical image comprising a series of two-dimensional images of one or more arterial beds of the subject, the series of two-dimensional images configured to be reconstructed into a three-dimensional image of the one or more arterial beds of the subject, wherein the second medical image comprises one or more regions of arterial plaque.

Embodiment 82: The non-transitory computer readable medium of Embodiment 81, wherein the first medical image and the second medical image are acquired using a single image acquisition system.

Embodiment 83: The non-transitory computer readable medium of Embodiment 81, wherein the first medical image and the second medical image are acquired using a different image acquisition system.

Embodiment 84: The non-transitory computer readable medium of Embodiment 81, wherein the one or more arterial beds comprises one or more of a coronary artery, aorta, carotid artery, lower extremity artery, or upper extremity artery.

Embodiment 85: The non-transitory computer readable medium of Embodiment 81, wherein the first medical image and the second medical image comprises a computed tomography (CT) image.

Embodiment 86: The non-transitory computer readable medium of Embodiment 81, wherein one or more of the first medical image or the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 87: The non-transitory computer readable medium of Embodiment 81, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 1: A computer-implemented method of estimating volume of arterial plaque in an arterial bed region of a subject based at least in part on analysis of visceral adiposity on a medical image, the method comprising: accessing, by a computer system, a medical image, the medical image comprising an axial slice of an abdomen of the subject; analyzing, by the computer system, the medical image to identify one or more regions of visceral adiposity; quantifying, by the computer system, an amount of the one or more regions of visceral adiposity identified on the medical image; estimating, by the computer system, volume of arterial plaque in an arterial bed region based at least in part on the quantified amount of the one or more regions of visceral adiposity identified on the medical image, the volume of arterial plaque comprising volume of low-density non-calcified plaque, volume of non-calcified plaque, or volume of calcified plaque, wherein the volume of arterial plaque in the arterial bed region is estimated using a plurality of reference values of volume of arterial plaque in the arterial bed and amount of visceral adiposity obtained from a plurality of reference subjects, wherein the estimated volume of arterial plaque is indicative of risk of artery disease for the subject, and wherein the estimated volume of arterial plaque above a predetermined threshold is indicative of additional treatment or testing of the subject for artery disease, wherein the computer system comprises a computer processor and an electronic storage medium.

Embodiment 2: The computer-implemented method of Embodiment 1, wherein the additional testing of the subject for artery disease comprises obtaining a computed tomography (CT) image of the arterial bed.

Embodiment 3: The computer-implemented method of Embodiment 2, wherein the CT image of the arterial bed comprises a coronary CT angiography (CCTA).

Embodiment 4: The computer-implemented method of Embodiment 2, wherein the additional testing of the subject for artery disease further comprises quantitative analysis of the CCTA.

Embodiment 5: The computer-implemented method of Embodiment 4, wherein the quantitative analysis of the CCTA is based at least in part on artificial intelligence (AI) or machine learning (ML).

Embodiment 6: The computer-implemented method of Embodiment 1, wherein the medical image comprises a single axial computed tomography (CT) image acquired at or near a level of the umbilicus of the subject.

Embodiment 7: The computer-implemented method of Embodiment 1, wherein the arterial bed region comprises one or more of a coronary artery, aorta, carotid artery, lower extremity artery, or upper extremity artery.

Embodiment 8: The computer-implemented method of Embodiment 1, wherein the volume of arterial plaque in the arterial bed region is estimated using an AI or ML algorithm.

Embodiment 9: The computer-implemented method of Embodiment 1, wherein the estimated volume of arterial plaque in the arterial bed region comprises one or more ranges of volume of arterial plaque.

Embodiment 10: The computer-implemented method of Embodiment 1, wherein the estimated volume of arterial plaque in the arterial bed region comprises a value of volume of arterial plaque.

Embodiment 11: The computer-implemented method of Embodiment 1, wherein the quantified amount of the one or more regions of visceral adiposity comprises a two-dimensional area of the one or more regions of visceral adiposity identified on the medical image.

Embodiment 12: The computer-implemented method of Embodiment 1, wherein the quantified amount of the one or more regions of visceral adiposity comprises volume of the one or more regions of visceral adiposity identified on the medical image.

Embodiment 13: The computer-implemented method of Embodiment 1, further comprising estimating, by the computer system, one or more of extent of vascular remodeling or stenosis of the arterial bed region based at least in part on the quantified amount of the one or more regions of visceral adiposity identified on the medical image.

Embodiment 14: The computer-implemented method of Embodiment 1, wherein the treatment comprises one or more of a medication treatment, lifestyle treatment, or revascularization treatment.

Embodiment 15: The computer-implemented method of Embodiment 1, wherein identifying the one or more regions of visceral adiposity comprises segmenting subcutaneous fat.

Embodiment 16: The computer-implemented method of Embodiment 1, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 17: A computer-implemented method of estimating amount of visceral adiposity of a subject based at least in part on analysis of arterial plaque in an arterial bed region of the subject using image analysis, the method comprising: accessing, by a computer system, a medical image of the arterial bed region of the subject; analyzing, by the computer system, the medical image to identify one or more regions of arterial plaque; characterizing, by the computer system, the identified one or more regions of arterial plaque as one or more of low-density non-calcified plaque, non-calcified plaque, or calcified plaque based at least in part on density; quantifying, by the computer system, a volume of the characterized one or more regions of arterial plaque; estimating, by the computer system, amount of visceral adiposity of the subject based at least in part on the quantified volume of the characterized one or more regions of arterial plaque, wherein the amount of visceral adiposity of the subject is estimated using a plurality of reference values of volume of characterized arterial plaque in the arterial bed and amount of visceral adiposity obtained from a plurality of reference subjects, wherein the estimated amount of visceral adiposity is configured to be used to determine a treatment for the subject, wherein the computer system comprises a computer processor and an electronic storage medium.

Embodiment 18: The computer-implemented method of Embodiment 17, wherein the arterial bed region comprises one or more of a coronary artery, aorta, carotid artery, lower extremity artery, or upper extremity artery.

Embodiment 19: The computer-implemented method of Embodiment 17, wherein the amount of visceral adiposity of the subject comprises a two-dimensional area of visceral adiposity on an axial slice medical image acquired at or near a level of the umbilicus of the subject.

Embodiment 20: The computer-implemented method of Embodiment 17, wherein the amount of visceral adiposity of the subject comprises volume of visceral adiposity in the abdomen of the subject.

Embodiment 21: The computer-implemented method of Embodiment 17, wherein one or more regions of arterial plaque is identified using an artificial intelligence (AI) or machine learning (ML) algorithm.

Embodiment 22: The computer-implemented method of Embodiment 17, wherein the medical image comprises a Computed Tomography (CT) image.

Embodiment 23: The computer-implemented method of Embodiment 17, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 24: The computer-implemented method of Embodiment 17, wherein density comprises material density.

Embodiment 25: The computer-implemented method of Embodiment 17, wherein density comprises radiodensity.

Embodiment 26: The computer-implemented method of Embodiment 25, wherein the medical image comprises a CT image, and wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 27: The computer-implemented method of Embodiment 17, wherein the treatment comprises one or more of a medication treatment, lifestyle treatment, or revascularization treatment.

Embodiment 28: A system for estimating volume of arterial plaque in an arterial bed region of a subject based at least in part on analysis of visceral adiposity on a medical image, the system comprising: a non-transitory computer storage medium configured to at least store computer executable instructions; and one or more computer hardware processors in communication with the first non-transitory computer storage medium, the one or more computer hardware processors configured to execute the computer-executable instructions to at least: access a medical image, the medical image comprising an axial slice of an abdomen of the subject; analyze the medical image to identify one or more regions of visceral adiposity; quantify an amount of the one or more regions of visceral adiposity identified on the medical image; estimate volume of arterial plaque in an arterial bed region based at least in part on the quantified amount of the one or more regions of visceral adiposity identified on the medical image, the volume of arterial plaque comprising volume of low-density non-calcified plaque, volume of non-calcified plaque, or volume of calcified plaque, wherein the volume of arterial plaque in the arterial bed region is estimated using a plurality of reference values of volume of arterial plaque in the arterial bed and amount of visceral adiposity obtained from a plurality of reference subjects, wherein the estimated volume of arterial plaque is indicative of risk of artery disease for the subject, and wherein the estimated volume of arterial plaque above a predetermined threshold is indicative of additional treatment or testing of the subject for artery disease.

Embodiment 29: The system of Embodiment 28, wherein the additional testing of the subject for artery disease comprises obtaining a computed tomography (CT) image of the arterial bed.

Embodiment 30: The system of Embodiment 29, wherein the CT image of the arterial bed comprises a coronary CT angiography (CCTA).

Embodiment 31: The system of Embodiment 29, wherein the additional testing of the subject for artery disease further comprises quantitative analysis of the CCTA.

Embodiment 32: The system of Embodiment 31, wherein the quantitative analysis of the CCTA is based at least in part on artificial intelligence (AI) or machine learning (ML).

Embodiment 33: The system of Embodiment 28, wherein the medical image comprises a single axial computed tomography (CT) image acquired at or near a level of the umbilicus of the subject.

Embodiment 34: The system of Embodiment 28, wherein the arterial bed region comprises one or more of a coronary artery, aorta, carotid artery, lower extremity artery, or upper extremity artery.

Embodiment 35: The system of Embodiment 28, wherein the volume of arterial plaque in the arterial bed region is estimated using an AI or ML algorithm.

Embodiment 36: The system of Embodiment 28, wherein the estimated volume of arterial plaque in the arterial bed region comprises one or more ranges of volume of arterial plaque.

Embodiment 37: The system of Embodiment 28, wherein the estimated volume of arterial plaque in the arterial bed region comprises a value of volume of arterial plaque.

Embodiment 38: The system of Embodiment 28, wherein the quantified amount of the one or more regions of visceral adiposity comprises a two-dimensional area of the one or more regions of visceral adiposity identified on the medical image.

Embodiment 39: The system of Embodiment 28, wherein the quantified amount of the one or more regions of visceral adiposity comprises volume of the one or more regions of visceral adiposity identified on the medical image.

Embodiment 40: The system of Embodiment 28, further comprising estimating one or more of extent of vascular remodeling or stenosis of the arterial bed region based at least in part on the quantified amount of the one or more regions of visceral adiposity identified on the medical image.

Embodiment 41: The system of Embodiment 28, wherein the treatment comprises one or more of a medication treatment, lifestyle treatment, or revascularization treatment.

Embodiment 42: The system of Embodiment 28, wherein identifying the one or more regions of visceral adiposity comprises segmenting subcutaneous fat.

Embodiment 43: The system of Embodiment 28, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 44: A system of estimating amount of visceral adiposity of a subject based at least in part on analysis of arterial plaque in an arterial bed region of the subject using image analysis, the system comprising: a non-transitory computer storage medium configured to at least store computer executable instructions; and one or more computer hardware processors in communication with the first non-transitory computer storage medium, the one or more computer hardware processors configured to execute the computer-executable instructions to at least: access a medical image of the arterial bed region of the subject; analyze the medical image to identify one or more regions of arterial plaque; characterize the identified one or more regions of arterial plaque as one or more of low-density non-calcified plaque, non-calcified plaque, or calcified plaque based at least in part on density; quantify a volume of the characterized one or more regions of arterial plaque; estimate amount of visceral adiposity of the subject based at least in part on the quantified volume of the characterized one or more regions of arterial plaque, wherein the amount of visceral adiposity of the subject is estimated using a plurality of reference values of volume of characterized arterial plaque in the arterial bed and amount of visceral adiposity obtained from a plurality of reference subjects, wherein the estimated amount of visceral adiposity is configured to be used to determine a treatment for the subject.

Embodiment 45: The system of Embodiment 44, wherein the arterial bed region comprises one or more of a coronary artery, aorta, carotid artery, lower extremity artery, or upper extremity artery.

Embodiment 46: The system of Embodiment 44, wherein the amount of visceral adiposity of the subject comprises a two-dimensional area of visceral adiposity on an axial slice medical image acquired at or near a level of the umbilicus of the subject.

Embodiment 47: The system of Embodiment 44, wherein the amount of visceral adiposity of the subject comprises volume of visceral adiposity in the abdomen of the subject.

Embodiment 48: The system of Embodiment 44, wherein one or more regions of arterial plaque is identified using an artificial intelligence (AI) or machine learning (ML) algorithm.

Embodiment 49: The system of Embodiment 44, wherein the medical image comprises a Computed Tomography (CT) image.

Embodiment 50: The system of Embodiment 44, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 51: The system of Embodiment 44, wherein density comprises material density.

Embodiment 52: The system of Embodiment 44, wherein density comprises radiodensity.

Embodiment 53: The system of Embodiment 52, wherein the medical image comprises a CT image, and wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 54: The system of Embodiment 44, wherein the treatment comprises one or more of a medication treatment, lifestyle treatment, or revascularization treatment.

Embodiment 55: A non-transitory computer readable medium configured for estimating volume of arterial plaque in an arterial bed region of a subject based at least in part on analysis of visceral adiposity on a medical image, the computer readable medium having program instructions for causing a hardware processor to perform a method of: accessing a medical image, the medical image comprising an axial slice of an abdomen of the subject; analyzing the medical image to identify one or more regions of visceral adiposity; quantifying an amount of the one or more regions of visceral adiposity identified on the medical image; estimating volume of arterial plaque in an arterial bed region based at least in part on the quantified amount of the one or more regions of visceral adiposity identified on the medical image, the volume of arterial plaque comprising volume of low-density non-calcified plaque, volume of non-calcified plaque, or volume of calcified plaque, wherein the volume of arterial plaque in the arterial bed region is estimated using a plurality of reference values of volume of arterial plaque in the arterial bed and amount of visceral adiposity obtained from a plurality of reference subjects, wherein the estimated volume of arterial plaque is indicative of risk of artery disease for the subject, and wherein the estimated volume of arterial plaque above a predetermined threshold is indicative of additional treatment or testing of the subject for artery disease.

Embodiment 56: The non-transitory computer readable medium of Embodiment 55, wherein the additional testing of the subject for artery disease comprises obtaining a computed tomography (CT) image of the arterial bed.

Embodiment 57: The non-transitory computer readable medium of Embodiment 56, wherein the CT image of the arterial bed comprises a coronary CT angiography (CCTA).

Embodiment 58: The non-transitory computer readable medium of Embodiment 56, wherein the additional testing of the subject for artery disease further comprises quantitative analysis of the CCTA.

Embodiment 59: The non-transitory computer readable medium of Embodiment 58, wherein the quantitative analysis of the CCTA is based at least in part on artificial intelligence (AI) or machine learning (ML).

Embodiment 60: The non-transitory computer readable medium of Embodiment 55, wherein the medical image comprises a single axial computed tomography (CT) image acquired at or near a level of the umbilicus of the subject.

Embodiment 61: The non-transitory computer readable medium of Embodiment 55, wherein the arterial bed region comprises one or more of a coronary artery, aorta, carotid artery, lower extremity artery, or upper extremity artery.

Embodiment 62: The non-transitory computer readable medium of Embodiment 55, wherein the volume of arterial plaque in the arterial bed region is estimated using an AI or ML algorithm.

Embodiment 63: The non-transitory computer readable medium of Embodiment 55, wherein the estimated volume of arterial plaque in the arterial bed region comprises one or more ranges of volume of arterial plaque.

Embodiment 64: The non-transitory computer readable medium of Embodiment 55, wherein the estimated volume of arterial plaque in the arterial bed region comprises a value of volume of arterial plaque.

Embodiment 65: The non-transitory computer readable medium of Embodiment 55, wherein the quantified amount of the one or more regions of visceral adiposity comprises a two-dimensional area of the one or more regions of visceral adiposity identified on the medical image.

Embodiment 66: The non-transitory computer readable medium of Embodiment 55, wherein the quantified amount of the one or more regions of visceral adiposity comprises volume of the one or more regions of visceral adiposity identified on the medical image.

Embodiment 67: The non-transitory computer readable medium of Embodiment 55, further comprising estimating one or more of extent of vascular remodeling or stenosis of the arterial bed region based at least in part on the quantified amount of the one or more regions of visceral adiposity identified on the medical image.

Embodiment 68: The non-transitory computer readable medium of Embodiment 55, wherein the treatment comprises one or more of a medication treatment, lifestyle treatment, or revascularization treatment.

Embodiment 69: The non-transitory computer readable medium of Embodiment 55, wherein identifying the one or more regions of visceral adiposity comprises segmenting subcutaneous fat.

Embodiment 70: The non-transitory computer readable medium of Embodiment 55, wherein low-density non-calcified plaque comprises a region of plaque on a CT image comprising a radiodensity value between about −189 and about 30 Hounsfield units, wherein non-calcified plaque comprises a region of plaque on a CT image comprising a radiodensity value between about 31 and about 350 Hounsfield units, and wherein calcified plaque comprises a region of plaque on a CT image comprising a radiodensity value between about 351 and 2500 Hounsfield units.

Embodiment 71: A non-transitory computer readable medium configured for estimating amount of visceral adiposity of a subject based at least in part on analysis of arterial plaque in an arterial bed region of the subject using image analysis, the computer readable medium having program instructions for causing a hardware processor to perform a method of: accessing, by a computer system, a medical image of the arterial bed region of the subject; analyzing the medical image to identify one or more regions of arterial plaque; characterizing the identified one or more regions of arterial plaque as one or more of low-density non-calcified plaque, non-calcified plaque, or calcified plaque based at least in part on density; quantifying a volume of the characterized one or more regions of arterial plaque; estimating amount of visceral adiposity of the subject based at least in part on the quantified volume of the characterized one or more regions of arterial plaque, wherein the amount of visceral adiposity of the subject is estimated using a plurality of reference values of volume of characterized arterial plaque in the arterial bed and amount of visceral adiposity obtained from a plurality of reference subjects, wherein the estimated amount of visceral adiposity is configured to be used to determine a treatment for the subject.

Embodiment 72: The non-transitory computer readable medium of Embodiment 71, wherein the arterial bed region comprises one or more of a coronary artery, aorta, carotid artery, lower extremity artery, or upper extremity artery.

Embodiment 73: The non-transitory computer readable medium of Embodiment 71, wherein the amount of visceral adiposity of the subject comprises a two-dimensional area of visceral adiposity on an axial slice medical image acquired at or near a level of the umbilicus of the subject.

Embodiment 74: The non-transitory computer readable medium of Embodiment 71, wherein the amount of visceral adiposity of the subject comprises volume of visceral adiposity in the abdomen of the subject.

Embodiment 75: The non-transitory computer readable medium of Embodiment 71, wherein one or more regions of arterial plaque is identified using an artificial intelligence (AI) or machine learning (ML) algorithm.

Embodiment 76: The non-transitory computer readable medium of Embodiment 71, wherein the medical image comprises a Computed Tomography (CT) image.

Embodiment 77: The non-transitory computer readable medium of Embodiment 71, wherein the medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 78: The non-transitory computer readable medium of Embodiment 71, wherein density comprises material density.

Embodiment 79: The non-transitory computer readable medium of Embodiment 71, wherein density comprises radiodensity.

Embodiment 80: The non-transitory computer readable medium of Embodiment 79, wherein the medical image comprises a CT image, and wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 81: The non-transitory computer readable medium of Embodiment 71, wherein the treatment comprises one or more of a medication treatment, lifestyle treatment, or revascularization treatment.

Embodiment 1: A computer-implemented method of facilitating risk assessment of arterial plaque disease for a subject based at least in part on image analysis, the method comprising: accessing, by a computer system, a first medical image, the first medical image comprising an axial slice of an abdomen of the subject; analyzing, by the computer system, the first medical image to identify one or more regions of visceral adiposity; quantifying, by the computer system, an amount of the one or more regions of visceral adiposity identified on the first medical image; accessing, by the computer system, a second medical image, the second medical image comprising an arterial bed region of the subject; analyzing, by the computer system, the second medical image to identify one or more regions of arterial plaque; characterizing, by the computer system, the identified one or more regions of arterial plaque as one or more of low-density non-calcified plaque, non-calcified plaque, or calcified plaque based at least in part on density; quantifying, by the computer system, a volume of the characterized one or more regions of arterial plaque; generating, by the computer system, a weighted measure of the quantified amount of the one or more regions of visceral adiposity identified on the first medical image and the quantified volume of the characterized one or more regions of arterial plaque; and determining, by the computer system, a risk of major adverse cardiovascular event (MACE) or arterial plaque disease for the subject based at least in part on the generated weighted measure, wherein the computer system comprises a computer processor and an electronic storage medium.

Embodiment 2: The computer-implemented method of Embodiment 1, further comprising determining a treatment for the subject based at least in part on the determined risk of MACE or arterial plaque disease, the treatment comprising one or more of lifestyle treatment, medication treatment, or invasive treatment.

Embodiment 3: The computer-implemented method of Embodiment 1, wherein the first medical image comprises a single axial computed tomography (CT) image acquired at or near a level of the umbilicus of the subject.

Embodiment 4: The computer-implemented method of Embodiment 1, wherein the arterial bed region comprises one or more of a coronary artery, aorta, carotid artery, lower extremity artery, or upper extremity artery.

Embodiment 5: The computer-implemented method of Embodiment 1, wherein the one or more regions of visceral adiposity are identified on the first medical image using an artificial intelligence (AI) or machine learning (ML) algorithm.

Embodiment 6: The computer-implemented method of Embodiment 1, wherein the one or more regions of arterial plaque are identified on the second medical image using an artificial intelligence (AI) or machine learning (ML) algorithm.

Embodiment 7: The computer-implemented method of Embodiment 1, wherein the second medical image comprises a Computed Tomography (CT) image.

Embodiment 8: The computer-implemented method of Embodiment 7, wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 9: The computer-implemented method of Embodiment 1, wherein the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 10: The computer-implemented method of Embodiment 1, wherein the density comprises material density.

Embodiment 11: The computer-implemented method of Embodiment 1, wherein the density comprises radiodensity.

Embodiment 12: The computer-implemented method of Embodiment 1, wherein the first medical image comprises a two-dimensional image, and wherein the second medical image comprises a series of two-dimensional images configured to be reconstructed into a three-dimensional image.

Embodiment 13: A computer-implemented method of facilitating risk assessment of arterial plaque disease for a subject based at least in part on image analysis, the method comprising: accessing, by a computer system, a first medical image, the first medical image comprising an axial slice of an abdomen of the subject; analyzing, by the computer system, the first medical image to identify one or more regions of visceral adiposity; quantifying, by the computer system, an amount of the one or more regions of visceral adiposity identified on the first medical image; accessing, by the computer system, a second medical image, the second medical image comprising an arterial bed region of the subject; analyzing, by the computer system, the second medical image to identify one or more regions of arterial plaque; characterizing, by the computer system, the identified one or more regions of arterial plaque as one or more of low-density non-calcified plaque, non-calcified plaque, or calcified plaque based at least in part on density; quantifying, by the computer system, a volume of the characterized one or more regions of arterial plaque; and determining, by the computer system, a risk of major adverse cardiovascular event (MACE) or arterial plaque disease for the subject based at least in part on analysis of the quantified amount of the one or more regions of visceral adiposity identified on the first medical image and the quantified volume of the characterized one or more regions of arterial plaque, wherein the computer system comprises a computer processor and an electronic storage medium.

Embodiment 14: The computer-implemented method of Embodiment 13, further comprising determining a treatment for the subject based at least in part on the determined risk of MACE or arterial plaque disease, the treatment comprising one or more of lifestyle treatment, medication treatment, or invasive treatment.

Embodiment 15: The computer-implemented method of Embodiment 13, wherein the first medical image comprises a single axial computed tomography (CT) image acquired at or near a level of the umbilicus of the subject.

Embodiment 16: The computer-implemented method of Embodiment 13, wherein the arterial bed region comprises one or more of a coronary artery, aorta, carotid artery, lower extremity artery, or upper extremity artery.

Embodiment 17: The computer-implemented method of Embodiment 13, wherein the one or more regions of visceral adiposity are identified on the first medical image using an artificial intelligence (AI) or machine learning (ML) algorithm.

Embodiment 18: The computer-implemented method of Embodiment 13, wherein the one or more regions of arterial plaque are identified on the second medical image using an artificial intelligence (AI) or machine learning (ML) algorithm.

Embodiment 19: The computer-implemented method of Embodiment 13, wherein the second medical image comprises a Computed Tomography (CT) image.

Embodiment 20: The computer-implemented method of Embodiment 19, wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 21: The computer-implemented method of Embodiment 13, wherein the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 22: The computer-implemented method of Embodiment 13, wherein the density comprises material density.

Embodiment 23: The computer-implemented method of Embodiment 13, wherein the density comprises radiodensity.

Embodiment 24: The computer-implemented method of Embodiment 13, wherein the first medical image comprises a two-dimensional image, and wherein the second medical image comprises a series of two-dimensional images configured to be reconstructed into a three-dimensional image.

Embodiment 25: A non-transitory computer readable medium configured for facilitating risk assessment of arterial plaque disease for a subject based at least in part on image analysis, the computer readable medium having program instructions for causing a hardware processor to perform a method of: accessing, by a computer system, a first medical image, the first medical image comprising an axial slice of an abdomen of the subject; analyzing, by the computer system, the first medical image to identify one or more regions of visceral adiposity; quantifying, by the computer system, an amount of the one or more regions of visceral adiposity identified on the first medical image; accessing, by the computer system, a second medical image, the second medical image comprising an arterial bed region of the subject; analyzing, by the computer system, the second medical image to identify one or more regions of arterial plaque; characterizing, by the computer system, the identified one or more regions of arterial plaque as one or more of low-density non-calcified plaque, non-calcified plaque, or calcified plaque based at least in part on density; quantifying, by the computer system, a volume of the characterized one or more regions of arterial plaque; generating, by the computer system, a weighted measure of the quantified amount of the one or more regions of visceral adiposity identified on the first medical image and the quantified volume of the characterized one or more regions of arterial plaque; and determining, by the computer system, a risk of major adverse cardiovascular event (MACE) or arterial plaque disease for the subject based at least in part on the generated weighted measure, wherein the computer system comprises a computer processor and an electronic storage medium.

Embodiment 26: The non-transitory computer readable medium configured as in Embodiment 25, further comprising determining a treatment for the subject based at least in part on the determined risk of MACE or arterial plaque disease, the treatment comprising one or more of lifestyle treatment, medication treatment, or invasive treatment.

Embodiment 27: The non-transitory computer readable medium configured as in Embodiment 25, wherein the first medical image comprises a single axial computed tomography (CT) image acquired at or near a level of the umbilicus of the subject.

Embodiment 28: The non-transitory computer readable medium configured as in Embodiment 25, wherein the arterial bed region comprises one or more of a coronary artery, aorta, carotid artery, lower extremity artery, or upper extremity artery.

Embodiment 29: The non-transitory computer readable medium configured as in Embodiment 25, wherein the one or more regions of visceral adiposity are identified on the first medical image using an artificial intelligence (AI) or machine learning (ML) algorithm.

Embodiment 30: The non-transitory computer readable medium configured as in Embodiment 25, wherein the one or more regions of arterial plaque are identified on the second medical image using an artificial intelligence (AI) or machine learning (ML) algorithm.

Embodiment 31: The non-transitory computer readable medium configured as in Embodiment 25, wherein the second medical image comprises a Computed Tomography (CT) image.

Embodiment 32: The non-transitory computer readable medium configured as in Embodiment 31, wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 33: The non-transitory computer readable medium configured as in Embodiment 25, wherein the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 34: The non-transitory computer readable medium configured as in Embodiment 25, wherein the density comprises material density.

Embodiment 35: The non-transitory computer readable medium configured as in Embodiment 25, wherein the density comprises radiodensity.

Embodiment 36: The non-transitory computer readable medium configured as in Embodiment 25, wherein the first medical image comprises a two-dimensional image, and wherein the second medical image comprises a series of two-dimensional images configured to be reconstructed into a three-dimensional image.

Embodiment 37: A non-transitory computer readable medium configured for facilitating risk assessment of arterial plaque disease for a subject based at least in part on image analysis, the computer readable medium having program instructions for causing a hardware processor to perform a method of: accessing a first medical image, the first medical image comprising an axial slice of an abdomen of the subject; analyzing the first medical image to identify one or more regions of visceral adiposity; quantifying an amount of the one or more regions of visceral adiposity identified on the first medical image; accessing a second medical image, the second medical image comprising an arterial bed region of the subject; analyzing the second medical image to identify one or more regions of arterial plaque; characterizing the identified one or more regions of arterial plaque as one or more of low-density non-calcified plaque, non-calcified plaque, or calcified plaque based at least in part on density; quantifying a volume of the characterized one or more regions of arterial plaque; and determining a risk of major adverse cardiovascular event (MACE) or arterial plaque disease for the subject based at least in part on analysis of the quantified amount of the one or more regions of visceral adiposity identified on the first medical image and the quantified volume of the characterized one or more regions of arterial plaque, wherein the computer system comprises a computer processor and an electronic storage medium.

Embodiment 38: The non-transitory computer readable medium configured as in Embodiment 37, further comprising determining a treatment for the subject based at least in part on the determined risk of MACE or arterial plaque disease, the treatment comprising one or more of lifestyle treatment, medication treatment, or invasive treatment.

Embodiment 39: The non-transitory computer readable medium configured as in Embodiment 37, wherein the first medical image comprises a single axial computed tomography (CT) image acquired at or near a level of the umbilicus of the subject.

Embodiment 40: The non-transitory computer readable medium configured as in Embodiment 37, wherein the arterial bed region comprises one or more of a coronary artery, aorta, carotid artery, lower extremity artery, or upper extremity artery.

Embodiment 41: The non-transitory computer readable medium configured as in Embodiment 37, wherein the one or more regions of visceral adiposity are identified on the first medical image using an artificial intelligence (AI) or machine learning (ML) algorithm.

Embodiment 42: The non-transitory computer readable medium configured as in Embodiment 37, wherein the one or more regions of arterial plaque are identified on the second medical image using an artificial intelligence (AI) or machine learning (ML) algorithm.

Embodiment 43: The non-transitory computer readable medium configured as in Embodiment 37, wherein the second medical image comprises a Computed Tomography (CT) image.

Embodiment 44: The non-transitory computer readable medium configured as in Embodiment 43, wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 45: The non-transitory computer readable medium configured as in Embodiment 37, wherein the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 46: The non-transitory computer readable medium configured as in Embodiment 37, wherein the density comprises material density.

Embodiment 47: The non-transitory computer readable medium configured as in Embodiment 37, wherein the density comprises radiodensity.

Embodiment 48: The non-transitory computer readable medium configured as in Embodiment 37, wherein the first medical image comprises a two-dimensional image, and wherein the second medical image comprises a series of two-dimensional images configured to be reconstructed into a three-dimensional image.

Embodiment 49: A system comprising one or more processors and one or more memories storing instructions to cause the processors to perform a method comprising:

accessing a first medical image, the first medical image comprising an axial slice of an abdomen of the subject; analyzing the first medical image to identify one or more regions of visceral adiposity; quantifying an amount of the one or more regions of visceral adiposity identified on the first medical image; accessing a second medical image, the second medical image comprising an arterial bed region of the subject; analyzing the second medical image to identify one or more regions of arterial plaque; characterizing the identified one or more regions of arterial plaque as one or more of low-density non-calcified plaque, non-calcified plaque, or calcified plaque based at least in part on density; quantifying a volume of the characterized one or more regions of arterial plaque; generating a weighted measure of the quantified amount of the one or more regions of visceral adiposity identified on the first medical image and the quantified volume of the characterized one or more regions of arterial plaque; and determining a risk of major adverse cardiovascular event (MACE) or arterial plaque disease for the subject based at least in part on the generated weighted measure, wherein the computer system comprises a computer processor and an electronic storage medium.

Embodiment 50: The system of Embodiment 49, further comprising determining a treatment for the subject based at least in part on the determined risk of MACE or arterial plaque disease, the treatment comprising one or more of lifestyle treatment, medication treatment, or invasive treatment.

Embodiment 51: The system of Embodiment 49, wherein the first medical image comprises a single axial computed tomography (CT) image acquired at or near a level of the umbilicus of the subject.

Embodiment 52: The system of Embodiment 49, wherein the arterial bed region comprises one or more of a coronary artery, aorta, carotid artery, lower extremity artery, or upper extremity artery.

Embodiment 53: The system of Embodiment 49, wherein the one or more regions of visceral adiposity are identified on the first medical image using an artificial intelligence (AI) or machine learning (ML) algorithm.

Embodiment 54: The system of Embodiment 49, wherein the one or more regions of arterial plaque are identified on the second medical image using an artificial intelligence (AI) or machine learning (ML) algorithm.

Embodiment 55: The system of Embodiment 49, wherein the second medical image comprises a Computed Tomography (CT) image.

Embodiment 56: The system of Embodiment 55, wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 57: The system of Embodiment 49, wherein the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 58: The system of Embodiment 49, wherein the density comprises material density.

Embodiment 59: The system of Embodiment 49, wherein the density comprises radiodensity.

Embodiment 60: The system of Embodiment 49, wherein the first medical image comprises a two-dimensional image, and wherein the second medical image comprises a series of two-dimensional images configured to be reconstructed into a three-dimensional image.

Embodiment 61: A system comprising at least one processor and at least one memory storing instructions that cause the processor to perform a method of: accessing a first medical image, the first medical image comprising an axial slice of an abdomen of the subject; analyzing the first medical image to identify one or more regions of visceral adiposity; quantifying an amount of the one or more regions of visceral adiposity identified on the first medical image; accessing a second medical image, the second medical image comprising an arterial bed region of the subject; analyzing the second medical image to identify one or more regions of arterial plaque; characterizing the identified one or more regions of arterial plaque as one or more of low-density non-calcified plaque, non-calcified plaque, or calcified plaque based at least in part on density; quantifying a volume of the characterized one or more regions of arterial plaque; and determining a risk of major adverse cardiovascular event (MACE) or arterial plaque disease for the subject based at least in part on analysis of the quantified amount of the one or more regions of visceral adiposity identified on the first medical image and the quantified volume of the characterized one or more regions of arterial plaque, wherein the computer system comprises a computer processor and an electronic storage medium.

Embodiment 62: The system of Embodiment 61, further comprising determining a treatment for the subject based at least in part on the determined risk of MACE or arterial plaque disease, the treatment comprising one or more of lifestyle treatment, medication treatment, or invasive treatment.

Embodiment 63: The system of Embodiment 61, wherein the first medical image comprises a single axial computed tomography (CT) image acquired at or near a level of the umbilicus of the subject.

Embodiment 64: The system of Embodiment 61, wherein the arterial bed region comprises one or more of a coronary artery, aorta, carotid artery, lower extremity artery, or upper extremity artery.

Embodiment 65: The system of Embodiment 61, wherein the one or more regions of visceral adiposity are identified on the first medical image using an artificial intelligence (AI) or machine learning (ML) algorithm.

Embodiment 66: The system of Embodiment 61, wherein the one or more regions of arterial plaque are identified on the second medical image using an artificial intelligence (AI) or machine learning (ML) algorithm.

Embodiment 67: The system of Embodiment 61, wherein the second medical image comprises a Computed Tomography (CT) image.

Embodiment 68: The system of Embodiment 67, wherein low-density non-calcified plaque comprises a region of plaque comprising a radiodensity value between about −189 and about 30 Hounsfield units, wherein non-calcified plaque comprises a region of plaque comprising a radiodensity value between about 31 and about 350 Hounsfield units, and wherein calcified plaque comprises a region of plaque comprising a radiodensity value between about 351 and 2500 Hounsfield units.

Embodiment 69: The system of Embodiment 61, wherein the second medical image is obtained using an imaging technique comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 70: The system of Embodiment 61, wherein the density comprises material density.

Embodiment 71: The system of Embodiment 61, wherein the density comprises radiodensity.

Embodiment 72: The system of Embodiment 61, wherein the first medical image comprises a two-dimensional image, and wherein the second medical image comprises a series of two-dimensional images configured to be reconstructed into a three-dimensional image.

Determination of a Medical Facility Based at Least in Part on Image-Based Plaque Analysis Disclosed herein are systems, devices, and methods for determination of a medical facility based at least in part on image-based plaque analysis. In some embodiments, the image to be analyzed is obtained remote from a medical care facility, such as in an ambulance or at other remote sites. For example, a patient undergoing cardiac distress may be imaged by emergency responders before being taken to or in route to a medical facility such as a hospital. In some embodiments, a patient may be imaged using a portable medical imager, such as a portable CT scanner. The portable CT scanner can be, for example, in an ambulance. The medical image can be analyzed, for example, on a remote server, to determine one or more characteristics of the patient's medical condition. In some embodiments, the medical image is analyzed to determine one or more plaque parameters associated with coronary arteries of the patient. For example, in some embodiments, the medical image can be analyzed using one or more machine learning or artificial intelligence algorithms. The analysis of the medical image can be used to determine to which type of medical facility (e.g., general hospital, catheterization lab, etc.) the patient should be taken. In some embodiments, in response to analyzing the medical image, instructions for taking the patient to a medical facility (e.g., GPS instructions) and/or care instructions can be provided to the emergency responders and/or healthcare providers at the healthcare facility to which the patient will be transported. In some embodiments, the systems, devices, and methods described herein are configured to determine a risk of coronary artery disease (CAD), such as for example myocardial infarction (MI), while on an ambulance at another location away from a catheter lab based on one or more plaque analyses described herein. In some embodiments, the systems, devices, and methods described herein are configured to generate a list of medical facilities and determine which the patient should be taken to based on their risk of MI.

As discussed herein, disclosed herein are systems, methods, and devices for determination of a medical facility based at least in part on image-based plaque analysis. In some embodiments, an image to be analyzed is obtained remote from a medical care facility, such as in an ambulance or at other remote sites. For example, a patient undergoing cardiac distress may be imaged by emergency responders before being taken to or in route to a medical facility such as a hospital. In some embodiments, a patient may be imaged using a portable medical imager, such as a portable CT scanner. The portable CT scanner can be, for example, in an ambulance. The medical image can be analyzed, for example, on a remote server, to determine one or more characteristics of the patient's medical condition. In some embodiments, the medical image is analyzed to determine one or more plaque parameters associated with coronary arteries of the patient. For example, in some embodiments, the medical image can be analyzed using one or more machine learning or artificial intelligence algorithms. The analysis of the medical image can be used to determine to which type of medical facility (e.g., general hospital, catheterization lab, etc.) the patient should be taken. In some embodiments, in response to analyzing the medical image, instructions for taking the patient to a medical facility (e.g., GPS instructions) and/or care instructions can be provided to the emergency responders and/or healthcare providers at the healthcare facility to which the patient will be transported. In some embodiments, the systems, devices, and methods described herein are configured to determine a risk of coronary artery disease (CAD), such as for example myocardial infarction (MI), while on an ambulance at another location away from a catheter lab based on one or more plaque analyses described herein. In some embodiments, the systems, devices, and methods described herein are configured to generate a list of medical facilities and determine which the patient should be taken to based on their risk of MI.

More specifically, in some embodiments, the systems, methods, and devices can be configured to analyze a medical image to perform one or more analyses of plaque and/or types of plaque, such as for example low density non-calcified plaque, calcified plaque, non-calcified plaque, and/or the like. In particular, in some embodiments, low density non-calcified plaque can be a focus due to the high-risk generally associated with low density non-calcified plaque. For example, low density non-calcified plaque can have a higher risk of potential rupture compared to other types of plaque, such as regular non-calcified plaque or calcified plaque. A plaque rupture can, in some instances, clog or block a vessel, thereby causing a heart attack or MI. As such, it can be advantageous to analyze one or more features of low density non-calcified plaque, and/or non-calcified plaque and/or calcified plaque, which may correspond to high or low risk of CAD and/or stability or instability of plaque. In some embodiments, the systems, devices, and methods are configured to analyze a medical image, such as a CT or CCTA image, to derive one or more features, measures, and/or characterizations of plaque, such as low density non-calcified plaque, non-calcified plaque, and/or calcified plaque, and use the same to facilitate an assessment or and/or generate an assessment of risk of CAD and/or stability or instability of plaque. Using this determination, the system can generate lists of medical facilities. The list can be separated into facilities with catheter labs or without catheter labs. Depending on the plaque analysis, the system can determine which facility to which the subject should be taken.

Figure 17:
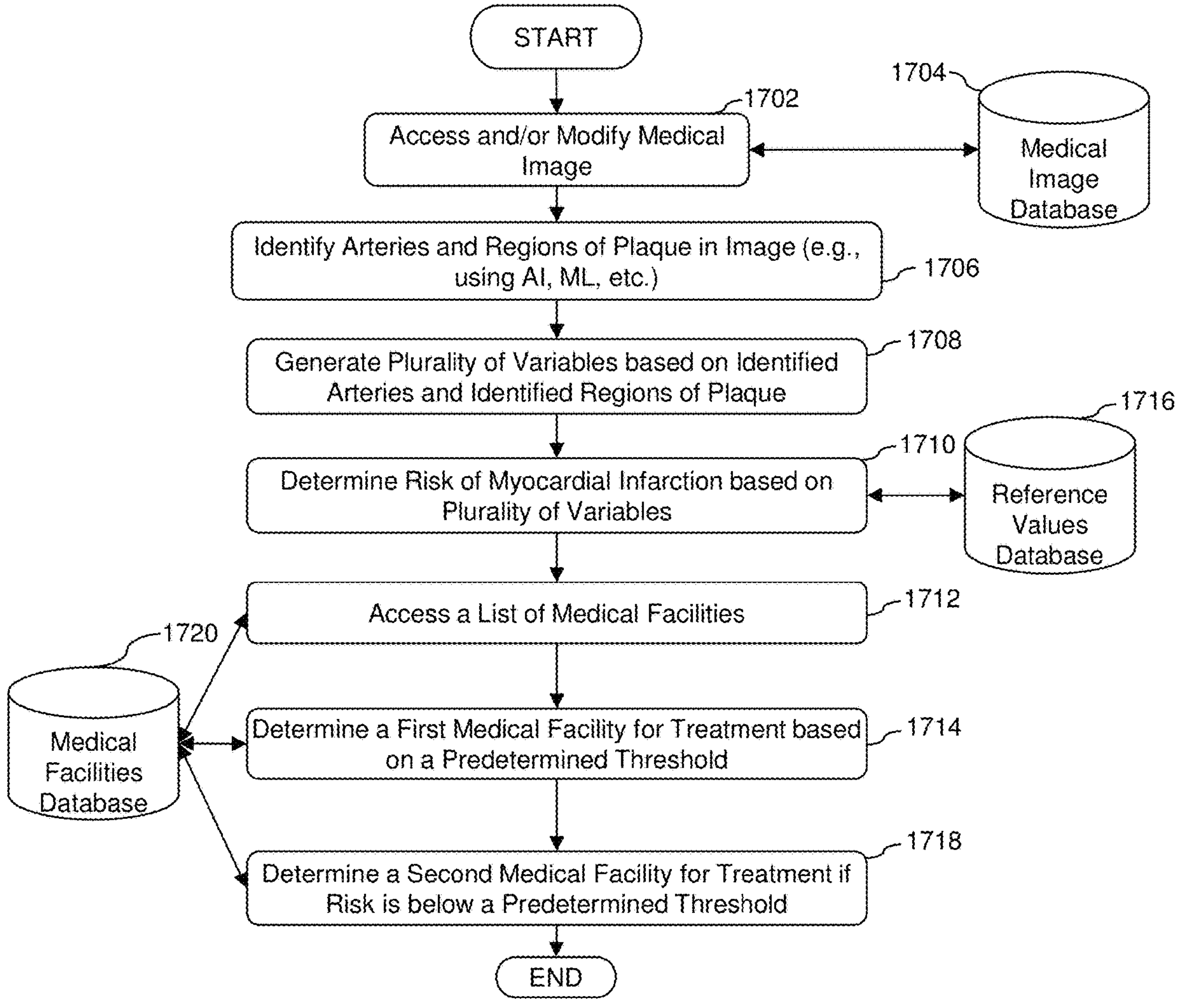
FIG. 17 is a flowchart illustrating an example embodiment(s) of systems, devices, and methods for determination of a medical facility based on image-based analysis.

FIG. 17 is a flowchart illustrating an example embodiment(s) of systems, devices, and methods for determination of a medical facility based at least in part on image-based plaque analysis. As illustrated in FIG. 17, in some embodiments, the system can be configured to access and/or modify one or more medical images at block 1702. In some embodiments, the medical image of the patient can be taken while the patient is remotely located from a healthcare facility using, for example, a portable or remotely located medical imager. In some embodiments, the medical image is taken by emergency responders responding to a patient undergoing medical distress, such as an adverse cardiac event. In some embodiments, the medical image is taken using a medical imaging device located in an ambulance, helicopter, or other emergency medical transport. In some embodiments, the system can access the medical image of a subject, the medical image comprising a representation of a portion of one or more coronary arteries, wherein the medical image is obtained using an imaging modality on an ambulance. In some embodiments, the medical image can include one or more arteries, such as coronary, carotid, and/or other arteries of a subject. In some embodiments, the medical image can be stored in a medical image database 1704. In some embodiments, the medical image database 1704 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above. In some embodiments, the imaging modality comprises computed tomography (CT).

In some embodiments, the system can be configured to automatically and/or dynamically perform one or more analyses of the medical image as discussed herein. For example, in some embodiments, at block 1706, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the one or more coronary arteries comprising one or more regions of plaque. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1706, the system can further be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque.

In some embodiments, at block 1708, the system can be configured to analyze the identified one or more coronary arteries and the one or more regions of plaque to generate a plurality of image-derived variables. The plurality of image-derived variables can include one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis.

In some embodiments, at block 1710, the system can be configured to determine a risk of myocardial infarction based on the determined plurality of variables and/or other features of the medical image. For example, in some embodiments, the system can be configured to use a reference values database 1716 of other subjects. The reference values database 1716 can include images of other subjects which have been analyzed to determine risk of CAD or MI. In some embodiments, using the images can help the system to determine if the risk to the current subject of MI. In some embodiments, a machine learning algorithm is applied to determine risk of myocardial infarction for the subject based at least in part on the plurality of image-derived variables, wherein the machine learning algorithm is trained based at least in part on the plurality of image-derived variables derived from medical images of other subjects with known risk of myocardial infarction.

In some embodiments, at block 1712, the system can be configured to access a list of medical facilities from a medical facilities database 1720. In some embodiments, the system accesses a first list of medical facilities comprising a cardiac catheterization lab and a second list of medical facilities not comprising a cardiac catheterization lab. In some embodiments, the list includes other factors such as distance from the current location of the ambulance, capacity, and insurance compatibility.

In some embodiments, at block 1714, the system can be configured to determine a first medical facility for treating the subject from the first list of medical facilities comprising a cardiac catheterization lab when the determined risk of myocardial infarction for the subject is above a predetermined threshold. In some embodiments, determining the first medical facility comprises accessing, by the computer system, availability of cardiac catheterization labs at one or more medical facilities on the first list of medical facilities; and determining, by the computer system, as the first medical facility a medical facility with highest availability of the cardiac catheterization lab within a predetermined distance from a current location of the subject. In some embodiments, the system only determines one list that contains medical facilities for treating the subject from the list of medical facilities comprising a cardiac catheterization lab when the determined risk of myocardial infarction for the subject is above a predetermined threshold.

In some embodiments, at block 1718, the system can be configured to determine a second medical facility for treating the subject from the second list of medical facilities not comprising a cardiac catheterization lab when the determined risk of myocardial infarction for the subject is below a predetermined threshold. In some embodiments the second medical facility comprises a closest medical facility from a location of the subject.

In some embodiments, the system can generate driving instructions for the ambulance to one or more of the first medical facility or the second medical facility. In some embodiments, the system can cause self-driving of the ambulance to one or more of the first medical facility or the second medical facility. In some embodiments, the system can transmit the determined risk of myocardial infarction for the subject and the medical image to one or more of the first medical facility or the second medical facility. In some embodiments, the system can create a weighted measure of the plurality of image-derived variables, wherein the risk of myocardial infarction is determined based at least in part on the weighted measure of the plurality of image-derived variables. In some embodiments, the system determines a medical facility for treating the subject that is closest to a current location of the subject when the determined risk of myocardial infarction for the subject is below a predetermined threshold.

The computer system 902 of FIG. 9, and in some instances, the analysis and/or risk assessment module 940, can be configured to carry out the functions, methods, acts, and/or processes for determination of a medical facility based at least in part on image-based plaque analysis described herein, such as those described above with reference to FIG. 17.

The following are non-limiting examples of certain embodiments of systems and methods for determination of a medical facility based at least in part on image-based plaque analysis. Other embodiments may include one or more other features, or different features, that are discussed herein.

Embodiment 1: A computer-implemented method of determining a medical facility for a subject based at least in part on image-based analysis of plaque from a medical image, the method comprising: accessing, by a computer system, a medical image of a subject, the medical image comprising a representation of a portion of one or more coronary arteries, wherein the medical image is obtained using an imaging modality on an ambulance; analyzing, by the computer system, the medical image to identify one or more coronary arteries, the one or more coronary arteries comprising one or more regions of plaque; analyzing, by the computer system, the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis; applying, by the computer system, a machine learning algorithm to determine risk of myocardial infarction for the subject based at least in part on the plurality of image-derived variables, wherein the machine learning algorithm is trained based at least in part on the plurality of image-derived variables derived from medical images of other subjects with known risk of myocardial infarction; accessing, by the computer system, a first list of medical facilities comprising a cardiac catheterization lab and a second list of medical facilities not comprising a cardiac catheterization lab; determining, by the computer system, a first medical facility for treating the subject from the first list of medical facilities comprising a cardiac catheterization lab when the determined risk of myocardial infarction for the subject is above a predetermined threshold; and determining, by the computer system, a second medical facility for treating the subject from the second list of medical facilities not comprising a cardiac catheterization lab when the determined risk of myocardial infarction for the subject is below a predetermined threshold, wherein the computer system comprises a computer processor and an electronic storage medium.

Embodiment 2: The computer-implemented method of Embodiment 1, wherein the second medical facility comprises a closest medical facility from a location of the subject.

Embodiment 3: The computer-implemented method of Embodiment 1, wherein determining the first medical facility comprises: accessing, by the computer system, availability of cardiac catheterization labs at one or more medical facilities on the first list of medical facilities; and determining, by the computer system, as the first medical facility a medical facility with highest availability of the cardiac catheterization lab within a predetermined distance from a current location of the subject.

Embodiment 4: The computer-implemented method of Embodiment 1, further comprising causing, by the computer system, generation of driving instructions for the ambulance to one or more of the first medical facility or the second medical facility.

Embodiment 5: The computer-implemented method of Embodiment 4, further comprising causing, by the computer system, self-driving of the ambulance to one or more of the first medical facility or the second medical facility.

Embodiment 6: The computer-implemented method of Embodiment 1, further comprising transmitting, by the computer system, the determined risk of myocardial infarction for the subject and the medical image to one or more of the first medical facility or the second medical facility.

Embodiment 7: The computer-implemented method of Embodiment 1, further comprising generating, by the computer system, a weighted measure of the plurality of image-derived variables, wherein the risk of myocardial infarction is determined based at least in part on the weighted measure of the plurality of image-derived variables.

Embodiment 8: The computer-implemented method of Embodiment 1, wherein the imaging modality comprises computed tomography (CT).

Embodiment 9: The computer-implemented method of Embodiment 8, wherein the medical image comprises a coronary CT angiography (CCTA).

Embodiment 10: The computer-implemented method of Embodiment 1, wherein the imaging modality comprises one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 11: A computer-implemented method of determining a medical facility for a subject based at least in part on image-based analysis of plaque from a medical image, the method comprising: accessing, by a computer system, a medical image of a subject, the medical image comprising a representation of a portion of one or more coronary arteries, wherein the medical image is obtained using an imaging modality on an ambulance; analyzing, by the computer system, the medical image to identify one or more coronary arteries, the one or more coronary arteries comprising one or more regions of plaque; analyzing, by the computer system, the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis; applying, by the computer system, a machine learning algorithm to determine risk of myocardial infarction for the subject based at least in part on the plurality of image-derived variables, wherein the machine learning algorithm is trained based at least in part on the plurality of image-derived variables derived from medical images of other subjects with known risk of myocardial infarction; accessing, by the computer system, a list of medical facilities comprising a cardiac catheterization lab; and determining, by the computer system, a medical facility for treating the subject from the list of medical facilities comprising a cardiac catheterization lab when the determined risk of myocardial infarction for the subject is above a predetermined threshold; wherein the computer system comprises a computer processor and an electronic storage medium.

Embodiment 12: The computer-implemented method of Embodiment 11, further comprising determining, by the computer system, a medical facility for treating the subject that is closest to a current location of the subject when the determined risk of myocardial infarction for the subject is below a predetermined threshold.

Embodiment 13: The computer-implemented method of Embodiment 11, wherein determining the medical facility comprises: accessing, by the computer system, availability of cardiac catheterization labs at one or more medical facilities on the list of medical facilities; and determining, by the computer system, as the medical facility a medical facility with highest availability of the cardiac catheterization lab within a predetermined distance from a current location of the subject.

Embodiment 14: The computer-implemented method of Embodiment 11, further comprising causing, by the computer system, generation of driving instructions for the ambulance to the medical facility.

Embodiment 15: The computer-implemented method of Embodiment 11, further comprising causing, by the computer system, self-driving of the ambulance to the medical facility.

Embodiment 16: The computer-implemented method of Embodiment 11, further comprising transmitting, by the computer system, the determined risk of myocardial infarction for the subject and the medical image to the medical facility.

Embodiment 17: The computer-implemented method of Embodiment 11, further comprising generating, by the computer system, a weighted measure of the plurality of image-derived variables, wherein the risk of myocardial infarction is determined based at least in part on the weighted measure of the plurality of image-derived variables.

Embodiment 18: The computer-implemented method of Embodiment 11, wherein the imaging modality comprises computed tomography (CT).

Embodiment 19: The computer-implemented method of Embodiment 18, wherein the medical image comprises a coronary CT angiography (CCTA).

Embodiment 20: The computer-implemented method of Embodiment 11, wherein the imaging modality comprises one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 21: A system for determining a medical facility for a subject based at least in part on image-based analysis of plaque from a medical image, the system comprising: a non-transitory computer storage medium configured to at least store computer executable instructions; and one or more computer hardware processors in communication with the first non-transitory computer storage medium, the one or more computer hardware processors configured to execute the computer-executable instructions to at least: access a medical image of a subject, the medical image comprising a representation of a portion of one or more coronary arteries, wherein the medical image is obtained using an imaging modality on an ambulance; analyze the medical image to identify one or more coronary arteries, the one or more coronary arteries comprising one or more regions of plaque; analyze the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis; apply a machine learning algorithm to determine risk of myocardial infarction for the subject based at least in part on the plurality of image-derived variables, wherein the machine learning algorithm is trained based at least in part on the plurality of image-derived variables derived from medical images of other subjects with known risk of myocardial infarction; access a first list of medical facilities comprising a cardiac catheterization lab and a second list of medical facilities not comprising a cardiac catheterization lab; determine a first medical facility for treating the subject from the first list of medical facilities comprising a cardiac catheterization lab when the determined risk of myocardial infarction for the subject is above a predetermined threshold; and determine a second medical facility for treating the subject from the second list of medical facilities not comprising a cardiac catheterization lab when the determined risk of myocardial infarction for the subject is below a predetermined threshold.

Embodiment 22: The system of Embodiment 21, wherein the second medical facility comprises a closest medical facility from a location of the subject.

Embodiment 23: The system of Embodiment 21, wherein determining the first medical facility comprises: accessing availability of cardiac catheterization labs at one or more medical facilities on the first list of medical facilities; and determining as the first medical facility a medical facility with highest availability of the cardiac catheterization lab within a predetermined distance from a current location of the subject.

Embodiment 24: The system of Embodiment 21, wherein the system is further configured to generate driving instructions for the ambulance to one or more of the first medical facility or the second medical facility.

Embodiment 25: The system of Embodiment 24, wherein the system is further configured for self-driving of the ambulance to one or more of the first medical facility or the second medical facility.

Embodiment 26: The system of Embodiment 21, wherein the system is further configured for transmitting the determined risk of myocardial infarction for the subject and the medical image to one or more of the first medical facility or the second medical facility.

Embodiment 27: The system of Embodiment 21, wherein the system is further configured to generate a weighted measure of the plurality of image-derived variables, wherein the risk of myocardial infarction is determined based at least in part on the weighted measure of the plurality of image-derived variables.

Embodiment 28: The system of Embodiment 21, wherein the imaging modality comprises computed tomography (CT).

Embodiment 29: The system of Embodiment 28, wherein the medical image comprises a coronary CT angiography (CCTA).

Embodiment 30: The system of Embodiment 21, wherein the imaging modality comprises one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 31: A system for determining a medical facility for a subject based at least in part on image-based analysis of plaque from a medical image, the system comprising: a non-transitory computer storage medium configured to at least store computer executable instructions; and one or more computer hardware processors in communication with the first non-transitory computer storage medium, the one or more computer hardware processors configured to execute the computer-executable instructions to at least: access a medical image of a subject, the medical image comprising a representation of a portion of one or more coronary arteries, wherein the medical image is obtained using an imaging modality on an ambulance; analyze the medical image to identify one or more coronary arteries, the one or more coronary arteries comprising one or more regions of plaque; analyze the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis; apply a machine learning algorithm to determine risk of myocardial infarction for the subject based at least in part on the plurality of image-derived variables, wherein the machine learning algorithm is trained based at least in part on the plurality of image-derived variables derived from medical images of other subjects with known risk of myocardial infarction; access a list of medical facilities comprising a cardiac catheterization lab; and determine a medical facility for treating the subject from the list of medical facilities comprising a cardiac catheterization lab when the determined risk of myocardial infarction for the subject is above a predetermined threshold.

Embodiment 32: The system of Embodiment 31, the system further configured to determine a medical facility for treating the subject that is closest to a current location of the subject when the determined risk of myocardial infarction for the subject is below a predetermined threshold.

Embodiment 33: The system of Embodiment 31, wherein determining the medical facility comprises: accessing availability of cardiac catheterization labs at one or more medical facilities on the list of medical facilities; and determining as the medical facility a medical facility with highest availability of the cardiac catheterization lab within a predetermined distance from a current location of the subject.

Embodiment 34: The system of Embodiment 31, wherein the system further comprises generation of driving instructions for the ambulance to the medical facility.

Embodiment 35: The system of Embodiment 31, wherein the system further comprises self-driving of the ambulance to the medical facility.

Embodiment 36: The system of Embodiment 31, wherein the system further comprises transmitting the determined risk of myocardial infarction for the subject and the medical image to the medical facility.

Embodiment 37: The system of Embodiment 31, wherein the system further comprises generating a weighted measure of the plurality of image-derived variables, wherein the risk of myocardial infarction is determined based at least in part on the weighted measure of the plurality of image-derived variables.

Embodiment 38: The system of Embodiment 31, wherein the imaging modality comprises computed tomography (CT).

Embodiment 39: The system of Embodiment 38, wherein the medical image comprises a coronary CT angiography (CCTA).

Embodiment 40: The system of Embodiment 31, wherein the imaging modality comprises one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 41: A non-transitory computer readable medium configured for determining a medical facility for a subject based at least in part on image-based analysis of plaque from a medical image, the computer readable medium having program instructions for causing a hardware processor to perform a method of: accessing a medical image of a subject, the medical image comprising a representation of a portion of one or more coronary arteries, wherein the medical image is obtained using an imaging modality on an ambulance; analyzing the medical image to identify one or more coronary arteries, the one or more coronary arteries comprising one or more regions of plaque; analyzing the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis; applying a machine learning algorithm to determine risk of myocardial infarction for the subject based at least in part on the plurality of image-derived variables, wherein the machine learning algorithm is trained based at least in part on the plurality of image-derived variables derived from medical images of other subjects with known risk of myocardial infarction; accessing a first list of medical facilities comprising a cardiac catheterization lab and a second list of medical facilities not comprising a cardiac catheterization lab; determining a first medical facility for treating the subject from the first list of medical facilities comprising a cardiac catheterization lab when the determined risk of myocardial infarction for the subject is above a predetermined threshold; and determining a second medical facility for treating the subject from the second list of medical facilities not comprising a cardiac catheterization lab when the determined risk of myocardial infarction for the subject is below a predetermined threshold.

Embodiment 42: The non-transitory computer readable medium of Embodiment 41, wherein the second medical facility comprises a closest medical facility from a location of the subject.

Embodiment 43: The non-transitory computer readable medium of Embodiment 41, wherein determining the first medical facility comprises: accessing availability of cardiac catheterization labs at one or more medical facilities on the first list of medical facilities; and determining as the first medical facility a medical facility with highest availability of the cardiac catheterization lab within a predetermined distance from a current location of the subject.

Embodiment 44: The non-transitory computer readable medium of Embodiment 41, wherein the method further comprises generation of driving instructions for the ambulance to one or more of the first medical facility or the second medical facility.

Embodiment 45: The non-transitory computer readable medium of Embodiment 44, wherein the method further comprises self-driving of the ambulance to one or more of the first medical facility or the second medical facility.

Embodiment 46: The non-transitory computer readable medium of Embodiment 41, wherein the method further comprises transmitting the determined risk of myocardial infarction for the subject and the medical image to one or more of the first medical facility or the second medical facility.

Embodiment 47: The non-transitory computer readable medium of Embodiment 41, wherein the method further comprises generation of a weighted measure of the plurality of image-derived variables, wherein the risk of myocardial infarction is determined based at least in part on the weighted measure of the plurality of image-derived variables.

Embodiment 48: The non-transitory computer readable medium of Embodiment 41, wherein the imaging modality comprises computed tomography (CT).

Embodiment 49: The non-transitory computer readable medium of Embodiment 48, wherein the medical image comprises a coronary CT angiography (CCTA).

Embodiment 50: The non-transitory computer readable medium of Embodiment 41, wherein the imaging modality comprises one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 51: A non-transitory computer readable medium for determining a medical facility for a subject based at least in part on image-based analysis of plaque from a medical image, the computer readable medium having program instructions for causing a hardware processor to perform a method of: accessing a medical image of a subject, the medical image comprising a representation of a portion of one or more coronary arteries, wherein the medical image is obtained using an imaging modality on an ambulance; analyzing the medical image to identify one or more coronary arteries, the one or more coronary arteries comprising one or more regions of plaque; analyzing the identified one or more coronary arteries and the one or more regions of plaque to generate a plurality of image-derived variables, the plurality of image-derived variables comprising one or more of percent atheroma volume of total plaque, total plaque volume, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, vessel length, segment length, lesion length, lumen volume, number of chronic total occlusion (CTO), vessel volume, number of stenosis, severity of stenosis, remodeling index, minimum lumen diameter, maximum lumen diameter, mean lumen diameter, stenosis area percentage, stenosis diameter percentage, number of mild stenosis, number of moderate stenosis, number of zero stenosis, number of severe stenosis, presence of high-risk anatomy, presence of positive remodeling, number of severe stenosis excluding CTO, vessel area, lumen area, diameter stenosis percentage, reference lumen diameter before stenosis, perivascular fat attenuation, or reference lumen diameter after stenosis; applying a machine learning algorithm to determine risk of myocardial infarction for the subject based at least in part on the plurality of image-derived variables, wherein the machine learning algorithm is trained based at least in part on the plurality of image-derived variables derived from medical images of other subjects with known risk of myocardial infarction; accessing a list of medical facilities comprising a cardiac catheterization lab; and determining a medical facility for treating the subject from the list of medical facilities comprising a cardiac catheterization lab when the determined risk of myocardial infarction for the subject is above a predetermined threshold.

Embodiment 52: The non-transitory computer readable medium of Embodiment 51, wherein the method further comprises determining a medical facility for treating the subject that is closest to a current location of the subject when the determined risk of myocardial infarction for the subject is below a predetermined threshold.

Embodiment 53: The non-transitory computer readable medium of Embodiment 51, wherein determining the medical facility comprises: accessing availability of cardiac catheterization labs at one or more medical facilities on the list of medical facilities; and determining as the medical facility a medical facility with highest availability of the cardiac catheterization lab within a predetermined distance from a current location of the subject.

Embodiment 54: The non-transitory computer readable medium of Embodiment 51, wherein the method further comprises generation of driving instructions for the ambulance to the medical facility.

Embodiment 55: The non-transitory computer readable medium of Embodiment 51, wherein the method further comprises self-driving of the ambulance to the medical facility.

Embodiment 56: The non-transitory computer readable medium of Embodiment 51, wherein the method further comprises transmitting the determined risk of myocardial infarction for the subject and the medical image to the medical facility.

Embodiment 57: The non-transitory computer readable medium of Embodiment 51, wherein the method further comprises generation of a weighted measure of the plurality of image-derived variables, wherein the risk of myocardial infarction is determined based at least in part on the weighted measure of the plurality of image-derived variables.

Embodiment 58: The non-transitory computer readable medium of Embodiment 51, wherein the imaging modality comprises computed tomography (CT).

Embodiment 59: The non-transitory computer readable medium of Embodiment 58, wherein the medical image comprises a coronary CT angiography (CCTA).

Embodiment 60: The non-transitory computer readable medium of Embodiment 51, wherein the imaging modality comprises one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Multivariable Image-Based Analysis of Endothelial Shear Stress and Plaque Analysis Disclosed herein are systems, devices, and methods for determination of plaque progression based on multivariable image-based analysis of plaque parameters and/or endothelial shear stress. In particular, in some embodiments, the systems, devices, and methods described herein are related to analysis of one or more regions of plaque, such as for example coronary plaque, based on one or more distances, volumes, shapes, morphologies, embeddedness, and/or axes measurements. For example, in some embodiments, the systems, devices, and methods described herein are related to plaque analysis based on one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque, and/or the like. In some embodiments, the systems, devices, and methods described herein are configured to determine a risk of coronary artery disease (CAD), such as for example myocardial infarction (MI), based on one or more plaque analyses described herein, by determining a level of endothelial shear stress for one or more regions of the one or more artery vessels. In some embodiments, the systems, devices, and methods described herein the determined level of endothelial stress is used to determine a risk of arterial disease.

As discussed herein, disclosed herein are systems, methods, and devices for multivariable image-based analysis of endothelial shear stress. In particular, in some embodiments the systems, devices, and methods for determination of plaque progression based on multivariable image-based analysis of plaque parameters and/or endothelial shear stress. In particular, in some embodiments, the systems, devices, and methods described herein are related to analysis of one or more regions of plaque, such as for example coronary plaque, based on one or more distances, volumes, shapes, morphologies, embeddedness, and/or axes measurements. For example, in some embodiments, the systems, devices, and methods described herein are related to plaque analysis based on one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque, and/or the like. In some embodiments, the systems, devices, and methods described herein are configured to determine a risk of coronary artery disease (CAD), such as for example myocardial infarction (MI), based on one or more plaque analyses described herein, by determining a level of endothelial shear stress for one or more regions of the one or more artery vessels. In some embodiments, the systems, devices, and methods described herein the determined level of endothelial stress is used to determine a risk of arterial disease.

More specifically, in some embodiments, the systems, methods, and devices can be configured to analyze a medical image to perform one or more analyses of levels of endothelial shear stress. In particular, in some embodiments, endothelial shear stress can indicate a higher risk of coronary artery disease. Endothelial shear stress is the stress created on an artery wall by flowing blood. When the blood flows along the endothelial surface of an arterial wall, the blood creates friction that can weaken the arterial wall. In circumstances where plaque has developed, the protrusion of the endothelial surface changes the flow of blood through the artery, changing the friction on the endothelial surface, weakening the endothelial surface increasing a chance for a plaque rupture. A plaque rupture can, in some instances, clog or block a vessel, thereby causing a heart attack or MI. As such, it can be advantageous to analyze one or more features of an artery to determine levels of endothelial shear stress, which may correspond to high or low risk of CAD. In some embodiments, the systems, devices, and methods are configured to analyze a medical image, such as a CT or CCTA image, to derive one or more features, measures, and/or characterizations of plaque and use the same to facilitate an assessment or and/or generate an assessment of risk of CAD using levels of endothelial shear stress. Thus, in some embodiments, the systems, devices, and methods can provide an efficient and/or non-invasive method of assessing risk of CAD.

In some embodiments, through use of the methods and systems described herein, computational fluid dynamics may not be needed to predict coronary arterial disease. Using plaque features, in some embodiments, such as, volume, morphology, composite, eccentricity, stenosis, downstream plaque, upstream plaque, size of the vessel, and/or size of the lumen, etc., the system can determine a level of endothelial wall shear stress, for example, directly from analysis of medical image. Using a pixel-by-pixel analysis, in some embodiments, the variables can be used to determine if the level is low, intermediate, or high. Using the weighted number, in some embodiments, the system can be configured to classify the endothelial wall shear stress to determine a risk of coronary artery disease.

Figure 18:
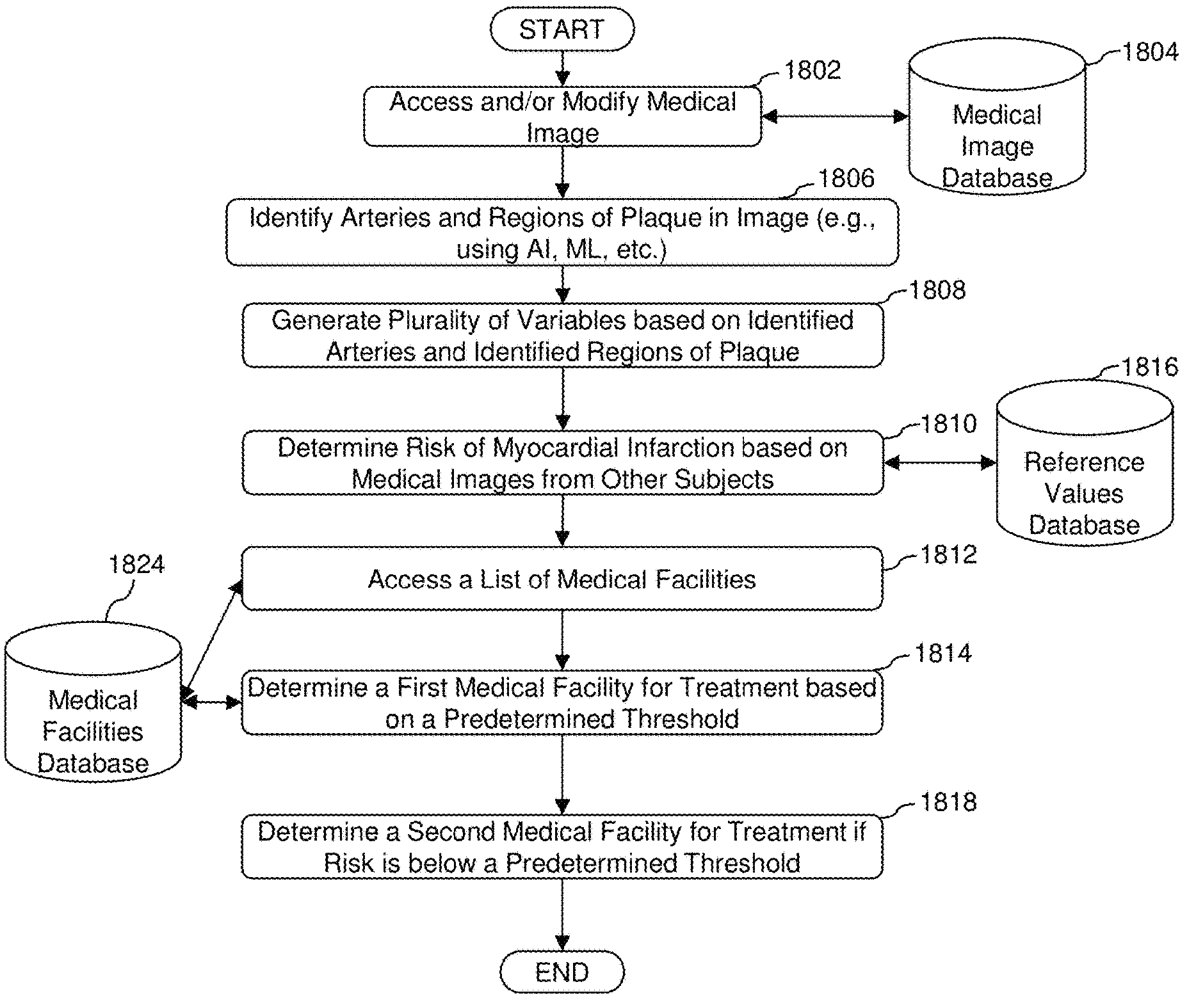
FIG. 18 is a flowchart illustrating an example embodiment(s) of systems, devices, and methods for predicting plaque progression.

FIG. 18 is a flowchart illustrating an example embodiment(s) of systems, devices, and methods for predicting plaque progression. In some embodiments, plaque progression can be predicted based at least in part on a risk level of a region of plaque and/or a level of endothelial shear stress on the region of plaque determined. In some embodiments, risk level of CAD and/or level of endothelial shear stress can be determined based at least in part on a plurality of variables derived from non-invasive medical image analysis.

As illustrated in FIG. 18, in some embodiments, the system can be configured to access and/or modify one or more medical images at block 1802. In some embodiments, the medical image can include one or more arteries, such as coronary, carotid, and/or other arteries of a subject. In some embodiments, the medical image can be stored in and/or retrieved from a medical image database 1804. In some embodiments, the medical image database 1804 can be locally accessible by the system and/or can be located remotely and accessible through a network connection. The medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1806, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1806, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque. In some embodiments, the system is configured to identify one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque.

In some embodiments, at block 1808, the system is configured to generate a plurality of variables based on the one or more arteries and regions of plaque identified at block 206. For example, the plurality of variables can be generated by using an artificial intelligence (AI) and/or machine learning (ML) algorithm trained on a plurality of medical images with the plurality of variables pre-identified. In some embodiments, the plurality of variables can include one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque.

In some embodiments, the system can be further be configured to analyze the region(s) of plaque for one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

In some embodiments, at block 1810, the system can be configured to generate a first weighted measure of the generated plurality of variables. For example, in some embodiments, the system can determine one or more variables of the plurality of variables are more useful in determining a risk level associated with a region of plaque. The system can weight the variables according to their use in determining risk level in an analysis.

In some embodiments, at block 1812, the system can be configured to determine a risk level of a particular region of plaque of the one or more regions of plaque based at least in part on the first weighted measure of the generated plurality of variables. The risk level for the one or more regions of the one or more artery vessels can be determined using a machine learning algorithm trained based at least in part on a plurality of weighted measures of the plurality of variables generated from a plurality of medical images of a plurality of other subjects with known risk levels stored within a reference values database 1816.

In some embodiments, at block 1814, the system can be configured to generate a second weighted measure based on the plurality of variable determined at block 1808. For example, in some embodiments, the system can determine one or more variables of the plurality of variables are more useful in determining a level of endothelial shear stress associated with the region of plaque. The system can weight the variables according to their use in determining endothelia shear stress in an analysis.

In some embodiments, at block 1818, the system can be configured to determine a level of endothelial shear stress for one or more regions of one or more artery vessels based at least in part of the second weighted measure of the generated plurality of variables. The level of endothelial shear stress for the one or more regions of the one or more artery vessels can be determined using a machine learning algorithm trained based at least in part on a plurality of weighted measures of the plurality of variables generated from a plurality of medical images of a plurality of other subjects with known levels of endothelial shear stress stored within a reference values database 1816. In some embodiments, the level of endothelial shear stress comprises one of low, medium, or high. In some embodiments, the level of endothelial shear stress is determined on a continuous scale. In some embodiments, the level of endothelial shear stress for the one or more regions of the one or more artery vessels is determined without using computational fluid dynamics. In some embodiments, the level of endothelial shear stress for the one or more regions of the one or more artery vessels is determined without using an invasive measurement of the subject. In some embodiments, the known levels of endothelial shear stress are generated based at least in part on computational fluid dynamics applies to the plurality of medical images of the plurality of other subjects. In some embodiments, the known levels of endothelial shear stress are generated based at least in part on an invasive measure. In some embodiments, the determined level of endothelial shear stress is configured to be used to determine a treatment for arterial disease for the subject.

In some embodiments, at block 120, the system can be configured to predict progression of the plaque based at least in part on the risk level determined at block 1812 and the level of endothelial shear stress determined at block 1818. In some embodiments, the progression of the particular region of plaque is predicted using a machine learning algorithm trained based at least in part on a plurality of first weighted measures and a plurality of second weighted measures generated from a plurality of medical images of a plurality of other subjects with known progressions of plaque. The plurality of first weighted measures and the plurality of second weighted measures can be stored in the reference values database 1816. In some embodiments, the known progression of plaque are derived from longitudinal analysis of medical images. In some embodiments, the predicted progression of the particular region of plaque comprises one or more of rapid progression, slow progression, or stabilization. In some embodiments, the endothelial shear stress being below a predetermined threshold is indicative of rapid progression of plaque. In some embodiments, the endothelial shear stress being above a predetermined threshold is indicative of slow progression of plaque or stabilization of plaque.

In some embodiments, at block 122, the system can generate and/or present a proposed treatment for arterial disease for the subject based at least in part on the determined risk of arterial disease for the subject. In some embodiments, the proposed treatment can be determined with reference to one or more reference values can be stored on a treatment reference values database 1824, which can be locally accessible by the system and/or can be located remotely and accessible through a network connection.

In some embodiments, the system can be configured to generate a graphical representation of the analyses results, determined risk of CAD, and/or proposed treatment for the subject. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1824, which can be locally accessible by the system and/or can be located remotely and accessible through a network connection. In some embodiments, the plaque risk/treatment database 1824 can include reference points or data that relate one or more treatment to cardiovascular disease risk or state determined based on one or more reference plaque analyses values. In some embodiments, a graphical representation can be configured to show the determined level of endothelial shear stress for the one or more regions of the one or more artery vessels.

In some embodiments, the system can be configured to repeat one or more processes described in relation to blocks 1802-1824, for example for one or more other vessels, segment, regions of plaque, different subjects, and/or for the same subject at a different time. As such, in some embodiments, the system can provide for longitudinal disease tracking and/or personalized treatment for a subject.

In some embodiments the system can accesses a subsequent medical image of the subject, the subsequent medical image comprising one or more artery vessels and one or more regions of plaque within the one or more artery vessels, analyze the subsequent medical image of the subject to generate the plurality of variables, determine a subsequent level of endothelial shear stress for one or more regions of one or more artery vessels based at least in part on the plurality of variables generated from analyzing the subsequent medical image, and generate a graphical representation of a comparison of the level of endothelial shear stress and the level of subsequent level of endothelial shear stress for one or more regions of one or more artery vessels, wherein the graphical representation of the comparison is configured to be used to track progression of arterial disease for the subject.

Figure 19:
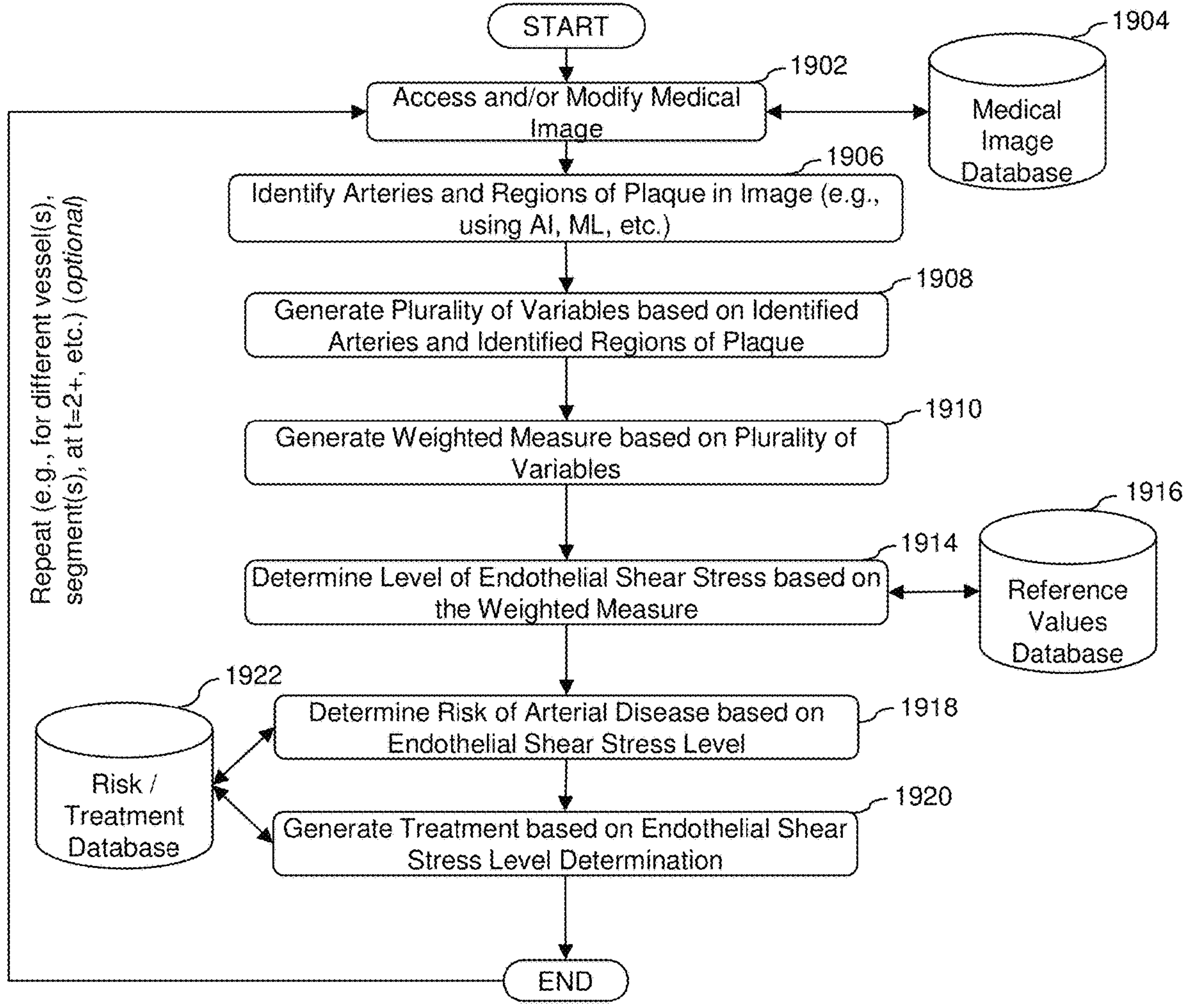
FIG. 19 is a flowchart illustrating an example embodiment(s) of systems, devices, and methods for non-invasive image-based plaque analysis and determination of endothelial shear stress.

FIG. 19 is a flowchart illustrating an example embodiment(s) of systems, devices, and methods for determination of endothelial shear stress. As illustrated in FIG. 19, in some embodiments, the system can be configured to access and/or modify one or more medical images at block 1902. In some embodiments, the medical image can include one or more arteries, such as coronary, carotid, and/or other arteries of a subject. In some embodiments, the medical image can be stored in and/or retrieved from a medical image database 1904. In some embodiments, the medical image database 1904 can be locally accessible by the system and/or can be located remotely and accessible through a network connection. The medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 1906, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 1906, the system can further be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque. In some embodiments, the system is configured to identify one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque.

In some embodiments, at block 1908, the system is configured to generate a plurality of variables based on the one or more arteries and regions of plaque identified at block 1906. For example, the plurality of variables can be generated by using an artificial intelligence (AI) and/or machine learning (ML) algorithm trained on a plurality of medical images with the plurality of variables pre-identified. In some embodiments, the plurality of variables can include one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque.

In some embodiments, the system can be further be configured to analyze the region(s) of plaque for one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

In some embodiments, at block 1910, the system can be configured to generate a weighted measure of the generated plurality of variables. For example, in some embodiments, the system can determine one or more variables of the plurality of variables are more useful in determining endothelial shear stress. The system can weight the variables according to their use in determining endothelial shear stress to use in an analysis.

In some embodiments, at block 1914, the system can be used to determine a level of endothelial shear stress for one or more regions of one or more artery vessels based at least in part of the weighted measure of the generated plurality of variables. In some embodiments, the level of endothelial shear stress for the one or more regions of the one or more artery vessels is determined using a machine learning algorithm trained based at least in part on a plurality of weighted measures of the plurality of variables generated from a plurality of medical images of a plurality of other subjects with known levels of endothelial shear stress stored within a reference values database 1916. In some embodiments, the level of endothelial shear stress comprises one of low, medium, or high. In some embodiments, the level of endothelial shear stress is determined on a continuous scale. In some embodiments, the level of endothelial shear stress for the one or more regions of the one or more artery vessels is determined without using computational fluid dynamics. In some embodiments, the level of endothelial shear stress for the one or more regions of the one or more artery vessels is determined without using an invasive measurement of the subject. In some embodiments, the known levels of endothelial shear stress are generated based at least in part on computational fluid dynamics applies to the plurality of medical images of the plurality of other subjects. In some embodiments, the known levels of endothelial shear stress are generated based at least in part on an invasive measure. In some embodiments, the determined level of endothelial shear stress is configured to be used to determine a treatment for arterial disease for the subject.

In some embodiments, at block 1918, the system can be configured to use the determined level of endothelial shear stress to determine a risk of arterial disease for the subject. In some embodiments, the endothelial shear stress below a predetermined threshold is indicative of high risk of arterial disease. In some embodiments, the endothelial shear stress above a predetermined threshold is indicative of low risk of arterial disease. In some embodiments, at block 1918, the system can be configured to determine a risk of CAD or MI based at least in part endothelial shear stress levels described herein, for example in relation to one or more of blocks

1902-1918. In some embodiments, the system can be configured to utilize some or all of the plaque analyses results. In some embodiments, the system can be configured to generate a weighted measure of some or all of the plaque analyses described herein in determining a risk of CAD. In some embodiments, the risk can be determined with reference to one or more reference values can be stored on a risk reference values database 1922, which can be locally accessible by the system and/or can be located remotely and accessible through a network connection.

In some embodiments, at block 1920, the system can generate and/or present a proposed treatment for arterial disease for the subject based at least in part on the determined risk of arterial disease for the subject. In some embodiments, the proposed treatment can be determined with reference to one or more reference values can be stored on a treatment reference values database 1922, which can be locally accessible by the system and/or can be located remotely and accessible through a network connection.

In some embodiments, the system can be configured to generate a graphical representation of the analyses results, determined risk of CAD, and/or proposed treatment for the subject. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 1922, which can be locally accessible by the system and/or can be located remotely and accessible through a network connection. In some embodiments, the plaque risk/treatment database 1922 can include reference points or data that relate one or more treatment to cardiovascular disease risk or state determined based on one or more reference plaque analyses values. In some embodiments a graphical representation can be configured to show the determined level of endothelial shear stress for the one or more regions of the one or more artery vessels.

In some embodiments, the system can be configured to repeat one or more processes described in relation to blocks 1902-1922, for example for one or more other vessels, segment, regions of plaque, different subjects, and/or for the same subject at a different time. As such, in some embodiments, the system can provide for longitudinal disease tracking and/or personalized treatment for a subject.

In some embodiments the system can accesses a subsequent medical image of the subject, the subsequent medical image comprising one or more artery vessels and one or more regions of plaque within the one or more artery vessels, analyze the subsequent medical image of the subject to generate the plurality of variables, determine a subsequent level of endothelial shear stress for one or more regions of one or more artery vessels based at least in part on the plurality of variables generated from analyzing the subsequent medical image, and generate a graphical representation of a comparison of the level of endothelial shear stress and the level of subsequent level of endothelial shear stress for one or more regions of one or more artery vessels, wherein the graphical representation of the comparison is configured to be used to track progression of arterial disease for the subject.

The computer system 902 of FIG. 9, and in some instances, the analysis and/or risk assessment module 940, can be configured to carry out the functions, methods, acts, and/or processes for multivariable image-based analysis of endothelial shear stress described herein, such as those described above with reference to FIGS. 18-19.

The following are non-limiting examples of certain embodiments of systems and methods for multivariable image-based analysis of endothelial shear stress. Other embodiments may include one or more other features, or different features, that are discussed herein.

Embodiment 1: A computer-implemented method of predicting plaque progression based at least in part on a risk level of a region of plaque and a level of endothelial shear stress on the region of plaque determined based at least in part on a plurality of variables derived from non-invasive medical image analysis, the method comprising: accessing, by a computer system, a medical image of a subject, the medical image comprising a portion of one or more arteries; analyzing, by the computer system, the medical image of the subject to identify one or more artery vessels and one or more regions of plaque within the one or more artery vessels; analyzing, by the computer system, the one or more artery vessels and the one or more regions of plaque to generate a plurality of variables, the plurality of variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque; generating, by the computer system, a first weighted measure of the generated plurality of variables; determining, by the computer system, a risk level of a particular region of plaque of the one or more regions of plaque based at least in part on the first weighted measure of the generated plurality of variables; generating, by the computer system, a second weighted measure of the generated plurality of variables; determining, by the computer system, a level of endothelial shear stress for the particular region of plaque based at least in part of the second weighted measure of the generated plurality of variables; and predicting, by the computer system, progression of the particular region of plaque based at least in part on the risk level and the level of endothelial shear stress for the particular region of plaque, wherein the computer system comprises a computer processor and an electronic storage medium.

Embodiment 2: The computer-implemented method of Embodiment 1, wherein the progression of the particular region of plaque is predicted using a machine learning algorithm trained based at least in part on a plurality of first weighted measures and a plurality of second weighted measures generated from a plurality of medical images of a plurality of other subjects with known progressions of plaque.

Embodiment 3: The computer-implemented method of Embodiment 2, wherein the known progressions of plaque are derived from longitudinal analysis of medical images.

Embodiment 4: The computer-implemented method of Embodiment 1, wherein the risk level of the particular region of plaque is determined using a machine learning algorithm trained based at least in part on a plurality of first weighted measures generated from a plurality of medical images of a plurality of other subjects with identified risks of plaque.

Embodiment 5: The computer-implemented method of Embodiment 1, wherein the level of endothelial shear stress for the particular region of plaque is determined using a machine learning algorithm trained based at least in part on a plurality of second weighted measures of the plurality of variables generated from a plurality of medical images of a plurality of other subjects with known levels of endothelial shear stress.

Embodiment 6: The computer-implemented method of Embodiment 5, wherein the known levels of endothelial shear stress are generated based at least in part on computational fluid dynamics applies to the plurality of medical images of the plurality of other subjects.

Embodiment 7: The computer-implemented method of Embodiment 5, wherein the known levels of endothelial shear stress are generated based at least in part on an invasive measure.

Embodiment 8: The computer-implemented method of Embodiment 1, wherein the level of endothelial shear stress comprises one of low, medium, or high.

Embodiment 9: The computer-implemented method of Embodiment 1, wherein the level of endothelial shear stress is determined on a continuous scale.

Embodiment 10: The computer-implemented method of Embodiment 1, further comprising generating, by the computer system, a graphical representation of the determined level of endothelial shear stress for the particular region of plaque.

Embodiment 11: The computer-implemented method of Embodiment 1, further comprising generating, by the computer system, a graphical representation of the determined level of endothelial shear stress for the particular region of plaque, the determined risk level of the particular region of plaque, and the predicted progression of the particular region of plaque.

Embodiment 12: The computer-implemented method of Embodiment 1, wherein the predicted progression of the particular region of plaque comprises one or more of rapid progression, slow progression, or stabilization.

Embodiment 13: The computer-implemented method of Embodiment 1, wherein the endothelial shear stress below a predetermined threshold is indicative of rapid progression of plaque.

Embodiment 14: The computer-implemented method of Embodiment 1, wherein the endothelial shear stress above a predetermined threshold is indicative of slow progression of plaque or stabilization of plaque.

Embodiment 15: The computer-implemented method of Embodiment 1, wherein the plurality of variables are generated by using an artificial intelligence (AI) and/or machine learning (ML) algorithm trained on a plurality of medical images with the plurality of variables pre-identified.

Embodiment 16: The computer-implemented method of Embodiment 1, wherein the level of endothelial shear stress for the one or more regions of the one or more artery vessels is determined without using computational fluid dynamics.

Embodiment 17: The computer-implemented method of Embodiment 1, wherein the level of endothelial shear stress for the one or more regions of the one or more artery vessels is determined without using an invasive measurement of the subject.

Embodiment 18: The computer-implemented method of Embodiment 1, wherein the plurality of variables further comprises one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 19: The computer-implemented method of Embodiment 1, wherein the one or more arteries comprises one or more coronary arteries.

Embodiment 20: The computer-implemented method of Embodiment 1, wherein the one or more arteries comprises one or more coronary arteries, carotid, arteries, aorta, upper extremity arteries, or lower extremity arteries.

Embodiment 21: The computer-implemented method of Embodiment 1, wherein the predicted progression of the particular region of plaque is configured to be used to determine a treatment for arterial disease for the subject.

Embodiment 22: The computer-implemented method of Embodiment 1, further comprising determining, by the computer system, a risk of arterial disease for the subject based at least in part on the predicted progression of the particular region of plaque.

Embodiment 23: The computer-implemented method of Embodiment 22, further comprising generating, by the computer system, a graphical representation of the determined risk of arterial disease for the subject.

Embodiment 24: The computer-implemented method of Embodiment 22, further comprising determining, by the computer system, a proposed treatment for arterial disease for the subject based at least in part on the predicted progression of the particular region of plaque.

Embodiment 25: The computer-implemented method of Embodiment 24, further comprising generating, by the computer system, a graphical representation of the determined proposed treatment for arterial disease for the subject.

Embodiment 26: The computer-implemented method of Embodiment 1, further comprising: accessing, by the computer system, a subsequent medical image of the subject obtained after treating the subject for arterial disease with a treatment, the subsequent medical image comprising the one or more artery vessels and the one or more regions of plaque; analyzing, by the computer system, the subsequent medical image of the subject to generate the plurality of variables; generating, by the computer system, a first weighted measure of the plurality of variables generated from the subsequent medical image; determining, by the computer system, a subsequent risk level of the particular region of plaque of the one or more regions of plaque based at least in part on the first weighted measure of the plurality of variables generated from the subsequent medical image; and generating, by the computer system, a graphical representation of a comparison of the subsequent risk level of the particular region of plaque to the predicted progression of the particular region of plaque, wherein the graphical representation of the comparison is configured to be used to track efficacy of the treatment.

Embodiment 27: The computer-implemented method of Embodiment 1, wherein the medical image of the subject is obtained non-invasively.

Embodiment 28: The computer-implemented method of Embodiment 1, wherein the medical image is obtained using computed tomography (CT).

Embodiment 29: The computer-implemented method of Embodiment 1, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 30: A system for predicting plaque progression based at least in part on a risk level of a region of plaque and a level of endothelial shear stress on the region of plaque determined based at least in part on a plurality of variables derived from non-invasive medical image analysis, the system comprising: a non-transitory computer storage medium configured to at least store computer executable instructions; and one or more computer hardware processors in communication with the first non-transitory computer storage medium, the one or more computer hardware processors configured to execute the computer-executable instructions to at least: access a medical image of a subject, the medical image comprising a portion of one or more arteries; analyze the medical image of the subject to identify one or more artery vessels and one or more regions of plaque within the one or more artery vessels; analyze the one or more artery vessels and the one or more regions of plaque to generate a plurality of variables, the plurality of variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque; generate a first weighted measure of the generated plurality of variables; determine a risk level of a particular region of plaque of the one or more regions of plaque based at least in part on the first weighted measure of the generated plurality of variables; generate a second weighted measure of the generated plurality of variables; determine a level of endothelial shear stress for the particular region of plaque based at least in part of the second weighted measure of the generated plurality of variables; and predict progression of the particular region of plaque based at least in part on the risk level and the level of endothelial shear stress for the particular region of plaque.

Embodiment 31: The system of Embodiment 30, wherein the progression of the particular region of plaque is predicted using a machine learning algorithm trained based at least in part on a plurality of first weighted measures and a plurality of second weighted measures generated from a plurality of medical images of a plurality of other subjects with known progressions of plaque.

Embodiment 32: The system of Embodiment 31, wherein the known progressions of plaque are derived from longitudinal analysis of medical images.

Embodiment 33: The system of Embodiment 30, wherein the risk level of the particular region of plaque is determined using a machine learning algorithm trained based at least in part on a plurality of first weighted measures generated from a plurality of medical images of a plurality of other subjects with identified risks of plaque.

Embodiment 34: The system of Embodiment 30, wherein the level of endothelial shear stress for the particular region of plaque is determined using a machine learning algorithm trained based at least in part on a plurality of second weighted measures of the plurality of variables generated from a plurality of medical images of a plurality of other subjects with known levels of endothelial shear stress.

Embodiment 35: The system of Embodiment 34, wherein the known levels of endothelial shear stress are generated based at least in part on computational fluid dynamics applies to the plurality of medical images of the plurality of other subjects.

Embodiment 36: The system of Embodiment 34, wherein the known levels of endothelial shear stress are generated based at least in part on an invasive measure.

Embodiment 37: The system of Embodiment 30, wherein the level of endothelial shear stress comprises one of low, medium, or high.

Embodiment 38: The system of Embodiment 30, wherein the level of endothelial shear stress is determined on a continuous scale.

Embodiment 39: The system of Embodiment 30, wherein the system is further configured to generate a graphical representation of the determined level of endothelial shear stress for the particular region of plaque.

Embodiment 40: The system of Embodiment 30, wherein the system is further configured to generate a graphical representation of the determined level of endothelial shear stress for the particular region of plaque, the determined risk level of the particular region of plaque, and the predicted progression of the particular region of plaque.

Embodiment 41: The system of Embodiment 30, wherein the predicted progression of the particular region of plaque comprises one or more of rapid progression, slow progression, or stabilization.

Embodiment 42: The system of Embodiment 30, wherein the endothelial shear stress below a predetermined threshold is indicative of rapid progression of plaque.

Embodiment 43: The system of Embodiment 30, wherein the endothelial shear stress above a predetermined threshold is indicative of slow progression of plaque or stabilization of plaque.

Embodiment 44: The system of Embodiment 30, wherein the plurality of variables are generated by using an artificial intelligence (AI) and/or machine learning (ML) algorithm trained on a plurality of medical images with the plurality of variables pre-identified.

Embodiment 45: The system of Embodiment 30, wherein the level of endothelial shear stress for the one or more regions of the one or more artery vessels is determined without using computational fluid dynamics.

Embodiment 46: The system of Embodiment 30, wherein the level of endothelial shear stress for the one or more regions of the one or more artery vessels is determined without using an invasive measurement of the subject.

Embodiment 47: The system of Embodiment 30, wherein the plurality of variables further comprises one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 48: The system of Embodiment 30, wherein the one or more arteries comprises one or more coronary arteries.

Embodiment 49: The system of Embodiment 30, wherein the one or more arteries comprises one or more coronary arteries, carotid, arteries, aorta, upper extremity arteries, or lower extremity arteries.

Embodiment 50: The system of Embodiment 30, wherein the predicted progression of the particular region of plaque is configured to be used to determine a treatment for arterial disease for the subject.

Embodiment 51: The system of Embodiment 30, wherein the system is further configured to determine a risk of arterial disease for the subject based at least in part on the predicted progression of the particular region of plaque.

Embodiment 52: The system of Embodiment 51, wherein the system is further configured to generate a graphical representation of the determined risk of arterial disease for the subject.

Embodiment 53: The system of Embodiment 51, wherein the system is further configured to determine a proposed treatment for arterial disease for the subject based at least in part on the predicted progression of the particular region of plaque.

Embodiment 54: The system of Embodiment 53, wherein the system is further configured to generate a graphical representation of the determined proposed treatment for arterial disease for the subject.

Embodiment 55: The system of Embodiment 30, wherein the system is further configured to: access a subsequent medical image of the subject obtained after treating the subject for arterial disease with a treatment, the subsequent medical image comprising the one or more artery vessels and the one or more regions of plaque; analyze the subsequent medical image of the subject to generate the plurality of variables; generate a first weighted measure of the plurality of variables generated from the subsequent medical image; determine a subsequent risk level of the particular region of plaque of the one or more regions of plaque based at least in part on the first weighted measure of the plurality of variables generated from the subsequent medical image; and generate a graphical representation of a comparison of the subsequent risk level of the particular region of plaque to the predicted progression of the particular region of plaque, wherein the graphical representation of the comparison is configured to be used to track efficacy of the treatment.

Embodiment 56: The system of Embodiment 30, wherein the medical image of the subject is obtained non-invasively.

Embodiment 57: The system of Embodiment 30, wherein the medical image is obtained using computed tomography (CT).

Embodiment 58: The system of Embodiment 30, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 59: A non-transitory computer readable medium configured for predicting plaque progression based at least in part on a risk level of a region of plaque and a level of endothelial shear stress on the region of plaque determined based at least in part on a plurality of variables derived from non-invasive medical image analysis, the computer readable medium having program instructions for causing a hardware processor to perform a method of: access a medical image of a subject, the medical image comprising a portion of one or more arteries; analyze the medical image of the subject to identify one or more artery vessels and one or more regions of plaque within the one or more artery vessels; analyze the one or more artery vessels and the one or more regions of plaque to generate a plurality of variables, the plurality of variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque; generate a first weighted measure of the generated plurality of variables; determine a risk level of a particular region of plaque of the one or more regions of plaque based at least in part on the first weighted measure of the generated plurality of variables; generate a second weighted measure of the generated plurality of variables; determine a level of endothelial shear stress for the particular region of plaque based at least in part of the second weighted measure of the generated plurality of variables; and predict progression of the particular region of plaque based at least in part on the risk level and the level of endothelial shear stress for the particular region of plaque.

Embodiment 60: The non-transitory computer readable medium of Embodiment 59, wherein the progression of the particular region of plaque is predicted using a machine learning algorithm trained based at least in part on a plurality of first weighted measures and a plurality of second weighted measures generated from a plurality of medical images of a plurality of other subjects with known progressions of plaque.

Embodiment 61: The non-transitory computer readable medium of Embodiment 60, wherein the known progressions of plaque are derived from longitudinal analysis of medical images.

Embodiment 62: The non-transitory computer readable medium of Embodiment 59, wherein the risk level of the particular region of plaque is determined using a machine learning algorithm trained based at least in part on a plurality of first weighted measures generated from a plurality of medical images of a plurality of other subjects with identified risks of plaque.

Embodiment 63: The non-transitory computer readable medium of Embodiment 59, wherein the level of endothelial shear stress for the particular region of plaque is determined using a machine learning algorithm trained based at least in part on a plurality of second weighted measures of the plurality of variables generated from a plurality of medical images of a plurality of other subjects with known levels of endothelial shear stress.

Embodiment 64: The non-transitory computer readable medium of Embodiment 63, wherein the known levels of endothelial shear stress are generated based at least in part on computational fluid dynamics applies to the plurality of medical images of the plurality of other subjects.

Embodiment 65: The non-transitory computer readable medium of Embodiment 63, wherein the known levels of endothelial shear stress are generated based at least in part on an invasive measure.

Embodiment 66: The non-transitory computer readable medium of Embodiment 59, wherein the level of endothelial shear stress comprises one of low, medium, or high.

Embodiment 67: The non-transitory computer readable medium of Embodiment 59, wherein the level of endothelial shear stress is determined on a continuous scale.

Embodiment 68: The non-transitory computer readable medium of Embodiment 59, further comprising generating, by the computer system, a graphical representation of the determined level of endothelial shear stress for the particular region of plaque.

Embodiment 69: The non-transitory computer readable medium of Embodiment 59, further comprising generating, by the computer system, a graphical representation of the determined level of endothelial shear stress for the particular region of plaque, the determined risk level of the particular region of plaque, and the predicted progression of the particular region of plaque.

Embodiment 70: The non-transitory computer readable medium of Embodiment 59, wherein the predicted progression of the particular region of plaque comprises one or more of rapid progression, slow progression, or stabilization.

Embodiment 71: The non-transitory computer readable medium of Embodiment 59, wherein the endothelial shear stress below a predetermined threshold is indicative of rapid progression of plaque.

Embodiment 72: The non-transitory computer readable medium of Embodiment 59, wherein the endothelial shear stress above a predetermined threshold is indicative of slow progression of plaque or stabilization of plaque.

Embodiment 73: The non-transitory computer readable medium of Embodiment 59, wherein the plurality of variables are generated by using an artificial intelligence (AI) and/or machine learning (ML) algorithm trained on a plurality of medical images with the plurality of variables pre-identified.

Embodiment 74: The non-transitory computer readable medium of Embodiment 59, wherein the level of endothelial shear stress for the one or more regions of the one or more artery vessels is determined without using computational fluid dynamics.

Embodiment 75: The non-transitory computer readable medium of Embodiment 59, wherein the level of endothelial shear stress for the one or more regions of the one or more artery vessels is determined without using an invasive measurement of the subject.

Embodiment 76: The non-transitory computer readable medium of Embodiment 59, wherein the plurality of variables further comprises one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 77: The non-transitory computer readable medium of Embodiment 59, wherein the one or more arteries comprises one or more coronary arteries.

Embodiment 78: The non-transitory computer readable medium of Embodiment 59, wherein the one or more arteries comprises one or more coronary arteries, carotid, arteries, aorta, upper extremity arteries, or lower extremity arteries.

Embodiment 79: The non-transitory computer readable medium of Embodiment 59, wherein the predicted progression of the particular region of plaque is configured to be used to determine a treatment for arterial disease for the subject.

Embodiment 80: The non-transitory computer readable medium of Embodiment 59, further comprising determining, by the computer system, a risk of arterial disease for the subject based at least in part on the predicted progression of the particular region of plaque.

Embodiment 81: The non-transitory computer readable medium of Embodiment 80, further comprising generating, by the computer system, a graphical representation of the determined risk of arterial disease for the subject.

Embodiment 82: The non-transitory computer readable medium of Embodiment 80, further comprising determining, by the computer system, a proposed treatment for arterial disease for the subject based at least in part on the predicted progression of the particular region of plaque.

Embodiment 83: The non-transitory computer readable medium of Embodiment 82, further comprising generating, by the computer system, a graphical representation of the determined proposed treatment for arterial disease for the subject.

Embodiment 84: The non-transitory computer readable medium of Embodiment 59, further comprising: accessing, by the computer system, a subsequent medical image of the subject obtained after treating the subject for arterial disease with a treatment, the subsequent medical image comprising the one or more artery vessels and the one or more regions of plaque; analyzing, by the computer system, the subsequent medical image of the subject to generate the plurality of variables; generating, by the computer system, a first weighted measure of the plurality of variables generated from the subsequent medical image; determining, by the computer system, a subsequent risk level of the particular region of plaque of the one or more regions of plaque based at least in part on the first weighted measure of the plurality of variables generated from the subsequent medical image; and generating, by the computer system, a graphical representation of a comparison of the subsequent risk level of the particular region of plaque to the predicted progression of the particular region of plaque, wherein the graphical representation of the comparison is configured to be used to track efficacy of the treatment.

Embodiment 85: The non-transitory computer readable medium of Embodiment 59, wherein the medical image of the subject is obtained non-invasively.

Embodiment 86: The non-transitory computer readable medium of Embodiment 59, wherein the medical image is obtained using computed tomography (CT).

Embodiment 87: The non-transitory computer readable medium of Embodiment 59, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Figure 20:
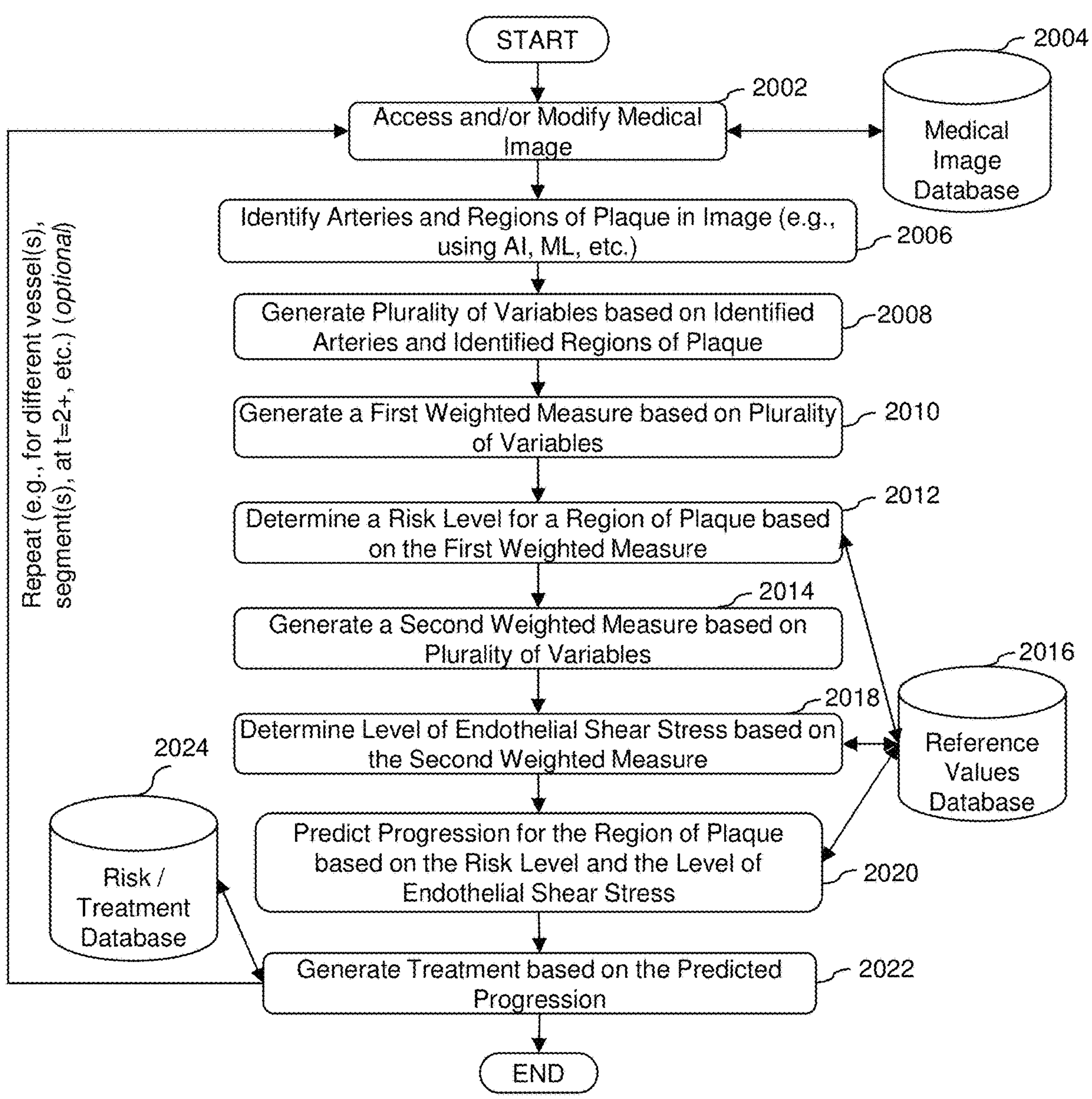
FIG. 20 is a flowchart illustrating an example embodiment(s) of systems, devices, and methods for predicting plaque progression.

FIG. 20 is a flowchart illustrating an example embodiment(s) of systems, devices, and methods for predicting plaque progression. In some embodiments, plaque progression can be predicted based at least in part on a risk level of a region of plaque and/or a level of endothelial shear stress on the region of plaque determined. In some embodiments, risk level of CAD and/or level of endothelial shear stress can be determined based at least in part on a plurality of variables derived from non-invasive medical image analysis.

As illustrated in FIG. 20, in some embodiments, the system can be configured to access and/or modify one or more medical images at block 2002. In some embodiments, the medical image can include one or more arteries, such as coronary, carotid, and/or other arteries of a subject. In some embodiments, the medical image can be stored in and/or retrieved from a medical image database 2004. In some embodiments, the medical image database 2004 can be locally accessible by the system and/or can be located remotely and accessible through a network connection. The medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 2006, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 2006, the system can be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque. In some embodiments, the system is configured to identify one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque.

In some embodiments, at block 108, the system is configured to generate a plurality of variables based on the one or more arteries and regions of plaque identified at block 2106. For example, the plurality of variables can be generated by using an artificial intelligence (AI) and/or machine learning (ML) algorithm trained on a plurality of medical images with the plurality of variables pre-identified. In some embodiments, the plurality of variables can include one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque.

In some embodiments, the system can be further be configured to analyze the region(s) of plaque for one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

In some embodiments, at block 2010, the system can be configured to generate a first weighted measure of the generated plurality of variables. For example, in some embodiments, the system can determine one or more variables of the plurality of variables are more useful in determining a risk level associated with a region of plaque. The system can weight the variables according to their use in determining risk level in an analysis.

In some embodiments, at block 2112, the system can be configured to determine a risk level of a particular region of plaque of the one or more regions of plaque based at least in part on the first weighted measure of the generated plurality of variables. The risk level for the one or more regions of the one or more artery vessels can be determined using a machine learning algorithm trained based at least in part on a plurality of weighted measures of the plurality of variables generated from a plurality of medical images of a plurality of other subjects with known risk levels stored within a reference values database 2016.

In some embodiments, at block 2014, the system can be configured to generate a second weighted measure based on the plurality of variable determined at block 108. For example, in some embodiments, the system can determine one or more variables of the plurality of variables are more useful in determining a level of endothelial shear stress associated with the region of plaque. The system can weight the variables according to their use in determining endothelia shear stress in an analysis.

In some embodiments, at block 2018, the system can be configured to determine a level of endothelial shear stress for one or more regions of one or more artery vessels based at least in part of the second weighted measure of the generated plurality of variables. The level of endothelial shear stress for the one or more regions of the one or more artery vessels can be determined using a machine learning algorithm trained based at least in part on a plurality of weighted measures of the plurality of variables generated from a plurality of medical images of a plurality of other subjects with known levels of endothelial shear stress stored within a reference values database 2016. In some embodiments, the level of endothelial shear stress comprises one of low, medium, or high. In some embodiments, the level of endothelial shear stress is determined on a continuous scale. In some embodiments, the level of endothelial shear stress for the one or more regions of the one or more artery vessels is determined without using computational fluid dynamics. In some embodiments, the level of endothelial shear stress for the one or more regions of the one or more artery vessels is determined without using an invasive measurement of the subject. In some embodiments, the known levels of endothelial shear stress are generated based at least in part on computational fluid dynamics applies to the plurality of medical images of the plurality of other subjects. In some embodiments, the known levels of endothelial shear stress are generated based at least in part on an invasive measure. In some embodiments, the determined level of endothelial shear stress is configured to be used to determine a treatment for arterial disease for the subject.

In some embodiments, at block 2020, the system can be configured to predict progression of the plaque based at least in part on the risk level determined at block 2012 and the level of endothelial shear stress determined at block 2018. In some embodiments, the progression of the particular region of plaque is predicted using a machine learning algorithm trained based at least in part on a plurality of first weighted measures and a plurality of second weighted measures generated from a plurality of medical images of a plurality of other subjects with known progressions of plaque. The plurality of first weighted measures and the plurality of second weighted measures can be stored in the reference values database 2016. In some embodiments, the known progression of plaque are derived from longitudinal analysis of medical images. In some embodiments, the predicted progression of the particular region of plaque comprises one or more of rapid progression, slow progression, or stabilization. In some embodiments, the endothelial shear stress being below a predetermined threshold is indicative of rapid progression of plaque. In some embodiments, the endothelial shear stress being above a predetermined threshold is indicative of slow progression of plaque or stabilization of plaque.

In some embodiments, at block 2022, the system can generate and/or present a proposed treatment for arterial disease for the subject based at least in part on the determined risk of arterial disease for the subject. In some embodiments, the proposed treatment can be determined with reference to one or more reference values can be stored on a treatment reference values database 2024, which can be locally accessible by the system and/or can be located remotely and accessible through a network connection.

In some embodiments, the system can be configured to generate a graphical representation of the analyses results, determined risk of CAD, and/or proposed treatment for the subject. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 2024, which can be locally accessible by the system and/or can be located remotely and accessible through a network connection. In some embodiments, the plaque risk/treatment database 2024 can include reference points or data that relate one or more treatment to cardiovascular disease risk or state determined based on one or more reference plaque analyses values. In some embodiments, a graphical representation can be configured to show the determined level of endothelial shear stress for the one or more regions of the one or more artery vessels.

In some embodiments, the system can be configured to repeat one or more processes described in relation to blocks 2002-2024, for example for one or more other vessels, segment, regions of plaque, different subjects, and/or for the same subject at a different time. As such, in some embodiments, the system can provide for longitudinal disease tracking and/or personalized treatment for a subject.

In some embodiments the system can accesses a subsequent medical image of the subject, the subsequent medical image comprising one or more artery vessels and one or more regions of plaque within the one or more artery vessels, analyze the subsequent medical image of the subject to generate the plurality of variables, determine a subsequent level of endothelial shear stress for one or more regions of one or more artery vessels based at least in part on the plurality of variables generated from analyzing the subsequent medical image, and generate a graphical representation of a comparison of the level of endothelial shear stress and the level of subsequent level of endothelial shear stress for one or more regions of one or more artery vessels, wherein the graphical representation of the comparison is configured to be used to track progression of arterial disease for the subject.

Figure 21:
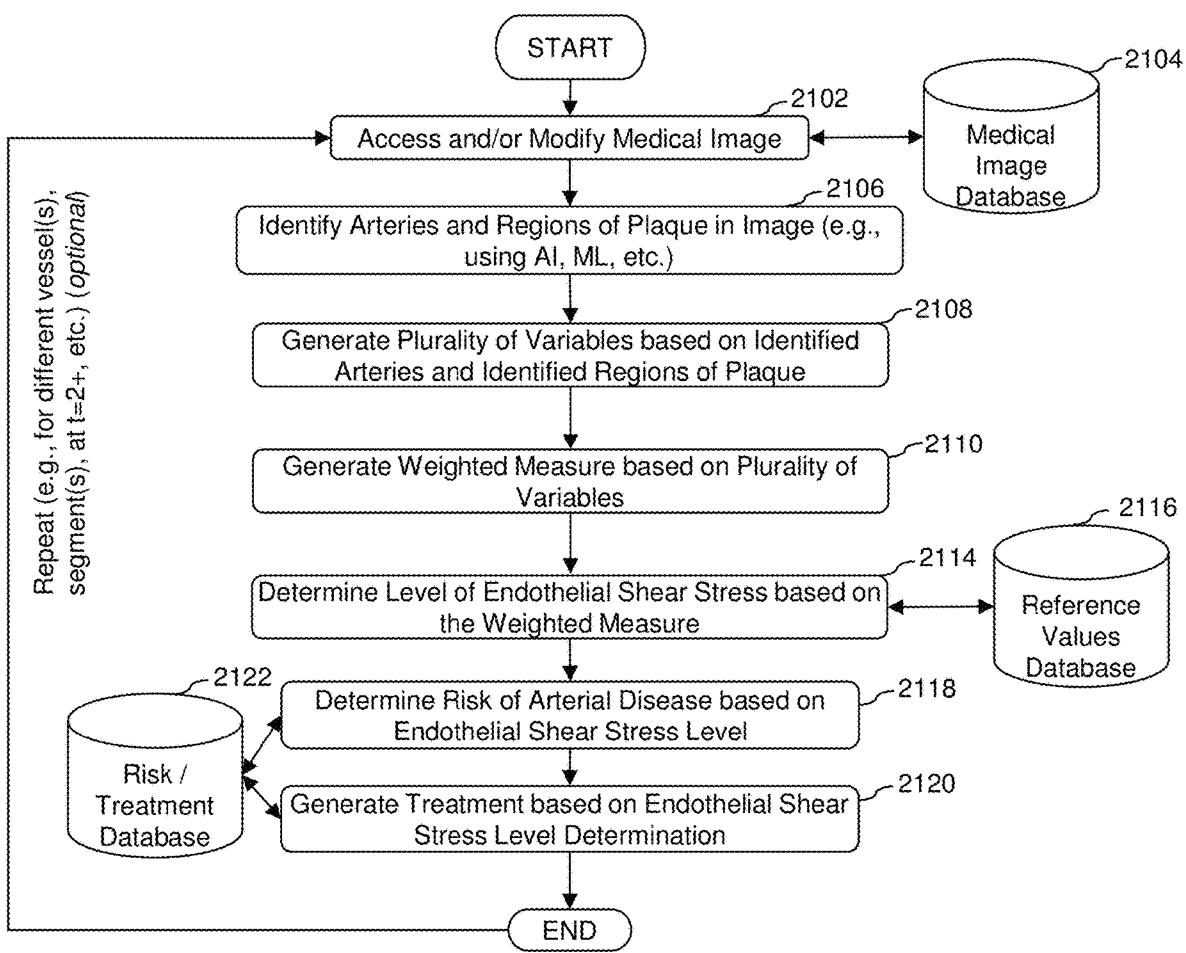
FIG. 21 is a flowchart illustrating an example embodiment(s) of systems, devices, and methods for non-invasive image-based plaque analysis and determination of endothelial shear stress.

FIG. 21 is a flowchart illustrating an example embodiment(s) of systems, devices, and methods for determination of endothelial shear stress. As illustrated in FIG. 21, in some embodiments, the system can be configured to access and/or modify one or more medical images at block 2102. In some embodiments, the medical image can include one or more arteries, such as coronary, carotid, and/or other arteries of a subject. In some embodiments, the medical image can be stored in and/or retrieved from a medical image database 2104. In some embodiments, the medical image database 2104 can be locally accessible by the system and/or can be located remotely and accessible through a network connection. The medical image can comprise an image obtained using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

In some embodiments, the system can be configured to automatically and/or dynamically perform one or more analyses of the medical image as discussed herein. For example, in some embodiments, at block 2106, the system can be configured to identify one or more vessels, such as of one or more arteries. The one or more arteries can include coronary arteries, carotid arteries, aorta, renal artery, lower extremity artery, upper extremity artery, and/or cerebral artery, amongst others. In some embodiments, the system can be configured to utilize one or more AI and/or ML algorithms to automatically and/or dynamically identify one or more arteries or coronary arteries using image processing. For example, in some embodiments, the one or more AI and/or ML algorithms can be trained using a Convolutional Neural Network (CNN) on a set of medical images on which arteries or coronary arteries have been identified, thereby allowing the AI and/or ML algorithm automatically identify arteries or coronary arteries directly from a medical image. In some embodiments, the arteries or coronary arteries are identified by size and/or location.

In some embodiments, at block 2106, the system can further be configured to identify one or more regions of plaque in the medical image. In some embodiments, the system can be configured to utilize one or more AI and/or ML algorithms to automatically and/or dynamically identify one or more regions of plaque using image processing. For example, in some embodiments, the one or more AI and/or ML algorithms can be trained using a Convolutional Neural Network (CNN) on a set of medical images on which regions of plaque have been identified, thereby allowing the AI and/or ML algorithm automatically identify regions of plaque directly from a medical image. In some embodiments, the system is configured to identify vessel and lumen walls and classify everything in between the vessel and lumen walls as plaque. In some embodiments, the system is configured to identify one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque.

In some embodiments, at block 2108, the system is configured to generate a plurality of variables based on the one or more arteries and regions of plaque identified at block 2106. For example, the plurality of variables can be generated by using an artificial intelligence (AI) and/or machine learning (ML) algorithm trained on a plurality of medical images with the plurality of variables pre-identified. In some embodiments, the plurality of variables can include one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque.

In some embodiments, the system can be further be configured to analyze the region(s) of plaque for one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

In some embodiments, at block 2110, the system can be configured to generate a weighted measure of the generated plurality of variables. For example, in some embodiments, the system can determine one or more variables of the plurality of variables are more useful in determining endothelial shear stress. The system can weight the variables according to their use in determining endothelial shear stress to use in an analysis.

In some embodiments, at block 2114, the system can be used to determine a level of endothelial shear stress for one or more regions of one or more artery vessels based at least in part of the weighted measure of the generated plurality of variables. In some embodiments, the level of endothelial shear stress for the one or more regions of the one or more artery vessels is determined using a machine learning algorithm trained based at least in part on a plurality of weighted measures of the plurality of variables generated from a plurality of medical images of a plurality of other subjects with known levels of endothelial shear stress stored within a reference values database 2116. In some embodiments, the level of endothelial shear stress comprises one of low, medium, or high. In some embodiments, the level of endothelial shear stress is determined on a continuous scale. In some embodiments, the level of endothelial shear stress for the one or more regions of the one or more artery vessels is determined without using computational fluid dynamics. In some embodiments, the level of endothelial shear stress for the one or more regions of the one or more artery vessels is determined without using an invasive measurement of the subject. In some embodiments, the known levels of endothelial shear stress are generated based at least in part on computational fluid dynamics applies to the plurality of medical images of the plurality of other subjects. In some embodiments, the known levels of endothelial shear stress are generated based at least in part on an invasive measure.

In some embodiments, the determined level of endothelial shear stress is configured to be used to determine a treatment for arterial disease for the subject.

In some embodiments, at block 2118, the system can be configured to use the determined level of endothelial shear stress to determine a risk of arterial disease for the subject. In some embodiments, the endothelial shear stress below a predetermined threshold is indicative of high risk of arterial disease. In some embodiments, the endothelial shear stress above a predetermined threshold is indicative of low risk of arterial disease. In some embodiments, at block 2118, the system can be configured to determine a risk of CAD or MI based at least in part endothelial shear stress levels described herein, for example in relation to one or more of blocks 2102-2118. In some embodiments, the system can be configured to utilize some or all of the plaque analyses results. In some embodiments, the system can be configured to generate a weighted measure of some or all of the plaque analyses described herein in determining a risk of CAD. In some embodiments, the risk can be determined with reference to one or more reference values can be stored on a risk reference values database 2122, which can be locally accessible by the system and/or can be located remotely and accessible through a network connection.

In some embodiments, at block 2120, the system can generate and/or present a proposed treatment for arterial disease for the subject based at least in part on the determined risk of arterial disease for the subject. In some embodiments, the proposed treatment can be determined with reference to one or more reference values can be stored on a treatment reference values database 2122, which can be locally accessible by the system and/or can be located remotely and accessible through a network connection.

In some embodiments, the system can be configured to generate a graphical representation of the analyses results, determined risk of CAD, and/or proposed treatment for the subject. In some embodiments, the analyses results can be displayed on a vessel, lesion, and/or subject basis. In some embodiments, the proposed treatment can include, for example, medical treatment such as statins, interventional treatment such as stent implantation, and/or lifestyle treatment such as exercise or diet. In some embodiments, in determining the risk or state of cardiovascular disease or health and/or treatment, the system can access a plaque risk/treatment database 2122, which can be locally accessible by the system and/or can be located remotely and accessible through a network connection. In some embodiments, the plaque risk/treatment database 2122 can include reference points or data that relate one or more treatment to cardiovascular disease risk or state determined based on one or more reference plaque analyses values. In some embodiments a graphical representation can be configured to show the determined level of endothelial shear stress for the one or more regions of the one or more artery vessels.

In some embodiments, the system can be configured to repeat one or more processes described in relation to blocks 2202-2122, for example for one or more other vessels, segment, regions of plaque, different subjects, and/or for the same subject at a different time. As such, in some embodiments, the system can provide for longitudinal disease tracking and/or personalized treatment for a subject.

In some embodiments the system can accesses a subsequent medical image of the subject, the subsequent medical image comprising one or more artery vessels and one or more regions of plaque within the one or more artery vessels, analyze the subsequent medical image of the subject to generate the plurality of variables, determine a subsequent level of endothelial shear stress for one or more regions of one or more artery vessels based at least in part on the plurality of variables generated from analyzing the subsequent medical image, and generate a graphical representation of a comparison of the level of endothelial shear stress and the level of subsequent level of endothelial shear stress for one or more regions of one or more artery vessels, wherein the graphical representation of the comparison is configured to be used to track progression of arterial disease for the subject.

The computer system 902 of FIG. 9, and in some instances, the analysis and/or risk assessment module 940, can be configured to carry out the functions, methods, acts, and/or processes for multivariable image-based analysis of endothelial shear stress described herein, such as those described above with reference to FIGS. 20-21.

The following are non-limiting examples of certain embodiments of systems and methods for multivariable image-based analysis of endothelial shear stress. Other embodiments may include one or more other features, or different features, that are discussed herein.

Embodiment 1: A computer-implemented method of determining a level of endothelial shear stress based at least in part on a plurality of variables derived from non-invasive medical image analysis, the method comprising: accessing, by a computer system, a medical image of a subject, the medical image comprising a portion of one or more arteries; analyzing, by the computer system, the medical image of the subject to identify one or more artery vessels and one or more regions of plaque within the one or more artery vessels; analyzing, by the computer system, the one or more artery vessels and the one or more regions of plaque to generate a plurality of variables, the plurality of variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque; generating, by the computer system, a weighted measure of the generated plurality of variables; determining, by the computer system, a level of endothelial shear stress for one or more regions of one or more artery vessels based at least in part of the weighted measure of the generated plurality of variables, wherein the level of endothelial shear stress for the one or more regions of the one or more artery vessels is determined using a machine learning algorithm trained based at least in part on a plurality of weighted measures of the plurality of variables generated from a plurality of medical images of a plurality of other subjects with known levels of endothelial shear stress, wherein the determined level of endothelial shear stress is configured to be used to determine a risk of arterial disease for the subject, wherein the computer system comprises a computer processor and an electronic storage medium.

Embodiment 2: The computer-implemented method of Embodiment 1, wherein the level of endothelial shear stress comprises one of low, medium, or high.

Embodiment 3: The computer-implemented method of Embodiment 1, wherein the level of endothelial shear stress is determined on a continuous scale.

Embodiment 4: The computer-implemented method of Embodiment 1, further comprising generating, by the computer system, a graphical representation of the determined level of endothelial shear stress for the one or more regions of the one or more artery vessels.

Embodiment 5: The computer-implemented method of Embodiment 1, wherein the endothelial shear stress below a predetermined threshold is indicative of high risk of arterial disease.

Embodiment 6: The computer-implemented method of Embodiment 1, wherein the endothelial shear stress above a predetermined threshold is indicative of low risk of arterial disease.

Embodiment 7: The computer-implemented method of Embodiment 1, wherein the plurality of variables are generated by using an artificial intelligence (AI) and/or machine learning (ML) algorithm trained on a plurality of medical images with the plurality of variables pre-identified.

Embodiment 8: The computer-implemented method of Embodiment 1, wherein the level of endothelial shear stress for the one or more regions of the one or more artery vessels is determined without using computational fluid dynamics.

Embodiment 9: The computer-implemented method of Embodiment 1, wherein the level of endothelial shear stress for the one or more regions of the one or more artery vessels is determined without using an invasive measurement of the subject.

Embodiment 10: The computer-implemented method of Embodiment 1, wherein the known levels of endothelial shear stress are generated based at least in part on computational fluid dynamics applies to the plurality of medical images of the plurality of other subjects.

Embodiment 11: The computer-implemented method of Embodiment 1, wherein the known levels of endothelial shear stress are generated based at least in part on an invasive measure.

Embodiment 12: The computer-implemented method of Embodiment 1, wherein the plurality of variables further comprises one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 13: The computer-implemented method of Embodiment 1, wherein the one or more arteries comprises one or more coronary arteries.

Embodiment 14: The computer-implemented method of Embodiment 1, wherein the one or more arteries comprises one or more coronary arteries, carotid, arteries, aorta, upper extremity arteries, or lower extremity arteries.

Embodiment 15: The computer-implemented method of Embodiment 1, wherein the determined level of endothelial shear stress is configured to be used to determine a treatment for arterial disease for the subject.

Embodiment 16: The computer-implemented method of Embodiment 1, further comprising determining, by the computer system, the risk of arterial disease for the subject based at least in part on the determined level of endothelial shear stress.

Embodiment 17: The computer-implemented method of Embodiment 1, further comprising generating, by the computer system, a graphical representation of the determined risk of arterial disease for the subject.

Embodiment 18: The computer-implemented method of Embodiment 1, further comprising determining, by the computer system, a proposed treatment for arterial disease for the subject based at least in part on the determined risk of arterial disease for the subject.

Embodiment 19: The computer-implemented method of Embodiment 1, further comprising generating, by the computer system, a graphical representation of the determined proposed treatment for arterial disease for the subject.

Embodiment 20: The computer-implemented method of Embodiment 1, further comprising: accessing, by the computer system, a subsequent medical image of the subject, the subsequent medical image comprising one or more artery vessels and one or more regions of plaque within the one or more artery vessels; analyzing, by the computer system, the subsequent medical image of the subject to generate the plurality of variables; determining, by the computer system, a subsequent level of endothelial shear stress for one or more regions of one or more artery vessels based at least in part on the plurality of variables generated from analyzing the subsequent medical image; and generating, by the computer system, a graphical representation of a comparison of the level of endothelial shear stress and the level of subsequent level of endothelial shear stress for one or more regions of one or more artery vessels, wherein the graphical representation of the comparison is configured to be used to track progression of arterial disease for the subject.

Embodiment 21: The computer-implemented method of Embodiment 1, wherein the medical image of the subject is obtained non-invasively.

Embodiment 22: The computer-implemented method of Embodiment 1, wherein the medical image is obtained using computed tomography (CT).

Embodiment 23: The computer-implemented method of Embodiment 1, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 24: A system for determining a level of endothelial shear stress based at least in part on a plurality of variables derived from non-invasive medical image analysis, the system comprising: a non-transitory computer storage medium configured to at least store computer executable instructions; and one or more computer hardware processors in communication with the first non-transitory computer storage medium, the one or more computer hardware processors configured to execute the computer-executable instructions to at least: access a medical image of a subject, the medical image comprising a portion of one or more arteries; analyze the medical image of the subject to identify one or more artery vessels and one or more regions of plaque within the one or more artery vessels; analyze the one or more artery vessels and the one or more regions of plaque to generate a plurality of variables, the plurality of variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque; generate a weighted measure of the generated plurality of variables; determine a level of endothelial shear stress for one or more regions of one or more artery vessels based at least in part of the weighted measure of the generated plurality of variables, wherein the level of endothelial shear stress for the one or more regions of the one or more artery vessels is determined using a machine learning algorithm trained based at least in part on a plurality of weighted measures of the plurality of variables generated from a plurality of medical images of a plurality of other subjects with known levels of endothelial shear stress, wherein the determined level of endothelial shear stress is configured to be used to determine a risk of arterial disease for the subject.

Embodiment 25: The system of Embodiment 24, wherein the level of endothelial shear stress comprises one of low, medium, or high.

Embodiment 26: The system of Embodiment 24, wherein the level of endothelial shear stress is determined on a continuous scale.

Embodiment 27: The system of Embodiment 24, wherein the system is further configured to generate a graphical representation of the determined level of endothelial shear stress for the one or more regions of the one or more artery vessels.

Embodiment 28: The system of Embodiment 24, wherein the endothelial shear stress below a predetermined threshold is indicative of high risk of arterial disease.

Embodiment 29: The system of Embodiment 24, wherein the endothelial shear stress above a predetermined threshold is indicative of low risk of arterial disease.

Embodiment 30: The system of Embodiment 24, wherein the plurality of variables are generated by using an artificial intelligence (AI) and/or machine learning (ML) algorithm trained on a plurality of medical images with the plurality of variables pre-identified.

Embodiment 31: The system of Embodiment 24, wherein the level of endothelial shear stress for the one or more regions of the one or more artery vessels is determined without using computational fluid dynamics.

Embodiment 32: The system of Embodiment 24, wherein the level of endothelial shear stress for the one or more regions of the one or more artery vessels is determined without using an invasive measurement of the subject.

Embodiment 33: The system of Embodiment 24, wherein the known levels of endothelial shear stress are generated based at least in part on computational fluid dynamics applies to the plurality of medical images of the plurality of other subjects.

Embodiment 34: The system of Embodiment 24, wherein the known levels of endothelial shear stress are generated based at least in part on an invasive measure.

Embodiment 35: The system of Embodiment 24, wherein the plurality of variables further comprises one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 36: The system of Embodiment 24, wherein the one or more arteries comprises one or more coronary arteries.

Embodiment 37: The system of Embodiment 24, wherein the one or more arteries comprises one or more coronary arteries, carotid, arteries, aorta, upper extremity arteries, or lower extremity arteries.

Embodiment 38: The system of Embodiment 24, wherein the determined level of endothelial shear stress is configured to be used to determine a treatment for arterial disease for the subject.

Embodiment 39: The system of Embodiment 24, wherein the system is further configured to determine risk of arterial disease for the subject based at least in part on the determined level of endothelial shear stress.

Embodiment 40: The system of Embodiment 39, wherein the system is further configured to generate a graphical representation of the determined risk of arterial disease for the subject.

Embodiment 41: The system of Embodiment 39, wherein the system is further configured to determine a proposed treatment for arterial disease for the subject based at least in part on the determined risk of arterial disease for the subject.

Embodiment 42: The system of Embodiment 41, wherein the system is further configured to generate a graphical representation of the determined proposed treatment for arterial disease for the subject.

Embodiment 43: The system of Embodiment 24, wherein the system is further configured to: access a subsequent medical image of the subject, the subsequent medical image comprising one or more artery vessels and one or more regions of plaque within the one or more artery vessels; analyze the subsequent medical image of the subject to generate the plurality of variables; determine a subsequent level of endothelial shear stress for one or more regions of one or more artery vessels based at least in part on the plurality of variables generated from analyzing the subsequent medical image; and generate a graphical representation of a comparison of the level of endothelial shear stress and the level of subsequent level of endothelial shear stress for one or more regions of one or more artery vessels, wherein the graphical representation of the comparison is configured to be used to track progression of arterial disease for the subject.

Embodiment 44: The system of Embodiment 24, wherein the medical image of the subject is obtained non-invasively.

Embodiment 45: The system of Embodiment 24, wherein the medical image is obtained using computed tomography (CT).

Embodiment 46: The system of Embodiment 24, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 47: A non-transitory computer readable medium configured for determining a level of endothelial shear stress based at least in part on a plurality of variables derived from non-invasive medical image analysis, the computer readable medium having program instructions for causing a hardware processor to perform a method of: accessing, by a computer system, a medical image of a subject, the medical image comprising a portion of one or more arteries; analyzing, by the computer system, the medical image of the subject to identify one or more artery vessels and one or more regions of plaque within the one or more artery vessels; analyzing, by the computer system, the one or more artery vessels and the one or more regions of plaque to generate a plurality of variables, the plurality of variables comprising one or more of lesion length, remodeling index, plaque slice percentage, stenosis area percentage, presence of low-density plaque, stenosis diameter percentage, presence of positive remodeling, reference diameter after stenosis, reference diameter before stenosis, vessel length, lumen volume, number of chronic total occlusion (CTO), vessel volume, number of stenosis, total plaque volume, number of mild stenosis, low-density plaque volume, plaque morphology, embeddedness of a low density non-calcified plaque by non-calcified plaque or calcified plaque, distance between plaque and lumen wall or vessel wall, or eccentricity of plaque; generating, by the computer system, a weighted measure of the generated plurality of variables; determining, by the computer system, a level of endothelial shear stress for one or more regions of one or more artery vessels based at least in part of the weighted measure of the generated plurality of variables, wherein the level of endothelial shear stress for the one or more regions of the one or more artery vessels is determined using a machine learning algorithm trained based at least in part on a plurality of weighted measures of the plurality of variables generated from a plurality of medical images of a plurality of other subjects with known levels of endothelial shear stress, wherein the determined level of endothelial shear stress is configured to be used to determine a risk of arterial disease for the subject, wherein the computer system comprises a computer processor and an electronic storage medium.

Embodiment 48: The non-transitory computer readable medium of Embodiment 47, wherein the level of endothelial shear stress comprises one of low, medium, or high.

Embodiment 49: The non-transitory computer readable medium of Embodiment 47, wherein the level of endothelial shear stress is determined on a continuous scale.

Embodiment 50: The non-transitory computer readable medium of Embodiment 47, further comprising generating, by the computer system, a graphical representation of the determined level of endothelial shear stress for the one or more regions of the one or more artery vessels.

Embodiment 51: The non-transitory computer readable medium of Embodiment 47, wherein the endothelial shear stress below a predetermined threshold is indicative of high risk of arterial disease.

Embodiment 52: The non-transitory computer readable medium of Embodiment 47, wherein the endothelial shear stress above a predetermined threshold is indicative of low risk of arterial disease.

Embodiment 53: The non-transitory computer readable medium of Embodiment 47, wherein the plurality of variables are generated by using an artificial intelligence (AI) and/or machine learning (ML) algorithm trained on a plurality of medical images with the plurality of variables pre-identified.

Embodiment 54: The non-transitory computer readable medium of Embodiment 47, wherein the level of endothelial shear stress for the one or more regions of the one or more artery vessels is determined without using computational fluid dynamics.

Embodiment 55: The non-transitory computer readable medium of Embodiment 47, wherein the level of endothelial shear stress for the one or more regions of the one or more artery vessels is determined without using an invasive measurement of the subject.

Embodiment 56: The non-transitory computer readable medium of Embodiment 47, wherein the known levels of endothelial shear stress are generated based at least in part on computational fluid dynamics applies to the plurality of medical images of the plurality of other subjects.

Embodiment 57: The non-transitory computer readable medium of Embodiment 47, wherein the known levels of endothelial shear stress are generated based at least in part on an invasive measure.

Embodiment 58: The non-transitory computer readable medium of Embodiment 47, wherein the plurality of variables further comprises one or more of percent atheroma volume of total plaque, percent atheroma volume of low-density non-calcified plaque, percent atheroma volume of non-calcified plaque, percent atheroma volume, low-density non-calcified plaque volume, percent atheroma volume of total calcified plaque, non-calcified plaque volume, total calcified plaque volume, percent atheroma volume of total non-calcified plaque, percent atheroma volume of low-density calcified plaque, percent atheroma volume of high-density calcified plaque, total non-calcified plaque volume, low-density calcified plaque volume, percent atheroma volume of medium-density calcified plaque, high-density calcified plaque volume, medium-density calcified plaque volume, number of high-risk plaque regions, number of segments with calcified plaque, number of segments with non-calcified plaque, plaque area, plaque burden, necrotic core percentage, necrotic core volume, fatty fibrous volume, fatty fibrous percentage, dense calcium percentage, low-density calcium percentage, medium-density calcified percentage, high-density calcified percentage, presence of two-feature positive plaques, number of two-feature positive plaques, segment length, severity of stenosis, minimum lumen diameter, maximum lumen diameter, mean lumen diameter, number of moderate stenosis, number of zero stenosis, number of severe stenosis, presence of high-risk anatomy, number of severe stenosis excluding CTO, vessel area, lumen area, diameter stenosis percentage, presence of ischemia, number of stents, reference lumen diameter before stenosis, perivascular fat attenuation, or reference lumen diameter after stenosis.

Embodiment 59: The non-transitory computer readable medium of Embodiment 47, wherein the one or more arteries comprises one or more coronary arteries.

Embodiment 60: The non-transitory computer readable medium of Embodiment 47, wherein the one or more arteries comprises one or more coronary arteries, carotid, arteries, aorta, upper extremity arteries, or lower extremity arteries.

Embodiment 61: The non-transitory computer readable medium of Embodiment 47, wherein the determined level of endothelial shear stress is configured to be used to determine a treatment for arterial disease for the subject.

Embodiment 62: The non-transitory computer readable medium of Embodiment 47, further comprising determining, by the computer system, the risk of arterial disease for the subject based at least in part on the determined level of endothelial shear stress.

Embodiment 63: The non-transitory computer readable medium of Embodiment 62, further comprising generating, by the computer system, a graphical representation of the determined risk of arterial disease for the subject.

Embodiment 64: The non-transitory computer readable medium of Embodiment 62, further comprising determining, by the computer system, a proposed treatment for arterial disease for the subject based at least in part on the determined risk of arterial disease for the subject.

Embodiment 65: The non-transitory computer readable medium of Embodiment 64, further comprising generating, by the computer system, a graphical representation of the determined proposed treatment for arterial disease for the subject.

Embodiment 66: The non-transitory computer readable medium of Embodiment 47, further comprising: access a subsequent medical image of the subject, the subsequent medical image comprising one or more artery vessels and one or more regions of plaque within the one or more artery vessels; analyze the subsequent medical image of the subject to generate the plurality of variables; determine a subsequent level of endothelial shear stress for one or more regions of one or more artery vessels based at least in part on the plurality of variables generated from analyzing the subsequent medical image; and generate a graphical representation of a comparison of the level of endothelial shear stress and the level of subsequent level of endothelial shear stress for one or more regions of one or more artery vessels, wherein the graphical representation of the comparison is configured to be used to track progression of arterial disease for the subject.

Embodiment 67: The non-transitory computer readable medium of Embodiment 47, wherein the medical image of the subject is obtained non-invasively.

Embodiment 68: The non-transitory computer readable medium of Embodiment 47, wherein the medical image is obtained using computed tomography (CT).

Embodiment 69: The non-transitory computer readable medium of Embodiment 47, wherein the medical image is obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Image-Based Analysis of Aortic Stenosis and/or Risk Determination

Disclosed herein are systems, devices, and methods for image-based analysis of aortic stenosis and/or risk determination. In particular, in some embodiments, the systems, devices, and methods described herein are related to the determination of aortic stenosis for a subject based at least in part on one or more plaque parameters and one or more aortic leaflet parameters derived from medical image analysis. In some embodiments, the systems, devices, and methods described herein are configured to identify one or more aortic leaflets of an aortic valve and identify one or more regions of plaque within the leaflet(s). In some embodiments, the systems, devices, and methods described herein are further configured to generate aortic leaflet parameter(s) comprising one or more of a gap between the one or more aortic leaflets or gradient of a boundary of the one or more aortic leaflets and generate a preliminary risk assessment of aortic stenosis. In some embodiments, if the preliminary risk assessment of aortic stenosis is above a predetermined threshold, the systems, devices, and methods described herein are configured to analyze aortic leaflet(s) in a second medical image and determine a gap between the one or more aortic leaflets at a second point in time. In some embodiments, the systems, devices, and methods described herein are configured to generate a risk level of aortic stenosis based at least on comparing the determined gap between the one or more aortic leaflets at the second point in time to a plurality of reference values of gaps between one or more aortic leaflets generated from a plurality of other subjects with varying levels of aortic stenosis.

As discussed herein, disclosed herein are systems, methods, and devices for image-based analysis of aortic stenosis and/or risk determination. The aortic valve is one of the four valves that control blood flow in the heart. The aortic valve is made up of three cusps, called leaflets, that open and close to allow blood to flow between the aorta and left ventricle. Over time, plaque can build up on the leaflets and cause aortic valve stenosis. When this occurs, the gap between the leaflets in the "open" state is reduced, obstructing blood flow.

Echocardiography is the typical imaging test ordered by physicians for checking aortic stenosis in patients. Although non-invasive, echocardiographs may be more time-consuming and complicated than other forms of non-invasive imaging, such as a CT scanning. It would be advantageous to provide an initial, non-invasive analysis of aortic stenosis before ordering additional scans.

Because the aortic valve exists in an open and closed state, analysis of aortic stenosis may require images of the aortic valve at two different points in time. In some embodiments, the systems, devices, and methods described herein relate to analyzing a first CT scan of an aortic valve in a "closed state," in which the plaque on the leaflets may be quantified. In some embodiments, the systems, devices, and methods may be configured to determine, from the results of the first CT scan, whether an additional CT scan is needed of the aortic valve in an "open state" to analyze the gap.

Figure 22A:
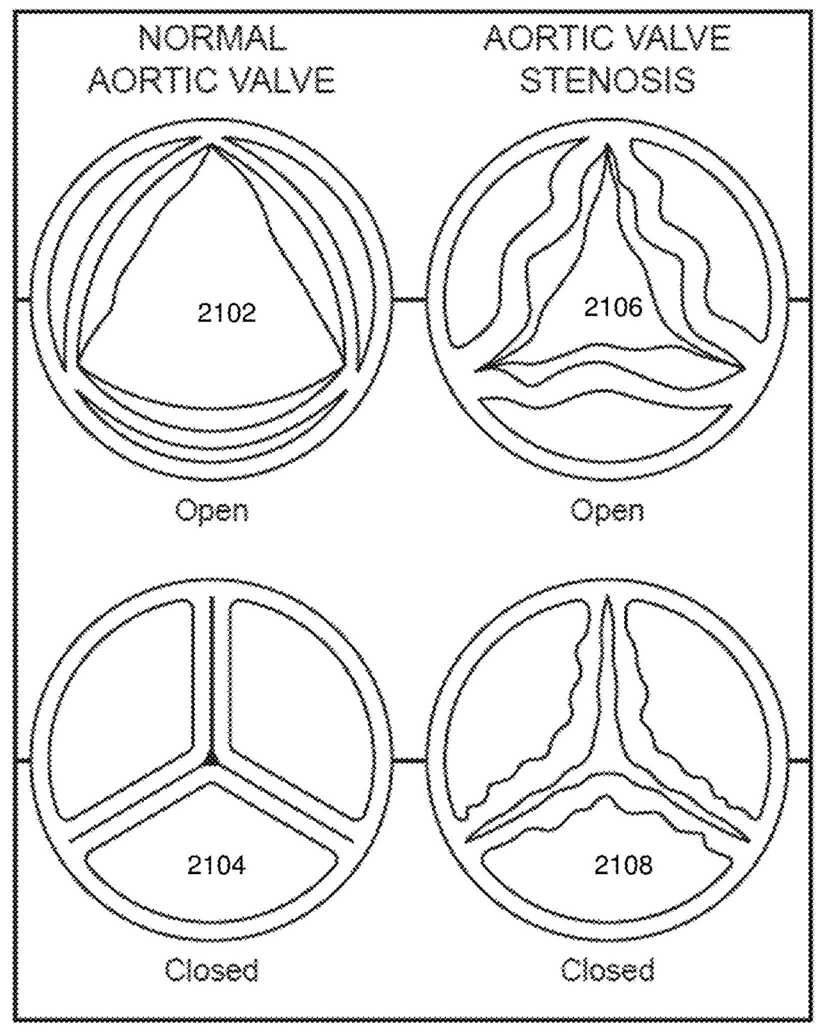
FIG. 22A illustrates sample diagrams of a normal aortic valve in open and closed configurations and a stenotic aortic value in open and closed configurations.

FIG. 22A illustrates sample diagrams of a normal aortic valve in open and closed configurations and a stenotic aortic value in open and closed configurations. As illustrated in FIG. 22A, a normal aortic valve in an open configuration is shown as 2102. Additionally, a normal aortic valve in a closed configuration is shown as 2104.

As illustrated, the blood flow in the open and closed normal aortic valves 2102 and 2104 is not obstructed. As illustrated in FIG. 22A, a stenotic aortic valve in an open configuration is shown as 2106. Additionally, a stenotic aortic valve in a closed configuration is shown as 2108. As illustrated, leaflets of the stenotic aortic valve include regions of plaque. It is noted that the gap through which the blood may flow through the stenotic aortic valve is smaller than the gap of normal aortic valve 2102.

Figure 22B:
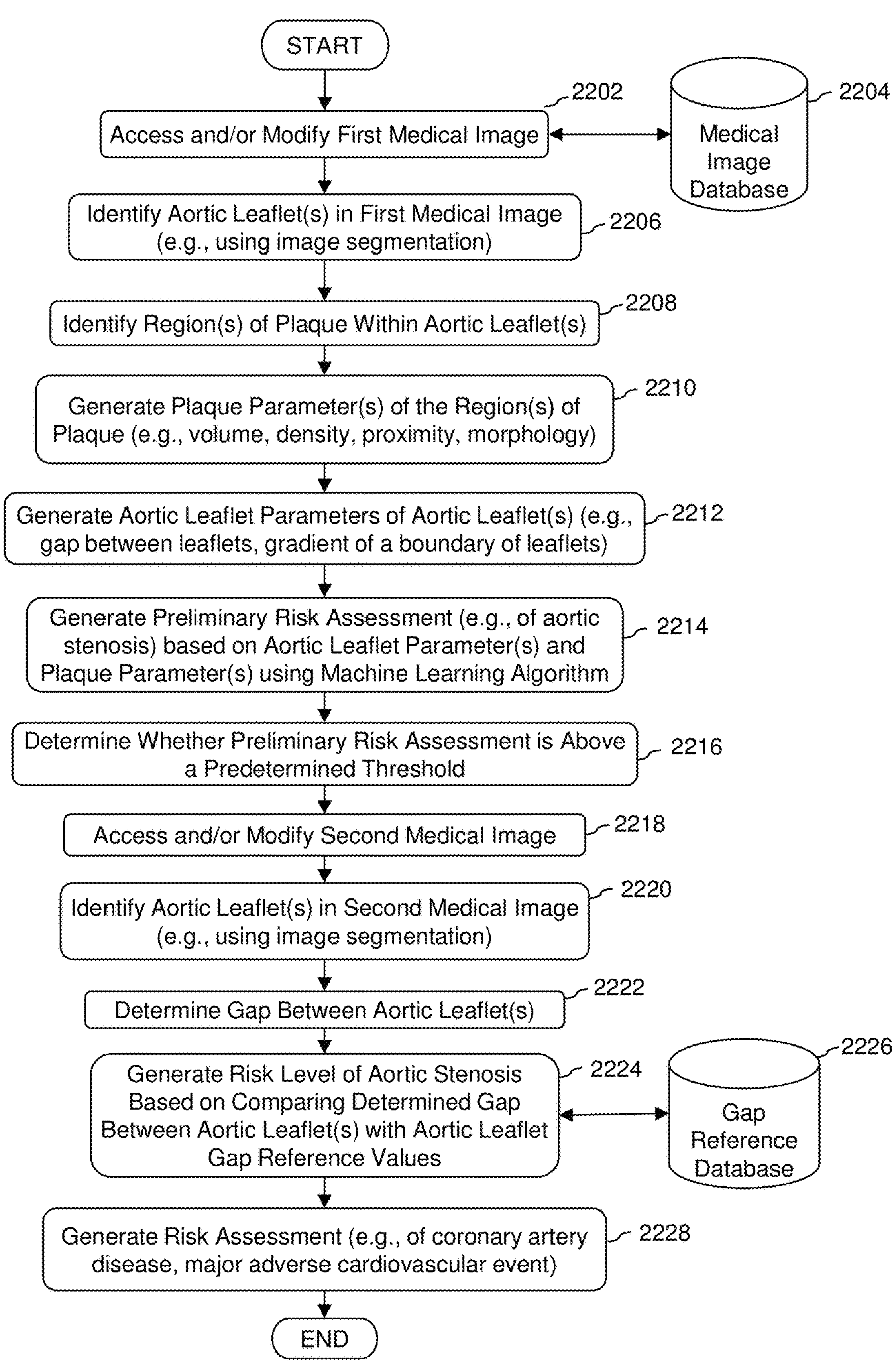
FIG. 22B is a flowchart illustrating an example embodiment(s) of systems, devices, and methods for image-based analysis of aortic stenosis and/or risk determination.

FIG. 22B is a flowchart illustrating an example embodiment(s) of systems, devices, and methods for image-based analysis of aortic stenosis and/or risk determination. As illustrated in FIG. 22B, in some embodiments, at block 2202, the system can be configured to access a first medical image of a subject obtained at a first point in time, the first medical image comprising a portion of an aortic valve of the subject at the first point in time.

In some embodiments, the medical image can be stored in a medical image database 2204. In some embodiments, the medical image database 2204 can be locally accessible by the system and/or can be located remotely and accessible through a network connection.

In some embodiments, the first medical image is obtained from a coronary computed tomography angiography (CCTA). Other medical imaging types, as described throughout this application, can also be used. For example, in some embodiments, the first medical image is obtained from computed tomography (CT). In some embodiments, the first medical image is obtained from an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

In some embodiments, the first point in time comprises a point in a cardiac cycle when a CCTA is obtained. In some embodiments, the first point in time comprises a point in a cardiac cycle when coronary arteries are stable.

In some embodiments, at block 2206, the system can be configured to analyze the first medical image of the subject to identify one or more aortic leaflets of the aortic valve of the subject using image segmentation. In some embodiments, the aortic leaflets are in a closed configuration at the first point in time. AI or ML algorithms can be trained and used for this purpose in some embodiments.

In some embodiments, at block 2208, the system can be configured to identify one or more regions of plaque within the one or more aortic leaflets.

In some embodiments, at block 2210, the system can be configured to generate one or more plaque parameters of the one or more regions of plaque identified within the one or more aortic leaflets, the one or more plaque parameters comprising one or more of total plaque volume, low-density non-calcified plaque volume, non-calcified plaque volume, calcified plaque volume, proximity of plaque to the one or more aortic leaflets, or plaque morphology.

In some embodiments, one or more of low-density non-calcified plaque volume, non-calcified plaque volume, or calcified plaque volume is determined based at least in part on analyzing density of one or more pixels corresponding to the one or more regions of plaque in the first medical image. In some embodiments, the density comprises material density. In some embodiments, the density comprises radiodensity.

In some embodiments, low density non-calcified plaque corresponds to one or more pixels with a radiodensity value between about −189 and about 30 Hounsfield units (HU). In some embodiments, the Hounsfield units in this range are, or between, about −189 HU, about −180 HU, about −170 HU, about −160 HU, about −150 HU, about −140 HU, about −130 HU, about −120 HU, about −110 HU, about −100 HU, about −90 HU, about −80 HU, about −70 HU, about −60 HU, about −50 HU, about −40 HU, about −30, about −20, about −10, about 0, about 10, about 20, and about 30 HU. In some embodiments, non-calcified plaque corresponds to one or more pixels with a radiodensity value between about 190 and about 350 Hounsfield units. In some embodiments, the Hounsfield units in this range are, or between, about 190 HU, about 200 HU, about 210 HU, about 220 HU, about 230 HU, about 230 HU, about 240 HU, about 250 HU, about 260 HU, about 270 HU, about 280 HU, 290 HU, 300 HU, about 310 HU, about 320 HU, about 330 HU, about 340 HU, and about 350 HU.

In some embodiments, calcified plaque corresponds to one or more pixels with a radiodensity value between about 351 and 2500 Hounsfield units. In some embodiments, the Hounsfield units in this range are, or between, two of about 351 HU, about 400 HU, about 500 HU, about 600 HU, about 700 HU, about 800 HU, about 900 HU, about 1000 HU, about 1100 HU, about 1200 HU, about 1300 HU, about 1400 HU, about 1500 HU, about 1600 HU, about 1700 HU, about 1800 HU, about 1900 HU, about 2000 HU, about 2100 HU, about 2200 HU, about 2300 HU, about 2400 HU, and about 2500 HU.

In some embodiments, the plaque morphology is determined as one or more of a crescent, round, lobular, or bean shape. In some embodiments, the plaque morphology comprising a round or bean shape is indicative of unstable plaque.

In some embodiments, at block 2212, the system can be configured to generate one or more aortic leaflet parameters of the one or more aortic leaflets, the one or more aortic leaflet parameters comprising one or more of a gap between the one or more aortic leaflets or gradient of a boundary of the one or more aortic leaflets.

In some embodiments, at block 2214, the system can be configured to generate a preliminary risk assessment of aortic stenosis of the subject based at least in part on the one or more plaque parameters and the one or more aortic leaflet parameters using a machine learning algorithm, the machine learning algorithm trained on the one or more plaque parameters and the one or more aortic leaflet parameters generated from a plurality of other subjects with known levels of aortic stenosis.

In some embodiments, at block 2216, the system can be configured to determine whether the preliminary risk assessment of aortic stenosis is above a predetermined threshold is indicative of further assessment of aortic stenosis for the subject. In some embodiments, further assessment t of aortic stenosis for the subject comprises an echocardiography.

In some embodiments, at block 2218, the system can be configured to access a second medical image of the subject obtained at a second point in time when the preliminary risk assessment of aortic stenosis is above the predetermined threshold, the second medical image comprising a portion of the aortic valve of the subject at the second point in time.

In some embodiments, the second medical image can be stored in medical image database 2204. In some embodiments, the medical image database 2204 can be locally accessible by the system and/or can be located remotely and accessible through a network connection.

In some embodiments, the second medical image is obtained from echocardiography. In some embodiments, the second medical image is obtained from an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

In some embodiments, at block 2220, the system can be configured to analyze the second medical image of the subject to identify one or more aortic leaflets of the aortic valve of the subject using image segmentation. In some embodiments, the aortic leaflets are in an open configuration at the second point in time. In some embodiments, the first point in time and the second point in time comprise different points in a cardiac cycle of the subject.

In some embodiments, at block 2222, the system can be configured to determine a gap between the one or more aortic leaflets at the second point in time, wherein the gap between the one or more aortic leaflets at the second point in time being below a predetermined threshold is indicative of aortic stenosis.

In some embodiments, at block 2224, the system can be configured to generate a risk level of aortic stenosis for the subject based at least on comparing the determined gap between the one or more aortic leaflets at the second point in time to a plurality of reference values of gaps between one or more aortic leaflets generated from a plurality of other subjects with varying levels of aortic stenosis. Reference values of gaps between one or more aortic leaflets generated from a plurality of other subjects with varying levels of aortic stenosis may be stored in gap reference database 2226.

In some embodiments, at block 2228, the system can be configured to generate an assessment of risk of coronary artery disease (CAD) or major adverse cardiovascular event (MACE) of the subject based at least in part on the gap between the one or more aortic leaflets at the second point in time.

In some embodiments, the system can be configured to determine a need for aortic valve replacement for the subject based at least in part on the determined gap between the one or more aortic leaflets at the second point in time.

In some embodiments, the system can be configured to generate a risk level of aortic stenosis for the subject based at least on comparing the preliminary risk assessment of aortic stenosis of the subject to a plurality of reference values of preliminary risk assessments of aortic stenosis generated from a plurality of other subjects with varying levels of aortic stenosis.

The computer system 902 of FIG. 9, and in some instances, the analysis and/or risk assessment module 940, can be configured to carry out the functions, methods, acts, and/or processes for image-based analysis of aortic stenosis and/or risk determination described herein, such as those described above with reference to FIGS. 22A-22B.

The following are non-limiting examples of certain embodiments of systems and methods for image-based analysis of aortic stenosis and/or risk determination. Other embodiments may include one or more other features, or different features, that are discussed herein.

Embodiment 1: A computer-implemented method of determination of aortic stenosis for a subject based at least in part on one or more plaque parameters and one or more aortic leaflet parameters derived from medical image analysis, the method comprising: accessing, by the computer system, a first medical image of a subject obtained at a first point in time, the first medical image comprising a portion of an aortic valve of the subject at the first point in time; analyzing, by the computer system, the first medical image of the subject to identify one or more aortic leaflets of the aortic valve of the subject using image segmentation; identifying, by the computer system, one or more regions of plaque within the one or more aortic leaflets; generating, by the computer system, one or more plaque parameters of the one or more regions of plaque identified within the one or more aortic leaflets, the one or more plaque parameters comprising one or more of total plaque volume, low-density non-calcified plaque volume, non-calcified plaque volume, calcified plaque volume, proximity of plaque to the one or more aortic leaflets, or plaque morphology; generating, by the computer system, one or more aortic leaflet parameters of the one or more aortic leaflets, the one or more aortic leaflet parameters comprising one or more of a gap between the one or more aortic leaflets or gradient of a boundary of the one or more aortic leaflets; and generating, by the computer system, a preliminary risk assessment of aortic stenosis of the subject based at least in part on the one or more plaque parameters and the one or more aortic leaflet parameters using a machine learning algorithm, the machine learning algorithm trained on the one or more plaque parameters and the one or more aortic leaflet parameters generated from a plurality of other subjects with known levels of aortic stenosis, wherein the preliminary risk assessment of aortic stenosis being above a predetermined threshold is indicative of further assessment of aortic stenosis for the subject, wherein the computer system comprises a computer processor and an electronic storage medium.

Embodiment 2: The computer-implemented method of Embodiment 1, further comprising: accessing, by the computer system, a second medical image of the subject obtained at a second point in time when the preliminary risk assessment of aortic stenosis is above the predetermined threshold, the second medical image comprising a portion of the aortic valve of the subject at the second point in time; analyzing, by the computer system, the second medical image of the subject to identify one or more aortic leaflets of the aortic valve of the subject using image segmentation; and determining, by the computer system, a gap between the one or more aortic leaflets at the second point in time, wherein the gap between the one or more aortic leaflets at the second point in time being below a predetermined threshold is indicative of aortic stenosis.

Embodiment 3: The computer-implemented method of Embodiment 2, further comprising: generating, by the computer system, a risk level of aortic stenosis for the subject based at least on comparing the determined gap between the one or more aortic leaflets at the second point in time to a plurality of reference values of gaps between one or more aortic leaflets generated from a plurality of other subjects with varying levels of aortic stenosis.

Embodiment 4: The computer-implemented method of Embodiment 2, further comprising generating, by the computer system, an assessment of risk of coronary artery disease (CAD) or major adverse cardiovascular event (MACE) of the subject based at least in part on the gap between the one or more aortic leaflets at the second point in time.

Embodiment 5: The computer-implemented method of Embodiment 2, further comprising determining, by the computer system, a need for aortic valve replacement for the subject based at least in part on the determined gap between the one or more aortic leaflets at the second point in time.

Embodiment 6: The computer-implemented method of Embodiment 1, further comprising: generating, by the computer system, a risk level of aortic stenosis for the subject based at least on comparing the preliminary risk assessment of aortic stenosis of the subject to a plurality of reference values of preliminary risk assessments of aortic stenosis generated from a plurality of other subjects with varying levels of aortic stenosis.

Embodiment 7: The computer-implemented method of Embodiment 1, wherein the aortic leaflets are in a closed configuration at the first point in time.

Embodiment 8: The computer-implemented method of Embodiment 2, wherein the aortic leaflets are in an open configuration at the second point in time.

Embodiment 9: The computer-implemented method of Embodiment 1, wherein the first medical image is obtained from a coronary computed tomography angiography (CCTA).

Embodiment 10: The computer-implemented method of Embodiment 1, wherein the first point in time comprises a point in a cardiac cycle when a CCTA is obtained.

Embodiment 11: The computer-implemented method of Embodiment 1, wherein the first point in time comprises a point in a cardiac cycle when coronary arteries are stable.

Embodiment 12: The computer-implemented method of Embodiment 2, wherein the first point in time and the second point in time comprise different points in a cardiac cycle of the subject.

Embodiment 13: The computer-implemented method of Embodiment 1, wherein further assessment of aortic stenosis for the subject comprises an echocardiography.

Embodiment 14: The computer-implemented method of Embodiment 2, wherein the second medical image is obtained from echocardiography.

Embodiment 15: The computer-implemented method of Embodiment 1, wherein the first medical image is obtained from computed tomography (CT).

Embodiment 16: The computer-implemented method of Embodiment 1, wherein the first medical image is obtained from an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 17: The computer-implemented method of Embodiment 2, wherein the second medical image is obtained from an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 18: The computer-implemented method of Embodiment 1, wherein one or more of low-density non-calcified plaque volume, non-calcified plaque volume, or calcified plaque volume is determined based at least in part on analyzing density of one or more pixels corresponding to the one or more regions of plaque in the first medical image.

Embodiment 19: The computer-implemented method of Embodiment 18, wherein the density comprises material density.

Embodiment 20: The computer-implemented method of Embodiment 18, wherein the density comprises radiodensity.

Embodiment 21: The computer-implemented method of Embodiment 18, wherein low density non-calcified plaque corresponds to one or more pixels with a radiodensity value between about −189 and about 30 Hounsfield units.

Embodiment 22: The computer-implemented method of Embodiment 18, wherein non-calcified plaque corresponds to one or more pixels with a radiodensity value between about 190 and about 350 Hounsfield units.

Embodiment 23: The computer-implemented method of Embodiment 18, wherein calcified plaque corresponds to one or more pixels with a radiodensity value between about 351 and 2500 Hounsfield units.

Embodiment 24: The computer-implemented method of Embodiment 1, wherein the plaque morphology is determined as one or more of a crescent, round, lobular, or bean shape.

Embodiment 25: The computer-implemented method of Embodiment 23, wherein the plaque morphology comprising a round or bean shape is indicative of unstable plaque.

Embodiment 26: A system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a first medical image of a subject obtained at a first point in time, the first medical image comprising a portion of an aortic valve of the subject at the first point in time; analyze the first medical image of the subject to identify one or more aortic leaflets of the aortic valve of the subject using image segmentation; identify one or more regions of plaque within the one or more aortic leaflets; generate one or more plaque parameters of the one or more regions of plaque identified within the one or more aortic leaflets, the one or more plaque parameters comprising one or more of total plaque volume, low-density non-calcified plaque volume, non-calcified plaque volume, calcified plaque volume, proximity of plaque to the one or more aortic leaflets, or plaque morphology; generate one or more aortic leaflet parameters of the one or more aortic leaflets, the one or more aortic leaflet parameters comprising one or more of a gap between the one or more aortic leaflets or gradient of a boundary of the one or more aortic leaflets; and generate a preliminary risk assessment of aortic stenosis of the subject based at least in part on the one or more plaque parameters and the one or more aortic leaflet parameters using a machine learning algorithm, the machine learning algorithm trained on the one or more plaque parameters and the one or more aortic leaflet parameters generated from a plurality of other subjects with known levels of aortic stenosis, wherein the preliminary risk assessment of aortic stenosis being above a predetermined threshold is indicative of further assessment of aortic stenosis for the subject.

Embodiment 27: The system of Embodiment 26, wherein the one or more computer hardware processors are further configured to: access a second medical image of the subject obtained at a second point in time when the preliminary risk assessment of aortic stenosis is above the predetermined threshold, the second medical image comprising a portion of the aortic valve of the subject at the second point in time; analyze the second medical image of the subject to identify one or more aortic leaflets of the aortic valve of the subject using image segmentation; and determine a gap between the one or more aortic leaflets at the second point in time, wherein the gap between the one or more aortic leaflets at the second point in time being below a predetermined threshold is indicative of aortic stenosis.

Embodiment 28: The system of Embodiment 27, wherein the one or more computer hardware processors are further configured to: generate a risk level of aortic stenosis for the subject based at least on comparing the determined gap between the one or more aortic leaflets at the second point in time to a plurality of reference values of gaps between one or more aortic leaflets generated from a plurality of other subjects with varying levels of aortic stenosis.

Embodiment 29: The system of Embodiment 27, wherein the one or more computer hardware processors are further configured to generate an assessment of risk of coronary artery disease (CAD) or major adverse cardiovascular event (MACE) of the subject based at least in part on the gap between the one or more aortic leaflets at the second point in time.

Embodiment 30: The system of Embodiment 27, wherein the one or more computer hardware processors are further configured to determine a need for aortic valve replacement for the subject based at least in part on the determined gap between the one or more aortic leaflets at the second point in time.

Embodiment 31: The system of Embodiment 26, wherein the one or more computer hardware processors are further configured to: generate a risk level of aortic stenosis for the subject based at least on comparing the preliminary risk assessment of aortic stenosis of the subject to a plurality of reference values of preliminary risk assessments of aortic stenosis generated from a plurality of other subjects with varying levels of aortic stenosis.

Embodiment 32: The system of Embodiment 26, wherein the aortic leaflets are in a closed configuration at the first point in time.

Embodiment 33: The system of Embodiment 27, wherein the aortic leaflets are in an open configuration at the second point in time.

Embodiment 34: The system of Embodiment 26, wherein the first medical image is obtained from a coronary computed tomography angiography (CCTA).

Embodiment 35: The system of Embodiment 26, wherein the first point in time comprises a point in a cardiac cycle when a CCTA is obtained.

Embodiment 36: The system of Embodiment 26, wherein the first point in time comprises a point in a cardiac cycle when coronary arteries are stable.

Embodiment 37: The system of Embodiment 27, wherein the first point in time and the second point in time comprise different points in a cardiac cycle of the subject.

Embodiment 38: The system of Embodiment 26, wherein further assessment of aortic stenosis for the subject comprises an echocardiography.

Embodiment 39: The system of Embodiment 27, wherein the second medical image is obtained from echocardiography.

Embodiment 40: The system of Embodiment 26, wherein the first medical image is obtained from computed tomography (CT).

Embodiment 41: The system of Embodiment 26, wherein the first medical image is obtained from an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 42: The system of Embodiment 27, wherein the second medical image is obtained from an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 43: The system of Embodiment 26, wherein one or more of low-density non-calcified plaque volume, non-calcified plaque volume, or calcified plaque volume is determined based at least in part on analyzing density of one or more pixels corresponding to the one or more regions of plaque in the first medical image.

Embodiment 44: The system of Embodiment 42, wherein the density comprises material density.

Embodiment 45: The system of Embodiment 42, wherein the density comprises radiodensity.

Embodiment 46: The system of Embodiment 45, wherein low density non-calcified plaque corresponds to one or more pixels with a radiodensity value between about −189 and about 30 Hounsfield units.

Embodiment 47: The system of Embodiment 45, wherein non-calcified plaque corresponds to one or more pixels with a radiodensity value between about 190 and about 350 Hounsfield units.

Embodiment 48: The system of Embodiment 45, wherein calcified plaque corresponds to one or more pixels with a radiodensity value between about 351 and 2500 Hounsfield units.

Embodiment 49: The system of Embodiment 26, wherein the plaque morphology is determined as one or more of a crescent, round, lobular, or bean shape.

Embodiment 50: The system of Embodiment 49, wherein the plaque morphology comprising a round or bean shape is indicative of unstable plaque.

Embodiment 51: A non-transitory computer readable medium configured for determination of aortic stenosis for a subject based at least in part on one or more plaque parameters and one or more aortic leaflet parameters derived from medical image analysis, the computer readable medium having program instructions for causing a hardware processor to perform a method of: accessing a first medical image of a subject obtained at a first point in time, the first medical image comprising a portion of an aortic valve of the subject at the first point in time; analyzing the first medical image of the subject to identify one or more aortic leaflets of the aortic valve of the subject using image segmentation; identifying one or more regions of plaque within the one or more aortic leaflets; generating one or more plaque parameters of the one or more regions of plaque identified within the one or more aortic leaflets, the one or more plaque parameters comprising one or more of total plaque volume, low-density non-calcified plaque volume, non-calcified plaque volume, calcified plaque volume, proximity of plaque to the one or more aortic leaflets, or plaque morphology; generating one or more aortic leaflet parameters of the one or more aortic leaflets, the one or more aortic leaflet parameters comprising one or more of a gap between the one or more aortic leaflets or gradient of a boundary of the one or more aortic leaflets; and generating a preliminary risk assessment of aortic stenosis of the subject based at least in part on the one or more plaque parameters and the one or more aortic leaflet parameters using a machine learning algorithm, the machine learning algorithm trained on the one or more plaque parameters and the one or more aortic leaflet parameters generated from a plurality of other subjects with known levels of aortic stenosis, wherein the preliminary risk assessment of aortic stenosis being above a predetermined threshold is indicative of further assessment of aortic stenosis for the subject.

Embodiment 52: The non-transitory computer readable medium of Embodiment 51, wherein the method performed by the hardware processor further comprises: accessing a second medical image of the subject obtained at a second point in time when the preliminary risk assessment of aortic stenosis is above the predetermined threshold, the second medical image comprising a portion of the aortic valve of the subject at the second point in time; analyzing the second medical image of the subject to identify one or more aortic leaflets of the aortic valve of the subject using image segmentation; and determining a gap between the one or more aortic leaflets at the second point in time, wherein the gap between the one or more aortic leaflets at the second point in time being below a predetermined threshold is indicative of aortic stenosis.

Embodiment 53: The non-transitory computer readable medium of Embodiment 52, wherein the method performed by the hardware processor further comprises: generating a risk level of aortic stenosis for the subject based at least on comparing the determined gap between the one or more aortic leaflets at the second point in time to a plurality of reference values of gaps between one or more aortic leaflets generated from a plurality of other subjects with varying levels of aortic stenosis.

Embodiment 54: The non-transitory computer readable medium of Embodiment 52, wherein the method performed by the hardware processor further comprises: generating, by the computer system, an assessment of risk of coronary artery disease (CAD) or major adverse cardiovascular event (MACE) of the subject based at least in part on the gap between the one or more aortic leaflets at the second point in time.

Embodiment 55: The non-transitory computer readable medium of Embodiment 52, wherein the method performed by the hardware processor further comprises: determining, by the computer system, a need for aortic valve replacement for the subject based at least in part on the determined gap between the one or more aortic leaflets at the second point in time.

Embodiment 56: The non-transitory computer readable medium of Embodiment 51, wherein the method performed by the hardware processor further comprises: generating a risk level of aortic stenosis for the subject based at least on comparing the preliminary risk assessment of aortic stenosis of the subject to a plurality of reference values of preliminary risk assessments of aortic stenosis generated from a plurality of other subjects with varying levels of aortic stenosis.

Embodiment 57: The non-transitory computer readable medium of Embodiment 51, wherein the aortic leaflets are in a closed configuration at the first point in time.

Embodiment 58: The non-transitory computer readable medium of Embodiment 52, wherein the aortic leaflets are in an open configuration at the second point in time.

Embodiment 59: The non-transitory computer readable medium of Embodiment 51, wherein the first medical image is obtained from a coronary computed tomography angiography (CCTA).

Embodiment 60: The non-transitory computer readable medium of Embodiment 51, wherein the first point in time comprises a point in a cardiac cycle when a CCTA is obtained.

Embodiment 61: The non-transitory computer readable medium of Embodiment 51, wherein the first point in time comprises a point in a cardiac cycle when coronary arteries are stable.

Embodiment 62: The non-transitory computer readable medium of Embodiment 52, wherein the first point in time and the second point in time comprise different points in a cardiac cycle of the subject.

Embodiment 63: The non-transitory computer readable medium of Embodiment 51, wherein further assessment of aortic stenosis for the subject comprises an echocardiography.

Embodiment 64: The non-transitory computer readable medium of Embodiment 52, wherein the second medical image is obtained from echocardiography.

Embodiment 65: The non-transitory computer readable medium of Embodiment 51, wherein the first medical image is obtained from computed tomography (CT).

Embodiment 66: The non-transitory computer readable medium of Embodiment 51, wherein the first medical image is obtained from an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 67: The non-transitory computer readable medium of Embodiment 52, wherein the second medical image is obtained from an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 68: The non-transitory computer readable medium of Embodiment 51, wherein one or more of low-density non-calcified plaque volume, non-calcified plaque volume, or calcified plaque volume is determined based at least in part on analyzing density of one or more pixels corresponding to the one or more regions of plaque in the first medical image.

Embodiment 69: The non-transitory computer readable medium of Embodiment 7, wherein the density comprises material density.

Embodiment 70: The non-transitory computer readable medium of Embodiment 67, wherein the density comprises radiodensity.

Embodiment 71: The non-transitory computer readable medium of Embodiment 70, wherein low density non-calcified plaque corresponds to one or more pixels with a radiodensity value between about −189 and about 30 Hounsfield units.

Embodiment 72: The non-transitory computer readable medium of Embodiment 70, wherein non-calcified plaque corresponds to one or more pixels with a radiodensity value between about 190 and about 350 Hounsfield units.

Embodiment 73: The non-transitory computer readable medium of Embodiment 70, wherein calcified plaque corresponds to one or more pixels with a radiodensity value between about 351 and 2500 Hounsfield units.

Embodiment 74: The non-transitory computer readable medium of Embodiment 51, wherein the plaque morphology is determined as one or more of a crescent, round, lobular, or bean shape.

Embodiment 75: The non-transitory computer readable medium of Embodiment 77, wherein the plaque morphology comprising a round or bean shape is indicative of unstable plaque.

Longitudinal Disease Tracking Based on Image Analysis of Cardiovascular Structures Disclosed herein are systems, devices, and methods for longitudinal disease tracking based on image analysis of cardiovascular structures. In particular, systems, devices, and methods can be configured to recognize anatomical structures in two medical images taken at different points in time and determine a difference in the structure between the two time points. The difference can be analyzed, for example, using a machine learning or artificial intelligence algorithm, to generate a measure of longitudinal progression of a disease.

In one example, the anatomical structure comprises the left ventricle. In two medical images obtained at different points in time, the left ventricular mass can be measured and compared to determine longitudinal tracking of left ventricular hypertrophy in a subject based at least in part on image-based analysis of one or more cardiovascular structural features, the method comprising. The difference can be analyzed in view of a plurality of reference values of differences in left ventricular mass generated from analyzing medical images of a plurality of other subjects obtained at different times and a plurality of reference measures of left ventricular hypertrophy generated based on the plurality of reference values of differences in left ventricular mass.

In another example, the anatomical structure comprises the profiles of the left and right atrial walls. In two medical images obtained at different points in time, the profiles of the left and right atrial walls can be compared and a change that has occurred over time can be determined in order to provide longitudinal tracking of atrial fibrillation. The change can be analyzed in view of a plurality of reference values of changes in profiles of left atrial wall and right atrial wall generated from analyzing medical images of a plurality of other subjects obtained at different times and a plurality of reference measures of atrial fibrillation of the plurality of subjects.

As described herein, systems, devices, and methods can be configured to recognize anatomical structures in two medical images taken at different points in time and determine a difference in the structure between the two time points. The difference can be analyzed, for example, using a machine learning or artificial intelligence algorithm, to generate a measure of longitudinal progression of a disease.

In one example, the anatomical structure comprises the left ventricle. In two medical images obtained at different points in time, the left ventricular mass can be measured and compared to determine longitudinal tracking of left ventricular hypertrophy in a subject based at least in part on image-based analysis of one or more cardiovascular structural features, the method comprising. The difference can be analyzed in view of a plurality of reference values of differences in left ventricular mass generated from analyzing medical images of a plurality of other subjects obtained at different times and a plurality of reference measures of left ventricular hypertrophy generated based on the plurality of reference values of differences in left ventricular mass.

In another example, the anatomical structure comprises the profiles of the left and right atrial walls. In two medical images obtained at different points in time, the profiles of the left and right atrial walls can be compared and a change that has occurred over time can be determined in order to provide longitudinal tracking of atrial fibrillation. The change can be analyzed in view of a plurality of reference values of changes in profiles of left atrial wall and right atrial wall generated from analyzing medical images of a plurality of other subjects obtained at different times and a plurality of reference measures of atrial fibrillation of the plurality of subjects.

Figure 23:
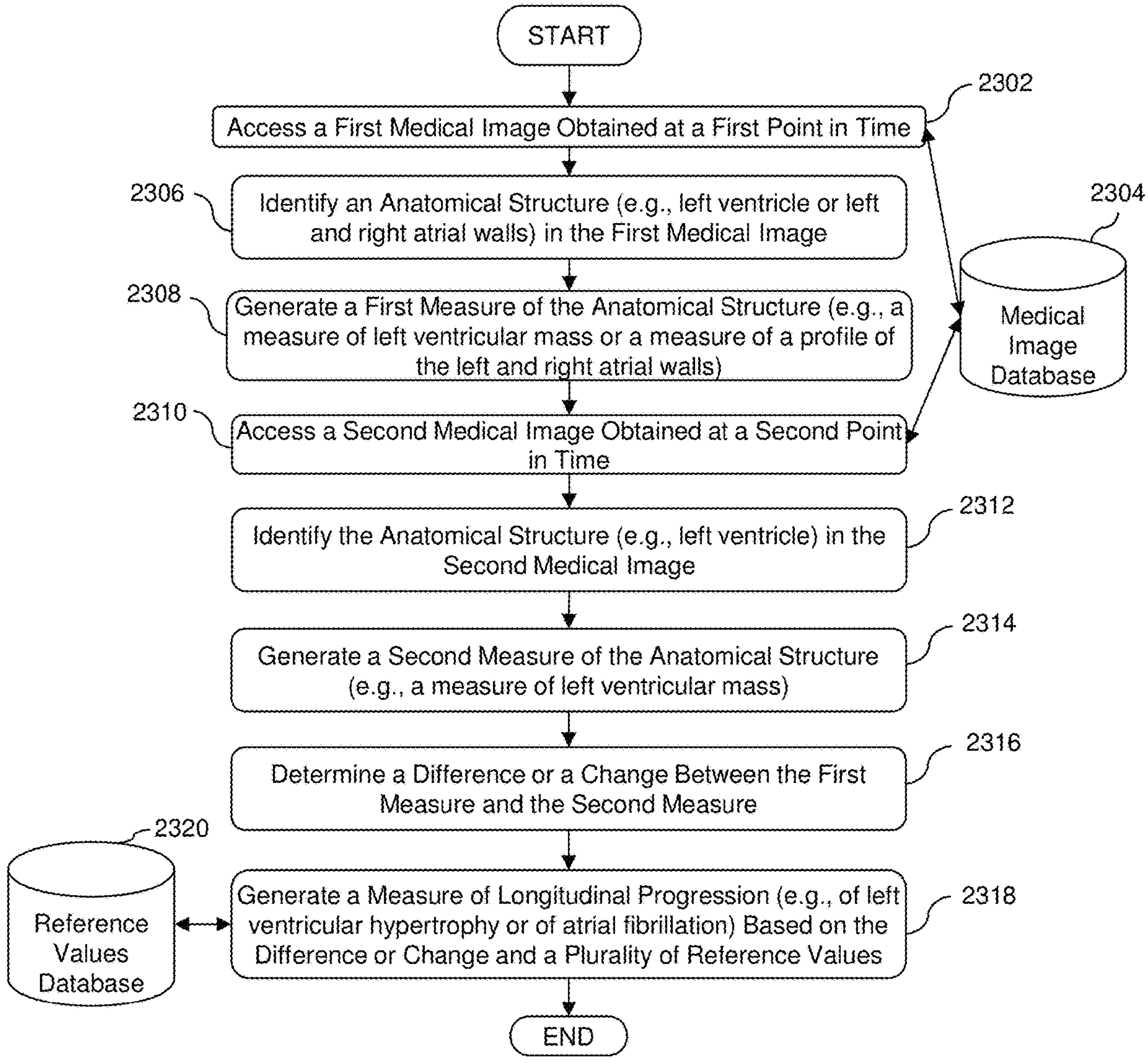
FIG. 23 is a flowchart illustrating an example embodiment(s) of systems, devices, and methods for longitudinal disease tracking based on image analysis of cardiovascular structures.

FIG. 23 is a flowchart illustrating an example embodiment(s) of systems, devices, and methods for longitudinal disease tracking based on image analysis of cardiovascular structures. As illustrated in FIG. 23, in some embodiments, the system can be configured to access a first medical image at block 2302. The first image can be obtained at a first point in time. For example, in some embodiments, the first medical image comprises or includes a portion of a myocardium of the subject. In some embodiments, the medical image can include one or more arteries, such as coronary, carotid, and/or other arteries of a subject. In some embodiments, the medical image can be stored in a medical image database 2304. In some embodiments, the medical image database 2304 can be locally accessible by the system and/or can be located remotely and accessible through a network connection. The medical image can comprise an image obtain using one or more modalities such as for example, CT, Dual-Energy Computed Tomography (DECT), Spectral CT, photon-counting CT, x-ray, ultrasound, echocardiography, intravascular ultrasound (IVUS), Magnetic Resonance (MR) imaging, optical coherence tomography (OCT), nuclear medicine imaging, positron-emission tomography (PET), single photon emission computed tomography (SPECT), or near-field infrared spectroscopy (NIRS). In some embodiments, the medical image comprises one or more of a contrast-enhanced CT image, non-contrast CT image, MR image, and/or an image obtained using any of the modalities described above.

At block 2306, the system can be configured to identify an anatomical structure in the first medical image. In some embodiments, the system is configured to identify the anatomical structure based at least in part on image segmentation. In some embodiments, the system can be configured to utilize one or more AI and/or ML algorithms to automatically and/or dynamically identify the anatomical structure using image processing. For example, in some embodiments, the one or more AI and/or ML algorithms can be trained using a Convolutional Neural Network (CNN) on a set of medical images on which the anatomical structures have been identified, thereby allowing the AI and/or ML algorithm automatically the anatomical structures directly from a medical image.

In some embodiments, the anatomical structure comprises a left ventricle of the subject. In some embodiments, the anatomical structure comprises a left atrial wall and a right atrial wall of the subject. Other anatomical structures can also be used.

At block 2308, the system can be determined to generate a measure of the first anatomical structure. For example, where the anatomical structure is the left ventricle of the subject, the first measure can be a first measure of left ventricular mass. As another example, where the anatomical structure comprises left and right atrial walls, the first measure can be a first profile of the left atrial wall and the right atrial wall.

As illustrated in FIG. 1, in some embodiments, the system can be configured to access a second medical image at block 2310. The second image can be obtained at a second point in time. The second point in time can be later than the first point in time. The second medical image can comprise or include a similar region of the subject as the first medical image. For example, in some embodiments, the second medical image comprises or includes a portion of the myocardium of the subject. The second medical image can be stored in the medical image database 2304.

In some embodiments, the first medical image and the second medical image are obtained at about a same point during a cardiac cycle. In some embodiments, the first medical image and the second medical image are obtained at a point during a cardiac cycle when movement of the myocardium is expected to be below a predetermined threshold.

In some embodiments, the second point in time is more than 12 months after the first point in time. In some embodiments, the second point in time is more than 24 months after the first point in time. In some embodiments, the second point in time is more than 36 months after the first point in time. In some embodiments, the second point in time is more than 48 months after the first point in time. Other time differences can also be used.

At block 2312, the system can be configured to identify the anatomical structure in the second medical image. The anatomical structure identified at block 2312 can be the same anatomical structure identified at block 2308. For example, similar steps as described with reference to block 2306 can be used to identify the anatomical structure in the second image.

For example, the anatomical structure comprises a left ventricle of the subject. As another example, the anatomical structure can comprise the left atrial wall and a right atrial wall of the subject. Other anatomical structures can also be used.

At block 2314 the system can be determined to generate a measure of the second anatomical structure. For example, where the anatomical structure is the left ventricle of the subject, the second measure can be a second measure of left ventricular mass. As another example, where the anatomical structure comprises left and right atrial walls, the first measure can be a first profile of the left atrial wall and the right atrial wall.

With continued reference to FIG. 23, in some embodiments, at block 2316 the system can be configured to determine a difference or a change between the first measure determined at block 2308 and the second measure determined at block 2314. Where the anatomical structure comprises the left ventricle, for example, the system can be configured to determine a difference between the left ventricular mass determined based on the first medical image and the left ventricular mass determined based on the first medical image. Where the anatomical structure comprises the left and right atrial walls, for example, the system can be configured to determine a difference between the profiles of the left and right atrial walls determined based on the first medical image and the left ventricular mass determined based on the first medical image.

At block 2318, the system can be configured to generate a measure of longitudinal progression, for example, of a disease, based on the difference or change determined at block 2316 and a plurality of reference values.

Where the anatomical structure comprises the left ventricle, for example, the system can be configured to generate a measure of longitudinal progression of left ventricular hypertrophy for the subject based at least in part on the difference between the first measure of left ventricular mass and the second measure of left ventricular mass and a plurality of reference values of differences in left ventricular mass generated from analyzing medical images of a plurality of other subjects obtained at different times and a plurality of reference measures of left ventricular hypertrophy generated based on the plurality of reference values of differences in left ventricular mass.

In some embodiments, the measure of longitudinal progression of left ventricular hypertrophy for the subject is generated using a machine learning algorithm. The machine learning algorithm can be trained on the plurality of reference values of differences in left ventricular mass generated from analyzing medical images of the plurality of other subjects obtained at different times and the plurality of reference measures of left ventricular hypertrophy generated based on the plurality of reference values of differences in left ventricular mass.

Where the anatomical structure comprises the left and right atrial walls, for example, the system can be configured to generate a measure of longitudinal progression of atrial fibrillation for the subject based at least in part on the change between the first profile of the left atrial wall and the right atrial wall at the first point in time and the second profile of the left atrial wall and the right atrial wall at the second point in time and a plurality of reference values of changes in profiles of left atrial wall and right atrial wall generated from analyzing medical images of a plurality of other subjects obtained at different times and a plurality of reference measures of atrial fibrillation of the plurality of subjects.

In some embodiments, the measure of longitudinal progression of atrial fibrillation for the subject is generated using a machine learning algorithm. The machine learning algorithm can be trained on the plurality of reference values of changes in profiles of left atrial wall and right atrial wall generated from analyzing medical images of the plurality of other subjects obtained at different times and the plurality of reference measures of atrial fibrillation of the plurality of subjects.

In some embodiments, the one or more reference values can be stored on a reference values database 2320, which can be locally accessible by the system and/or can be located remotely and accessible through a network connection.

In some embodiments, where the anatomical structure comprises the left ventricle, the system can further be configured to determine efficacy of treatment for hypertension for the subject between the first point in time and the second point in time. In some embodiments, the system can further be configured to determine risk of hypertension of the subject based at least in part on the generated measure of longitudinal progression of left ventricular hypertrophy. In some embodiments, the system can further be configured to generate a proposed treatment for the subject to treat hypertension based at least in part on the generated measure of longitudinal progression of left ventricular hypertrophy. In some embodiments, the difference between the first measure of left ventricular mass at the first point in time and the second measure of left ventricular mass at the second point in time being higher than a predetermined threshold is indicative of high left ventricular hypertrophy of the subject. In some embodiments, the difference between the first measure of left ventricular mass at the first point in time and the second measure of left ventricular mass at the second point in time being lower than a predetermined threshold is indicative of low left ventricular hypertrophy of the subject. In some embodiments, the measure of longitudinal progression of left ventricular hypertrophy comprises one of low, medium, or high. In some embodiments, the measure of longitudinal progression of left ventricular hypertrophy comprises a scaled value of a continuum of scaled values.

In some embodiments where the anatomical structure comprises the left and right atrial walls, the system can further be configured to determine efficacy of treatment for atrial fibrillation for the subject between the first point in time and the second point in time. In some embodiments, the system can further be configured to determine a risk of atrial fibrillation of the subject based at least in part on the generated measure of longitudinal progression of atrial fibrillation. In some embodiments, the system can further be configured to generating a proposed treatment for the subject to treat atrial fibrillation based at least in part on the generated measure of longitudinal progression of atrial fibrillation. In some embodiments, the measure of longitudinal progression of atrial fibrillation comprises one of low, medium, or high.

In some embodiments, the measure of longitudinal progression of atrial fibrillation comprises a scaled value of a continuum of scaled values.

The computer system 902 of FIG. 9, and in some instances, the analysis and/or risk assessment module 940, can be configured to carry out the functions, methods, acts, and/or processes for longitudinal disease tracking based on image analysis of cardiovascular structures described herein, such as those described above with reference to FIG. 23.

The following are non-limiting examples of certain embodiments of systems and methods for longitudinal disease tracking based on image analysis of cardiovascular structures. Other embodiments may include one or more other features, or different features, that are discussed herein.

Embodiment 1: A computer-implemented method of longitudinal tracking of left ventricular hypertrophy in a subject based at least in part on image-based analysis of one or more cardiovascular structural features, the method comprising: accessing, by a computer system, a first medical image of a subject, the first medical image comprising a portion of a myocardium of the subject, the first medical image obtained at a first point in time; identifying, by the computer system, the left ventricle of the subject in the first medical image based at least in part on image segmentation; analyzing, by the computer system, the left ventricle of the subject identified in the first medical image to generate a first measure of left ventricular mass at the first point in time; accessing, by a computer system, a second medical image of a subject, the second medical image comprising the portion of the myocardium of the subject, the second medical image obtained at a second point in time; identifying, by the computer system, the left ventricle of the subject in the second medical image based at least in part on image segmentation; analyzing, by the computer system, the left ventricle of the subject identified in the second medical image to generate a second measure of left ventricular mass at the second point in time; determining, by the computer system, a difference between the first measure of left ventricular mass at the first point in time and the second measure of left ventricular mass at the second point in time; generating, by the computer system, a measure of longitudinal progression of left ventricular hypertrophy for the subject based at least in part on the difference between the first measure of left ventricular mass and the second measure of left ventricular mass and a plurality of reference values of differences in left ventricular mass generated from analyzing medical images of a plurality of other subjects obtained at different times and a plurality of reference measures of left ventricular hypertrophy generated based on the plurality of reference values of differences in left ventricular mass, wherein the computer system comprises a computer processor and an electronic storage medium.

Embodiment 2: The computer-implemented method of Embodiment 1, further comprising determining efficacy of treatment for hypertension for the subject between the first point in time and the second point in time.

Embodiment 3: The computer-implemented method of Embodiment 1, further comprising determining risk of hypertension of the subject based at least in part on the generated measure of longitudinal progression of left ventricular hypertrophy.

Embodiment 4: The computer-implemented method of Embodiment 1, further comprising generating a proposed treatment for the subject to treat hypertension based at least in part on the generated measure of longitudinal progression of left ventricular hypertrophy.

Embodiment 5: The computer-implemented method of Embodiment 1, wherein the difference between the first measure of left ventricular mass at the first point in time and the second measure of left ventricular mass at the second point in time being higher than a predetermined threshold is indicative of high left ventricular hypertrophy of the subject.

Embodiment 6: The computer-implemented method of Embodiment 1, wherein the difference between the first measure of left ventricular mass at the first point in time and the second measure of left ventricular mass at the second point in time being lower than a predetermined threshold is indicative of low left ventricular hypertrophy of the subject.

Embodiment 7: The computer-implemented method of Embodiment 1, wherein the measure of longitudinal progression of left ventricular hypertrophy comprises one of low, medium, or high.

Embodiment 9: The computer-implemented method of Embodiment 1, wherein the measure of longitudinal progression of left ventricular hypertrophy comprises a scaled value of a continuum of scaled values.

Embodiment 9: The computer-implemented method of Embodiment 1, wherein the first medical image and the second medical image are obtained at about a same point during a cardiac cycle.

Embodiment 10: The computer-implemented method of Embodiment 1, wherein the first medical image and the second medical image are obtained at a point during a cardiac cycle when movement of the myocardium is expected to be below a predetermined threshold.

Embodiment 11: The computer-implemented method of Embodiment 1, wherein the second point in time is more than 12 months after the first point in time.

Embodiment 12: The computer-implemented method of Embodiment 1, wherein the second point in time is more than 24 months after the first point in time.

Embodiment 13: The computer-implemented method of Embodiment 1, wherein the second point in time is more than 36 months after the first point in time.

Embodiment 14: The computer-implemented method of Embodiment 1, wherein the second point in time is more than 48 months after the first point in time.

Embodiment 15: The computer-implemented method of Embodiment 1, wherein the first medical image and the second medical image comprise a computed tomography (CT) image.

Embodiment 16: The computer-implemented method of Embodiment 1, wherein one or more of the first medical or the second medical image comprises an image obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 17: The computer-implemented method of Embodiment 1, wherein the measure of longitudinal progression of left ventricular hypertrophy for the subject is generated using a machine learning algorithm, wherein the machine learning algorithm is trained on the plurality of reference values of differences in left ventricular mass generated from analyzing medical images of the plurality of other subjects obtained at different times and the plurality of reference measures of left ventricular hypertrophy generated based on the plurality of reference values of differences in left ventricular mass.

Embodiment 18: A computer-implemented method of longitudinal tracking of atrial fibrillation in a subject based at least in part on image-based analysis of one or more cardiovascular structural features, the method comprising: accessing, by a computer system, a first medical image of a subject, the first medical image comprising a portion of a myocardium of the subject, the first medical image obtained at a first point in time; identifying, by the computer system, the left atrial wall and the right atrial wall of the subject in the first medical image based at least in part on image segmentation; determining, by the computer system, a first profile of the left atrial wall and the right atrial wall in the first medical image at the first point in time; accessing, by a computer system, a second medical image of a subject, the second medical image comprising the portion of the myocardium of the subject, the second medical image obtained at a second point in time; identifying, by the computer system, the left atrial wall and the right atrial wall of the subject in the second medical image based at least in part on image segmentation; determining, by the computer system, a profile of the left atrial wall and the right atrial wall in the second medical image at the second point in time; determining, by the computer system, a change between the first profile of the left atrial wall and the right atrial wall at the first point in time and the second profile of the left atrial wall and the right atrial wall at the second point in time; generating, by the computer system, a measure of longitudinal progression of atrial fibrillation for the subject based at least in part on the change between the first profile of the left atrial wall and the right atrial wall at the first point in time and the second profile of the left atrial wall and the right atrial wall at the second point in time and a plurality of reference values of changes in profiles of left atrial wall and right atrial wall generated from analyzing medical images of a plurality of other subjects obtained at different times and a plurality of reference measures of atrial fibrillation of the plurality of subjects, wherein the computer system comprises a computer processor and an electronic storage medium.

Embodiment 19: The computer-implemented method of Embodiment 18, further comprising determining efficacy of treatment for atrial fibrillation for the subject between the first point in time and the second point in time.

Embodiment 20: The computer-implemented method of Embodiment 18, further comprising determining risk of atrial fibrillation of the subject based at least in part on the generated measure of longitudinal progression of atrial fibrillation.

Embodiment 21: The computer-implemented method of Embodiment 18, further comprising generating a proposed treatment for the subject to treat atrial fibrillation based at least in part on the generated measure of longitudinal progression of atrial fibrillation.

Embodiment 22: The computer-implemented method of Embodiment 18, wherein the measure of longitudinal progression of atrial fibrillation comprises one of low, medium, or high.

Embodiment 23: The computer-implemented method of Embodiment 18, wherein the measure of longitudinal progression of atrial fibrillation comprises a scaled value of a continuum of scaled values.

Embodiment 24: The computer-implemented method of Embodiment 18, wherein the first medical image and the second medical image are obtained at about a same point during a cardiac cycle.

Embodiment 25: The computer-implemented method of Embodiment 18, wherein the first medical image and the second medical image are obtained at a point during a cardiac cycle when movement of the myocardium is expected to be below a predetermined threshold.

Embodiment 26: The computer-implemented method of Embodiment 18, wherein the second point in time is more than 12 months after the first point in time.

Embodiment 27: The computer-implemented method of Embodiment 18, wherein the second point in time is more than 24 months after the first point in time.

Embodiment 28: The computer-implemented method of Embodiment 18, wherein the second point in time is more than 36 months after the first point in time.

Embodiment 29: The computer-implemented method of Embodiment 18, wherein the second point in time is more than 48 months after the first point in time.

Embodiment 30: The computer-implemented method of Embodiment 18, wherein the first medical image and the second medical image comprise a computed tomography (CT) image.

Embodiment 31: The computer-implemented method of Embodiment 18, wherein one or more of the first medical or the second medical image comprises an image obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 32: The computer-implemented method of Embodiment 18, wherein the measure of longitudinal progression of atrial fibrillation for the subject is generated using a machine learning algorithm, wherein the machine learning algorithm is trained on the plurality of reference values of changes in profiles of left atrial wall and right atrial wall generated from analyzing medical images of the plurality of other subjects obtained at different times and the plurality of reference measures of atrial fibrillation of the plurality of subjects.

Embodiment 33: A system for longitudinal tracking of left ventricular hypertrophy in a subject based at least in part on image-based analysis of one or more cardiovascular structural features, the system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a first medical image of a subject, the first medical image comprising a portion of a myocardium of the subject, the first medical image obtained at a first point in time; identify the left ventricle of the subject in the first medical image based at least in part on image segmentation; analyze the left ventricle of the subject identified in the first medical image to generate a first measure of left ventricular mass at the first point in time; access a second medical image of a subject, the second medical image comprising the portion of the myocardium of the subject, the second medical image obtained at a second point in time; identify the left ventricle of the subject in the second medical image based at least in part on image segmentation; analyze left ventricle of the subject identified in the second medical image to generate a second measure of left ventricular mass at the second point in time; determine a difference between the first measure of left ventricular mass at the first point in time and the second measure of left ventricular mass at the second point in time; generate a measure of longitudinal progression of left ventricular hypertrophy for the subject based at least in part on the difference between the first measure of left ventricular mass and the second measure of left ventricular mass and a plurality of reference values of differences in left ventricular mass generated from analyzing medical images of a plurality of other subjects obtained at different times and a plurality of reference measures of left ventricular hypertrophy generated based on the plurality of reference values of differences in left ventricular mass.

Embodiment 34: The system of Embodiment 33, wherein the one or more processors are configured to determine efficacy of treatment for hypertension for the subject between the first point in time and the second point in time.

Embodiment 35: The system of Embodiment 33, wherein the one or more processors are configured to determine risk of hypertension of the subject based at least in part on the generated measure of longitudinal progression of left ventricular hypertrophy.

Embodiment 36: The system of Embodiment 33, wherein the one or more processors are configured to generate a proposed treatment for the subject to treat hypertension based at least in part on the generated measure of longitudinal progression of left ventricular hypertrophy.

Embodiment 37: The system of Embodiment 33, wherein the difference between the first measure of left ventricular mass at the first point in time and the second measure of left ventricular mass at the second point in time being higher than a predetermined threshold is indicative of high left ventricular hypertrophy of the subject.

Embodiment 38: The system of Embodiment 33, wherein the difference between the first measure of left ventricular mass at the first point in time and the second measure of left ventricular mass at the second point in time being lower than a predetermined threshold is indicative of low left ventricular hypertrophy of the subject.

Embodiment 39: The system of Embodiment 33, wherein the measure of longitudinal progression of left ventricular hypertrophy comprises one of low, medium, or high.

Embodiment 40: The system of Embodiment 33, wherein the measure of longitudinal progression of left ventricular hypertrophy comprises a scaled value of a continuum of scaled values.

Embodiment 41: The system of Embodiment 33, wherein the first medical image and the second medical image are obtained at about a same point during a cardiac cycle.

Embodiment 42: The system of Embodiment 33, wherein the first medical image and the second medical image are obtained at a point during a cardiac cycle when movement of the myocardium is expected to be below a predetermined threshold.

Embodiment 43: The system of Embodiment 33, wherein the second point in time is more than 12 months after the first point in time.

Embodiment 44: The system of Embodiment 33, wherein the second point in time is more than 24 months after the first point in time.

Embodiment 45: The system of Embodiment 33, wherein the second point in time is more than 36 months after the first point in time.

Embodiment 46: The system of Embodiment 33, wherein the second point in time is more than 48 months after the first point in time.

Embodiment 47: The system of Embodiment 33, wherein the first medical image and the second medical image comprise a computed tomography (CT) image.

Embodiment 48: The system of Embodiment 33, wherein one or more of the first medical or the second medical image comprises an image obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 49: The system of Embodiment 33, wherein the measure of longitudinal progression of left ventricular hypertrophy for the subject is generated using a machine learning algorithm, wherein the machine learning algorithm is trained on the plurality of reference values of differences in left ventricular mass generated from analyzing medical images of the plurality of other subjects obtained at different times and the plurality of reference measures of left ventricular hypertrophy generated based on the plurality of reference values of differences in left ventricular mass.

Embodiment 50: A system longitudinal tracking of atrial fibrillation in a subject based at least in part on image-based analysis of one or more cardiovascular structural features, the system comprising: a non-transitory computer storage medium configured to at least store computer-executable instructions; and one or more computer hardware processors in communication with the first non-transitory computer storage medium, the one or more computer hardware processors configured to execute the computer-executable instructions to at least: access a first medical image of a subject, the first medical image comprising a portion of a myocardium of the subject, the first medical image obtained at a first point in time; identify the left atrial wall and the right atrial wall of the subject in the first medical image based at least in part on image segmentation; determine a first profile of the left atrial wall and the right atrial wall in the first medical image at the first point in time; access a second medical image of a subject, the second medical image comprising the portion of the myocardium of the subject, the second medical image obtained at a second point in time; identify the left atrial wall and the right atrial wall of the subject in the second medical image based at least in part on image segmentation; determine a profile of the left atrial wall and the right atrial wall in the second medical image at the second point in time; determine a change between the first profile of the left atrial wall and the right atrial wall at the first point in time and the second profile of the left atrial wall and the right atrial wall at the second point in time; generate a measure of longitudinal progression of atrial fibrillation for the subject based at least in part on the change between the first profile of the left atrial wall and the right atrial wall at the first point in time and the second profile of the left atrial wall and the right atrial wall at the second point in time and a plurality of reference values of changes in profiles of left atrial wall and right atrial wall generated from analyzing medical images of a plurality of other subjects obtained at different times and a plurality of reference measures of atrial fibrillation of the plurality of subjects.

Embodiment 51: The system of Embodiment 50, wherein the one or more processors are configured to determine efficacy of treatment for atrial fibrillation for the subject between the first point in time and the second point in time.

Embodiment 52: The system of Embodiment 50, wherein the one or more processors are configured to determine risk of atrial fibrillation of the subject based at least in part on the generated measure of longitudinal progression of atrial fibrillation.

Embodiment 53: The system of Embodiment 50, wherein the one or more processors are configured to generate a proposed treatment for the subject to treat atrial fibrillation based at least in part on the generated measure of longitudinal progression of atrial fibrillation.

Embodiment 54: The system of Embodiment 50, wherein the measure of longitudinal progression of atrial fibrillation comprises one of low, medium, or high.

Embodiment 55: The system of Embodiment 50, wherein the measure of longitudinal progression of atrial fibrillation comprises a scaled value of a continuum of scaled values.

Embodiment 56: The system of Embodiment 50, wherein the first medical image and the second medical image are obtained at about a same point during a cardiac cycle.

Embodiment 57: The system of Embodiment 50, wherein the first medical image and the second medical image are obtained at a point during a cardiac cycle when movement of the myocardium is expected to be below a predetermined threshold.

Embodiment 58: The system of Embodiment 50, wherein the second point in time is more than 12 months after the first point in time.

Embodiment 59: The system of Embodiment 50, wherein the second point in time is more than 24 months after the first point in time.

Embodiment 60: The system of Embodiment 50, wherein the second point in time is more than 36 months after the first point in time.

Embodiment 61: The system of Embodiment 50, wherein the second point in time is more than 48 months after the first point in time.

Embodiment 62: The system of Embodiment 50, wherein the first medical image and the second medical image comprise a computed tomography (CT) image.

Embodiment 63: The system of Embodiment 50, wherein one or more of the first medical or the second medical image comprises an image obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 64: The system of Embodiment 50, wherein the measure of longitudinal progression of atrial fibrillation for the subject is generated using a machine learning algorithm, wherein the machine learning algorithm is trained on the plurality of reference values of changes in profiles of left atrial wall and right atrial wall generated from analyzing medical images of the plurality of other subjects obtained at different times and the plurality of reference measures of atrial fibrillation of the plurality of subjects.

Embodiment 65: A non-transitory computer readable medium configured for longitudinal tracking of left ventricular hypertrophy in a subject based at least in part on image-based analysis of one or more cardiovascular structural features, the computer readable medium having program instructions for causing a hardware processor to perform a method of: accessing a first medical image of a subject, the first medical image comprising a portion of a myocardium of the subject, the first medical image obtained at a first point in time; identifying the left ventricle of the subject in the first medical image based at least in part on image segmentation; analyzing the left ventricle of the subject identified in the first medical image to generate a first measure of left ventricular mass at the first point in time; accessing a second medical image of a subject, the second medical image comprising the portion of the myocardium of the subject, the second medical image obtained at a second point in time; identifying the left ventricle of the subject in the second medical image based at least in part on image segmentation; analyzing the left ventricle of the subject identified in the second medical image to generate a second measure of left ventricular mass at the second point in time; determining a difference between the first measure of left ventricular mass at the first point in time and the second measure of left ventricular mass at the second point in time; generating a measure of longitudinal progression of left ventricular hypertrophy for the subject based at least in part on the difference between the first measure of left ventricular mass and the second measure of left ventricular mass and a plurality of reference values of differences in left ventricular mass generated from analyzing medical images of a plurality of other subjects obtained at different times and a plurality of reference measures of left ventricular hypertrophy generated based on the plurality of reference values of differences in left ventricular mass.

Embodiment 66: The computer readable medium of Embodiment 66, wherein the method further comprises determining efficacy of treatment for hypertension for the subject between the first point in time and the second point in time.

Embodiment 67: The computer readable medium of Embodiment 66, wherein the method further comprises determining risk of hypertension of the subject based at least in part on the generated measure of longitudinal progression of left ventricular hypertrophy.

Embodiment 68: The computer readable medium of Embodiment 66, wherein the method further comprises generating a proposed treatment for the subject to treat hypertension based at least in part on the generated measure of longitudinal progression of left ventricular hypertrophy.

Embodiment 69: The computer readable medium of Embodiment 66, wherein the difference between the first measure of left ventricular mass at the first point in time and the second measure of left ventricular mass at the second point in time being higher than a predetermined threshold is indicative of high left ventricular hypertrophy of the subject.

Embodiment 70: The computer readable medium of Embodiment 66, wherein the difference between the first measure of left ventricular mass at the first point in time and the second measure of left ventricular mass at the second point in time being lower than a predetermined threshold is indicative of low left ventricular hypertrophy of the subject.

Embodiment 71: The computer readable medium of Embodiment 66, wherein the measure of longitudinal progression of left ventricular hypertrophy comprises one of low, medium, or high.

Embodiment 72: The computer readable medium of Embodiment 66, wherein the measure of longitudinal progression of left ventricular hypertrophy comprises a scaled value of a continuum of scaled values.

Embodiment 73: The computer readable medium of Embodiment 66, wherein the first medical image and the second medical image are obtained at about a same point during a cardiac cycle.

Embodiment 74: The computer readable medium of Embodiment 66, wherein the first medical image and the second medical image are obtained at a point during a cardiac cycle when movement of the myocardium is expected to be below a predetermined threshold.

Embodiment 75: The computer readable medium of Embodiment 66, wherein the second point in time is more than 12 months after the first point in time.

Embodiment 76: The computer readable medium of Embodiment 66, wherein the second point in time is more than 24 months after the first point in time.

Embodiment 77: The computer readable medium of Embodiment 66, wherein the second point in time is more than 36 months after the first point in time.

Embodiment 78: The computer readable medium of Embodiment 66, wherein the second point in time is more than 48 months after the first point in time.

Embodiment 79: The computer readable medium of Embodiment 66, wherein the first medical image and the second medical image comprise a computed tomography (CT) image.

Embodiment 80: The computer readable medium of Embodiment 66, wherein one or more of the first medical or the second medical image comprises an image obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 81: The computer readable medium of Embodiment 66, wherein the measure of longitudinal progression of left ventricular hypertrophy for the subject is generated using a machine learning algorithm, wherein the machine learning algorithm is trained on the plurality of reference values of differences in left ventricular mass generated from analyzing medical images of the plurality of other subjects obtained at different times and the plurality of reference measures of left ventricular hypertrophy generated based on the plurality of reference values of differences in left ventricular mass.

Embodiment 82: A non-transitory computer readable medium configured for longitudinal tracking of atrial fibrillation in a subject based at least in part on image-based analysis of one or more cardiovascular structural features, the computer readable medium having program instructions for causing a hardware processor to perform a method of: accessing a first medical image of a subject, the first medical image comprising a portion of a myocardium of the subject, the first medical image obtained at a first point in time; identifying the left atrial wall and the right atrial wall of the subject in the first medical image based at least in part on image segmentation; determining a first profile of the left atrial wall and the right atrial wall in the first medical image at the first point in time; accessing a second medical image of a subject, the second medical image comprising the portion of the myocardium of the subject, the second medical image obtained at a second point in time; identifying the left atrial wall and the right atrial wall of the subject in the second medical image based at least in part on image segmentation; determining a profile of the left atrial wall and the right atrial wall in the second medical image at the second point in time; determining a change between the first profile of the left atrial wall and the right atrial wall at the first point in time and the second profile of the left atrial wall and the right atrial wall at the second point in time; generating a measure of longitudinal progression of atrial fibrillation for the subject based at least in part on the change between the first profile of the left atrial wall and the right atrial wall at the first point in time and the second profile of the left atrial wall and the right atrial wall at the second point in time and a plurality of reference values of changes in profiles of left atrial wall and right atrial wall generated from analyzing medical images of a plurality of other subjects obtained at different times and a plurality of reference measures of atrial fibrillation of the plurality of subjects.

Embodiment 83: The computer readable medium of Embodiment 82, wherein the method further comprises determining efficacy of treatment for atrial fibrillation for the subject between the first point in time and the second point in time.

Embodiment 84: The computer readable medium of Embodiment 82, wherein the method further comprises determining risk of atrial fibrillation of the subject based at least in part on the generated measure of longitudinal progression of atrial fibrillation.

Embodiment 85: The computer readable medium of Embodiment 82, wherein the method further comprises generating a proposed treatment for the subject to treat atrial fibrillation based at least in part on the generated measure of longitudinal progression of atrial fibrillation.

Embodiment 86: The computer readable medium of Embodiment 82, wherein the measure of longitudinal progression of atrial fibrillation comprises one of low, medium, or high.

Embodiment 87: The computer readable medium of Embodiment 82, wherein the measure of longitudinal progression of atrial fibrillation comprises a scaled value of a continuum of scaled values.

Embodiment 88: The computer readable medium of Embodiment 82, wherein the first medical image and the second medical image are obtained at about a same point during a cardiac cycle.

Embodiment 89: The computer readable medium of Embodiment 82, wherein the first medical image and the second medical image are obtained at a point during a cardiac cycle when movement of the myocardium is expected to be below a predetermined threshold.

Embodiment 90: The computer readable medium of Embodiment 82, wherein the second point in time is more than 12 months after the first point in time.

Embodiment 91: The computer readable medium of Embodiment 82, wherein the second point in time is more than 24 months after the first point in time.

Embodiment 92: The computer readable medium of Embodiment 82, wherein the second point in time is more than 36 months after the first point in time.

Embodiment 93: The computer readable medium of Embodiment 82, wherein the second point in time is more than 48 months after the first point in time.

Embodiment 94: The computer readable medium of Embodiment 82, wherein the first medical image and the second medical image comprise a computed tomography (CT) image.

Embodiment 95: The computer readable medium of Embodiment 82, wherein one or more of the first medical or the second medical image comprises an image obtained using an imaging modality comprising one or more of CT, x-ray, ultrasound, echocardiography, MR imaging, optical coherence tomography (OCT), nuclear medicine imaging, positron-emission tomography (PET), single photon emission computed tomography (SPECT), or near-field infrared spectroscopy (NIRS).

Embodiment 96: The computer readable medium of Embodiment 82, wherein the measure of longitudinal progression of atrial fibrillation for the subject is generated using a machine learning algorithm, wherein the machine learning algorithm is trained on the plurality of reference values of changes in profiles of left atrial wall and right atrial wall generated from analyzing medical images of the plurality of other subjects obtained at different times and the plurality of reference measures of atrial fibrillation of the plurality of subjects.

Other Embodiment(s)

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited.

The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

The invention claimed is:

1. A computer-implemented method of assessing microcirculatory resistance of coronary microvasculature based on non-invasive medical image analysis, the computer-implemented method comprising:

accessing, by a computer system, a first medical image of a subject, wherein the first medical image of the subject is obtained at a first point in time after injection of a contrast dye to the subject;

accessing, by the computer system, a second medical image of the subject, wherein the second medical image of the subject is obtained at a second point in time after injection of the contrast dye to the subject;

analyzing, by the computer system, the first medical image and the second medical image to identify a coronary artery;

mapping, by the computer system, myocardium subtended by the coronary artery in the first medical image and the second medical image;

analyzing, by the computer system, a difference in radiodensity between the myocardium subtended by the coronary artery in the first medical image and the second medical image, the difference in radiodensity arising from flow of the contrast dye through microvasculature of the myocardium subtended by the coronary artery;

determining, by the computer system, a generated measure of per-artery microcirculatory resistance of the coronary artery by relating the difference in radiodensity between the myocardium subtended by the coronary artery in the first medical image and the second medical image to a difference in time between the first point in time and the second point in time; and determining, by the computer system, an assessment of microcirculatory resistance of the coronary artery based at least in part on comparing the generated measure of the per-artery microcirculatory resistance of the coronary artery to a plurality of reference measures of per-artery microcirculatory resistance, the plurality of reference measures of per-artery microcirculatory resistance derived from a plurality of other subjects, wherein the assessment of microcirculatory resistance of the coronary artery is configured to be utilized to determine a treatment for the subject, wherein the computer system comprises a computer processor and an electronic storage medium.

2. The computer-implemented method of claim 1, wherein the assessment of microcirculatory resistance of the coronary artery is determined utilizing a machine learning algorithm trained based at least in part on the plurality of reference measures of per-artery microcirculatory resistance.

3. The computer-implemented method of claim 1, wherein the generated measure of per-artery microcirculatory resistance comprises an index of microcirculatory resistance (IMR) value.

4. The computer-implemented method of claim 3, wherein the index of microcirculatory resistance comprises Pd×Tmn at maximal hyperemia, wherein Pd comprises distal coronary pressure, and wherein Tmn comprises mean transit time.

5. The computer-implemented method of claim 1, wherein the microvasculature comprises vessels with a diameter less than about 500 μm.

6. The computer-implemented method of claim 1, wherein the first medical image and the second medical image comprise a resolution that does not allow for image segmentation of plaque within the microvasculature.

7. The computer-implemented method of claim 1, further comprising:

identifying, by the computer system, one or more regions of plaque on one or more of the first medical image or the second medical image; and generating, by the computer system, one or more quantified plaque parameters associated with the one or more regions of plaque, the one or more quantified plaque parameters comprising one or more of volume of low-density non-calcified plaque, volume of non-calcified plaque, or volume of calcified plaque, wherein a combination of the one or more quantified plaque parameters and the assessment of microcirculatory resistance of the coronary artery is configured to be used to determine a risk of major adverse cardiovascular event (MACE) for the subject.

8. The computer-implemented method of claim 7, wherein low density non-calcified plaque comprises a region of plaque having a radiodensity value of from about −189 to about 30 Hounsfield units, wherein non-calcified plaque comprises a region of plaque having a radiodensity value of from about 31 to about 350 Hounsfield units, and wherein calcified plaque comprises a region of plaque having a radiodensity value of from about 351 to about 2500 Hounsfield units.

9. The computer-implemented method of claim 1, wherein the difference in radiodensity between the myocardium subtended by the coronary artery in the first medical image and the second medical image is due to washout of the contrast dye.

10. The computer-implemented method of claim 1, further comprising:

generating, by the computer system, a measure of ischemia for the coronary artery, wherein a combination of the assessment of microcirculatory resistance of the coronary artery and the generated measure of ischemia for the coronary artery is configured to be used to determine a treatment for the subject.

11. The computer-implemented method of claim 10, wherein the measure of ischemia comprises fractional flow reserve.

12. A system for image-based assessment of microcirculatory resistance, the system comprising:

a non-transitory computer storage medium configured to at least store computer-executable instructions; and one or more computer hardware processors in communication with the non-transitory computer storage medium, the one or more computer hardware processors configured to execute the computer-executable instructions to at least:

access a first medical image of a subject, wherein the first medical image of the subject is obtained at a first point in time after injection of a contrast dye to the subject;

access a second medical image of a subject, wherein the second medical image of the subject is obtained at a second point in time after injection of the contrast dye to the subject;

analyze the first medical image and the second medical image to identify a coronary artery;

map myocardium subtended by the coronary artery in the first medical image and the second medical image;

analyze a difference in radiodensity between the myocardium subtended by the coronary artery in the first medical image and the second medical image, the difference in radiodensity arising from flow of the contrast dye through microvasculature of the myocardium subtended by the coronary artery;

determine a generated measure of per-artery microcirculatory resistance of the coronary artery by relating the difference in radiodensity between the myocardium subtended by the coronary artery in the first medical image and the second medical image to a difference in time between the first point in time and the second point in time; and determine an assessment of microcirculatory resistance of the coronary artery based at least in part on comparing the generated measure of the per-artery microcirculatory resistance of the coronary artery to a plurality of reference measures of per-artery microcirculatory resistance, the plurality of reference measures of per-artery microcirculatory resistance derived from a plurality of other subjects, wherein the assessment of microcirculatory resistance of the coronary artery is configured to be utilized to determine a treatment for the subject.

13. The system of claim 12, wherein the assessment of microcirculatory resistance of the coronary artery is determined utilizing a machine learning algorithm trained based at least in part on the plurality of reference measures of per-artery microcirculatory resistance.

14. The system of claim 12, wherein determining the assessment of microcirculatory resistance comprises determining an IMR value for the coronary artery utilizing a machine learning algorithm trained based at least in part on the plurality of reference measures of per-artery microcirculatory resistance and known IMR values.

15. The system of claim 12, wherein the first medical image and the second medical image comprise a resolution that does not allow for image segmentation of plaque within the microvasculature.

16. The system of claim 12, wherein the microvasculature comprises one or more regions of plaque, and wherein the one or more regions of plaque comprise a size that is not recognizable on the first medical image and the second medical image.

17. The system of claim 12, wherein the one or more computer hardware processors are further configured to:

identify one or more regions of plaque on one or more of the first medical image or the second medical image; and generate one or more quantified plaque parameters associated with the one or more regions of plaque, the one or more quantified plaque parameters comprising one or more of volume of low-density non-calcified plaque, volume of non-calcified plaque, or volume of calcified plaque, wherein a combination of the one or more quantified plaque parameters and the assessment of microcirculatory resistance of the coronary artery is configured to be used to determine a risk of major adverse cardiovascular event (MACE) for the subject.

18. The system of claim 12, wherein the difference in radiodensity between the myocardium subtended by the coronary artery in the first medical image and the second medical image is due to washout of the contrast dye.

19. The system of claim 12, wherein the one or more computer hardware processors are further configured to:

generate a measure of ischemia for the coronary artery, wherein a combination of the assessment of microcirculatory resistance of the coronary artery and the generated measure of ischemia for the coronary artery is configured to be used to determine a treatment for the subject.

20. A non-transitory computer readable medium configured for image-based assessment of microcirculatory resistance, the non-transitory computer readable medium having program instructions for causing a hardware processor to perform a method of:

accessing a first medical image of a subject, wherein the first medical image of the subject is obtained at a first point in time after injection of a contrast dye to the subject;

accessing a second medical image of a subject, wherein the second medical image of the subject is obtained at a second point in time after injection of the contrast dye to the subject;

analyzing the first medical image and the second medical image to identify a coronary artery;

mapping myocardium subtended by the coronary artery in the first medical image and the second medical image;

analyzing a difference in radiodensity between the myocardium subtended by the coronary artery in the first medical image and the second medical image, the difference in radiodensity arising from flow of the contrast dye through microvasculature of the myocardium subtended by the coronary artery;

determining a generated measure of per-artery microcirculatory resistance of the coronary artery by relating the difference in radiodensity between the myocardium subtended by the coronary artery in the first medical image and the second medical image to a difference in time between the first point in time and the second point in time; and determining an assessment of microcirculatory resistance of the coronary artery based at least in part on comparing the generated measure of the per-artery microcirculatory resistance of the coronary artery to a plurality of reference measures of per-artery microcirculatory resistance, the plurality of reference measures of per-artery microcirculatory resistance derived from a plurality of other subjects, wherein the assessment of microcirculatory resistance of the coronary artery is configured to be utilized to determine a treatment for the subject.

* * * * *